United States Patent [19]

Taniguchi et al.

[11] Patent Number: 6,059,718
[45] Date of Patent: *May 9, 2000

[54] ENDOSCOPE FORM DETECTING APPARATUS IN WHICH COIL IS FIXEDLY MOUNTED BY INSULATING MEMBER SO THAT FORM IS NOT DEFORMED WITHIN ENDOSCOPE

[75] Inventors: Akira Taniguchi, Hashioji; Sumihiro Uchimura, Sagamihara; Tsukasa Ishii, Hachioji; Masanao Hara, Tama; Nobuyuki Matsuura, Hino; Yasuo Miyano, Hachioji, all of Japan

[73] Assignee: Olympus Optical Co., Ltd., Tokyo, Japan

[*] Notice: This patent is subject to a terminal disclaimer.

[21] Appl. No.: 08/460,812

[22] Filed: Jun. 2, 1995

Related U.S. Application Data

[63] Continuation-in-part of application No. 08/281,668, Jul. 28, 1994, abandoned.

[30] Foreign Application Priority Data

| Oct. 18, 1993 | [JP] | Japan | 5-260148 |
| Oct. 18, 1993 | [JP] | Japan | 5-260149 |
| Apr. 21, 1994 | [JP] | Japan | 6-083291 |
| Jun. 20, 1994 | [JP] | Japan | 6-137468 |
| Aug. 18, 1994 | [JP] | Japan | 6-194312 |
| Sep. 30, 1994 | [JP] | Japan | 6-237955 |

[51] Int. Cl.[7] ..................................................... A61B 1/00

[52] U.S. Cl. ......................................... 600/117; 600/424

[58] Field of Search .................................. 128/653.1, 658, 128/662.06, 903, 737, 899, 656; 600/117, 145, 945, 407, 435, 433, 462, 550, 424, 109; 607/116, 122; 324/219, 246; 340/573; 125/45

[56] References Cited

U.S. PATENT DOCUMENTS

| 4,173,228 | 11/1979 | van Steenwyk et al. . |
| 4,176,662 | 12/1979 | Frazer . |
| 4,790,025 | 12/1988 | Inoue et al. ........................... 382/293 |
| 4,821,731 | 4/1989 | Martinelli et al. . |
| 5,005,592 | 4/1991 | Cartmell ............................... 128/653.1 |
| 5,073,960 | 12/1991 | Nakai et a. ........................... 382/199 |
| 5,099,845 | 3/1992 | Besz et al. ............................ 128/899 |
| 5,253,647 | 10/1993 | Takahashi et al. ................. 128/653.1 |
| 5,273,025 | 12/1993 | Sakiyama et al. . |
| 5,318,025 | 6/1994 | Dumoulin et al. ................... 128/899 |
| 5,325,873 | 7/1994 | Hirschi et al. ....................... 128/899 |
| 5,371,839 | 12/1994 | Fukunaga et al. ................... 395/131 |

(List continued on next page.)

FOREIGN PATENT DOCUMENTS

| 61-204364 | 9/1986 | Japan . |
| 63-59970 | 3/1988 | Japan . |
| 2-98524 | 4/1990 | Japan . |
| 5-80893 | 4/1993 | Japan . |
| 5-177000 | 7/1993 | Japan . |
| 92/03090 | 3/1992 | WIPO . |
| 94/04938 | 3/1994 | WIPO . |

*Primary Examiner*—Brian L. Casler
*Attorney, Agent, or Firm*—Armstrong, Westerman, Hattori, McLeland & Naughton

[57] ABSTRACT

Magnetic-field generating elements or magnetic-field detecting elements are fixed into an insertion part having elasticity, which is inserted into a subject, by an insulating material while ensuring that forms of the respective magnetic-field generating elements or the respective magnetic-field detecting elements are not changed. Even when the insertion part is bent, there is no change in either the function of magnetic-field generation or the function of magnetic-field detection. Magnetic-field detecting elements or magnetic-field generating elements which are arranged at known positions around the subject are combined with each other to calculate three-dimensional positions of the magnetic-field generating elements or the magnetic-field detecting elements within the insertion part. Further, a form of the insertion part is estimated, and a three-dimensional image corresponding to a form of the insertion part is produced. Moreover, a three-dimensional image is projected onto a screen surface to display a stereoscopic image corresponding to the form of the insertion part.

8 Claims, 116 Drawing Sheets

U.S. PATENT DOCUMENTS

| | | | |
|---|---|---|---|
| 5,425,367 | 6/1995 | Shapiro et al. | 128/899 |
| 5,425,382 | 6/1995 | Golden et al. | 128/899 |
| 5,445,150 | 8/1995 | Dumoulin et al. | 128/899 |
| 5,475,803 | 12/1995 | Stearns et al. | 395/137 |
| 5,490,246 | 2/1996 | Brotsky et al. | 395/161 |
| 5,558,091 | 9/1996 | Acker et al. | 128/899 |

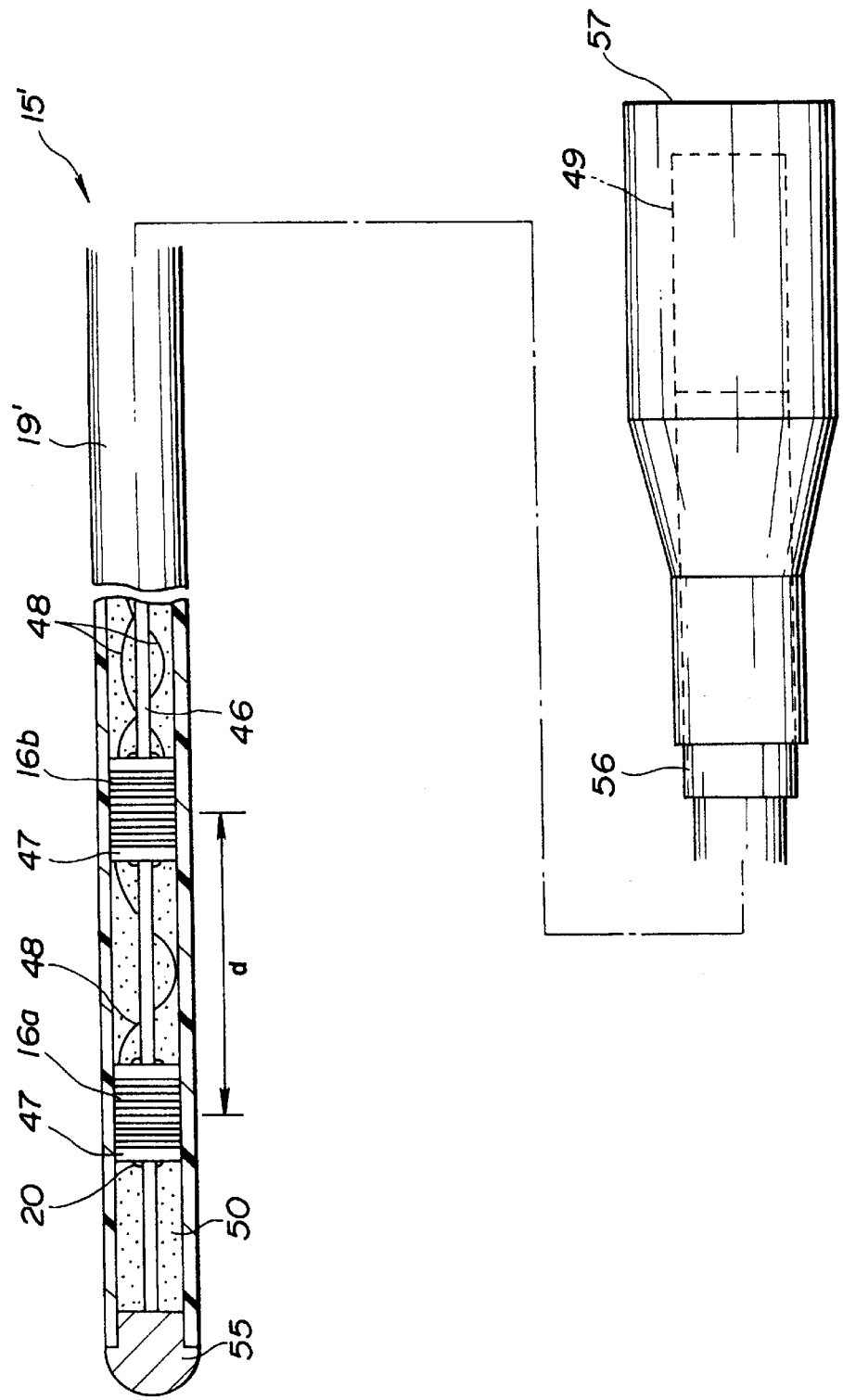

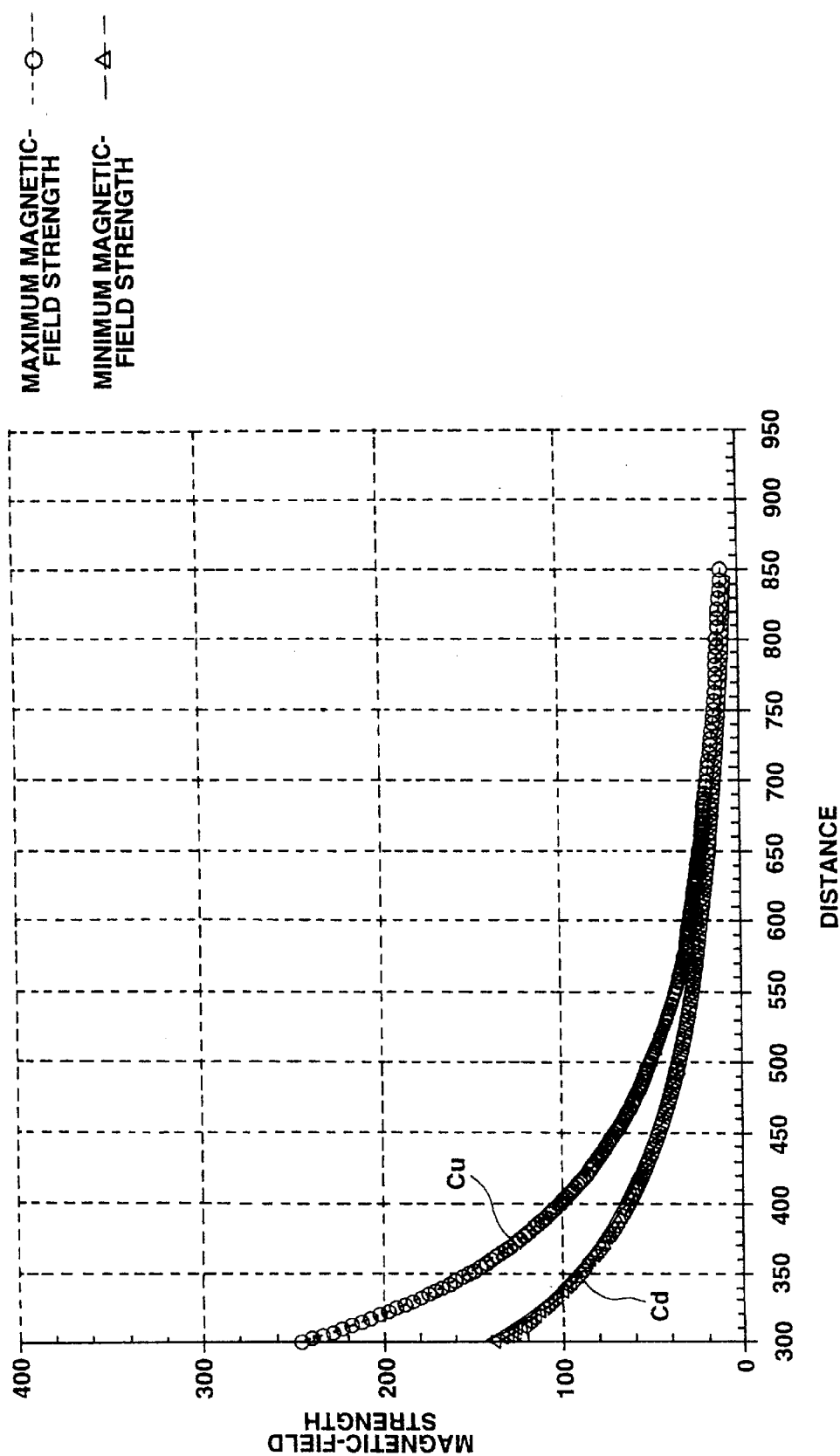

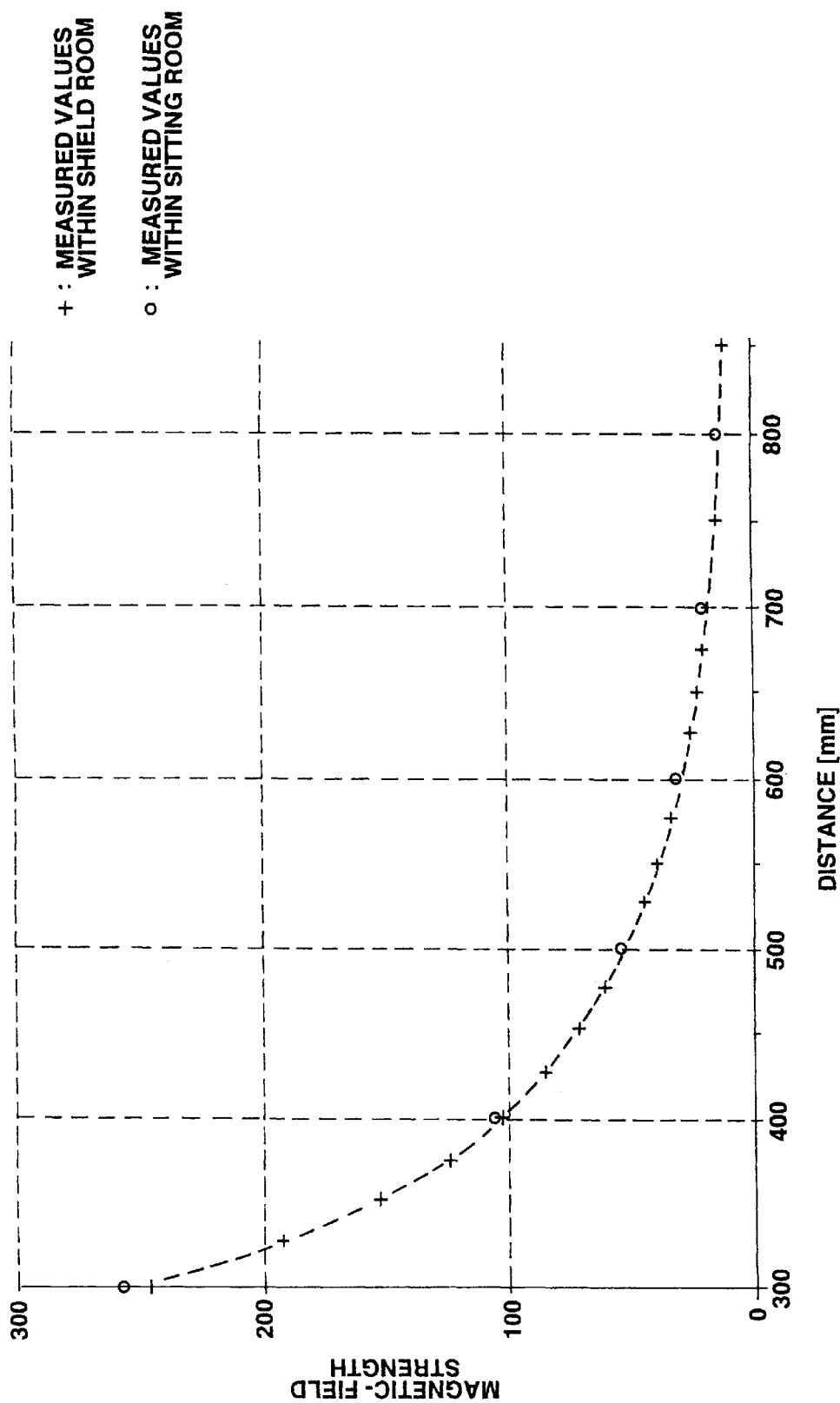

FIG.28a
FIG.28b
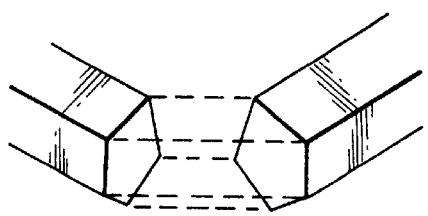
FIG.29
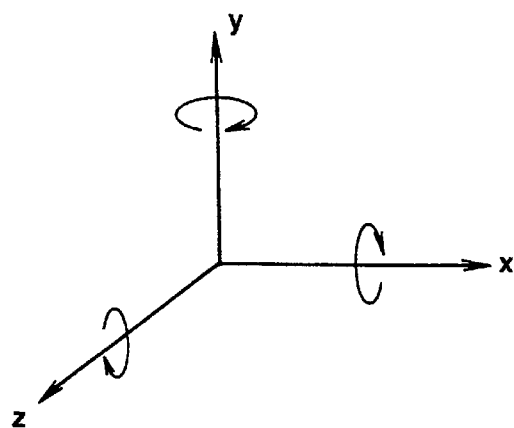
FIG.30
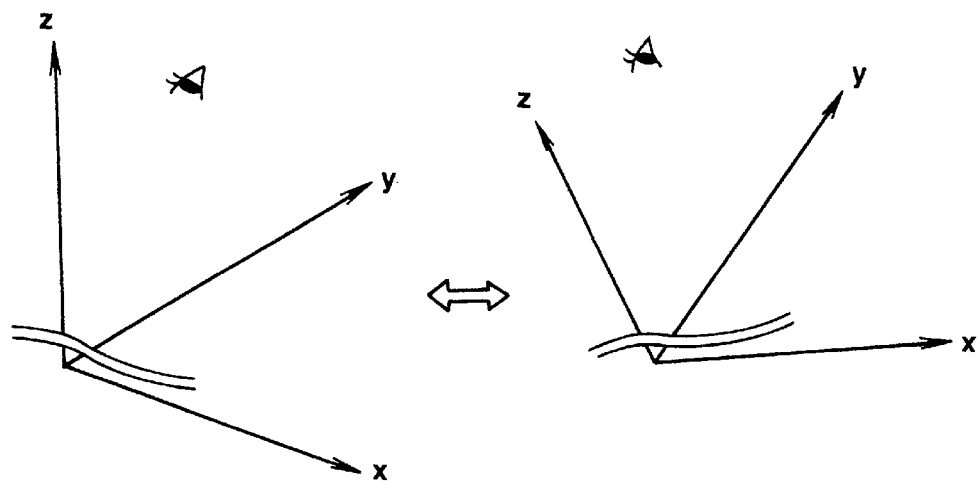

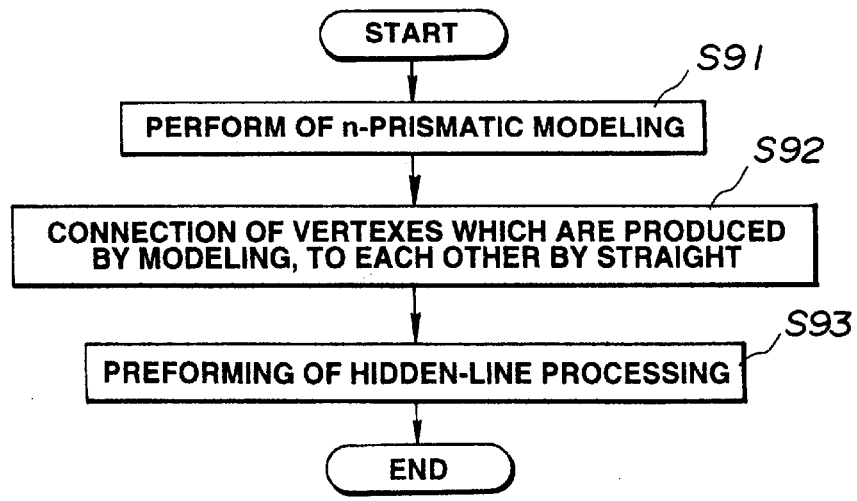
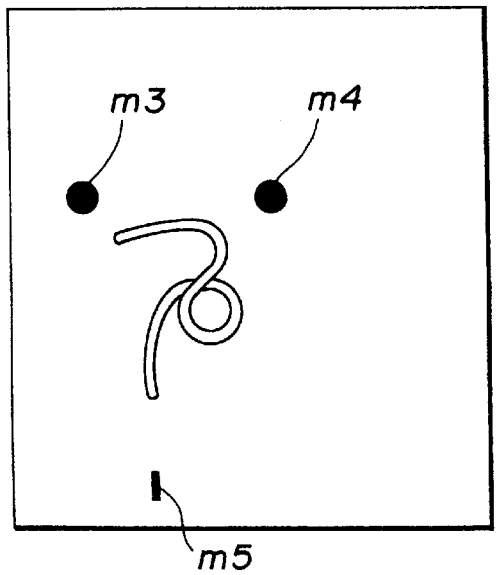
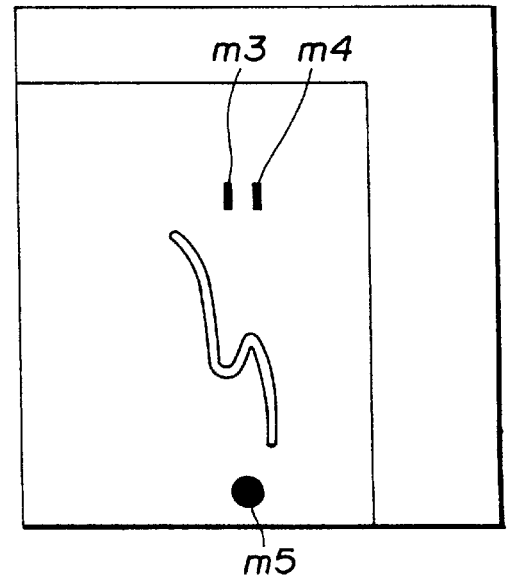

FIG.43a  FIG.43b
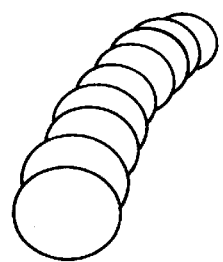
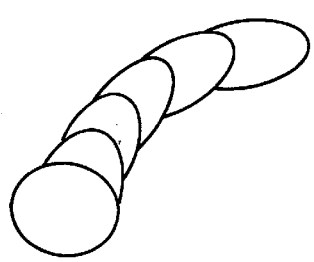
FIG.45a — SOURCE-COIL SWITCHING SIGNAL
FIG.45b — SOURCE-COIL CURRENT
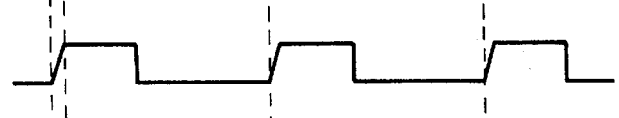
FIG.45c — SENSE-COIL DETECTING SIGNAL
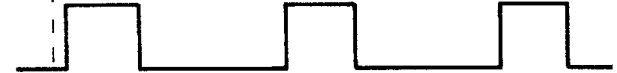
FIG.45d — READ TIMING
$\Delta t'$

FIG.63a ILLUMINATION (EXPOSURE) PERIOD OF TIME 
FIG.63b CCD DRIVE PERIOD OF TIME 
FIG.63c DRIVE SIGNAL PERIOD OF TIME 
FIG.66
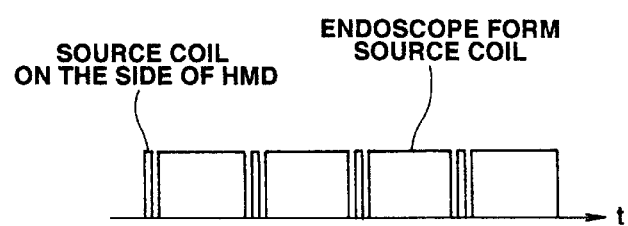

DETECTING DIRECTION

FIG.104
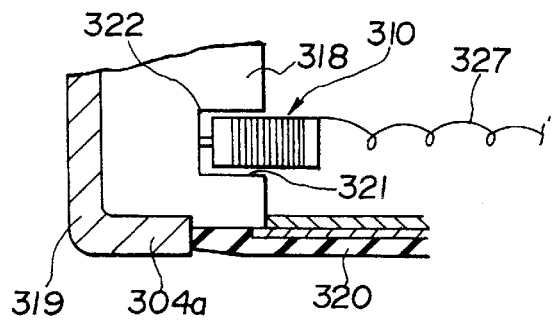
FIG.105
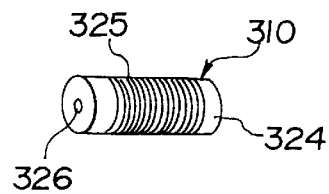
FIG.106a  FIG.106b
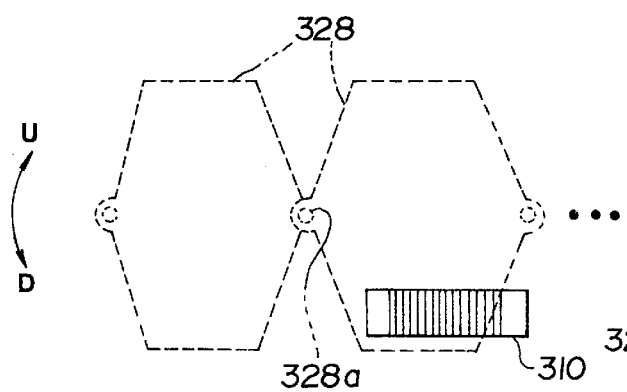 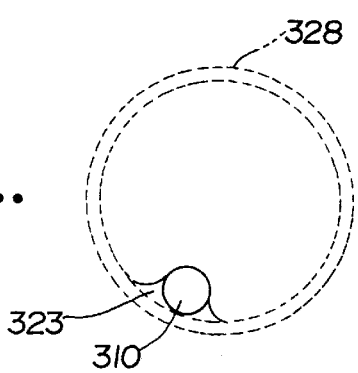
FIG.106c  FIG.106d  FIG.106e  FIG.106f
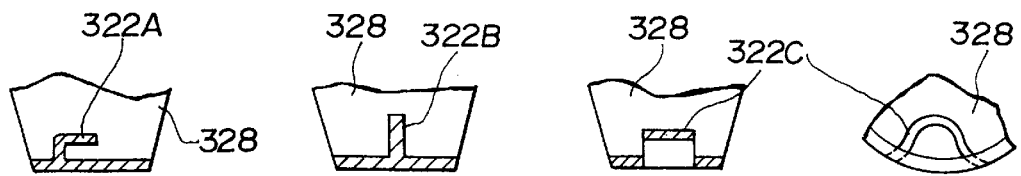

FIG.112
CORRECTION OF COORDINATE VALUE

| IN CASE WHERE ONLY 1α IS MATERIALIZED | IN CASE WHERE ONLY 2α IS MATERIALIZED | IN CASE WHERE ONLY 3α IS MATERIALIZED | ALL IS NOT MATERIALIZED |
|---|---|---|---|
| $X\gamma=(X\gamma+X\beta)/2$ | $X\alpha=(X\alpha+X\beta)/2$ | $X\beta=\{X\beta-(X\alpha+X\gamma)/2\}/2$ | |
| $Y\gamma=(Y\gamma+Y\beta)/2$ | $Y\alpha=(Y\alpha+Y\beta)/2$ | $Y\beta=\{Y\beta+(Y\alpha+Y\gamma)/2\}/2$ | |
| $Z\gamma=(Z\gamma+Z\beta)/2$ | $Z\alpha=(Z\alpha+Z\beta)/2$ | $Z\beta=\{Z\beta+(Z\alpha-Z\gamma)/2\}/2$ | |

ABNORMAL-VALUE FLAG SETTING

FIG.114

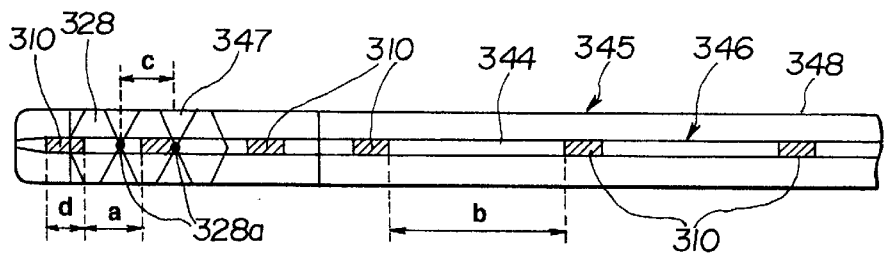

FIG.115

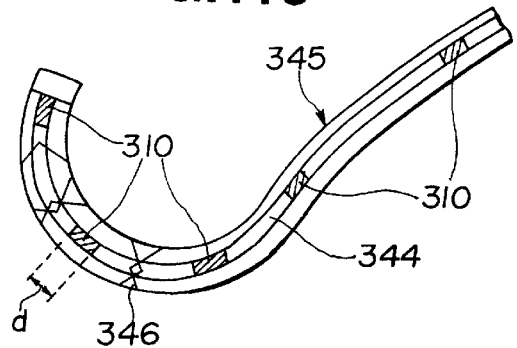

FIG.143

《INFORMATION》

TITLE SCREEN CAN DISPLAY SOME TEXT.

AND IT IS BACKED UP TO THIS SYSTEM MEMORY.■

FIG.144

```
PATIENT DATA LIST
  SEQ. NO.         ID. NO.                NAME
=================================================================
     1          000000000000001         ???Taniguchi
     2          000000000000002         S. Uchimura
     3          000000000000003         TukasaIshi
     4          000000000000004         ???Hiyama
     5          000000000000005         ???Watai
     6          000000000000006         HanakoMurata
     7
     8
     9
    10          000156                  MasanaHara
    11          000158                  YoshituguShida
    12          000163                  NaohikoKitamura
    13
    14
    15
    16
    17
    18
    19
    20          000000000000000         000000000000000000
                ALL CLEAR=HOMECLR       ENTER NO. : ■
```

FIG.145

PATIENT DATA ENTRY (INDIVIDUAL)

==========================================

---
SEQ. NO.   : 02

---

ID. NO.        : 000000000000002
      NAME           : S. Uchimura
      SEX            : M
      AGE            : 29
      D. O. BIRTH    :22/03/65 f·6 : PATIENT ENTRY     f·9 : GRAPHICS     f·10 : END

FIG.146

ID. NO : 000000000000002   NAME : S. Uchimura..
DATE : 12/07/94   SEX   : M... AGE : 29.
TIME : 19:21:16   D.O.BIRTH : 22/03/65

[CTRL+]
←,→:ROTATION +0.0[°]
↑,↓:ELEVATION +0.0[°]
+,−:VIEW POINT+0.0[cm]

vf·1      : RESET TO 0
f·10      : PROGRAM END

COMMENT :

ENDOSCOPE FORM DETECTING APPARATUS IN WHICH COIL IS FIXEDLY MOUNTED BY INSULATING MEMBER SO THAT FORM IS NOT DEFORMED WITHIN ENDOSCOPE

This application is a continuation-in-part of application Ser. No. 08/281,668, filed Jul. 28, 1994 now abandoned.

BACKGROUND OF THE INVENTION

1. Field of the Invention

The invention relates to an endoscope form detecting apparatus for detecting a form of an insertion part, in which a magnetic-field generation element or a magnetic detection element is fixedly mounted within the insertion part of the endoscope, by an insulating member so that the form is not deformed even when the insertion part is curved.

2. Description of the Related Art

In recent years, an endoscope has widely been used in the field of medical treatment and the industrial field. The endoscope, particularly, an endoscope whose insertion part is elastic is inserted into a curved body cavity, to thereby be able to diagnose internal organs in a depth within the body cavity without incision, and can perform medical treatment such as one in which a treatment tool is inserted into a channel, as occasion demands, to excise polyps, or the like.

In this case, as in the case where the interior of a distal or inferior digestive organ is inspected or examined from the side of an anus, for example, there is a certain measure of skill required for the insertion part to be smoothly inserted into the curved body cavity.

Specifically, whenever an inserting operation is performed, an operation where a bending section, which is provided on the insertion part, is curved in accordance with a bending of a line, or the like, is required for performing smooth insertion. To this end, it can be known where the position within the body cavity of a distal end or a forward end of the insertion part, in what manner the insertion part is curved at present, and the like.

For this reason, in the prior art of U.S. Pat. No. 5,273,025, there is disclosed an arrangement in which a non-scanning or standard antenna (antenna coil) which is provided outside the insertion part is scanned with respect to a receiving standard antenna (coil) which is provided on the insertion part, to detect an inserted condition or state of the insertion part.

Moreover, in a catheter guide device disclosed in Japanese Patent Laid-Open No. HEI 5-177000, an arrangements disclosed in which transmitting means is mounted on the forward end of the catheter or the like, and a signal thereof is received to establish a position of the transmitting means.

Further, an arrangement or the like is disclosed in U.S. Pat. No. 4,176,662 in which burst waves are outputted from a transducer at a forward end of an endoscope, the burst waves are detected by a plurality of surrounding antennas or transducers, and a position of the forward end is plotted onto a CRT.

Moreover, an apparatus is disclosed in U.S. Pat. No. 4,821,731 in which two (2) coils which are arranged outside a body and in the form of a cross are rotatable, and orientation adjacent to a forward end of a catheter is determined or decided on the basis of an output from a loop coil which is provided on the side of a forward end of the catheter which is inserted into the body.

The prior art disclosed in PCT Laid-Open Publication No. GB 91/01431 discloses an arrangement in which a plurality of dipole antennas are arranged in a grating or a lattice manner in X-Y direction around the periphery of a subject into which an endoscope is inserted, and are AC-driven, while a position of the endoscope is led-through or rendered by a signal which is produced by a coil built-in on the side of the endoscope.

However, in the above-described prior art, a method of fixing the coil which is built-in for detecting the position or the form, in the endoscope, or the like has not sufficiently been considered. For this reason, the internal organs or viscera within the endoscope are moved by curvature or bending of an insertion part whenever the endoscope is inserted into a patient. At that tine, a stress is applied to the position detecting coil by friction. Thus, there are situations where the coil is deformed.

If the coil is deformed, the magnetic field which is generated by the coil is changed or varies, or a level of an induced signal is changed. Accordingly, this produces a disadvantage in that it is impossible to perform positional detection or form detection with high accuracy.

Further, the above-described prior art discloses that the coil is arranged within the insertion part which is inserted into an organism, to detect the position of the coil. However, the above-described prior art does not disclose a method of telescopically displaying an image which corresponds to the form of the inserted insertion part, or a means for telescopically displaying the image. Since, generally, the insertion part which is inserted into the organism is curved, it is desirable that the form of the insertion part is displayed so as to be easily visualized.

SUMMARY OF THE INVENTION

It is an object of the invention to provide an endoscope form detecting apparatus which enables highly accurate form detection.

Further, it is another object of the invention to provide an endoscope position detecting apparatus which enables highly accurate positional detection.

Moreover, it is another object of the invention to provide an insertion-part form display apparatus which can display a form of an insertion part which is easily visualized.

According to the present invention, there are provided:

fixing means for fixing one of a magnetic-field generating element for generating a magnetic field and a magnetic-field detecting element for detecting the generated magnetic field, into an insertion part having elasticity of an endoscope through an insulating member such that a form of the magnetic-field generation element or the magnetic-field detecting element is not changed;

the other of the magnetic-field generation element and the magnetic-field detecting element which is arranged at a known position surrounding a subject into which the insertion part is inserted; and position calculation means for calculating a position of the magnetic-field generation element or the magnetic-field detecting element within the insertion part with respect to the magnetic-field generation element or the magnetic-field detecting element which is arranged at the known position, on the basis of a detecting signal which detects a magnetic field generated by the magnetic-field generation element by the magnetic-field detection element, whereby, whenever the insertion part is inserted into the interior of the subject, even if the insertion part is curved, the magnetic-field generation element or the magnetic-field detecting element within the insertion part is fixed such that a form thereof is not changed, by fixing means. Accordingly, the position of the insertion part of the endoscope can be detected with superior accuracy.

Furthermore, form estimation means which performs form estimation is provided with respect to an output from the position calculation means, whereby form estimation can be performed with high accuracy.

Further, a telescopic image corresponding to a telescopic form of the insertion part which is estimated by the form estimation means is constructed, and is converted into a two-dimensional image which is displayed by the display means, whereby an operator can easily visualize the form of the insertion part which is inserted into the subject. Thus, the operator can easily perform an inserting operation of the insertion part.

These objects and advantages of the present invention wild become further apparent from the following detailed explanation.

BRIEF DESCRIPTION OF THE DRAWINGS

FIGS. 1 to 43b relate to a first embodiment of the invention, where FIG. 1 is a schematic arrangement view of an endoscope system;

FIG. 2 is a block diagram of an arrangement of an endoscope form detecting apparatus;

FIG. 3 is a perspective view of the endoscope;

FIG. 4 is an arrangement view of a whole of an endoscope apparatus;

FIG. 5 is a cross-sectional view showing an arrangement on a distal side of a probe;

FIG. 6 is a cross-sectional view showing an arrangement of the probe;

FIG. 7 is an explanatory view showing a condition or state which detects a position of a source coil of the probe by the use of a sense coil;

FIG. 8b is a block diagram showing an arrangement of the circumference of a sense coil and an amplifier in FIG. 8a;

FIG. 9 is a flow chart for the description of operation of driving of a source coil and signal detection due to the sense coil;

FIGS. 10a~10g are timing diagrams for the description of operation of the driving of the source coil and signal detection operation due to the sense coil;

FIG. 11 is an explanatory view showing a condition or state for detecting an existing range or scope of a single source coil within the endoscope, by a plurality of sense coils which are provided on the periphery of the bed;

FIG. 12 is an explanatory view showing a form of an equal magnetic surface due to a single-axis coil;

FIG. 13 is an explanatory view showing a condition or state performing positional correction on the basis of inclination;

FIG. 14 is an explanatory view showing an output image of an endoscope form which is displayed on a monitor image plane:

FIG. 15 is a flow chart indicating the treatment or processing steps of the endoscope form detecting apparatus;

FIG. 16 is a characteristic view showing a graph of data in which orientation of the single-axis source coil is changed within a shield room, and values of the maximum magnetic-field strength and the minimum magnetic-field strength which are detected by the source coil and a three-axis sense coil of the known distance are measured by changing of the distance;

FIG. 18 is a comparison view showing measurement values within the shield room and a sitting room or a living room;

FIG. 19 is a flow chart of magnetic-field strength calculation treatment or processing;

FIG. 20 is a flow chart of a keyboard input treatment or processing;

FIG. 21 is a flow chart of command treatment or processing;

FIG. 22 is a flow chart of scope-image description treatment or processing;

FIGS. 23a~23d are flow charts of the scope-image description treatment or processing in an n-prismatic model;

FIG. 24 is a flow chart of construction the n-prismatic model;

FIGS. 28a and 28b are explanatory views showing a limit where the n-prismatic model data are generated;

FIG. 29 is an explanatory view showing rotation of an axis due to affine transformation;

FIG. 30 is an explanatory view showing the fact that sight-point-modification or—change is modified to rotation of a world coordinate system;

FIGS. 32a~32c are explanatory views of the world coordinate system or the like;

FIG. 33 is an explanatory view of processing for displaying a stereoscopic image and the adopted coordinate system;

FIG. 34 is a flow chart of hidden-line processing in the n-prismatic model;

FIG. 36 is a flow chart showing steps used to perform color shading processing;

FIG. 37 is a flow chart showing the steps used to perform the shading processing using color or hue;

FIG. 38 is a flow chart showing the steps used to perform the shading processing using luminance or intensity and chrominance or saturation;

FIG. 39 is a flow chart showing steps involved in an n-prismatic model due to a wire frame;

FIGS. 40a and 40b are explanatory views showing marker display examples upon display of an endoscope form;

FIG. 42 is a flow chart of steps involved in painting processing by means of the n-prismatic connection model;

FIGS. 43a and 43b are explanatory views showing an example display of display due to wire frame display;

FIGS. 45a~45d are timing diagrams describing the operation of FIG. 44;

FIG. 50 is a block diagram showing a more specific arrangement of the endoscope form detecting apparatus;

FIG. 51 is a flow chart showing steps involved in processing of magnetic-field generation and magnetic-field detection;

FIG. 52 is an explanatory view showing a monitor image plane which displays an endoscope form;

FIG. 54 is a block diagram showing an arrangement of an endoscope form detecting apparatus according to the third embodiment of the invention;

FIG. 56 is an explanatory diagram showing the relationship between sensors and a source;

FIG. 57 is an explanatory view showing a data table of a sensor A;

FIG. 58 is an explanatory view showing that a source position is determined from a spatial coordinate group which corresponds to output data;

FIG. 59 is an explanatory view showing a state which displays the source position determined in FIG. 58

FIGS. 63a~63c are explanatory views where driving is made such that a CCD drive-signal period and a drive-signal period are not piled up upon each other or do not lie one upon another;

FIGS. 64 to 66 relate to a seventh embodiment of the invention, FIG. 64 being an arrangement of an endoscope system according to the seventh embodiment of the invention;

FIG. 65 is an explanatory view showing detecting a position of a patient;

FIG. 66 is an explanatory view in which driving of positional detection and form detection is performed by time-sharing;

FIG. 74 is a flow chart showing the processing steps which generate a background image by the eleventh embodiment;

FIG. 87 is an explanatory view showing a top plan which is formed by two (2) source coils of a third modification, or the like;

FIGS. 92a and 92b are explanatory views showing a method of positioning the sensor, or the like;

FIGS. 103 to 106 relate to a sixteenth embodiment of the invention, FIG. 103 being an arrangement view of an endoscope form detecting apparatus;

FIG. 104 is a cross-sectional view showing a state in which a coil is fixedly mounted on a forward end of an endoscope;

FIG. 105 is a perspective view of the coil;

FIGS. 106a~106f are views showing fixing of the coil to a bending frame;

FIGS. 107 to 112 relate to a seventeenth embodiment of the invention, FIG. 107 being an arrangement view of an endoscope form detecting apparatus according to the seventeenth embodiment;

FIG. 108 is an explanatory view of a coordinate position;

FIG. 109 it a schematic block diagram of a detector;

FIG. 110 is a flow chart showing steps relating to insertion form detection;

FIG. 111 is a flow chart showing steps relating to coordinate positional detection;

FIG. 112 is a flow chart showing steps relating to coordinate positional correction;

FIGS. 114 and 115 relate to a modification of the eighteenth embodiment, FIG. 114 being a schematic arrangement view of an imaging probe which is arranged within an endoscope insertion part; and FIG. 115 is an explanatory view showing the relationship between a curved condition or state of a bending section and a length of a coil.

Figure 116:
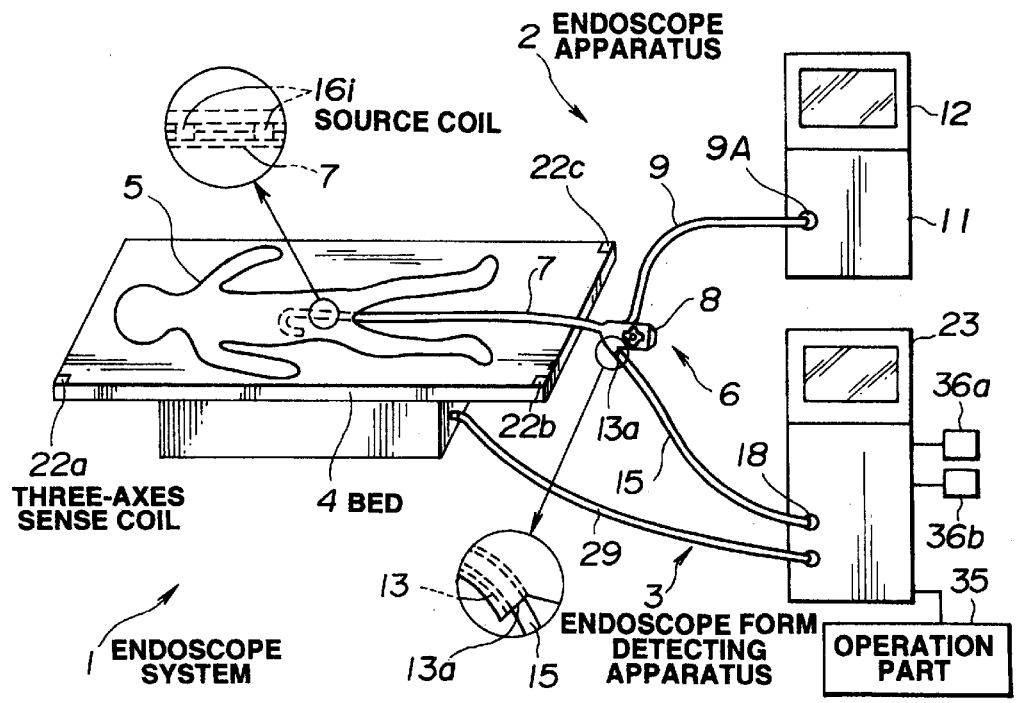
Figure 117:
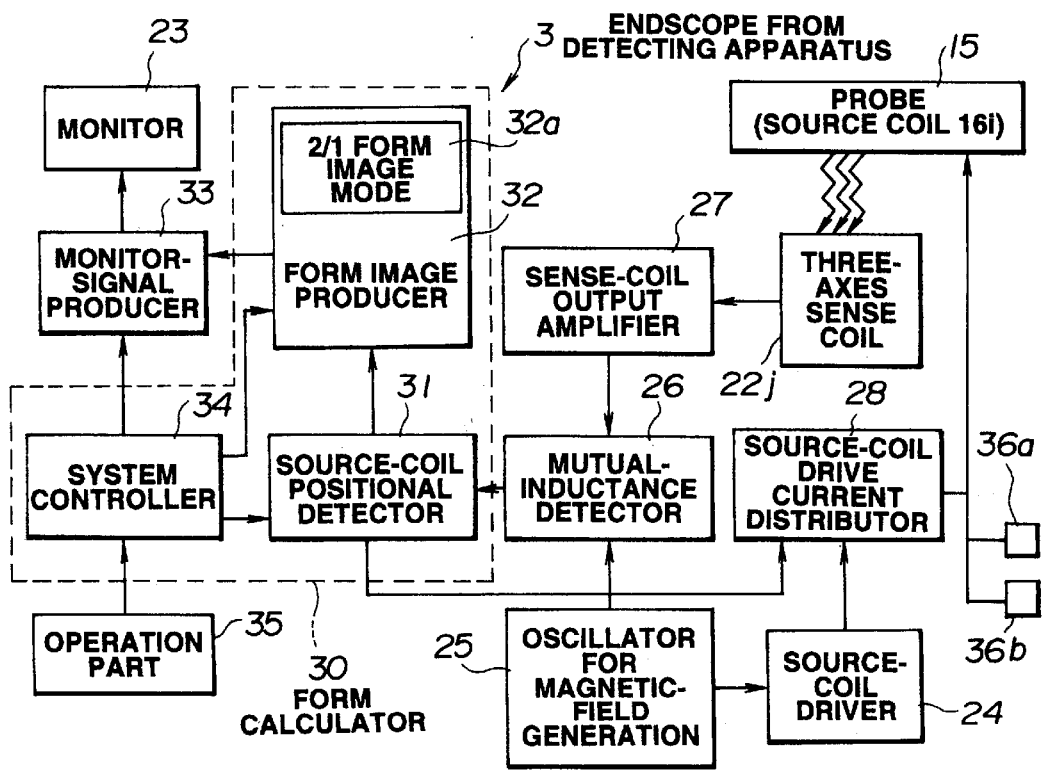
Figure 118:
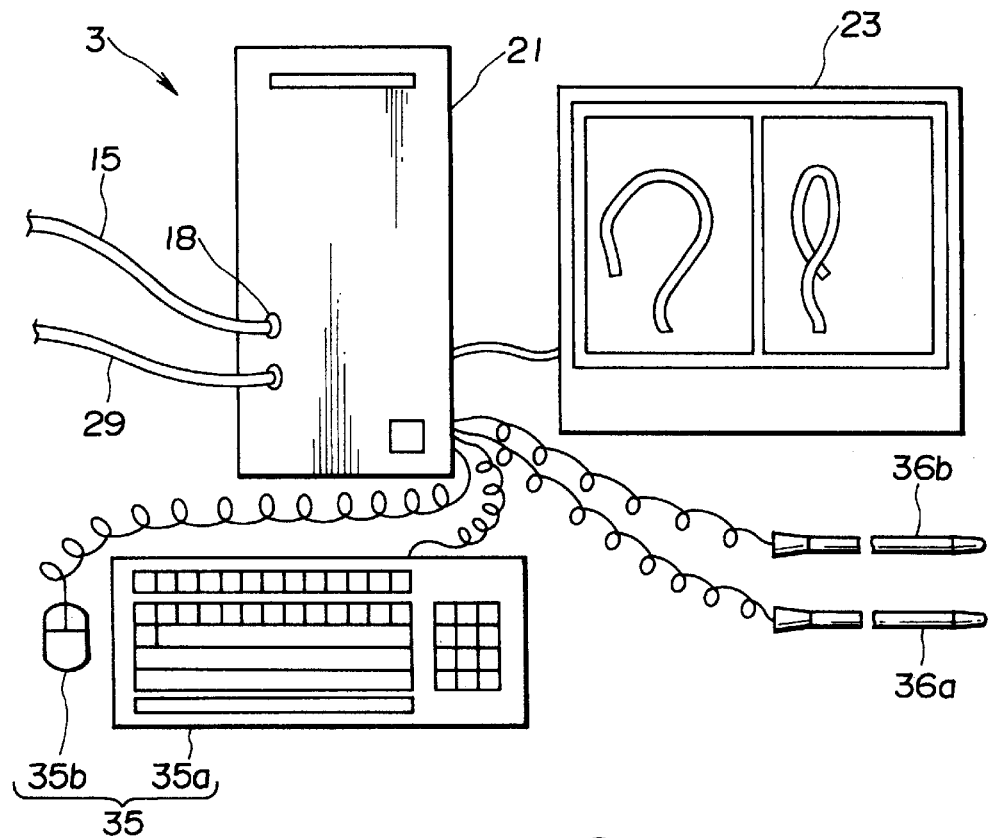
Figure 119:
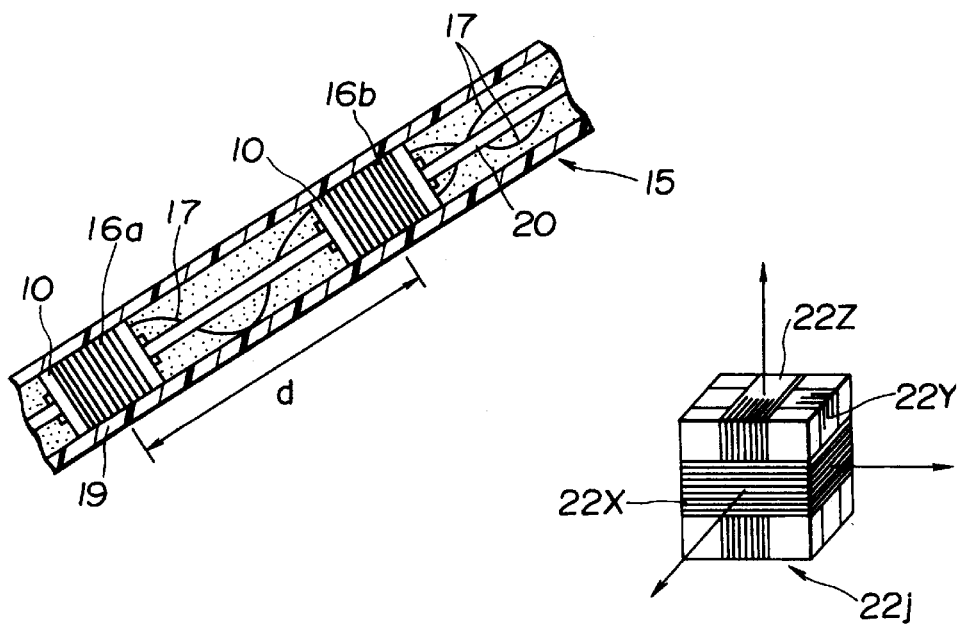
Figure 120:
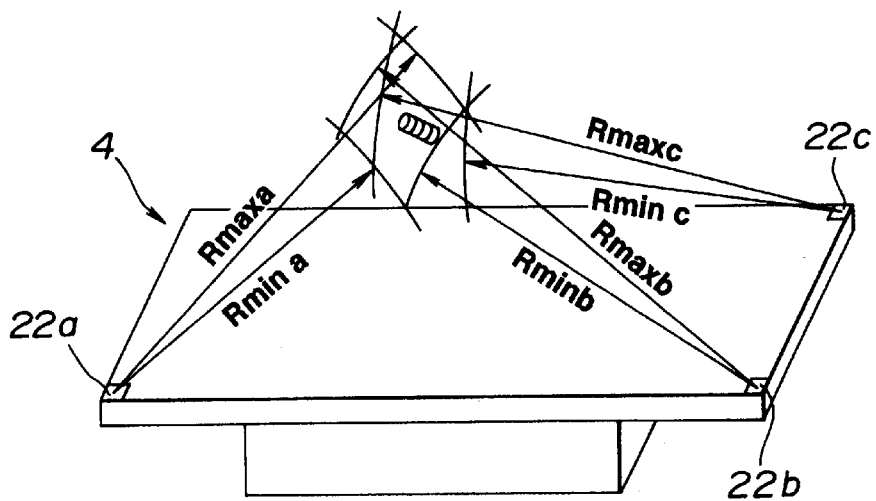
Figure 121:
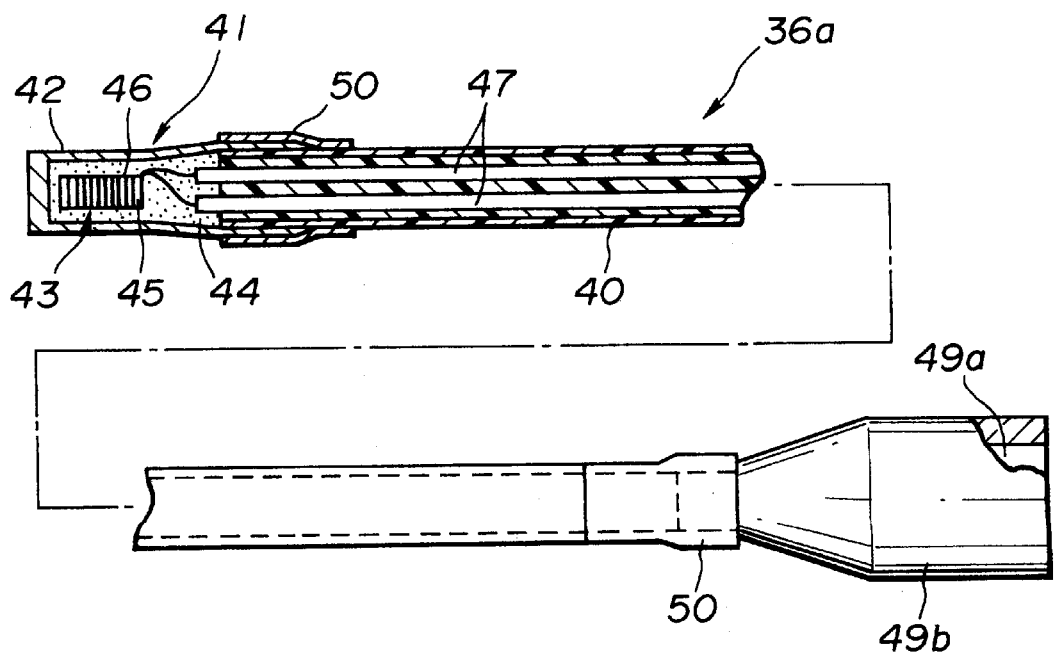
Figure 122:
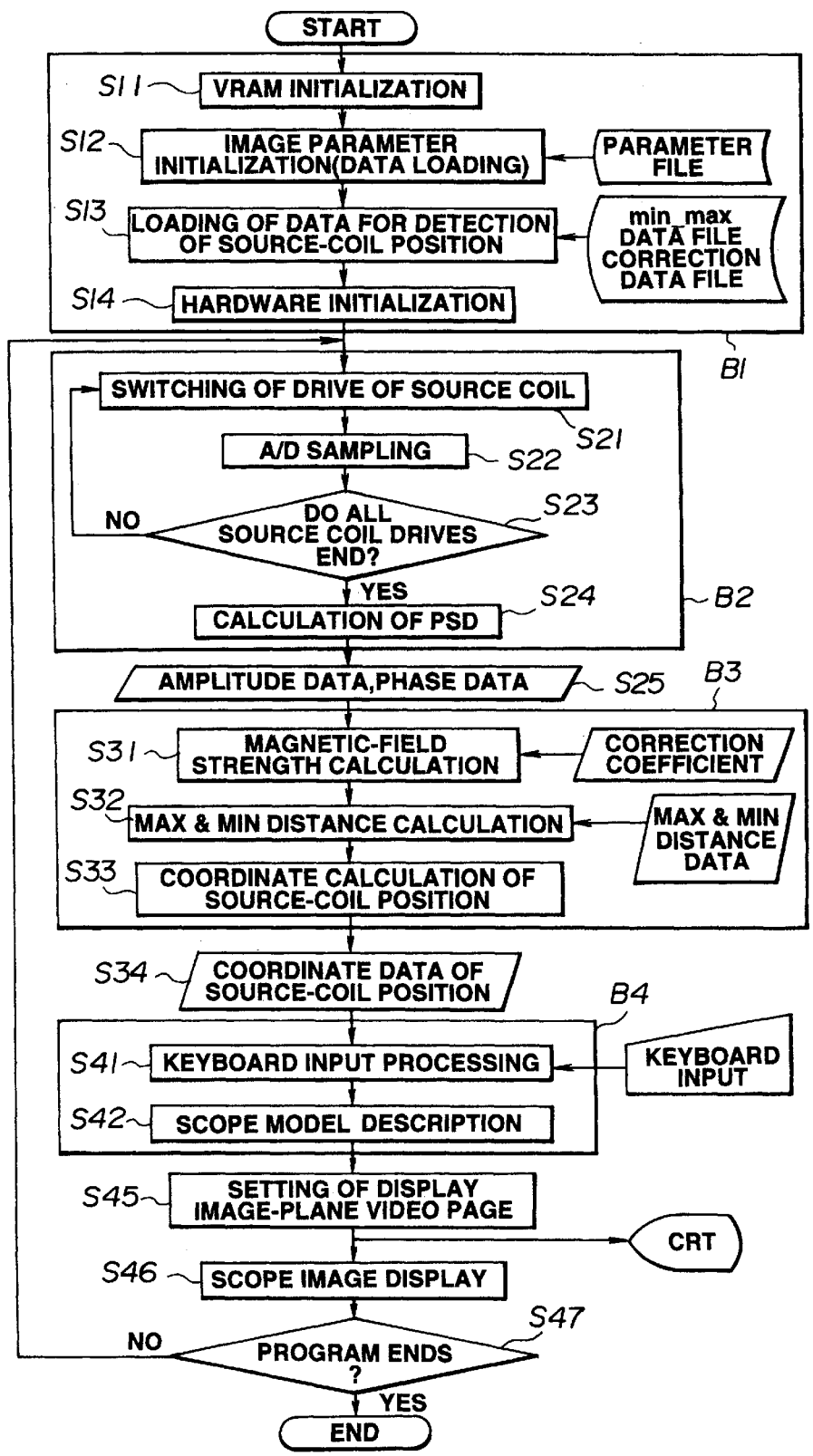
Figure 123:
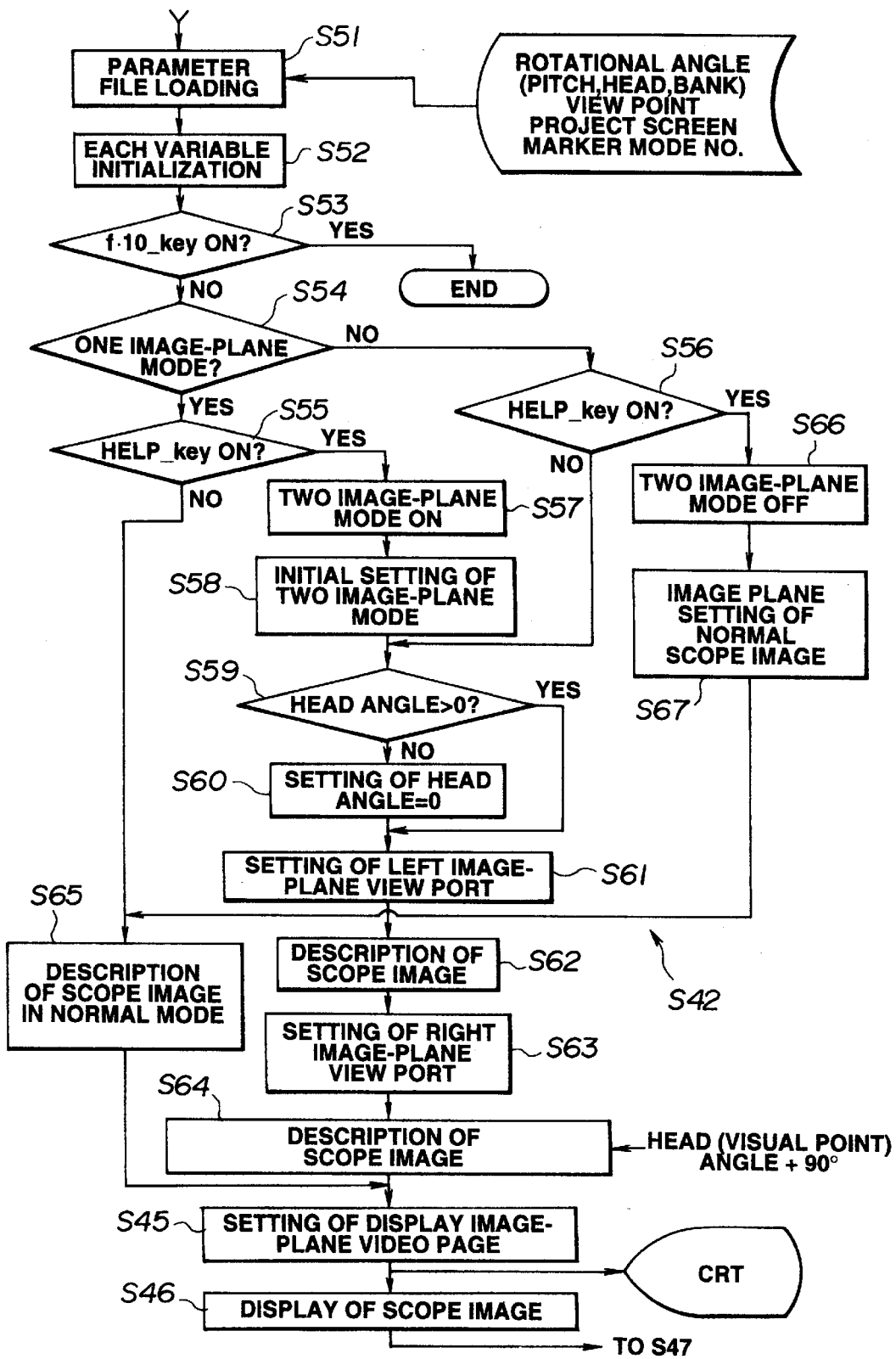
Figure 124:
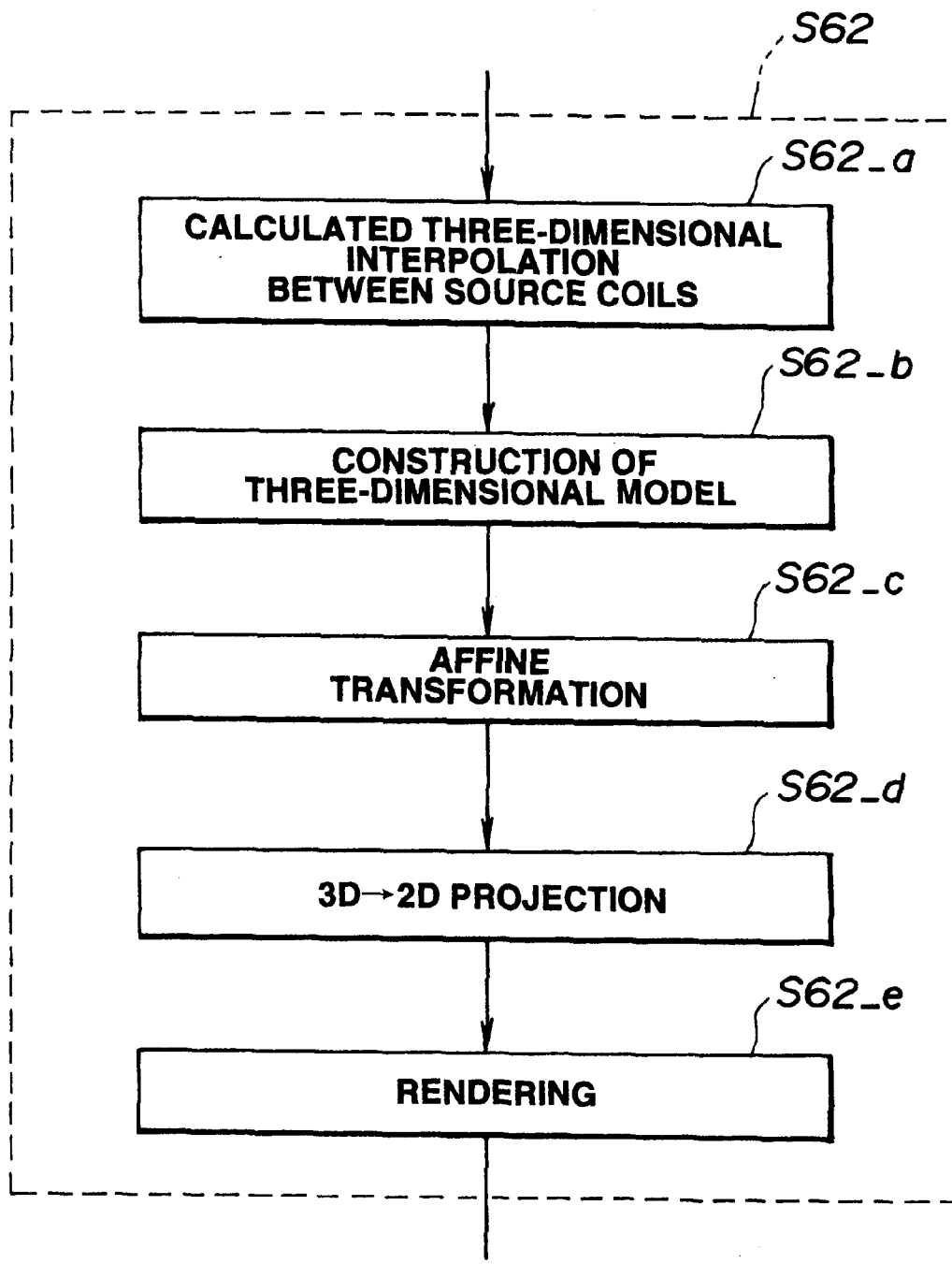
Figure 126:
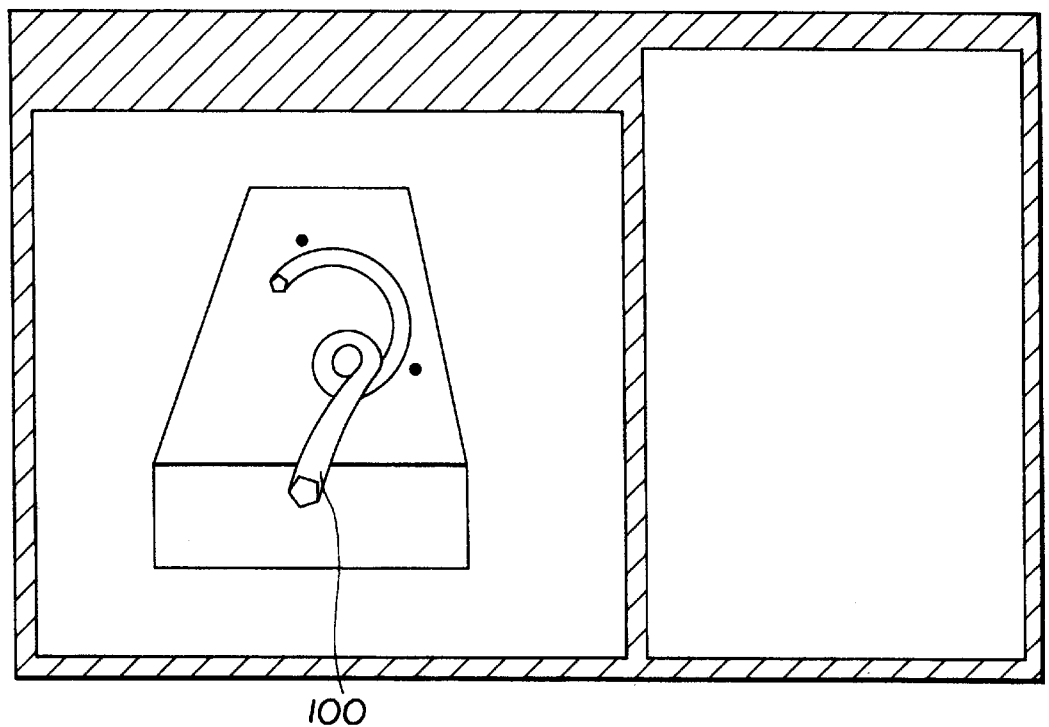
Figure 127:
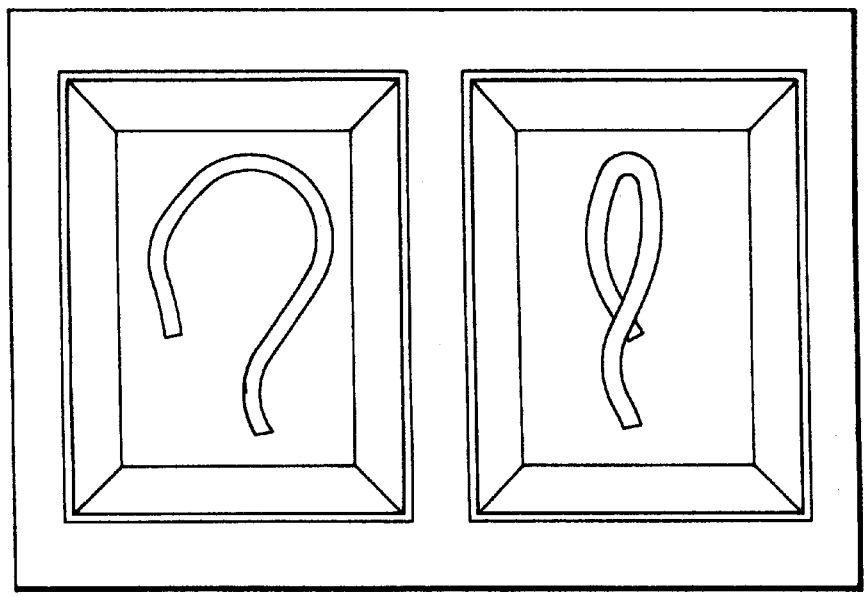
Figure 128:
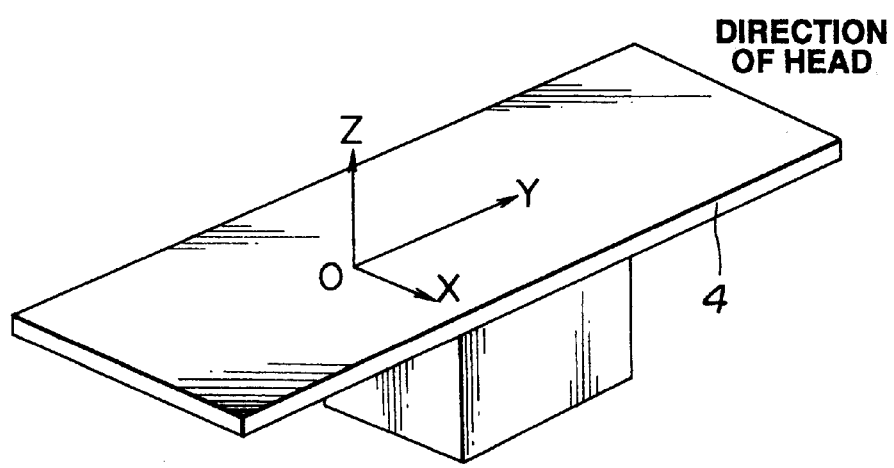
Figure 129:
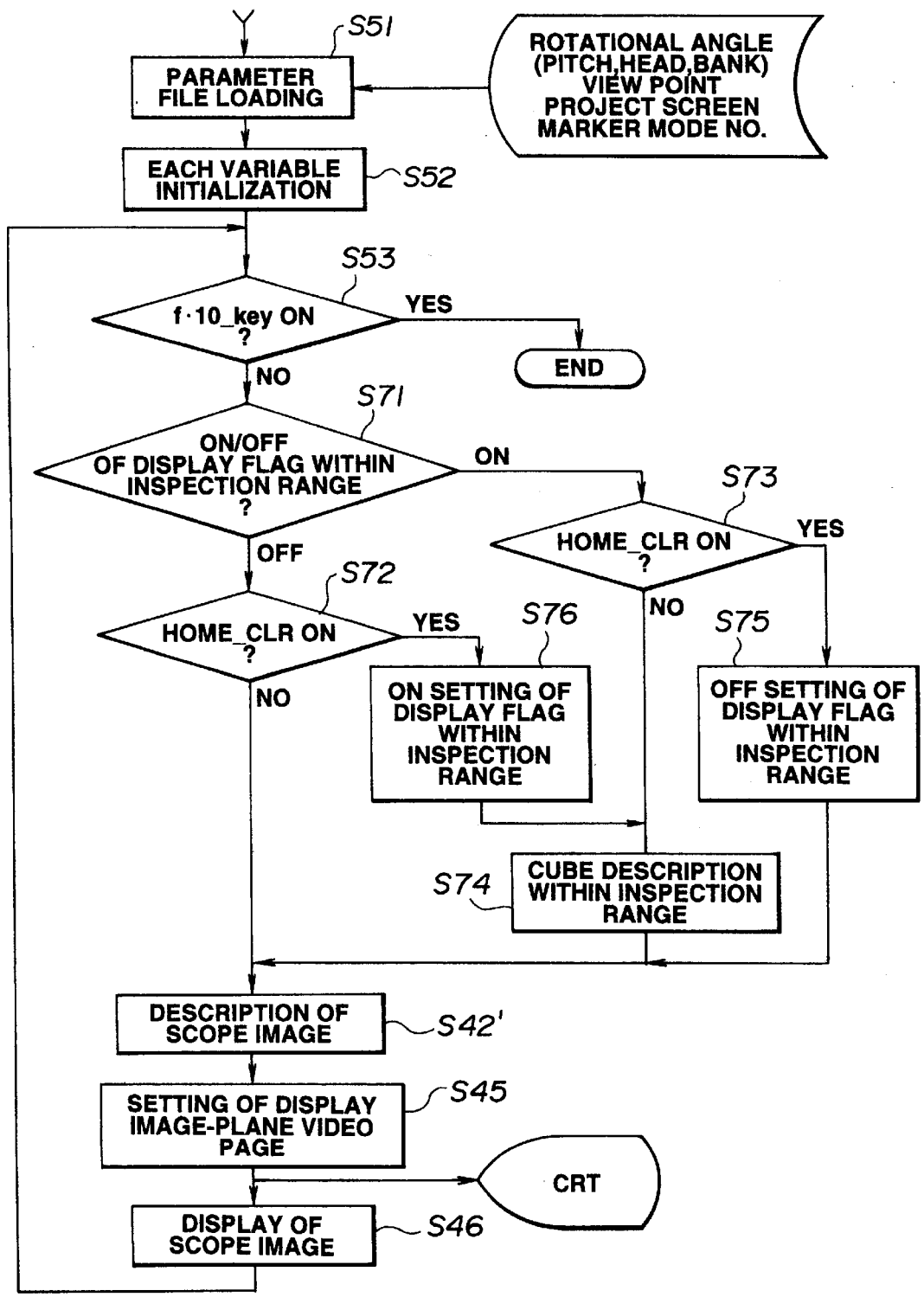
Figure 130B:
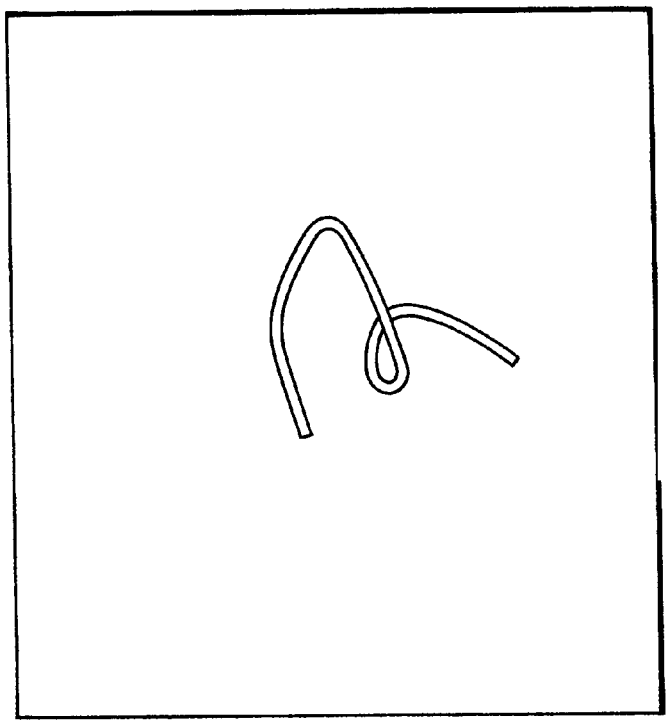
Figure 130A:
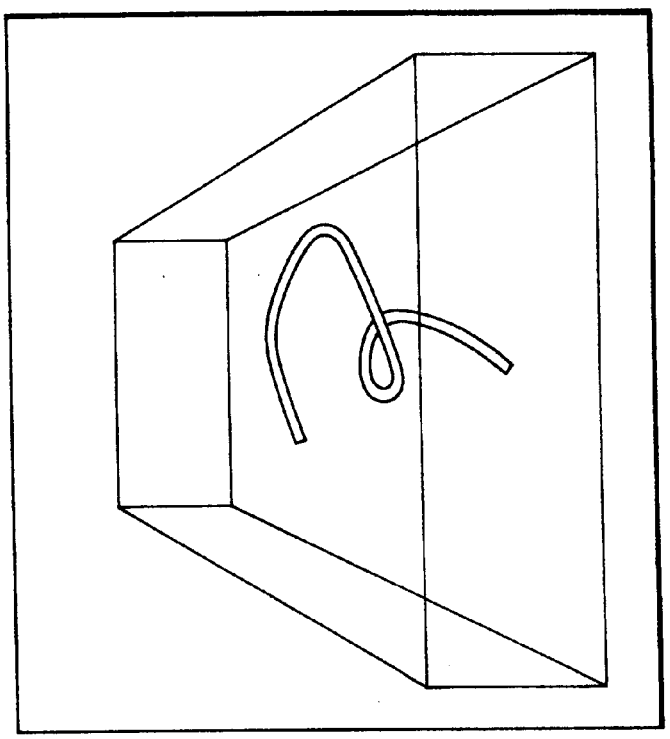
Figure 131:
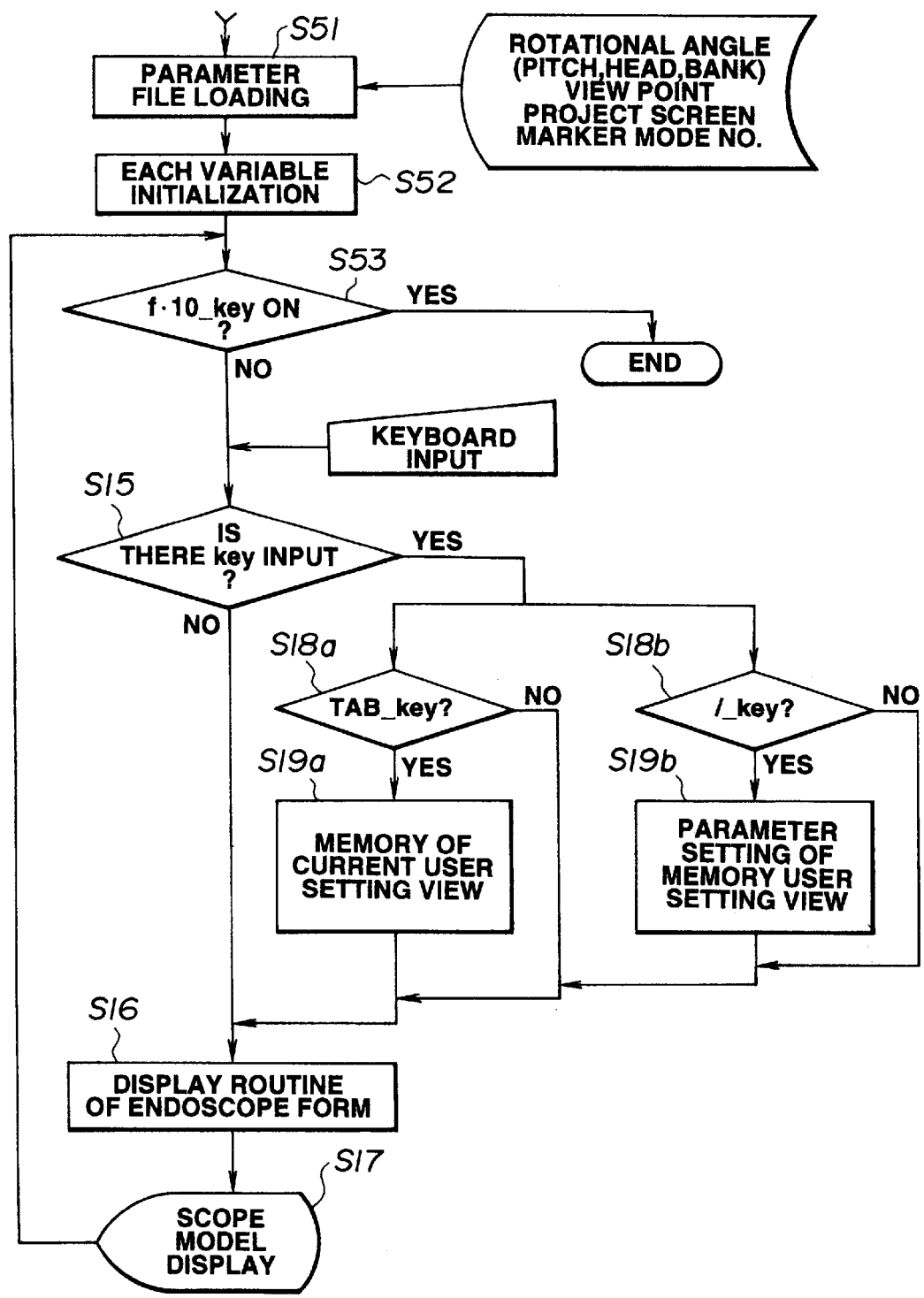
Figure 132:
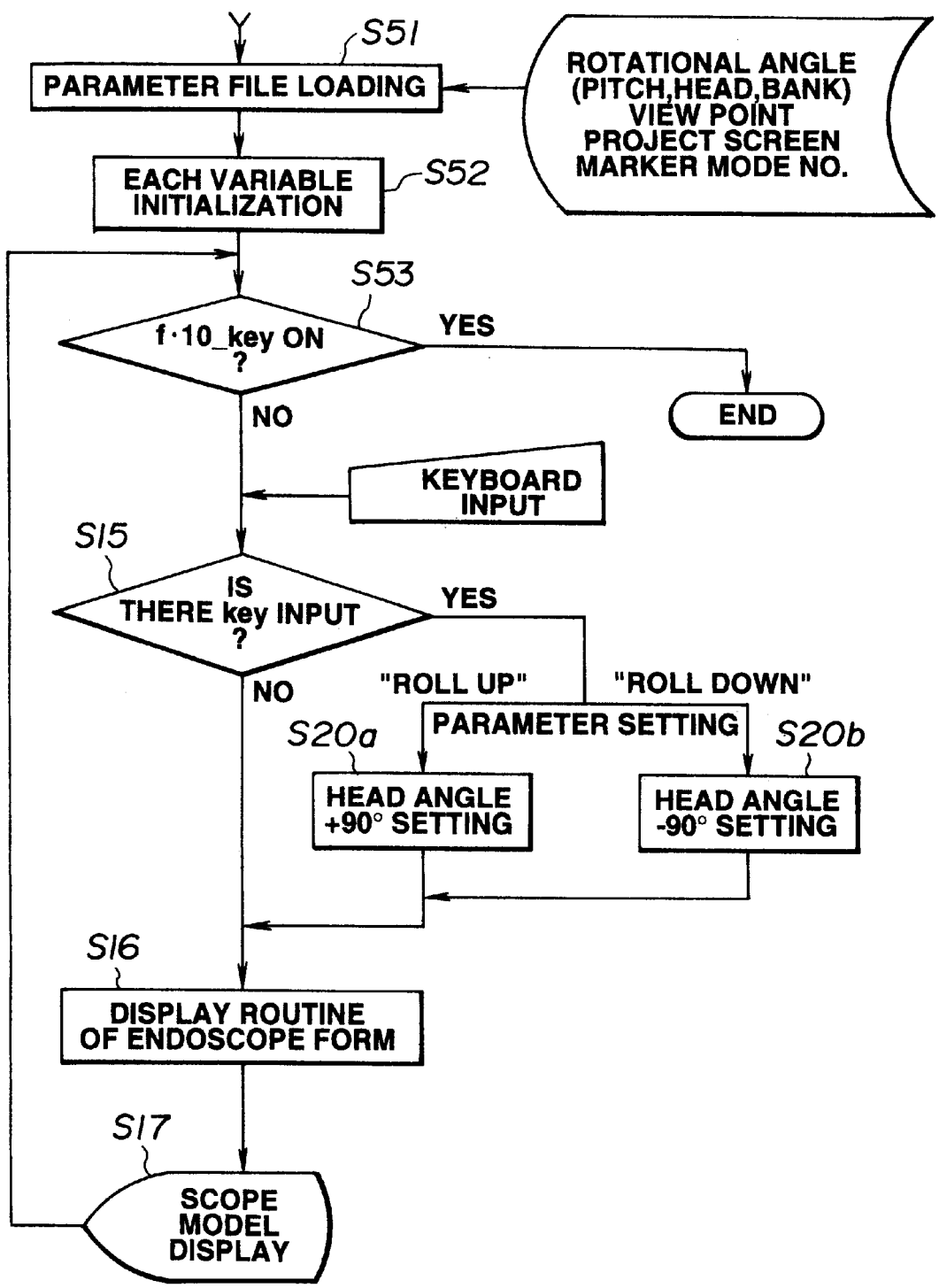
Figure 133:
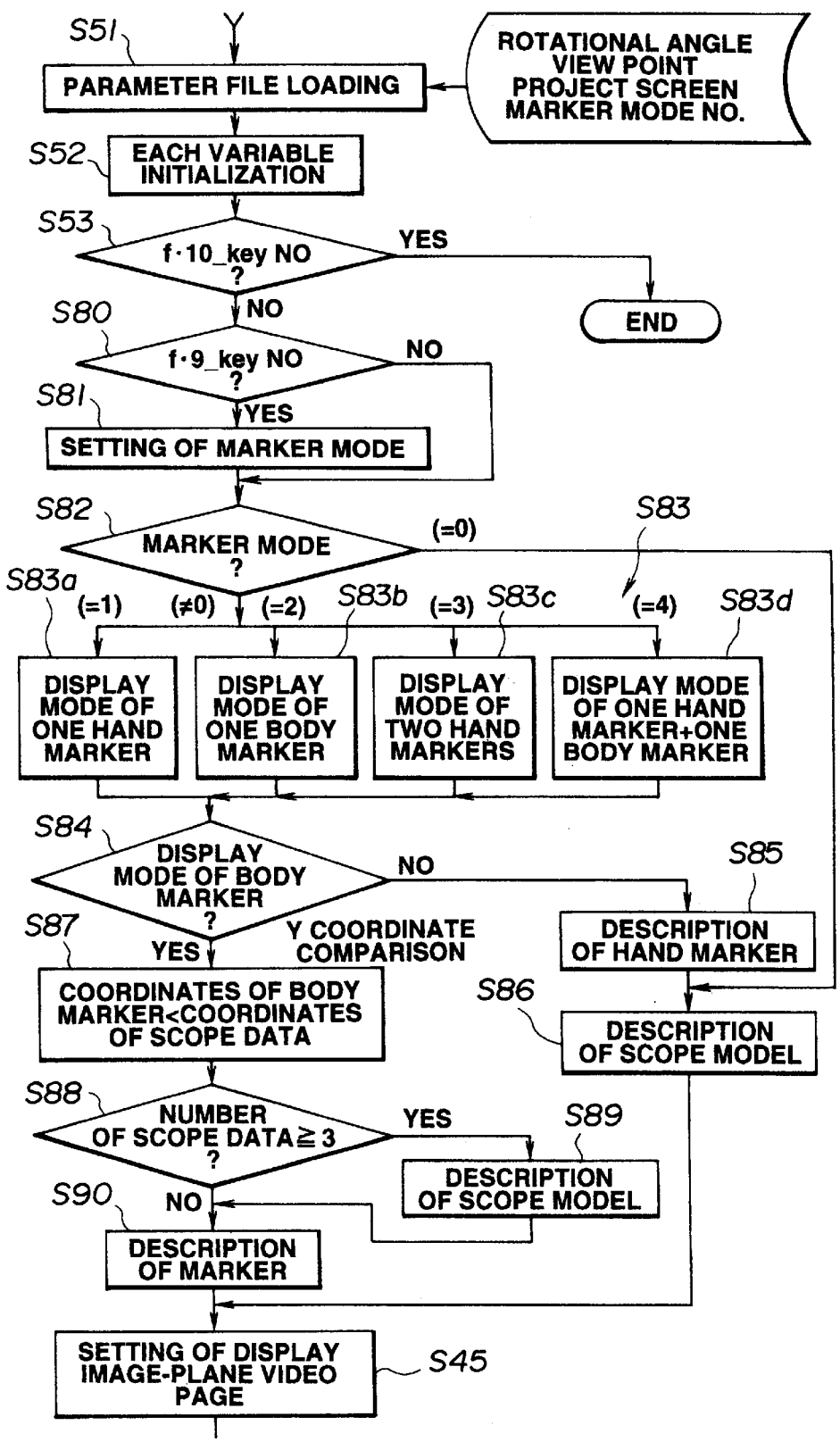
Figure 134:
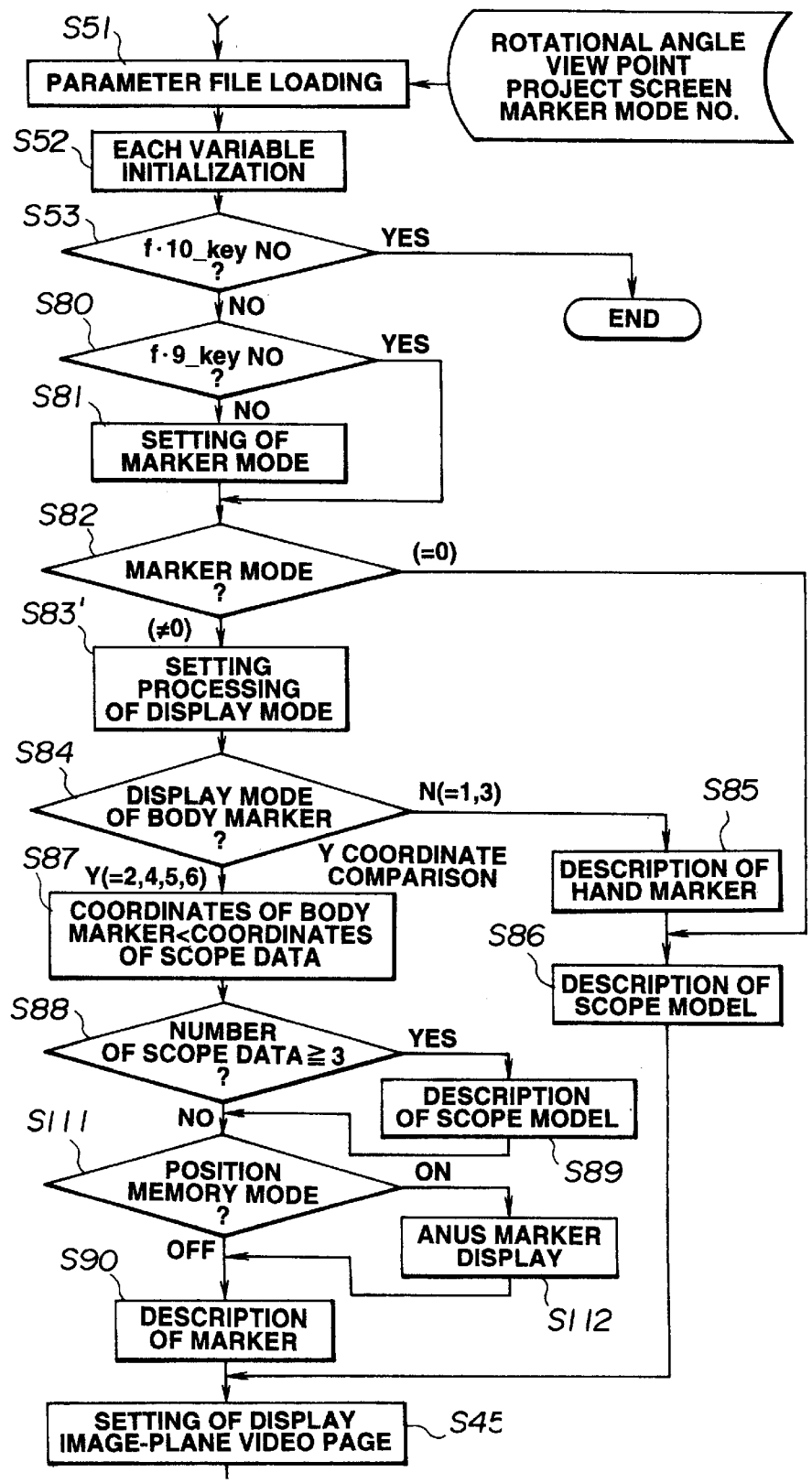
Figure 135:
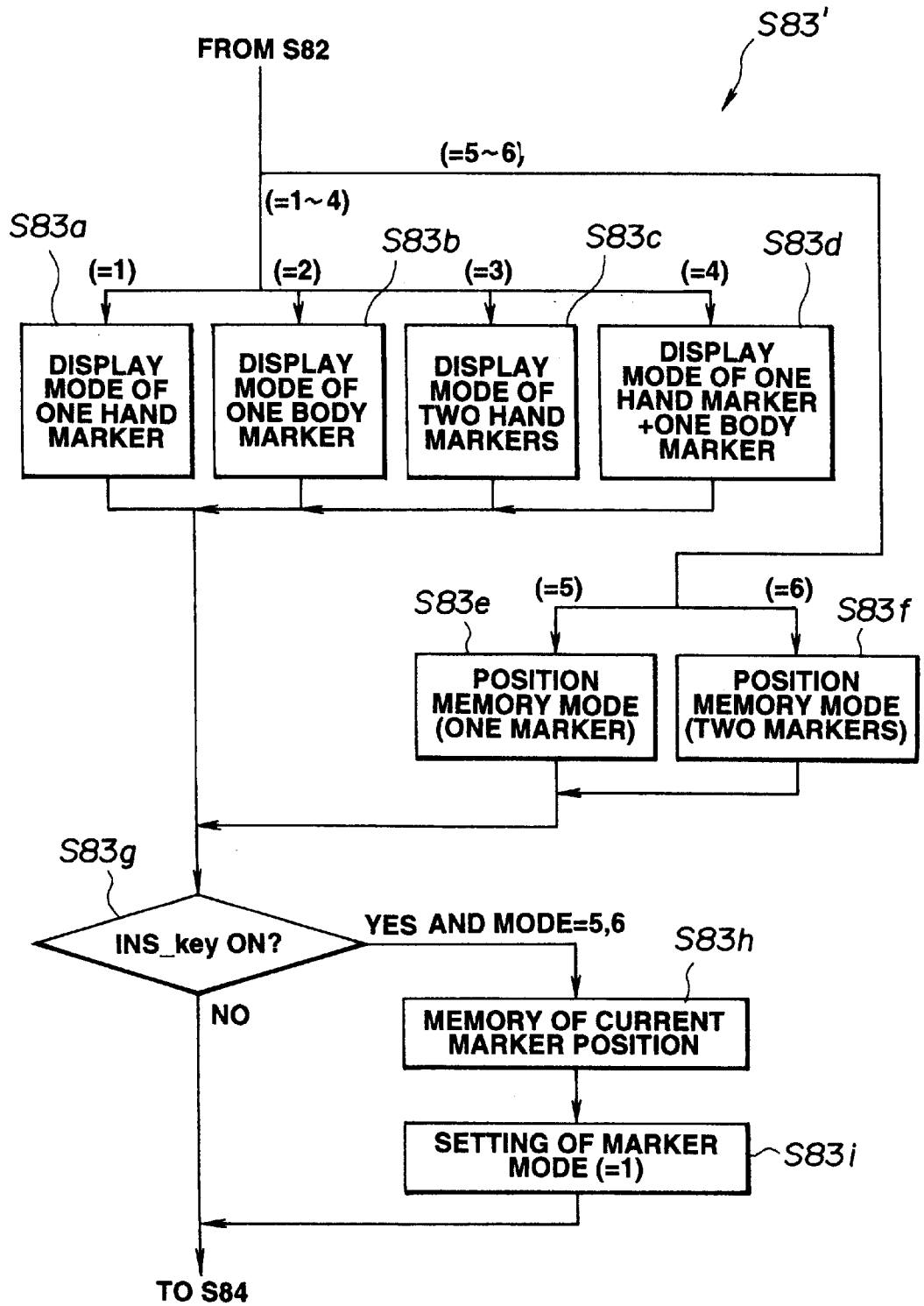
Figure 136:
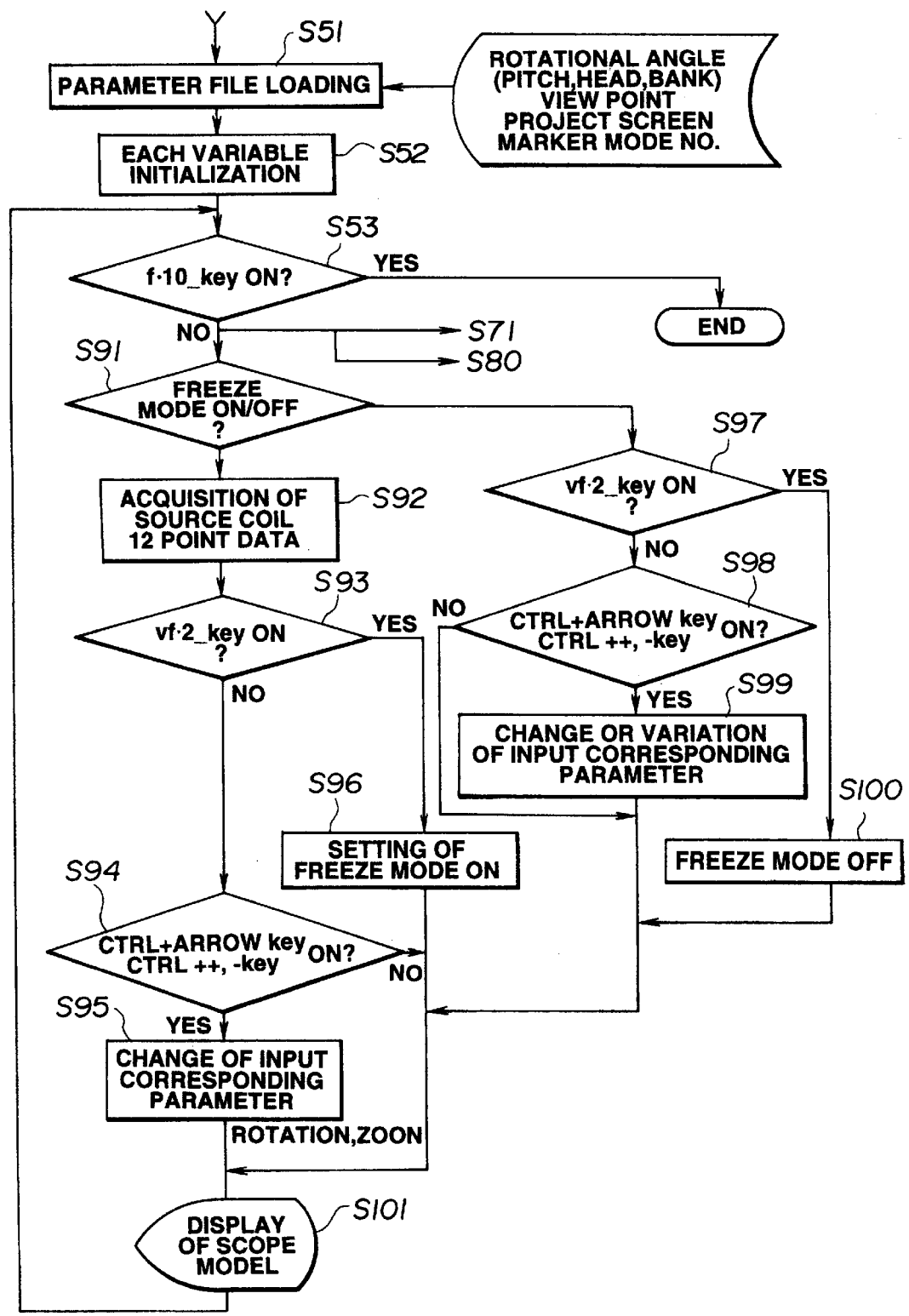
Figure 137:
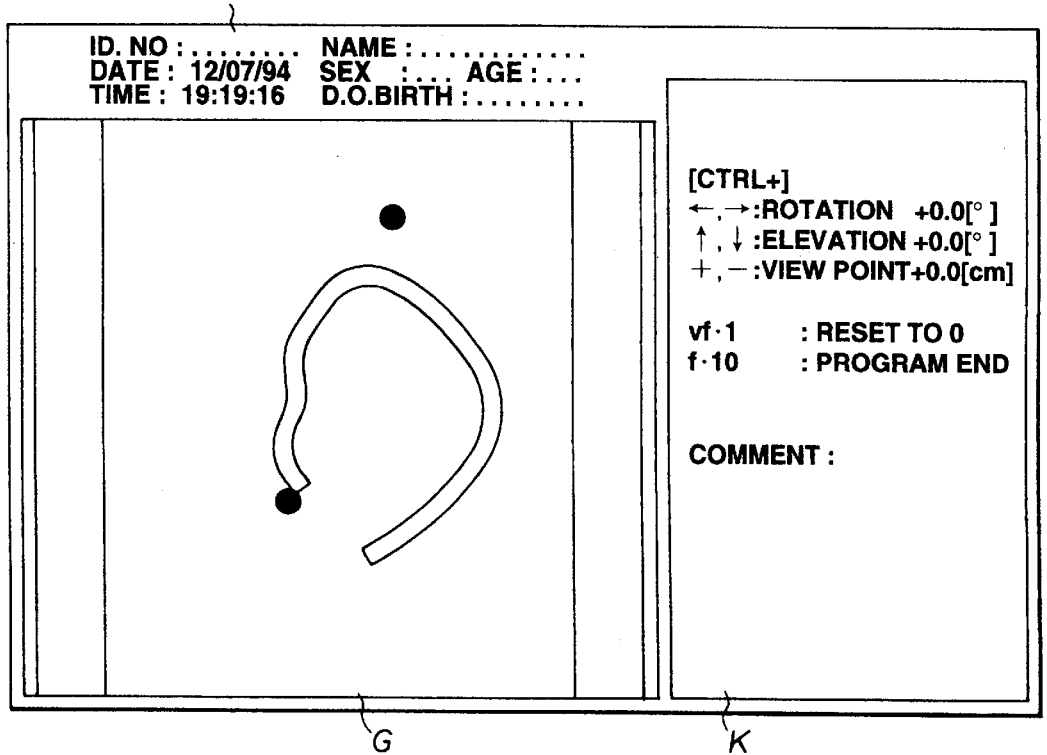
Figure 138:
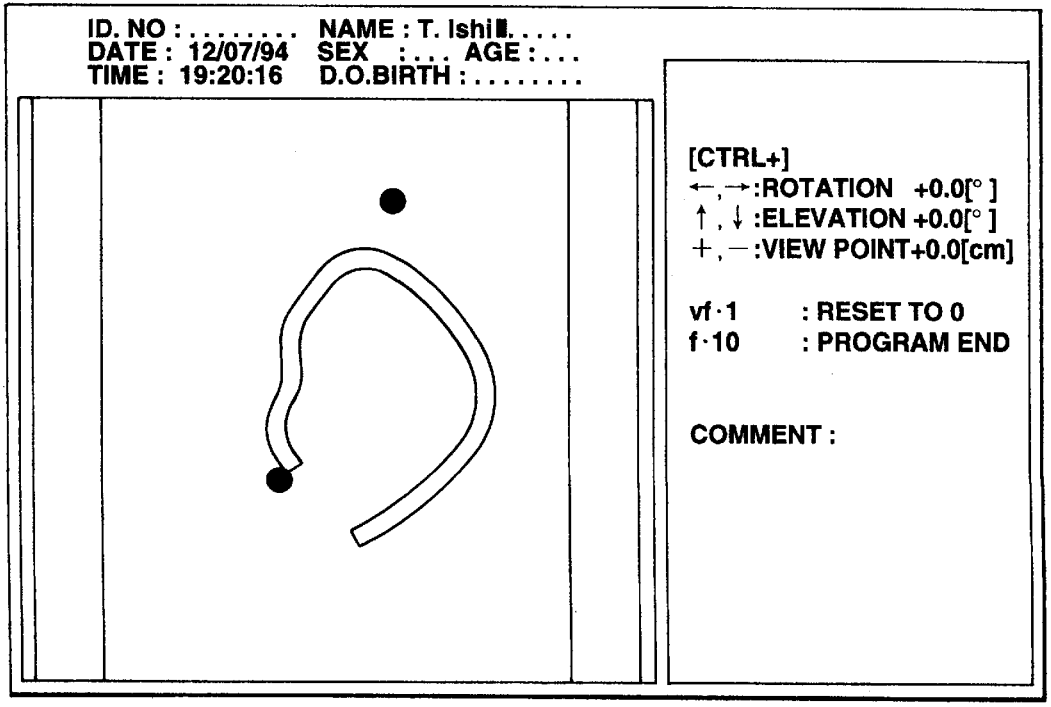
Figure 139:
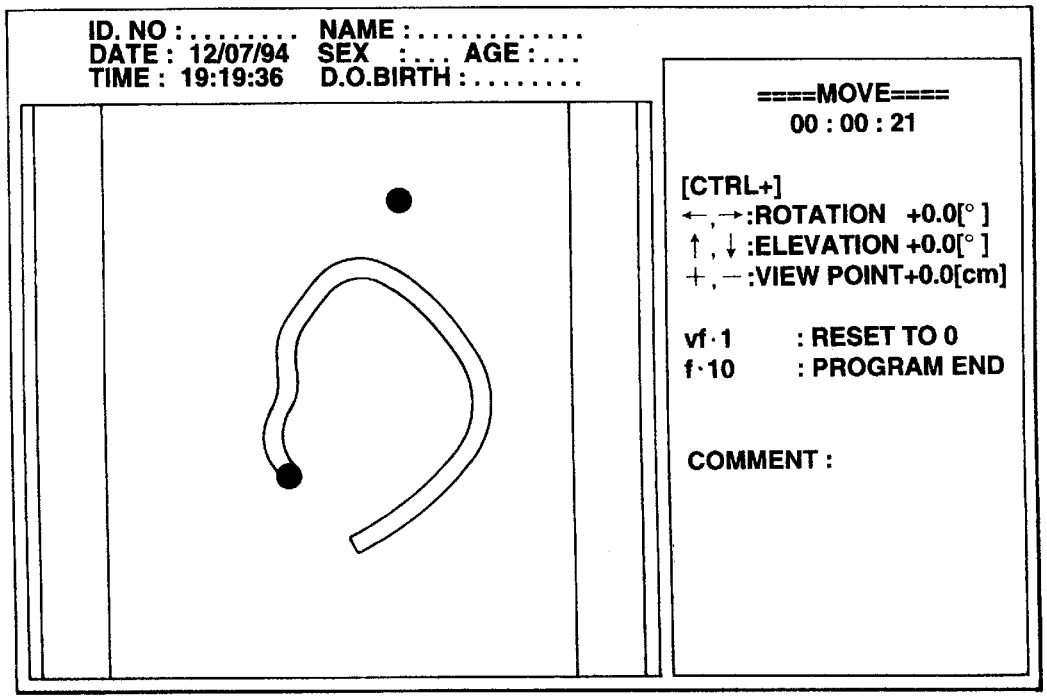
Figure 140:
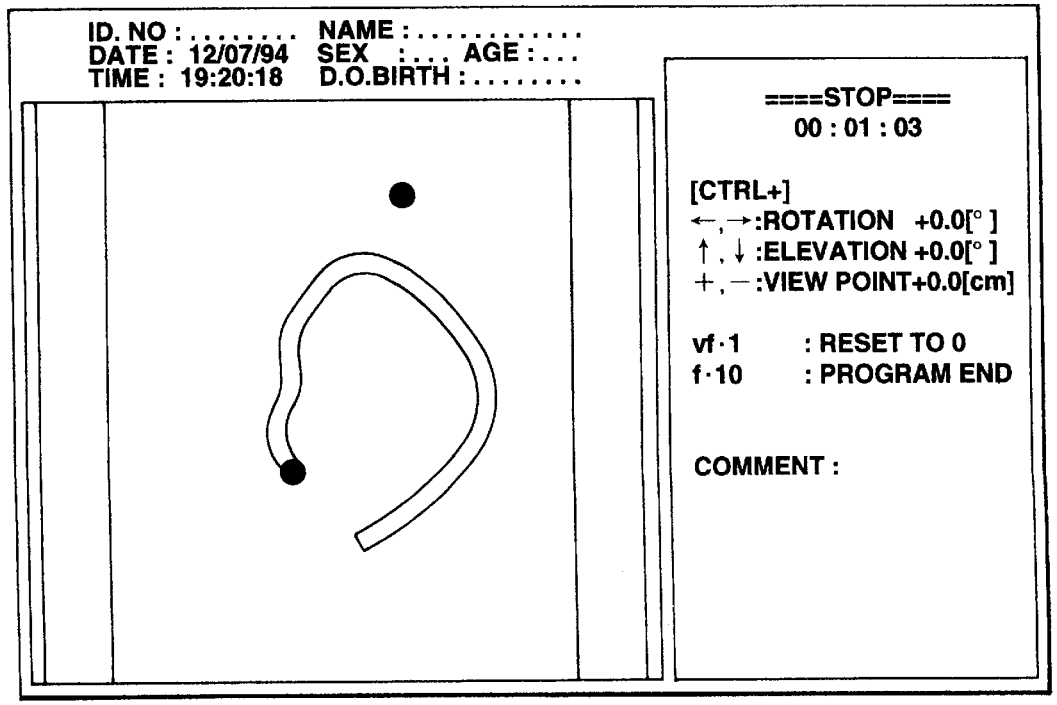
Figure 141:
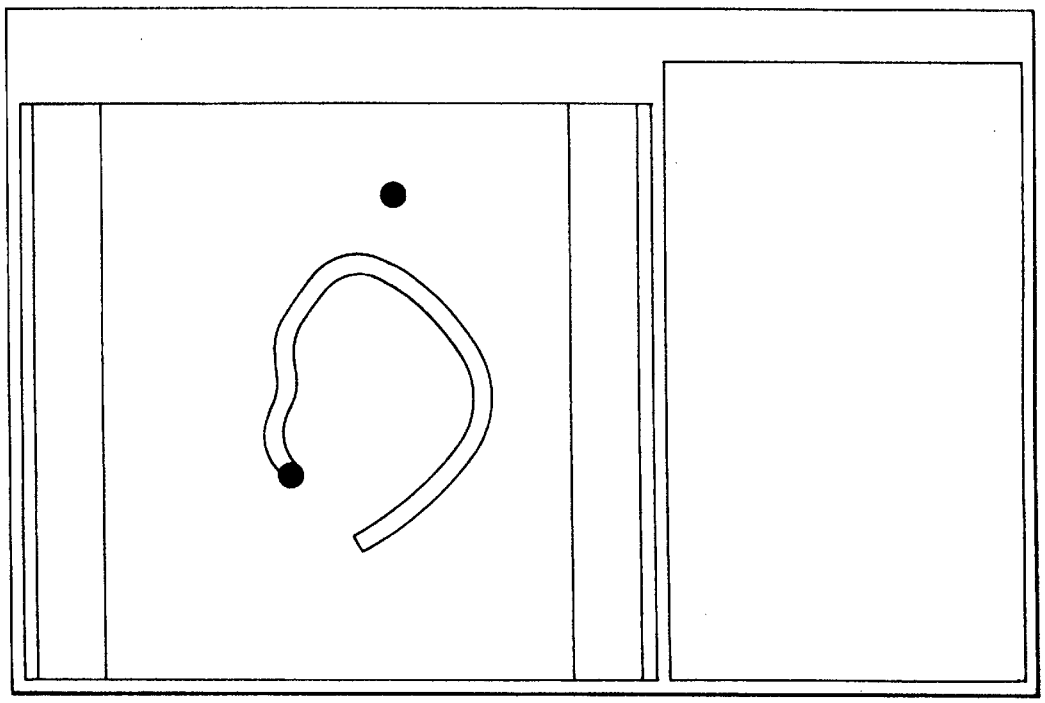
Figure 142:
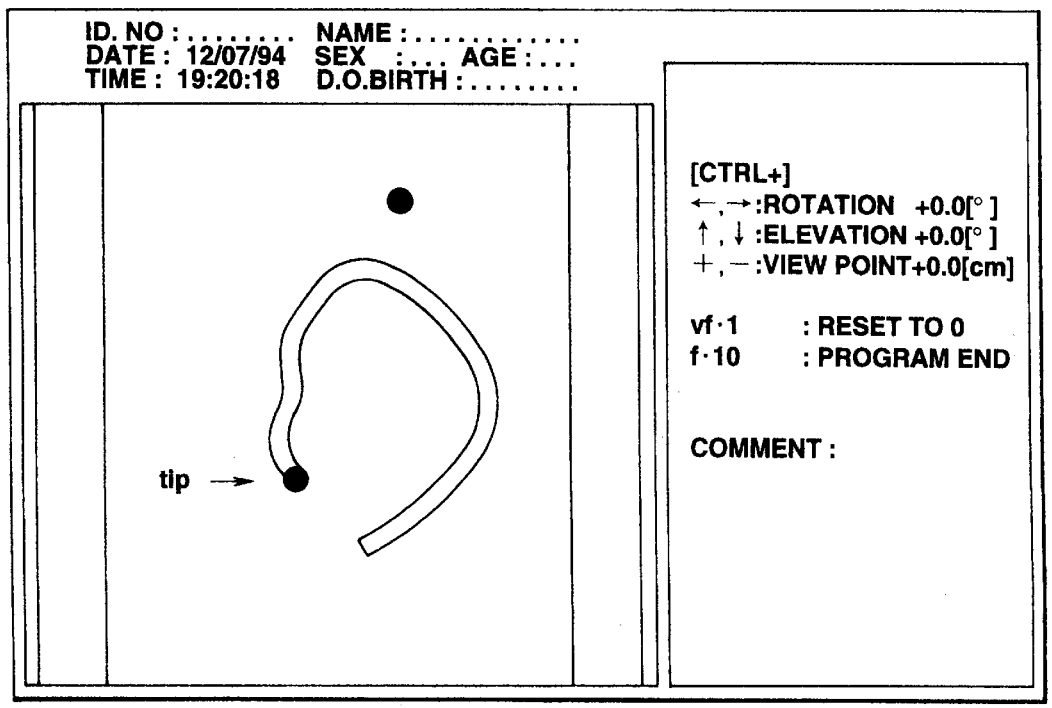
Figure 147:
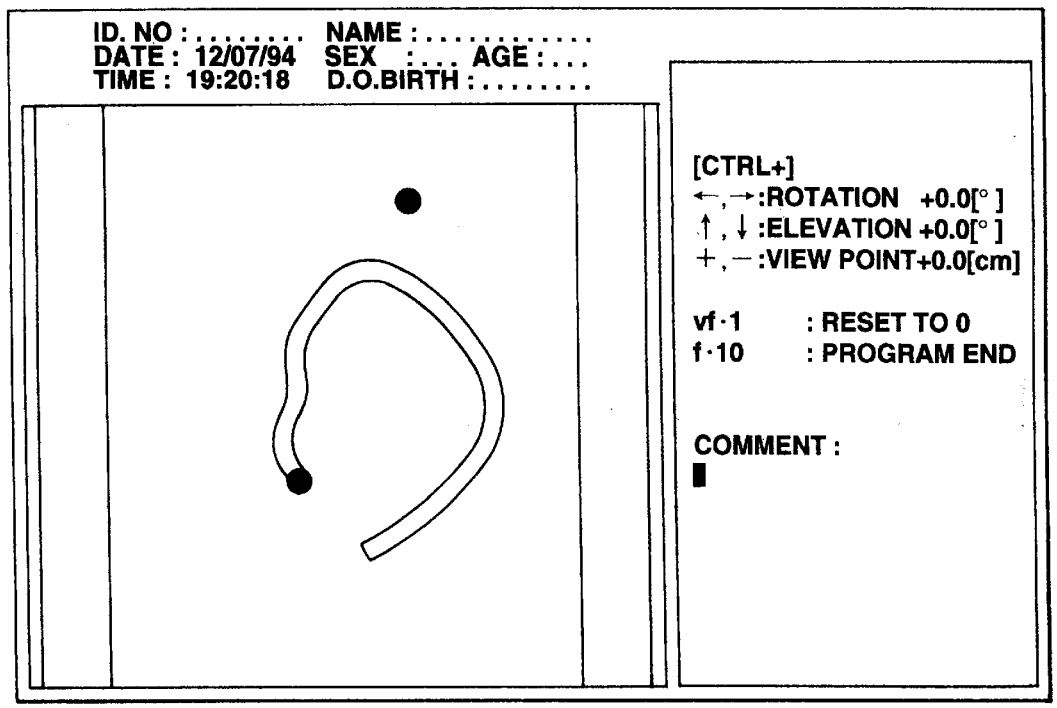
Figure 148:
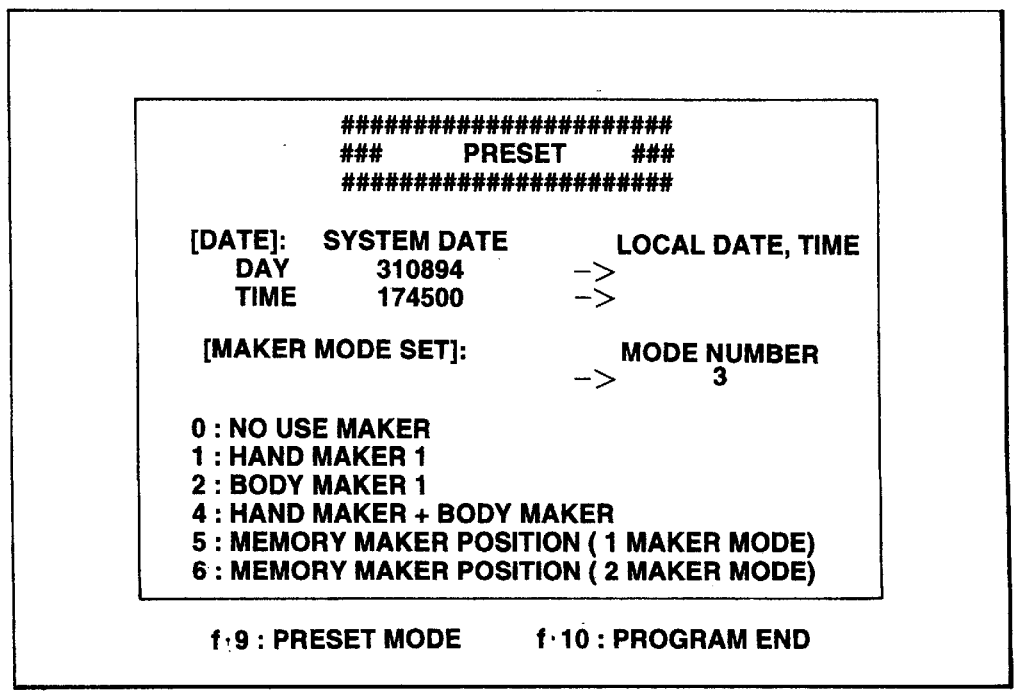
Figure 149:
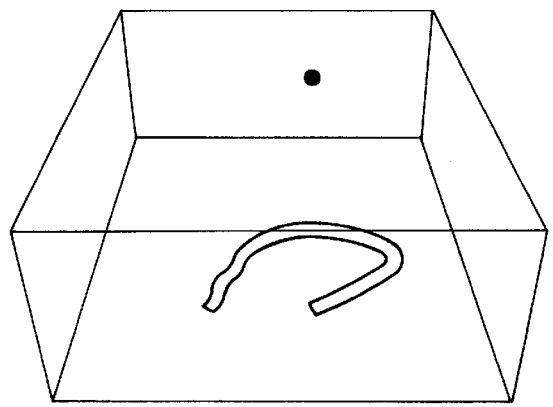
Figure 150:
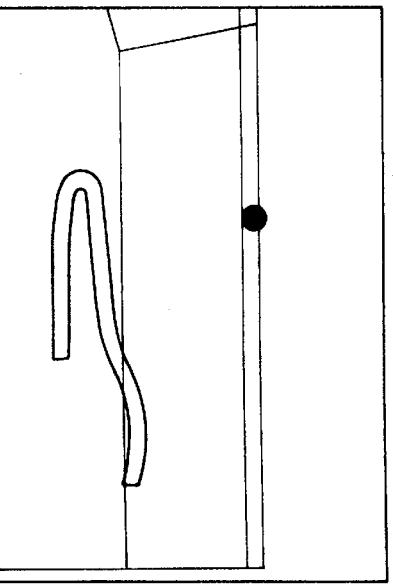
Figure 151:
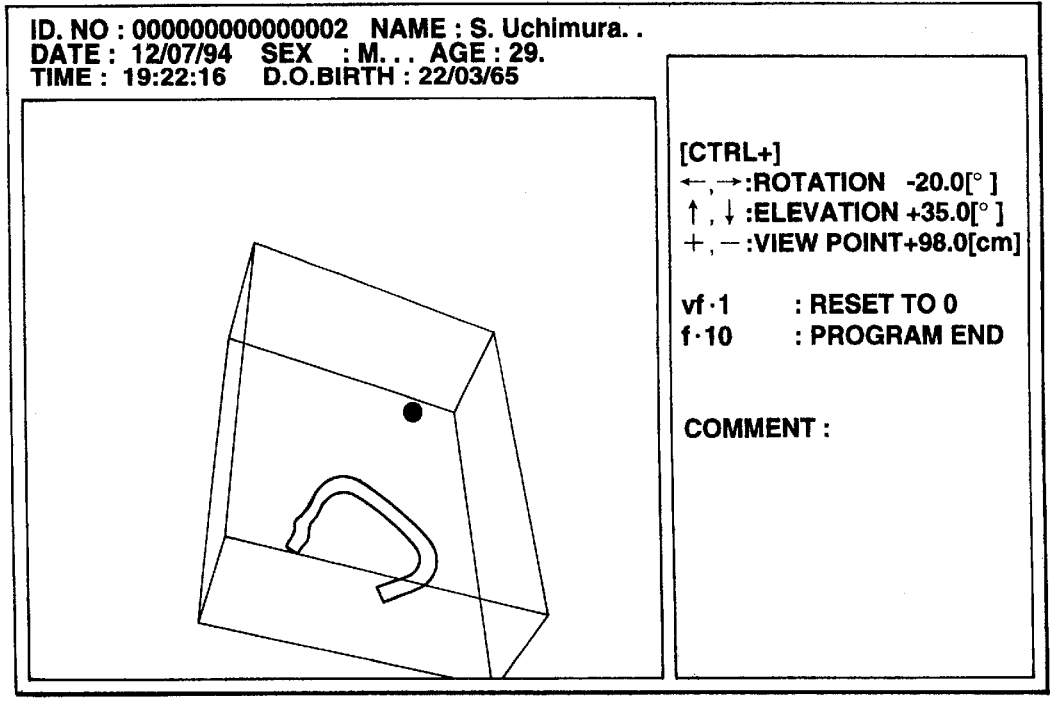
Figure 152:
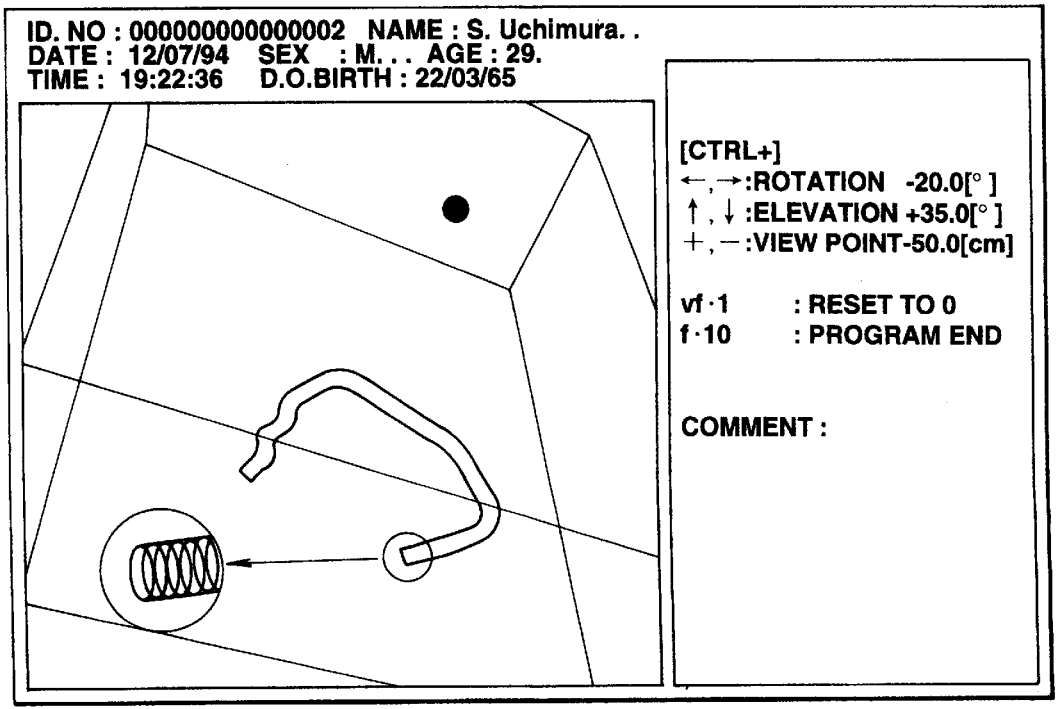
Figure 153:
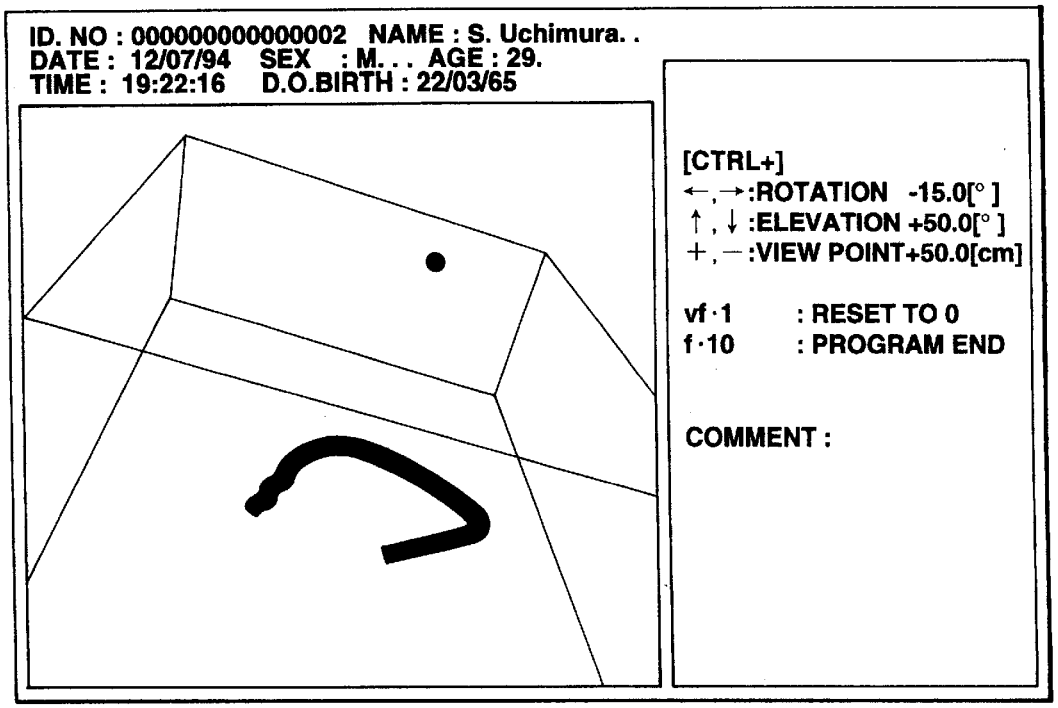
Figure 154:
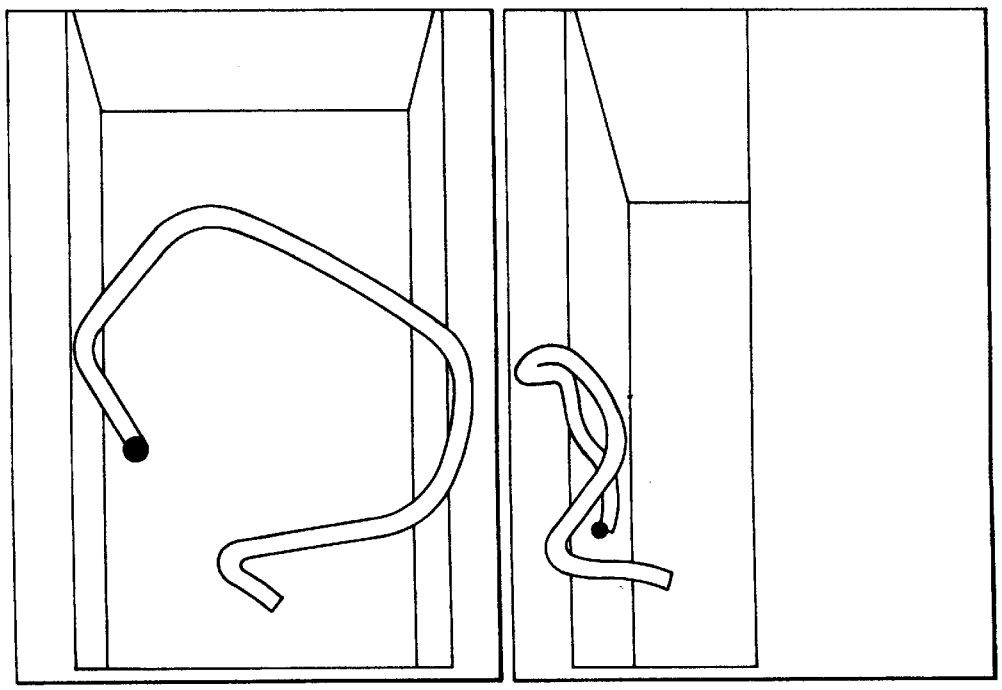
Figure 155:
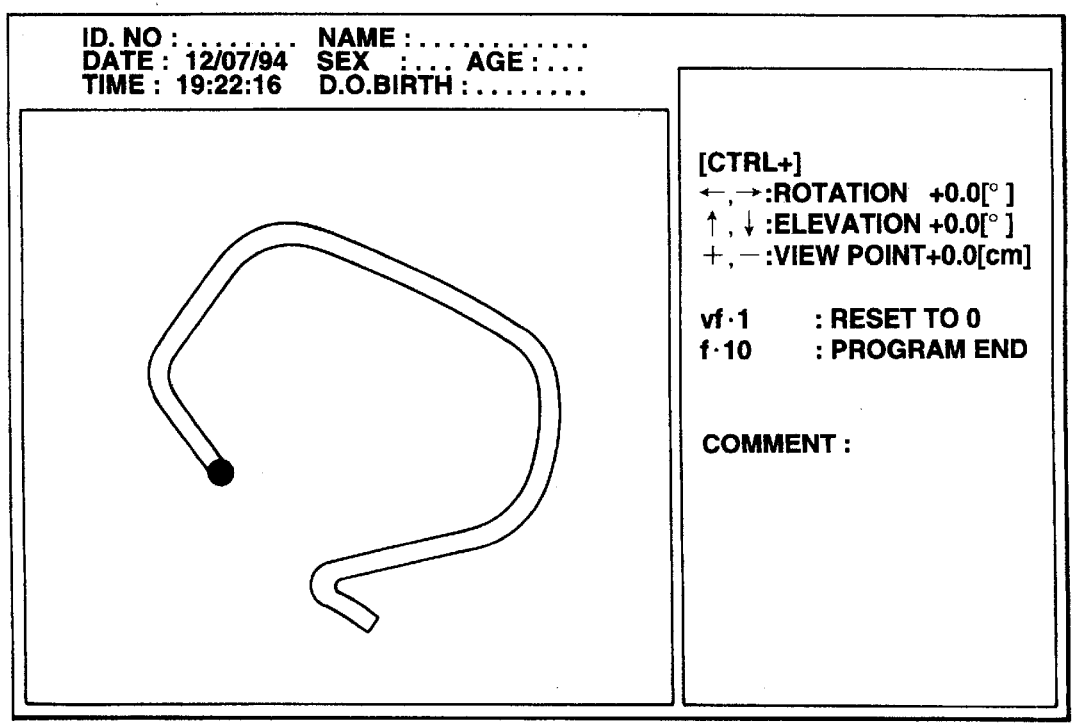
Figure 156:
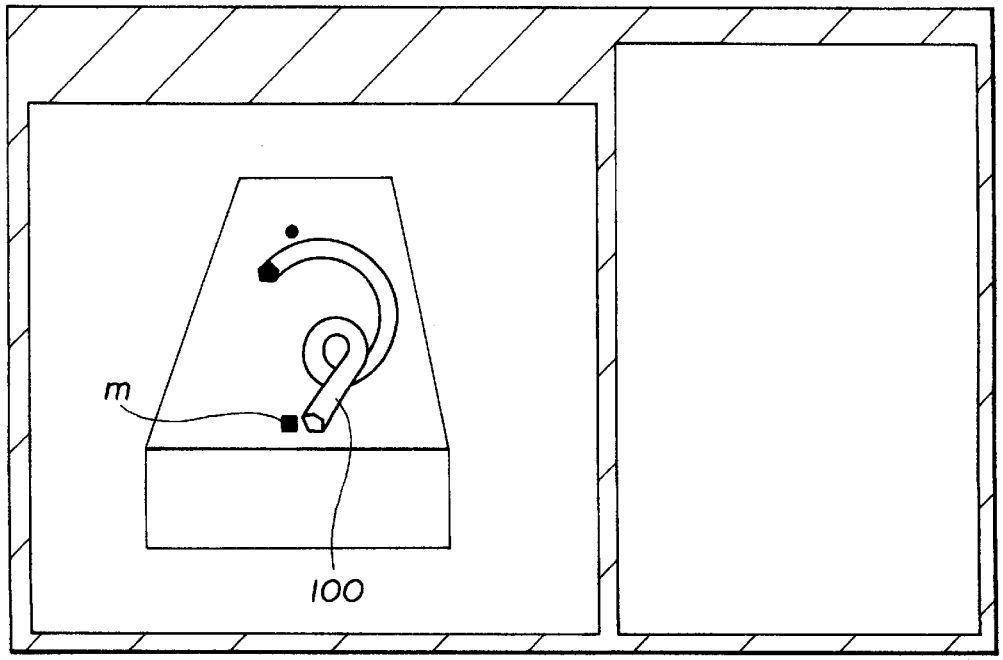
Figure 157:
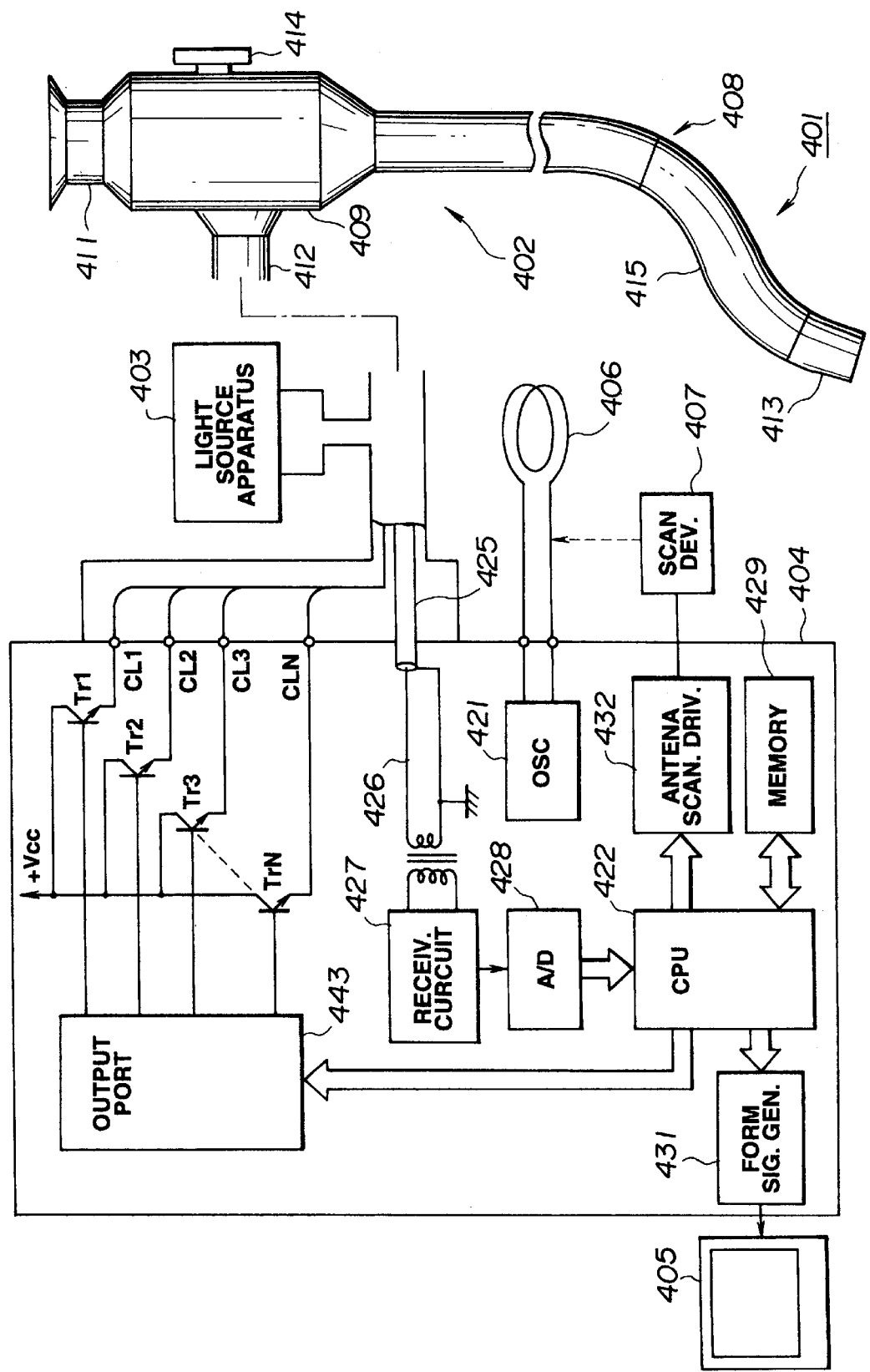
Figure 158:
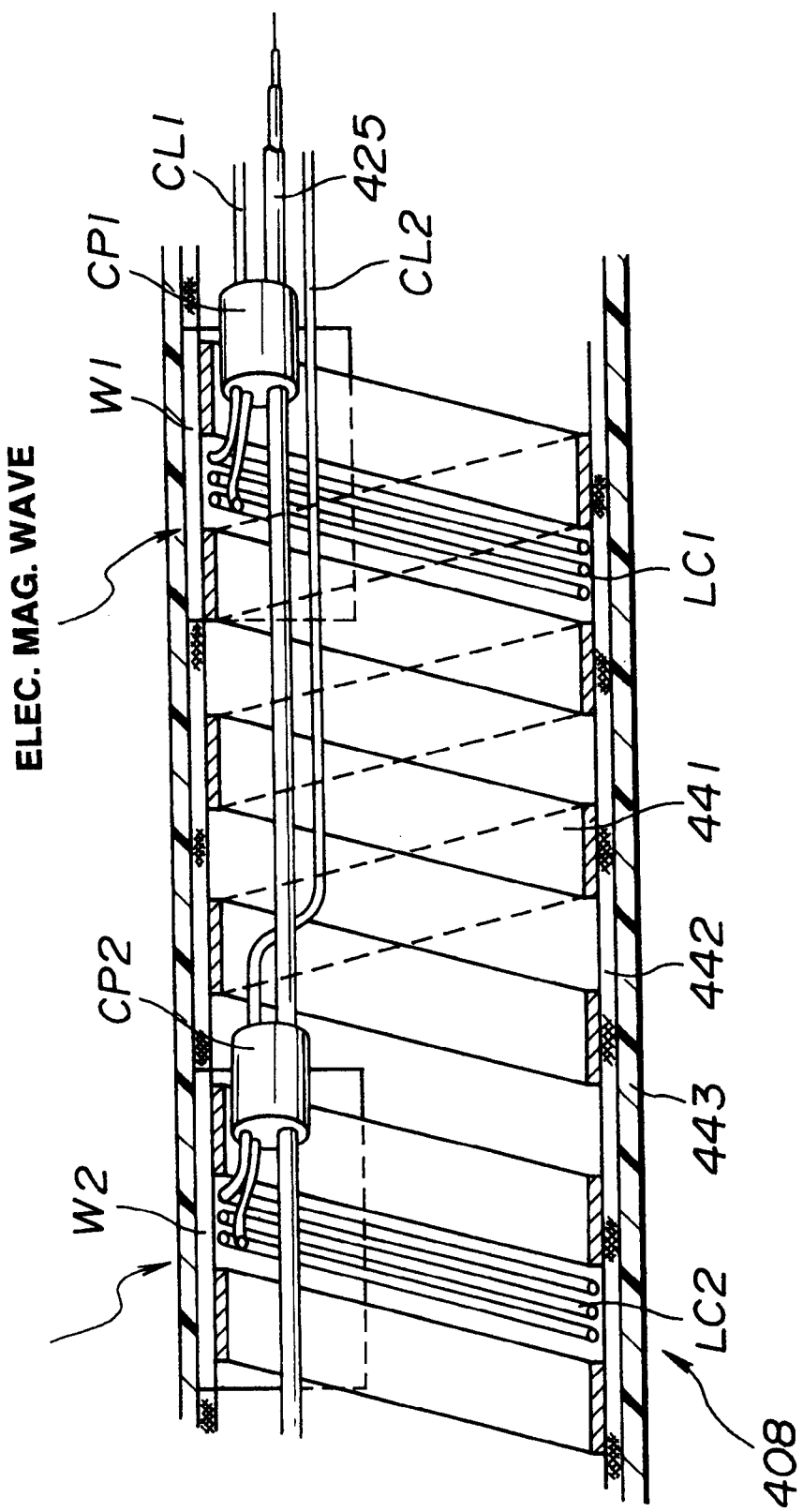
Figure 159:
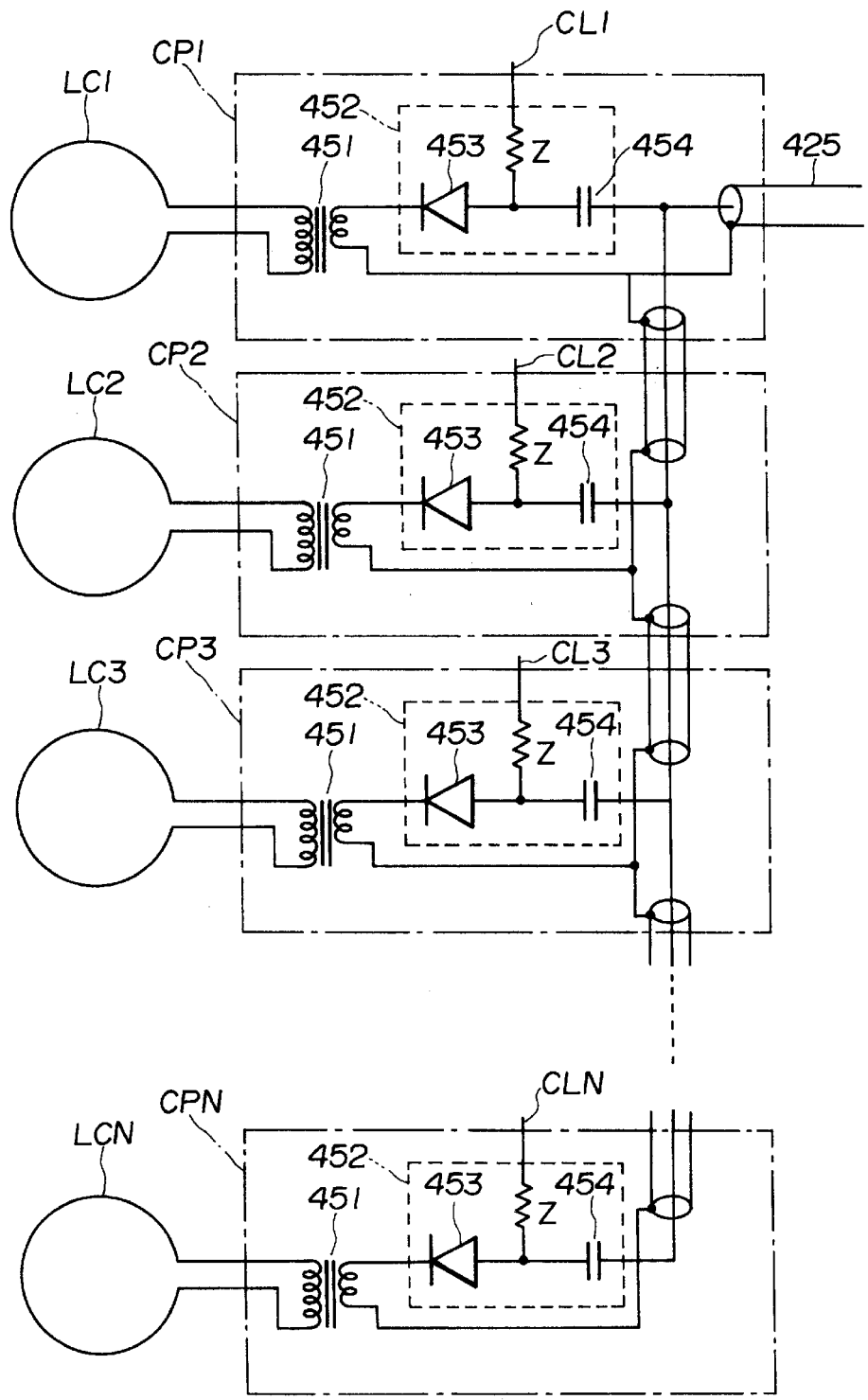
Figure 160:
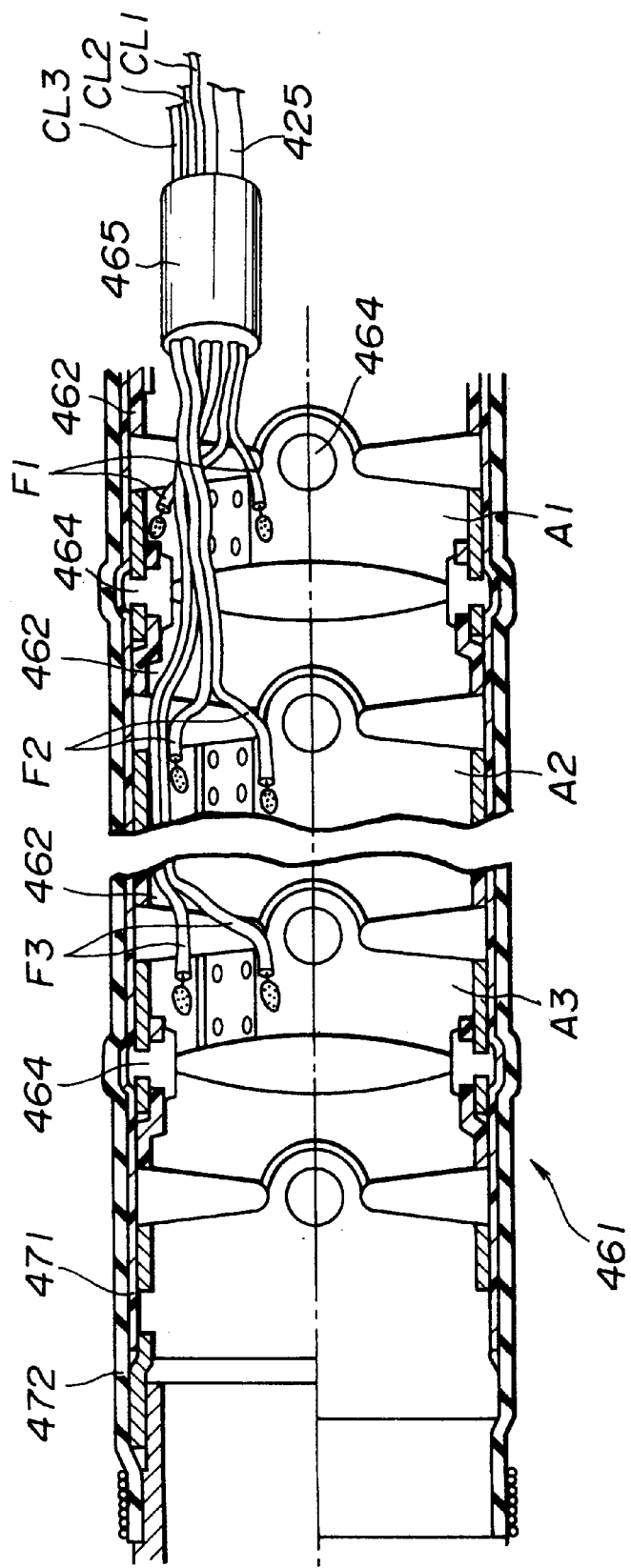
Figure 161:
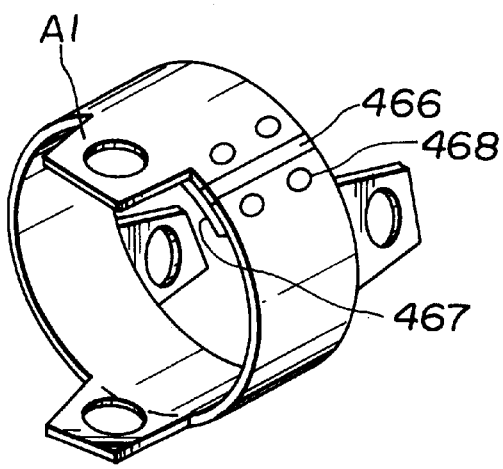
Figure 162:
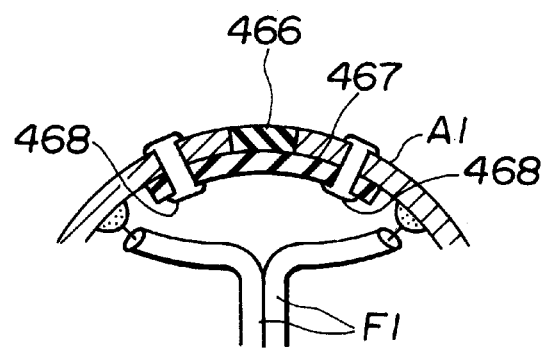

FIG. 116 to FIG. 128 relate to a nineteenth embodiment of the invention, FIG. 116 being a schematic arrangement view of an endoscope system which has the nineteenth embodiment;

FIG. 117 is a block diagram showing an arrangement of an endoscope form detecting apparatus according to the nineteenth embodiment;

FIG. 118 is a view of a whole arrangement of the endoscope form detecting apparatus;

FIG. 119 is an arrangement view of a three-axes sense coil and a probe;

FIG. 120 is an explanatory view showing a condition or aspect in which a plurality of sense coils are used to detect a position of a source coil within the probe;

FIG. 121 is a cross-sectional view showing an arrangement of a marker probe;

FIG. 122 is a flow view showing the processing contents of the endoscope form detecting apparatus;

FIG. 123 is a flow view of processing of scope model painting which displays an endoscope form by a two-image-plane mode and a one-image-plane mode;

FIG. 124 is a flow view of scope-image representation processing;

FIGS. 125a~125d are flow views of the scope-image representation processing by an n-prismatic model;

FIG. 126 is an explanatory view showing an output image of the endoscope form which is displayed on a monitor image plane by the one-image-plane mode;

FIG. 127 is an explanatory view showing the output image of the endoscope form which is displayed on the monitor image plane by the two-image-plane mode;

FIG. 128 is an explanatory view showing a coordinate system which is fixedly mounted on a bed;

FIG. 129 is a flow view in which display/non-display of a display frame within an inspection range is conducted in a first modification of the nineteenth embodiment;

FIG. 130a is an explanatory view showing an output image of an endoscope form, under a non-display state within the inspection range;

FIG. 130b is an explanatory view showing the output image of the endoscope form, under a display state within the inspection range;

FIG. 131 is a flow view in which memory and setting of a view parameter of the endoscope form display are conducted in a second modification of the nineteenth embodiment;

FIG. 132 is a flow view in which the endoscope form is rotated 90° in a horizontal direction to conduct the display, in a third modification of the nineteenth embodiment;

FIG. 133 to FIG. 135 relate to a twentieth embodiment of the invention, FIG. 133 being a flow view of processing which displays a marker by a selected marker mode in the twentieth embodiment;

FIG. 134 is a flow view showing processing of marker display having function of a position memory mode in a modification of the twentieth embodiment;

FIG. 135 is a flow view showing the contents of display-mode setting processing in FIG. 134;

FIG. 136 is a flow view of processing of operation in which freeze is conducted to display a form, in a twenty-first embodiment of the invention;

FIG. 137 is a view showing a specific example of a normal display image plane;

FIG. 138 is a view showing a specific example of a state of data input in a column of a name in a normal image plane;

FIG. 139 is a view showing a specific example during operation of a stop watch;

FIG. 140 is a view of a state under which the stop watch is stopped, in FIG. 139;

FIG. 141 is a view showing a specific example of a state in which full characters are erased;

FIG. 142 is a view showing a specific example of a state under which expanded comments are inputted;

FIG. 143 is a view showing a specific example of title screen display;

FIG. 144 is a view showing a specific example of a list of patient data;

FIG. 145 is a view showing a specific example of a pre-input image plane of the patient data;

FIG. 146 is a view showing a specific example of the display when the patient data in FIG. 145 are selected;

FIG. 147 is a view showing a specific example of a state under which a cursor is displayed on a comment frame;

FIG. 148 is a view showing a specific example of a pre-set image plane which conducts modification of initial setting;

FIG. 149 is a view showing a specific example of the display when a scope image is rotated about a Y-axis;

FIG. 150 is a view showing a specific example of the display when the scope image is rotated about an X-axis;

FIG. 151 is a view showing a specific example of the display when the scope image is zoomed out;

FIG. 152 is a view showing a specific example of the display when the scope image is zoomed in;

FIG. 153 is a view showing a specific example of display switching in case of being displayed by a painted-out scope image;

FIG. 154 is a view showing a specific example of the display in case of being displayed by the two-image-plane of the scope image;

FIG. 155 is a view showing a specific example of the display when a display range frame is erased;

FIG. 156 is a view showing a display example when portions on the side of the most distal end are displayed by a display mode which is different from the other model paintings;

FIG. 157 to FIG. 159 relate to a twenty-second embodiment of the invention, FIG. 157 being a block diagram showing a whole arrangement of an endoscope form detecting apparatus according to the twenty-second embodiment;

FIG. 158 is a cross-sectional view showing a structure of an insertion part;

FIG. 159 is a circuit view showing an arrangement of a coupler;

FIG. 160 to FIG. 164 relate to a twenty-third embodiment of the invention, FIG. 160 being a cross-sectional view showing a structure of a curvature part of an endoscope in the twenty-third embodiment;

FIG. 161 is a perspective view of an antenna piece;

FIG. 162 is a cross-sectional view showing a part of the antenna piece; and

Figure 163:
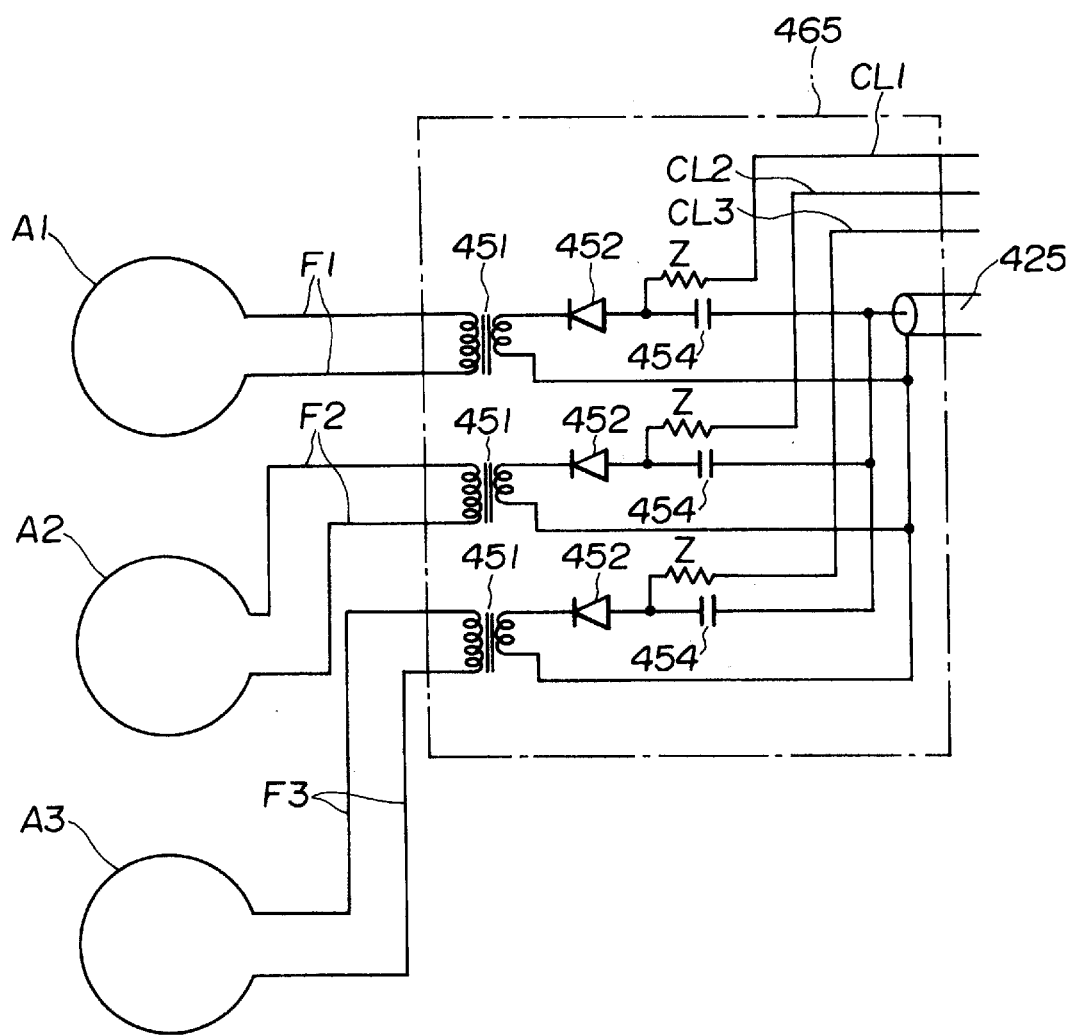

FIG. 163 is a circuit view showing an arrangement of a coupler.

DETAILED DESCRIPTION OF THE PREFERRED EMBODIMENTS

Various embodiments of the invention will hereunder be described specifically with reference to the accompanying drawings.

Figure 1:
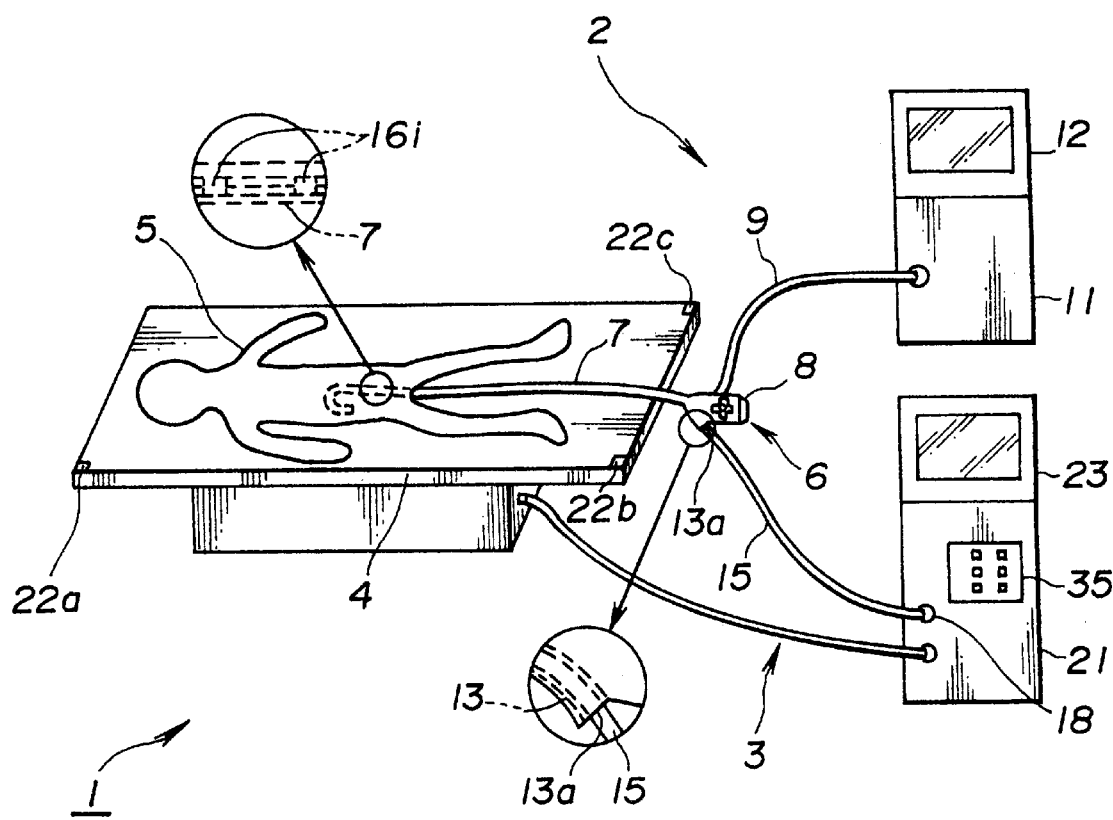

As shown in FIG. 1, an endoscope system 1 comprises an endoscope apparatus 2 which performs inspection or examination utilizing an endoscope 6, and an endoscope form detecting apparatus 3 which is used together with the endoscope apparatus 2, for detecting a position of inserting part 7 of the endoscope 6 and further which estimates a form of the inserting part 7 to display an image corresponding to the form.

Figure 3:
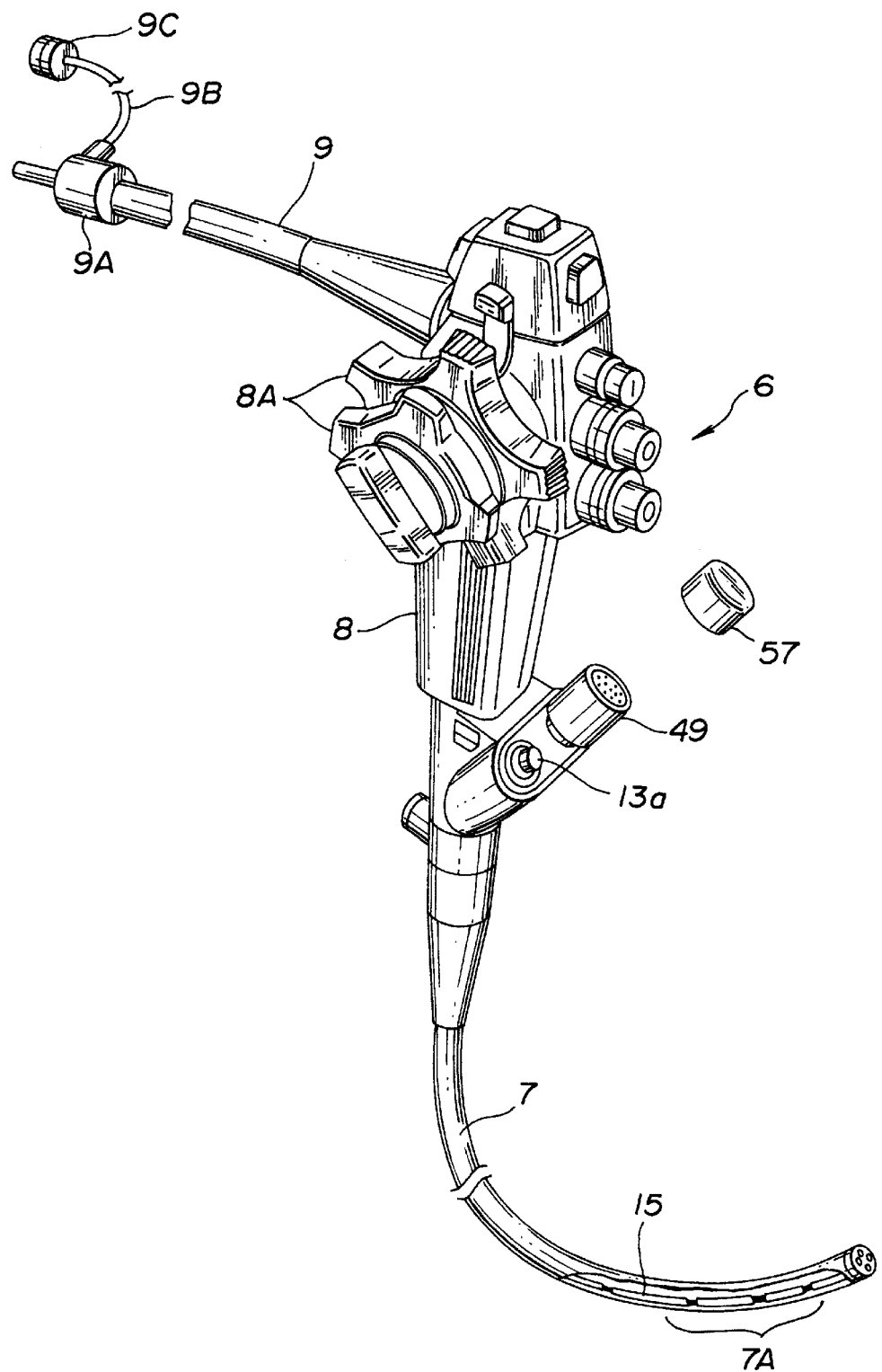

A patient 5 serving as a subject is mounted on a bed 4 (for endoscope inspection). The insertion part 7 of the endoscope 6 shown in FIG. 3 is inserted into a body cavity in the patient 5.

The endoscope 6 includes the inserting part 7 which is elongated in form and which has flexibility, an operating unit 8 having a large width and which is formed at a rearward end of the inserting part 7, and a universal cable 9 which extends from a side of the operating unit 8. A connector 9A is provided at a distal end of the universal cable 9. The connector 9A can be detachably connected to a light source 36 within a video processor 11.

Figure 4:
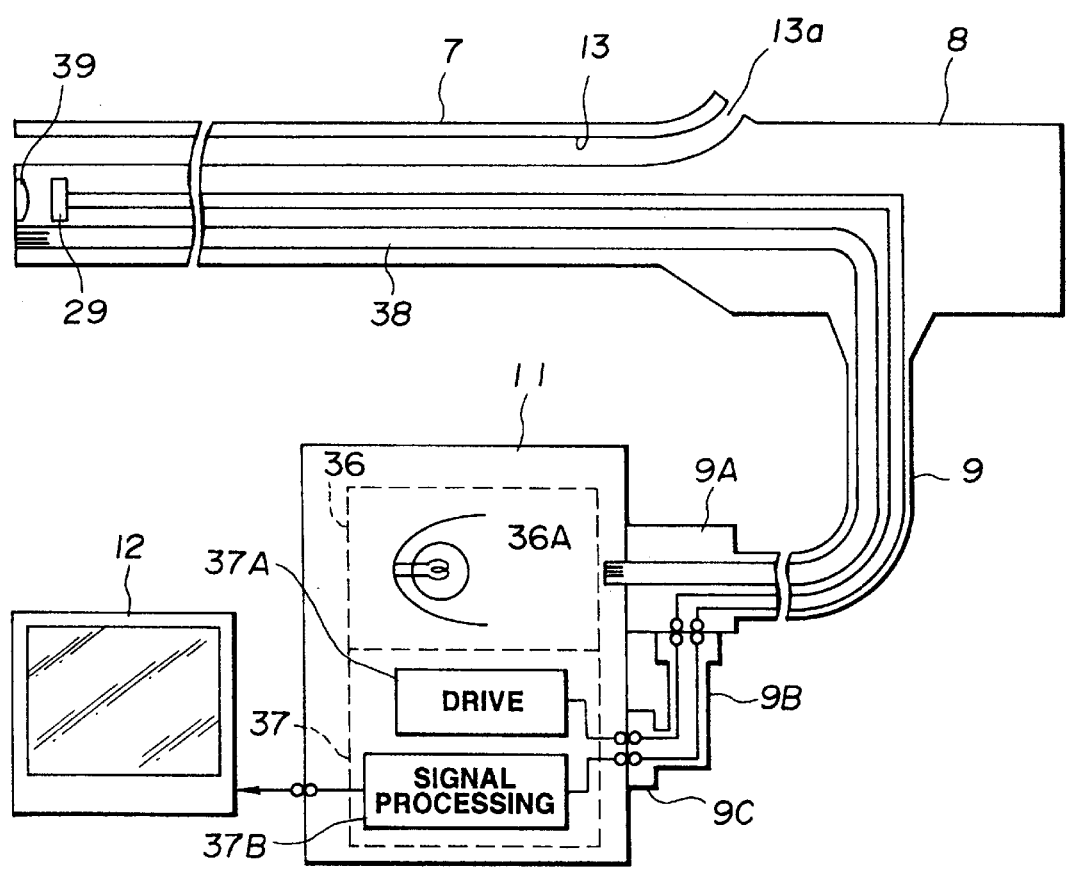

A signal cable 9B further extends from the connector 9A. A signal connector 9C which is provided at the distal end of the signal cable 9B can be detachably connected to a signal processor 37 within the video processor 11, as shown in FIG. 4.

A light guide 38 for transmitting an illumination light is inserted into the insertion part 7. The light guide 38 is further inserted into the universal cable 9 which extends from the operation unit 8 and which extends to the connector 9A at the distal end. An illumination light is supplied to the end face of the connector 9A from a lamp 36A within the light source 36 and is transmitted by the light guide 38 to output forwardly the illumination light which is transmitted from a forward-end surface which is mounted at an illumination window (which forms illumination-light output means) at the forward end of the inserting part 7.

The subject, such as an inner wall, an affected or diseased part or the like within a body cavity, which is illuminated by the illumination light which is outputted from the illumination window is focused to a CCD 29 serving as a solid-state image-pickup element which is arranged at a focusing surface of an objective lens 39 by the same which is mounted on an observation window which is formed adjacent to the illumination window at the forward end.

A CCD drive signal which is outputted from a CCD drive circuit 37A within the signal processing section 37 is applied to the CCD 29, whereby an image signal which is photoelectrically converted (by the CCD 29) is read out. The image signal passes through a signal line which is inserted into the insertion part 7 or the like, and is processed by a signal processing circuit 37B so as to be converted to a standard image signal. The image signal is outputted to a color monitor 12. Thus, an endoscope image which has its image formed onto a photoelectric-conversion surface of the CCD 29 by the objective lens 39 is displayed in color.

Further, a bending operation knob 8A is provided at an operation unit 8. Operation of angular movement of the knob 8A is performed whereby the bendable bending section 7A which is formed adjacent to the forward end of the insertion part 7 is made bendable. Thus, the forward-end side is curved so as to follow a curved surface of a curved path within the body cavity so as to be capable of smoothly being inserted into the curved path within the body cavity.

Moreover, as shown in FIG. 4, in the endoscope 6, a hollow channel 13 is formed within the insertion part 7. A treatment tool, such as forceps or the like, is inserted from an insertion port 13a in the proximal end of the channel 13, whereby the forward-end side of the treatment tool projects from a channel outlet in the forward-end surface of the insertion part 7 so as to be capable of performing biopsy, medical treatment or the like with respect to an affected or diseased part or the like.

Figure 5:
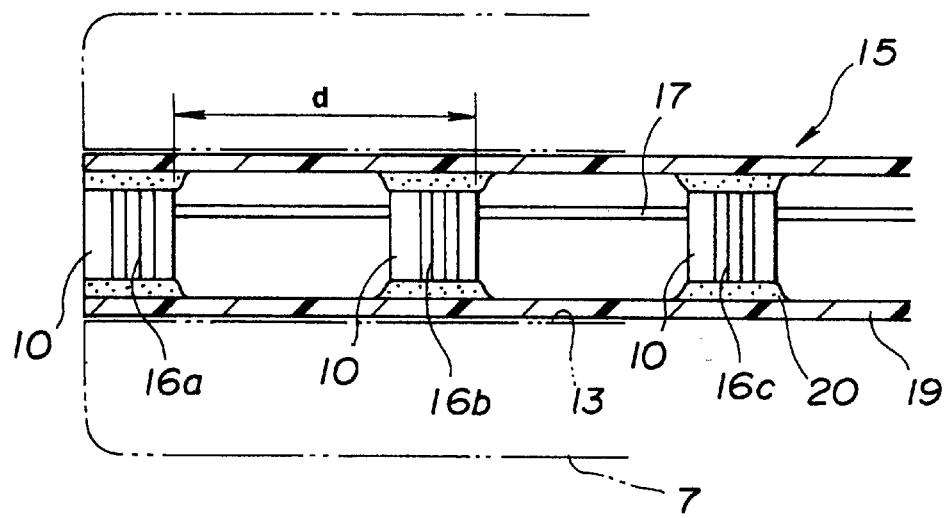

Furthermore, a probe 15 for detecting a position and a form (of the insertion part 7 which is inserted into the body cavity) is inserted through the channel 13 so that a forward-end side of the probe 15 can be set to a predetermined position within the channel 13. FIG. 5 shows an example of the forward-end side of the probe 15 where the probe 15 is fixedly mounted within the channel 13.

As shown in FIG. 5, in the probe 15, a plurality of source coils 16a, 16b, . . . (represented by the reference numeral 16i) each serving as a magnetic-field generation element for generating a magnetic field are fixedly mounted on an inner wall of a tube 19 by insulating adhesive 20, within a tube 19 which has a circular cross-section and which has electrical insulation and flexibility. The source coils 16i are arranged within tube 19 at predetermined intervals d, for example.

Each of the source coils 16i is formed by a solenoidal coil in which an insulation-covered lead wire is wound around an insulating hard columnar core 10, for example. Insulating adhesives 20 are applied to an outer peripheral surface of the coil, and the coil is fixedly mounted to the core 10 while being covered with insulation and is fixedly mounted also to the inner wall of the tube 19.

Each source coil 16i is of such construction that, even when the tube 19 is curved and is deformed, the source coil 16i per se is not deformed in form or shape thereof because the lead wire is wound around the hard core 10 and is fixedly mounted by the adhesives 20. Thus, the arrangement is such that magnetic-field generation is not affected when the tube 19 is deformed.

Further, a position of the source coil 16a at the distal end (forward end), for example, is so arranged that (the forward-end surface thereof) is in agreement with a surface of an outlet of the channel 13. Accordingly, a position of the source coil 16a at the most forward end is detected whereby a position of the forward-end surface of the insertion part 7 of the endoscope 6 (more accurately, a position more rearward only thorough ½ of the length of the source coil 16a in an axial direction of the insertion part 7) than the forward-end surface can be detected.

The position of the source coil 16a at the forward end is a known position of the endoscope 6, and the source coils 16i are provided at constant or predetermined intervals d. Accordingly, the position of each source coil 16i is set to the known position within the insertion part 7 of the endoscope 6. A position of each source coil 16i is detected whereby discrete positions of the insertion part 7 of the endoscope 6 (more accurately, a position of each source coil 16i) can be detected.

These discrete positions are detected whereby position therebetween can also substantially be estimated. Accordingly, it becomes possible to find out a form of the insertion part 7 of the endoscope 6 which is inserted into the body cavity, by detection of the discrete positions.

In this connection, an outer diameter adjacent to the forward end of the probe 15 may be slightly increased more than the other portions so that positioning and mounting can be made in intimate contact with the inner wall adjacent to the outlet of the channel 13. The arrangement may be such that if it becomes unnecessary to display the form of the endoscope (for example, display of the endoscope form is utilized so as to smoothly perform an insertion operation of the forward-end side of the insertion part 6 to a location adjacent to a part which is aimed at by a deep side within the body cavity), the hand side of the probe 15 is pulled, and the probe 15 is removed or unfastened from the grip of an operator so that the treatment tool or the like can be inserted into the channel 13.

Lead wires 17 which are connected respectively to the source coils 16i are connected to a connector 18 which is provided at the rearward end of the probe 15 or which is provided at a rearward end of the cable which extends from the rearward end of the probe 15. The connector 18 is connected to a connector receptacle of a body 21 of an (endoscope) form detecting apparatus. As described later, a drive signal is applied to each of the source coils 16i to generate a magnetic field which is utilized for positional detection.

FIG. 6 shows a structure or a probe 15' according to a modification of the embodiment. The probe 15' is arranged such that the source coils 16i are mounted on a support member 46 having flexibility within a sheath tube 19' which is an insulating member and which has flexibility, every predetermined distance d. The support member 46 is formed by a member which has no stretchability or elasticity with respect to a longitudinal direction thereof (an axial direction of the insertion part 7 in case of being arranged within the insertion part 7). Thus, the intervals between the source coils 16i are made constant even when the sheath tube 19' is curved.

Each of the source coils 16i is formed by a coil in which a copper wire 48 is wound about a magnetic material 47. One copper wire of a pair of terminals of the wound coil is made common, and extends along the support member 46, for example. The copper wire 48 which extends from the other terminal extends rearwardly from the respective source coils 16i, and is connected to a contact of a connector 49 (refer to FIG. 3) at the proximal end of the sheath tube 19'.

In this connection, the arrangement may be such that one of the pair of terminals of each of the coils which form the source coils 16i, respectively, extends rearwardly by a pair of copper wires, notwithstanding the fact that the pair of terminals are not made common.

A through-bore is provided in the magnetic material 47 of each of the source coils 16i. The support member 46 is passed through the through-bore and is fixed by the insulating adhesive 20 under a condition of constant or predetermined intervals d. Since there is the possibility that, if the wall of the sheath tube 19' is made thin, the sheath tube 19' is crushed or broken and is buckled by a force from the outside so that insertion becomes difficult, a bonding material 50 such as silicon or the like is filled in the periphery of each of the source coils 16*i* within the sheath tube 19'.

A substantially spherical forward-end tip 55 is mounted on a forward end of the sheath tube 19', to improve sliding upon insertion into the channel 13. Moreover, a failure prevention 56 is provided between a rearward end of the tube 19' and the connector 49.

Furthermore, the connector 49 is covered by a connector cap 57 in order to facilitate handling of an operator and in consideration of disinfection and sterilization processings.

FIG. 3 shows a state in which the probe 15' is mounted on the channel 13. In FIG. 3, the arrangement is such that forceps or the like can be inserted from the insertion port 13*a* in addition to the probe 15'. Also, the arrangement may be such that the probe 15' and the endoscope 6 are integrated with each other so as not to be detachable.

Figure 7:
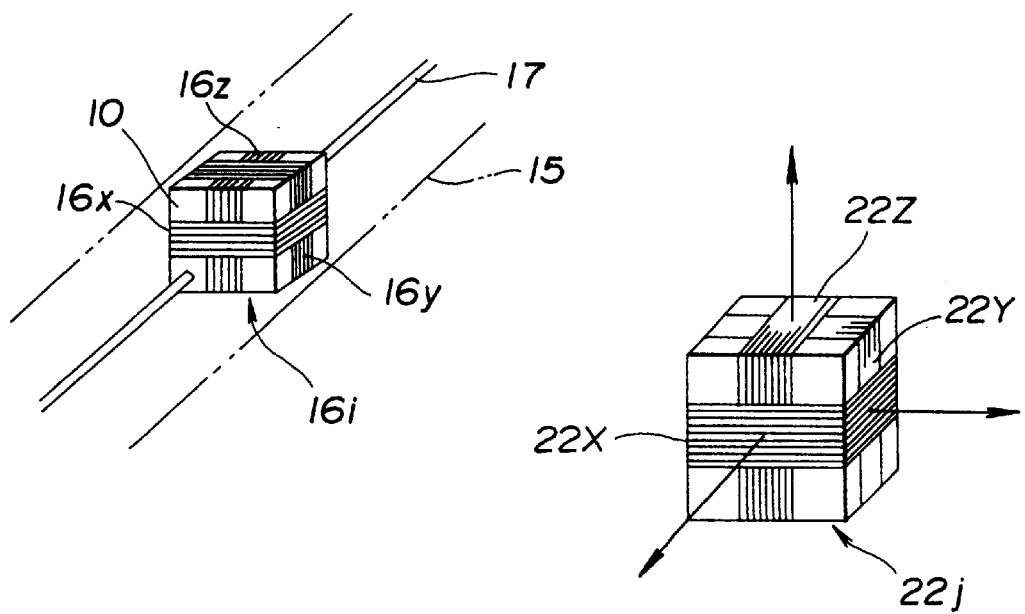

As shown in FIG. 5 or FIG. 6, the source coil 16*i* may be formed by a single-axis coil, or, as shown in FIG. 7, may be formed by a three-axis source coil 16*i*.

When the source coil 16*i* is formed by the three-axis source coil 16*i*, the source coil 16*i* is arranged such that three coils are wound about a hard core 10 which is formed by non-magnetic material or magnetic material and which is in the form of, for example, a cube. The core 10 made of non-magnetic material is used, whereby the core 10 may not be influenced by magnetic-field distribution which is generated by the other source coils which are located adjacent thereto or the like. Alternatively, when the source coil 16*i* does not access the adjacent source coil, the core serves as a magnetic core 10 to form a source coil which serves as a magnetic-field generation element about which the lead wire is wound.

Further, as shown in FIG. 7, a bore or hole is provided in a portion in the core 10 about which the coil is not wound so that the lead wire 17 connected to both ends of each coil is passed through the bore (the one end of each coil can be made common). In this connection, the arrangement may be made to a structure or construction which has no core 10 and in which three (3) coils including hollow portions of the three (3) coils, for example, are adhered to each other and are fixed to each other by insulating adhesives.

Moreover, as shown in FIG. 1, three-axis sense coils 22*a*, 22*b* and 22*c* (represented by 22*j*) which serve as magnetic-field detecting elements for detecting a magnetic field are mounted respectively on the known positions of the bed 4, for example, on three (3) corners. These three-axis sense coils 22*j* are connected to the body 21 of the form detecting apparatus through cables which extend from the bed 4.

As shown in FIG. 7, the three-axis sense coil 22*j* is wound respectively in three (3) directions such that respective coil surfaces thereof extend perpendicularly to each other. Each coil detects a signal which is in proportion to the strength of the magnetic field in an axial component which is perpendicular to a coil surface thereof.

The body 21 of the form detecting apparatus detects positions of the respective source coils 16*i* on the basis of an output from the three-axis sense coil 22*j*, to estimate a form of the insertion part 7 of the endoscope 6 which is inserted into the patient 5, to thereby display a computer graphic image corresponding to an estimated form, on the monitor 23.

Since the endoscope form detecting apparatus 3 utilizes magnetism, if metal exists which is not transparent with respect to magnetism, the endoscope form detecting apparatus 3 is influenced by iron loss or core loss or the like, so as to influence mutual inductance between the magnetic-field generation source coil 16*i* and the detecting three-axis sense coil 22*j*. Generally, if the mutual inductance is expressed as R+jX, (metal which is not transparent with respect to the magnetism) an influence is exerted upon both R and X.

In this case, amplitude and phase of the signal which is measured by orthogonal or cross detection, which is generally used in detection of a microscopic magnetic field, are varied. For this reason, it is desirable to set the environment upon which the generated magnetic field is not influenced.

In order to realize the same, the bed 4 may have to be made of a material which is magnetically transparent (in other words, a material which does not influence upon the magnetic field).

The material which is magnetically transparent may be resin such as Delrin or the like, for example, wood, or non-magnetic metal.

In actuality, since an alternating-current magnetic-field is used in detection of a position of the source coil 16*i*, the bed 4 may be made of a material which is not influenced magnetically in the frequency of a drive signal.

In view of the above, the bed 4 for inspection of the endoscope, shown in FIG. 1, which is used together with the present endoscope form detecting apparatus 3, is made of a non-magnetic material which is magnetically transparent in, at least, the frequency of the generated magnetic field.

Figure 2:
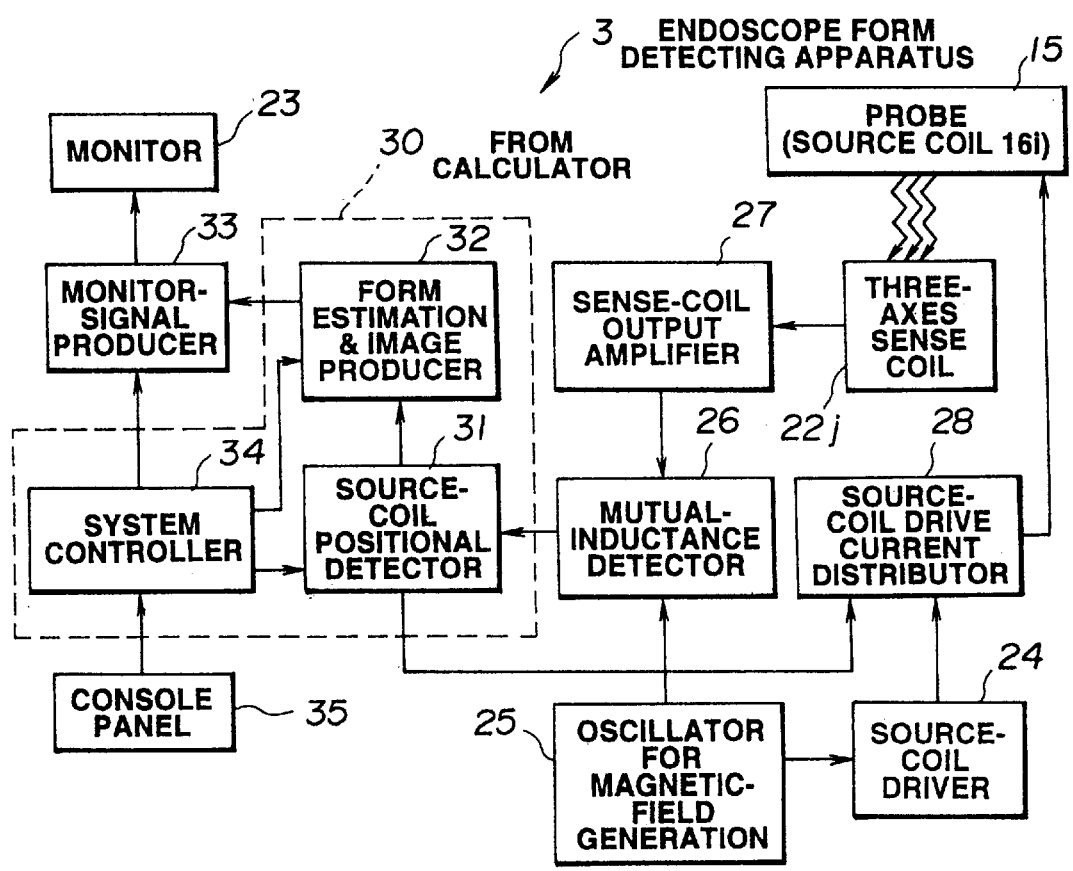

FIG. 2, is a block diagram showing a schematic arrangement of the endoscope form detecting apparatus 3.

A drive signal from a source-coil drive section 24 is supplied to the source coil 16*i* within the probe 15 which is set within the channel 13 of the endoscope 6. A magnetic field is generated in the vicinity of the source coil 16*i* to which the drive signal is applied.

The source-coil drive section 24 amplifies an alternate-current signal which is supplied from an (magnetic-field generating) oscillator 25, to output a drive signal for generating a required magnetic field. An alternate-current signal of the oscillator 25 is sent to a (mutual-inductance) detector 26, as a reference signed, for detecting a minute or microscopic magnetic field which is detected by the three-axis sense coil 22*j* which is provided on the bed 4.

The minute or microscopic magnetic-field detecting signal which is detected by the three-axis sense coil 22*j* is amplified by an (sense coil) output amplifier 27 and, subsequently, is inputted to the detector 26. The detector 26 performs amplifying and orthogonal detection (synchronous detection) with the reference signal serving as a reference, to produce a signal in relation to the mutual inductance between the coils.

Since the plurality of source coils 16*i* exist, a (source-coil drive current) distributor 28 which serves as a switching means for performing switching so as to successively supply the drive signal to the lead wire connected respectively to the source coils 16*i* exists between the source-coil drive section 24 and the source coil 16*i*.

The signal which is produced by the detector 26 is inputted to a (source coil) position detector (or a position estimator) 31 which forms a form computer or calculator 30 which performs processing which estimates a form of the insertion part 7 and which produces (calculates) an image corresponding to the estimated form. The inputted analog signal is converted to a digital signal to perform calculation of positional detection or operation or computation of positional estimation, to produce positional information estimated with respect to each source coil 16i. The positional detector 31 refers to reference information which serves as a reference which connects a magnetic-field strength and a distance with each other to be described subsequently, with respect to the detected magnetic-field strength, to calculate the positional information.

This each positional information is sent to a form estimation & image producer 32. By a form estimator within the form estimation & image producer 32, graphic processing, such as interpolation processing or the like, which interpolates an interval, from each discrete positional information produced is performed to estimate a form of (the insertion part 7 of) the endoscope 6.

Estimated image data of the form of the insertion part 7 produces a form image which corresponds to the form of the insertion part 7, by a (form) image generator within the form estimation & image producer 32, and are sent to a monitor-signal producer 33.

The monitor-signal producer 33 produces an image signal of an RGB system or an NTSC system or a PAL system which represents an image corresponding to the form, and outputs the same to a monitor 23 to thereby display an image corresponding to the insertion-part form of the endoscope 6 on a display surface of the monitor 23.

In this connection, the positional detector 31 sends a switching signal to the distributor 28 after calculation or computation of single positional detection has ended or has been completed. The positional detector 31 supplies the drive current to the next or subsequent source coil 16i to perform calculation or computation of positional detection thereof. The switching signal may be sent to the distributor 28 before calculation of each positional detection is completed, to successively store the signal detected by the sense coil 22j to a memory.

Further, a system controller 34 is formed by a CPU or the like to control operation or the like of the positional detector 31, the form estimation & image producer 32 and the monitor-signal producer 33. Moreover, a console panel 35 is connected to the system controller 34. A keyboard, a switch or the like of the console panel 35 is operated whereby a painting model of the endoscope form can be selected, the endoscope form displayed on the monitor 23 can be modified to a display condition with respect to a selected direction of a field-of-view or the like.

In this connection, the form calculator 30 indicated by the broken lines in FIG. 2 includes software. Furthermore, the endoscope form detecting apparatus 3 in FIG. 2 includes the endoscope position detecting apparatus according to the first embodiment. The endoscope position detecting apparatus is formed by the reference numerals 16i, 22j, 24~28, and 31 in FIG. 2.

Figure 8A:
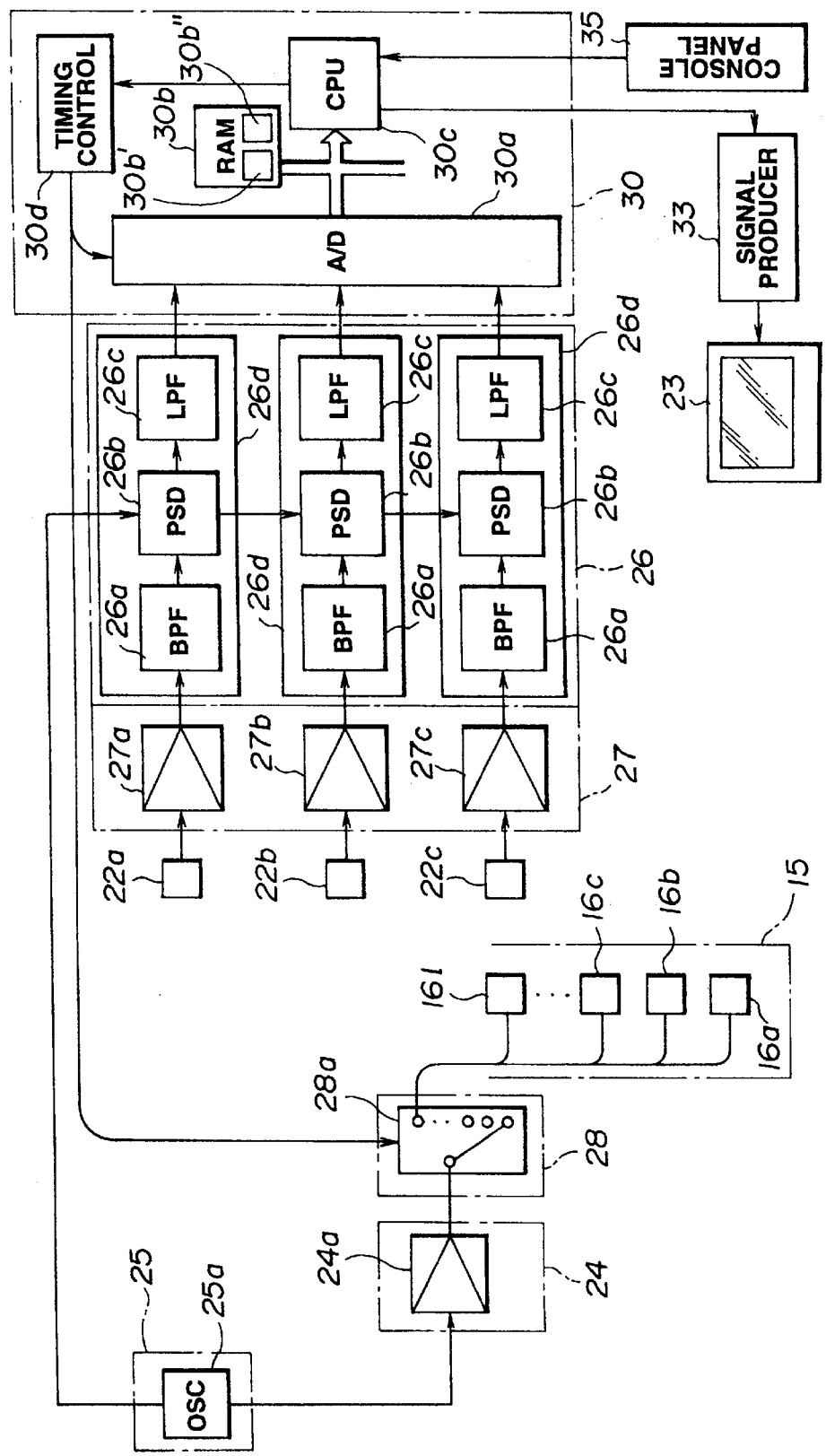
FIG. 8a is a block diagram showing a specific arrangement of the endoscope form detecting apparatus.

The arrangement of the endoscope form detecting apparatus 3 comes into one as shown in FIG. 8a if expressed more specifically. That is, the oscillator 25 is formed by an oscillator 25a, and an oscillating output thereof is amplified by an amplifier 24a which forms the driver 24. The oscillating output is switched by a source-coil switching circuit 28a which forms the distributor 28, so as to be successively applied to the plurality of source coils 16i to thereby generate a magnetic field around the applied source coils 16i.

Each magnetic field is detected by each sense coil 22j, and is amplified by each amplifier 27a which forms the amplifier 27. Subsequently, a signal including a phase difference with respect to the oscillation output together with the strength of the magnetic field is detected by a synchronous detecting circuit 26d which has a band-pass filter 26a, a phase detection circuit 26b and a low-pass filter 26c which cooperate with each other to form the inductance detector 26.

The phase detection circuit 26b refers to an output signal from the oscillator 25a to perform phase detection (cross detection). The output signal from a synchronous detection circuit 26d is converted to a digital signal through each channel of an A/D converter 30a which forms the form calculator 30 and, subsequently, is once stored in a storage 30b' of detected data of a RAM. The data in the storage 30b' are transferred to a CPU 30c, and calculation or computation of positional estimation, form estimation or the like is performed by the CPU 30c. Switching of each channel of the A/D converter 30a is performed by a timing control circuit 30d.

In this case, if computation or calculation with respect to a single source coil 16i is completed, for example, the CPU 30c sends an end signal to the timing control circuit 30d. If the timing control circuit 30d receives the end signal, a control signal of switching is sent to the source-coil switching circuit 28a, and a drive signal is applied to the subsequent source coil 16i.

The CPU 30c refers to reference information which is stored in a reference-information storage 30b" of the RAM 30b, for example, to estimate the position of the source coil 16i, and further uses information of each position which is produced by estimation to interpolate the interval, to perform estimation of the endoscope form. Moreover, the CPU 30c also produces a form image corresponding to the estimated form. The form image is outputted to the monitor 23 through the monitor-signal producer 33 similarly to FIG. 2. Thus, an image corresponding to the estimated endoscope form is displayed. In this connection, data (reference data for calculating a distance on the basis of a magnetic field strength) of two curved lines Cu and Cd in FIG. 16 to be described subsequently are stored in the reference-information storage 30b".

Figure 9:
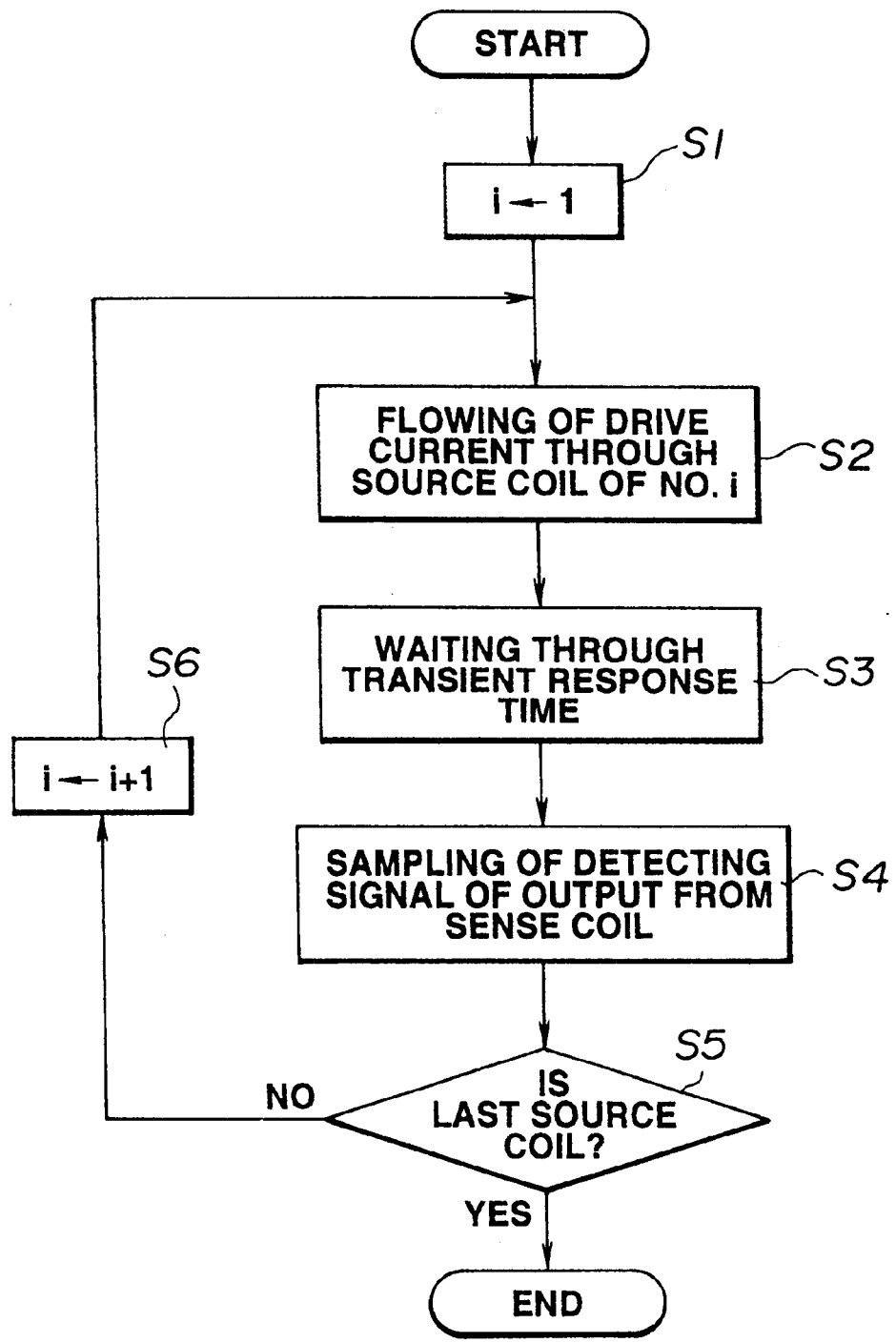

FIG. 9 is a flow chart of steps in a drive operation of the source coil and signal detection due to the sense coil for form detection. First, a parameter i is set is 1 (Step S1) and, thereafter, the source coil 16i of No. i is selected by the source-coil switching signal to cause drive current to flow through the source coil 16i (Step S2)

Subsequently, waiting is made through transient response time at (Step S3). A detecting signal which is detected by the sense coil 22j is sampled after the time at (Step S4). Subsequently, judgment as to whether or not the driven source coil of No. i is the last source coil is performed (Step S5). If the driven source coil of No. i is not the last source coil, i is increased to i+1 (Step S6), and the program is again returned to Step S2 of causing the drive current to flow through the source coil 16i of No. 1. Meanwhile, if the driven source coil of No. i is the last source coil, the program ends.

An explanatory view explains why the detecting signal due to the sense coil 22j is sampled after the transient response time Δt is shown in FIG. 10a~10d. If the source coil 16i is selected by the source-coil switching signal shown in FIG. 10a so that the drive current is caused to flow through the source coil 16i, the drive current which is caused to flow through the source coil 16i in fact indicates transient response characteristics between the times Δt as shown in FIG. 10b, with respect to the frequency of the drive current in accordance with the resistance component and the inductance component of the source coil 16i.

For this reason, the detecting signal which is detected by the sense coil 22j is influenced by the transient response characteristics as shown in FIG. 10c. For this reason, the timing control circuit 30d is controlled so as to perform reading with respect to the A/D converter 30a after the time Δt as shown in FIG. 10d. In this manner, the detecting signal which is not influenced by the transient response is used. In this connection, FIGS. 10e~10g are used in the description of FIG. 8b to be described subsequently.

FIG. 7 shows a state in which the position of the source coil 16i is detected by the three-axis sense coil 22j by the use of the three-axis source coil which serves as the source coil 16i. It is assumed that three (3) coils which are perpendicular to each other, in the three-axes source coil 16i are 16x, 16y and 16z, and three (3) coils of the three-axis sense coil 22j are 22X, 22Y and 22Z. Furthermore, it is assumed that there is no variation of the coils. Signal outputs which are detected by (three (3) coils 22X, 22Y and 22Z of) the three-axis sense coil 22j at the time when the coils 16x, 16y and 16z of the respective three-axis source coils 16i are driven are defined as follows;

It is assumed that, of the three-axis source coils 16i,
The sense coil output at the time the coil 16x is driven: Xx, Yx, Zx
The sense coil output at the time the coil 16y is driven: Xy, Yy, Zy
The sense coil output at the time the coil 16z is driven: Xz, Yz, Zz Eight (8) positions which are defined by values of detecting-signal outputs $Xx^2+Yx^2+Zx^2$, $Xy^2+Yy^2+Zy^2$ and $Xz^2+Yz^2+Zz^2$ corresponding to a square of the magnetic-field strength formed respectively by the three (3) coils 16x, 16y and 16z are produced as a candidate of the detecting position of the source coil 16i.

Further, a single quadrant (of eight (8) quadrants) in which the source coil 16i exists in coordinates whose origin is the sensor (three-axis sense coil 22j) is defined on the basis of the phase information of Xx, Yx, Zx, Xy, Yy, Zy, Xz, Yz and Zz which are produced by the synchronous detection of the detector 26.

Thus, the existing position of the source coil 16i is defined. In the present embodiment, the existing position of the source coil 16i not is found out directly by calculation or computation by the use of the signal which corresponds to the detected magnetic-field strength, but the existing position is calculated (estimated) with reference to reference data which is measured beforehand.

In this manner, if the source coil 16i of three axes and the three-axis sense coils 22j are used, the discrete position of the source coil 16i can be detected.

Moreover, as shown in FIG. 1, if the three-axis sense coils 22i are arranged respectively at a plurality of locations on the bed 4, it is made possible to detect the positions of the respective source coils 16i more accurately.

Figure 11:
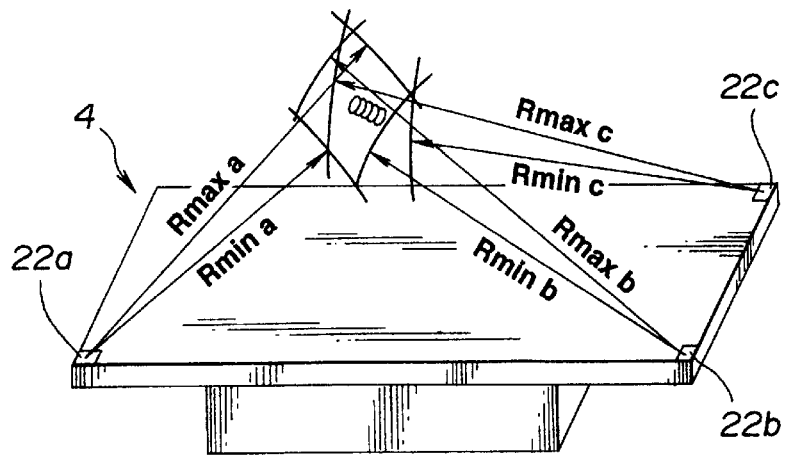

Furthermore, FIG. 11 shows a state under which a single-axis source coil 16i (expressed as being a single-core solenoid) is used to perform the positional detection by the three-axis sense coil 22j.

Typically, during the endoscope inspection or examination, the position of the endoscope 6 is on the bed 4 because the patient 5 is on the bed 4.

That is, if the three-axis sense coils 22j which serve as sensors are provided respectively at four corners of the bed 4, the endoscope 6 (the source coil 16i thereof) exists in the region which is surrounded by the sensor group. Accordingly, the quadrant in which the source coil 16i exists is limited every the installed three-axis sense coil 22j.

If it is assumed that the output from the single three-axis sense coil 22 at the time the source coil 16i is driven is Xi, Yi and Zi, the source coil 16i exists at a distance from the three-axis sense coil 22 which comes into the magnetic-field strength which is related in $Xi^2+Yi^2+Zi^2$.

Figure 12:
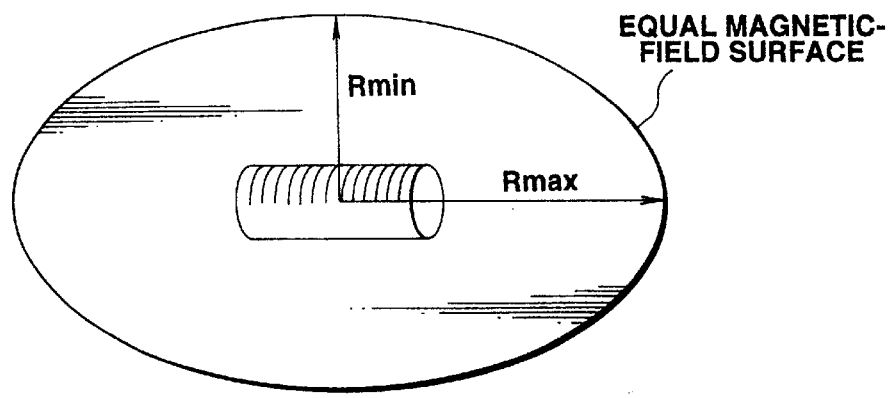

However, the single-axis coil is generally expressed as a dipole, and the equal magnetic-field surface thereof is not in the form of a spherical surface but is in the form of an elliptical surface instead as shown in FIG. 12.

For this reason, it is impossible to identify the position of the source coil 16i which is unknown as to in which direction the source coil 16i is oriented, on the basis of only the equal magnetic-field surface $Xi^2+Yi^2+Zi^2$ due to the single three-axis sense coil 22.

For this reason, distances associated by $Xj^2+Yj^2+Zj^2$ which are measured in relation respectively to the plurality of three-axis sense coils 22j provided on the bed 4 are used. In this case, since the establishment or installation positions of the three-axis sense coils 22j are already known, it is possible to express $Xj^2+Yj^2+Zj^2$ by single coordinates which are fixed to, for example, the bed 4.

It is considered that the magnetic-field strength in which the equal magnetic-field surface generated by the source coil 16i is expressed as being $Xs^2+Ys^2+Zs^2$ is detected by the sense coil 22j to estimate a distance therebetween.

Then, if the equal magnetic-field surface including the magnetic-field strength detected by the sense coil 22j from the magnetic-field strength is supposed, the sense coil 22j exists on the equal magnetic-field surface with respect to the central source coil 16i. If the maximum value and the minimum value of the distance from the center to the equal magnetic-field surface are assumed, respectively, to Rmaxj and Rminj, the sense coil 22j and the source coil 16i exist at a distance between them.

That is, if the sense coil 22j at the known position is made to a reference, the source coil 16i exists inside the distance of the maximum distance Rmaxj and outside the minimum distance Rminj as shown in FIG. 11.

Since the source coil 16i exists in overlap (volume) of a spherical shell which is expressed by Rmaxj and Rminj which correspond to Xj, Yj and Zj which are measured by the three-axis sense coils 22j and which are different from each other every three-axis sense coils 22j, the center of gravity of the region can be detected as being a coil position.

In this manner, the position can be determined. However, when a difference between Rmax and Rmin is great, there is the possibility that an error is generated.

In view of the above, an inclination of the source coil 16i is expressed in the phase information included in Xj, Yj and Zj, and the inclination in the volume found out previously is determined. Thus, the previous position determination is corrected so as to represent a more accurate position.

Figure 13:
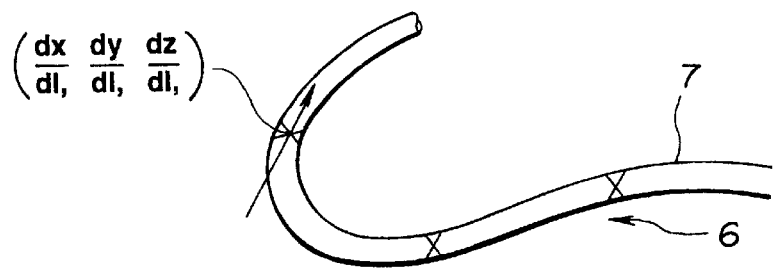

In this case, as shown in FIG. 13, since the endoscope 6 is continuous, the inclination (dx/dl, dy/dl and dz/dl) of the discrete positions of the source coil 16i (indicated by x marks) is equal to that in a tangential direction at the source-coil position of a curve 1 in which the source coil position is originally interpolated. Accordingly, correction of the position may be further performed.

Figure 14:
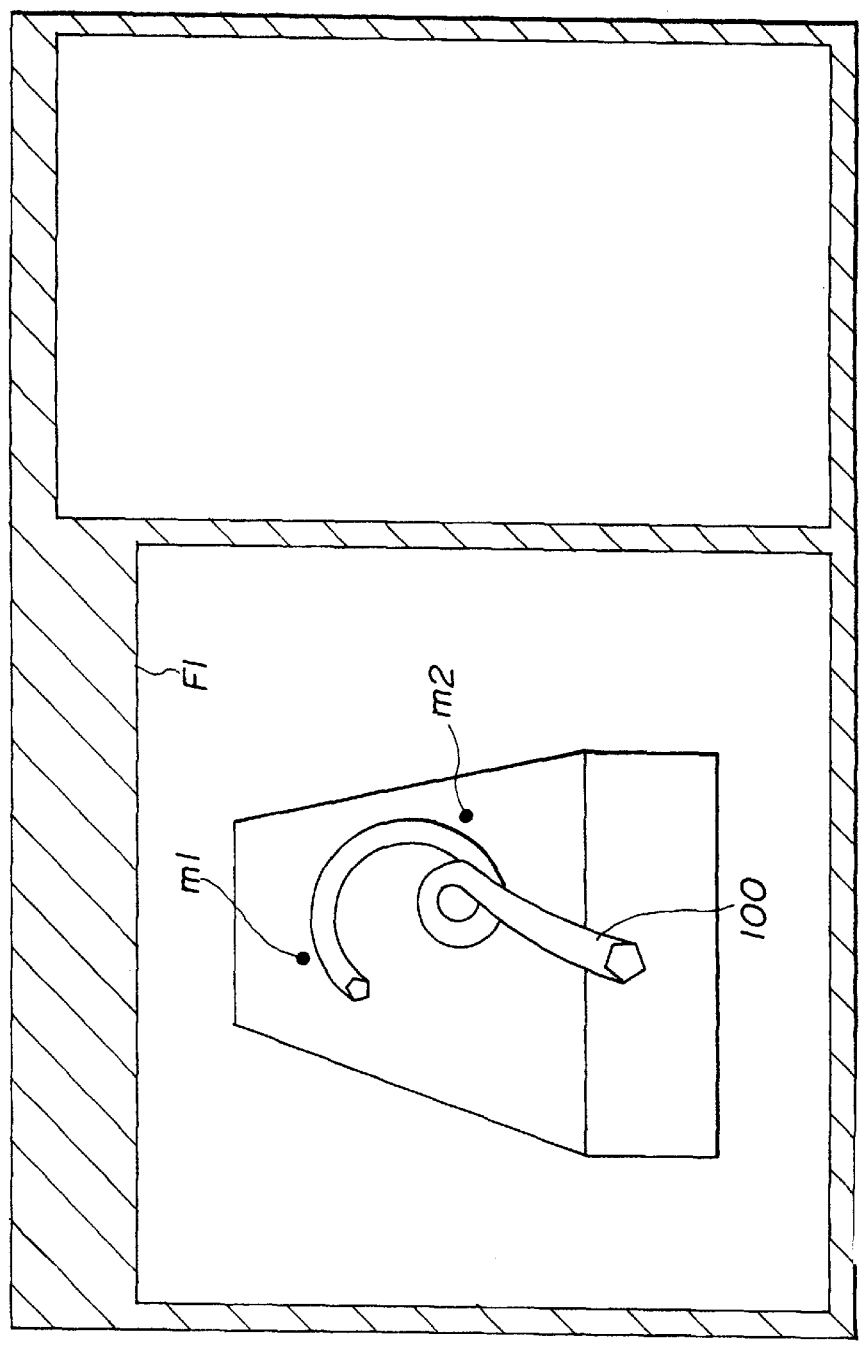

The form of the insertion part 7 of the endoscope 6 which is estimated by the plurality of positional information which is detected in this manner is displayed on the display surface of the monitor 23, for example, on the left-hand graphics output region as shown in FIG. 14 by an image 100 which is modeled as subsequently described. The right-hand region is a user interface region in which a user sets a point of view (a distance between the position and the origin), a rotational angle, an angle of elevation between the position of the point of view and the z-axis or the like, by key input from the console panel 35.

Figure 8B:
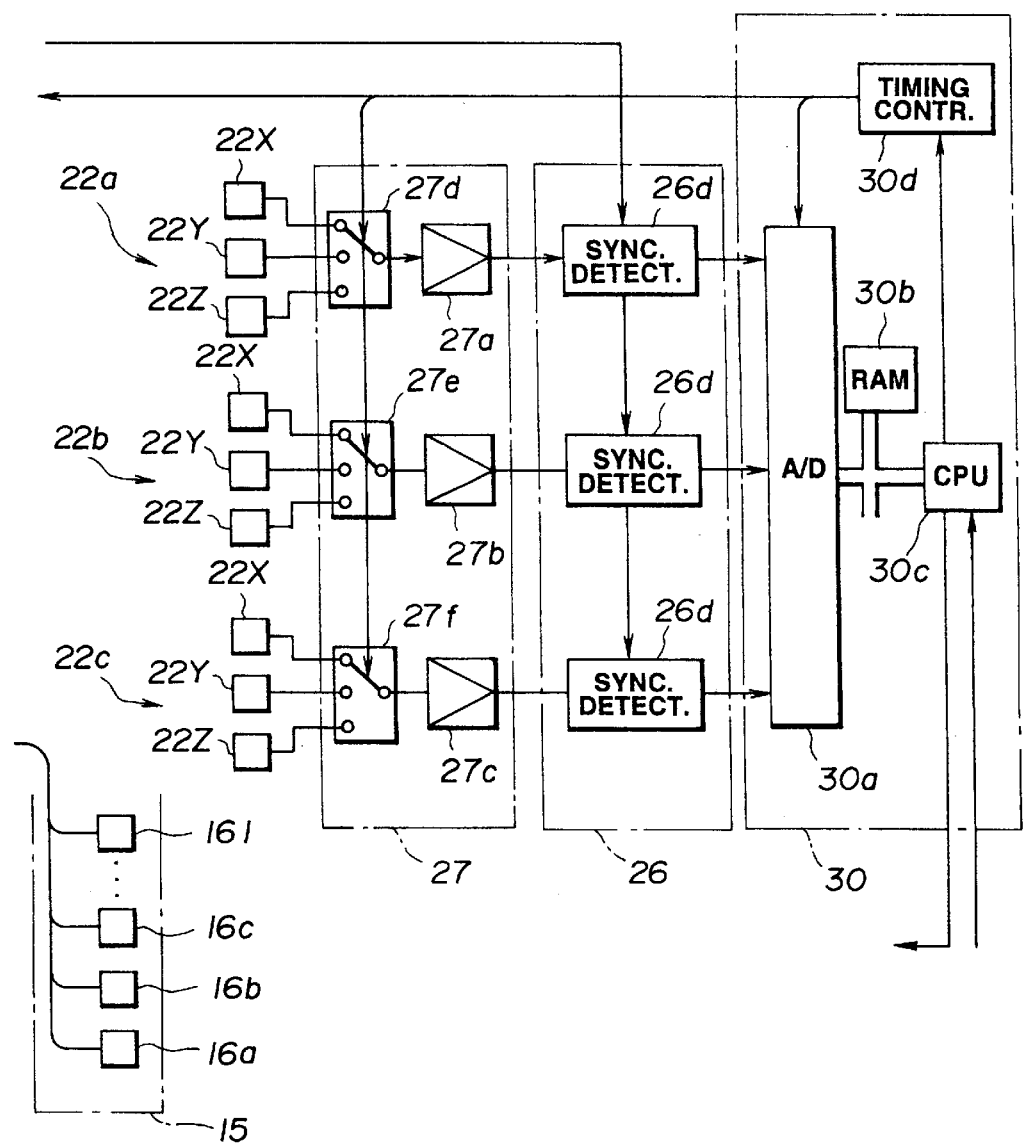

In the present embodiment, the sense coils 22*j* in FIG. 8*a* are formed by coils 22X, 22Y and 22Z having respective directionality and directionality thereof in three (3) directions extending perpendicularly to each other. Accordingly, the detailed arrangement in the vicinity of the sense coil 22*j* and the amplifier 27 in FIG. 8*a* is shown in FIG. 8*b*.

The coils 22J (J=X~Z) which form the sense coil 22*a* are inputted to the amplifier 27*a* through switch 27*d*.

Similarly, the coils 22J which form the sense coils 22*b* are inputted to the amplifier 27*b* through the switch 27*e*. The coils 22J which form the sense coil 22*c* are inputted to the amplifier 27*c* through the switch 27*f*.

Switching of the switches 27*d*, 27*e* and 27*f* is controlled by a switching signal due to the timing control circuit 30*d*, and the switching signal is inputted to the amplifier 27*j* on the order of the coils 22X, 22Y and 22Z.

Accordingly, the coils 22X, 22Y and 22Z are selected by the switching signal as shown in FIGS. 10*e*, 10*f* and 10*g*, with respect to a pulse period of time or duration through which reading shown in FIG. 10*d* is performed. In this connection, FIGS. 10*e*, 10*f* and 10*g* are indicated by the switching signals (each contact of the changing-over switch is turned ON/OFF) after having been decoded in order to facilitate understanding. Turning-ON is made at an "H" level, while turning-OFF is made at an "L" level.

In this connection, in FIG. 8*b*, the switches 27*d*, 27*e* and 27*f* can be formed as a single switch provided that the number of switching contacts is nine (9), and three (3) amplifiers 27*a*, 27*b* and 27*c* and three (3) synchronous detection circuits 26*d* can also be formed as one. This is because the signals taken into or fetched into the single A/D converter 30*a* come into singles, respectively, because two (2) or more signals are not fetched simultaneously.

When a plurality of A/D converters 30*a* are used, a plurality of signals of the sense coils can simultaneously be fetched. For example, in FIG. 8*b*, when the three (3) A/D converters which fetch respectively the outputs of the respective synchronous detection circuits 26*d* are used, when a single source coil 16*i* is driven, it is possible to fetch the signal of the detection of the magnetic-field strength simultaneously by three (3) coils (22X, 22X, 22X, for example).

Further, in FIG. 8*b*, if an arrangement is such that the outputs from the coils 22J are respectively amplified by the amplifiers, and the synchronous detection and the A/D conversion are performed without use of the switches 27*d*, 27*e* and 27*f*, when the single source coil 16*i* is driven, it is possible to produce a signal which is required with respect to the driven source coil 16*i* by all the coils which form three (3) sense coils 22 *a*, 22*b* and 22*c*. When the plurality of A/D converters are used, it is desirable to provide a memory such as a RAM or the like for temporarily storing A/D converted data into the A/D converters per se.

Figure 15:
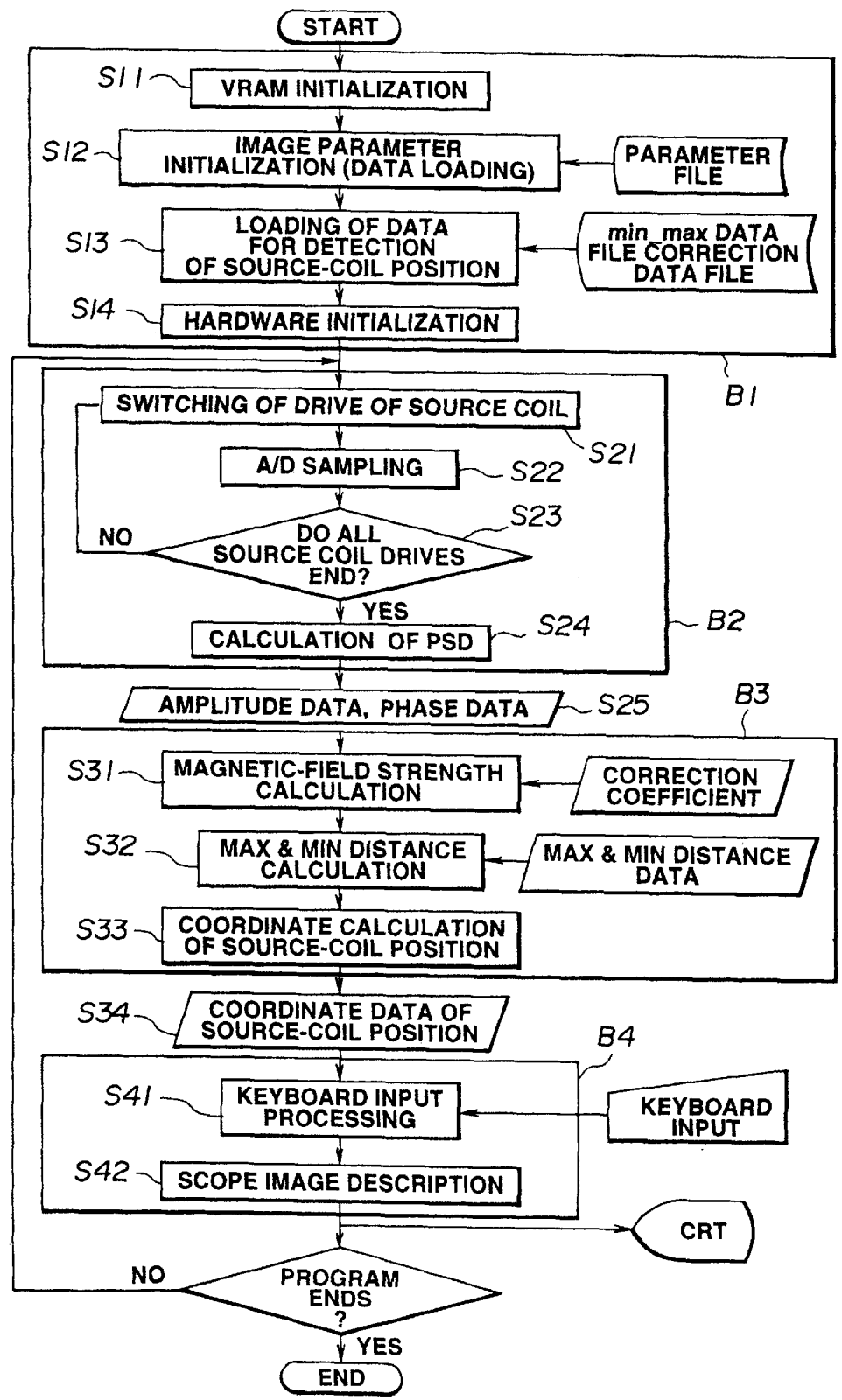

FIG. 15 is a flow chart showing steps in which the magnetic field created by the source coil 16*i* within the scope is detected by the three-axis sense coil 22*j* on the outside, a position of the source coil 16*i* is produced on the basis or the relationship between the magnetic-field strength and the distance between two points, and an insertion-part form under an inserted condition or state (also referred to as "scope form" in brief) on the basis of the positional detections of the plurality of source coils 16*i* is displayed on the monitor (referred also to as "CRT").

The whole arrangement of the flow can be divided into four (4) blocks of the below B1~B4, depending upon the processing contents thereof.

B1: Initialization Block

An initialization operation relating to all functions of the present program is ended or completed in the block. Specifically, setting of initial parameters on the basis of procedure for outputting the scope form onto a CRT, memory reading of basic or fundamental data which are used at the time the presence position of the source coil 16*i* are calculated, on the basis of phase information and the amplitude information which are produced from the magnetic-field strength detected by hardware, initialization of various kinds of boards for controlling the hardware, and the like are performed. In this connection, detailed processing contents will subsequently be performed by the following description of each of the blocks.

B2: Hardware Control Block

In the present system, the positional coordinates of the source coil 16*i* which are arranged and fixed within the insertion part 7 of the endoscope 6 are calculated on the basis of the magnetic-field strength which is generated by the source coil 16*i*, and the form of the insertion part 7 of the endoscope 6 under the inserted condition is estimated on the basis of the same.

This block is responsible for a period of time until the drive of the source coil 16*i* is switched to generate the magnetic field, the generated magnetic-field strength is detected by the sense coil 22*j*, and the detection output therefrom is converted to a form in which the source coil positional coordinates can be calculated or computed, and is outputted.

The drive switching of the source coil 16*i* is so arranged that where of the endoscope 6 the source coil is positioned. The sense coil 22*j* for detecting the magnetic-field strength of the source coil 16*i* is manufactured such that the surfaces or planes of the coils are parallel to the three (3) axes which extend perpendicularly to each other as shown in FIG. 6 so that the magnetic-field strength components in the three (3) axes directions which extend perpendicularly to each other regarding the single sense coil 22*j* can be detected. Data of the detected magnetic-field strength are separated into amplitude data and phase data which are required when the source coil position is calculated and are outputted.

B3: Source Position Calculation Block

On the basis of the amplitude data and the phase data which are produced by the magnetic-field detection at the previous block, this block is responsible for a period of time until the positional coordinates of the source coil 16*i* are calculated, by the utilization of the relationship between the magnetic-field strength and the distance between the two points. First, correction is performed on the relationship between a difference in magnitude of a diameter in axial directions of the sense coil 22*j* and the position between the source coil 16*i* and the sense coil 22*j* with respect to the amplitude data and the phase data, to calculate the magnetic-field strength which is considered as being detected at the establishment positions of the respective sense coils 22*j*.

On the basis of the magnetic-field strength calculated in this manner, the distance between the source coil 16*i* and the sense coil 22*j* is detected. In this connection, since the posture of the source coil 16*i* under the inserted condition (orientation of the solenoidal coil) is unknown, the existence position of the source coil 16*i* cannot be limited only within the range of a spherical shell. In view of this, the number of sense coils 22*j* is made equal to or greater than three (3), overlap of the region on which the source coil 16*i* is capable of existing is found, and the position of the center of gravity of the region is outputted as the positional coordinates of the source coil 16*i*.

B4: Image Display Block

This block is responsible for a period of time until the scope form is constructed on the basis of the data produced as the source-coil positional coordinates, and a painted image is outputted onto a CRT. Continuous coordinates which are smooth as a whole are constructed on the basis of one or more coordinates which are produced as being source-coil positional coordinates. On the basis of the continuous coordinates, modeling processing for showing a scope form is performed (utilization of a polygonal column, color gradation, chroma or saturation and intensity or luminance, hidden-line processing, perspective or the like).

Moreover, the scope image model which is displayed on the CRT is capable of being rotated, and which is capable of being enlarged and reduced in optional directions, and a body marker which can understand or see, at a glance, position of the point of sight and a head direction of the patient of the present display can also be displayed. A position of the point of sight upon completion is automatically stored or preserved, and comes into the next initial position of the point of sight. A hot key which stores a direction of the point of sight which is considered to be easy to see by the operator also exists.

The detailed contents of every block will be described below.

B1: Initialization Block

In initial Step S11, initialization of graphic pages (initialization of a VRAM) is performed. Moreover, when the scope image which is displayed on the CRT is updated, if a new image is superscribed, an impression of an image having excessive flicker is observed. In view of this, a plurality of graphic pages are continuously switched or changed over to display an image, whereby a smooth animated image is realized.

Furthermore, setting of the colors and gradation used is performed as follows:

The number of colors capable of being used is limited by hardware, and assignment or allocation is performed in the form of a pallet number. However, there are cases where only two (2) gradations are displayed as the default. In view of this, in order to realize more plentiful gradation within the scope of utilizable number of colors, setting of the pallet has been performed. For example, in FIG. 14, it is used in gradation display of the image 100 in which three (3) colors are applied respectively to a frame F1, markers m1 and m2 and a portion of a displayed model name (not shown), and all the remainder is applied to modeling of the insertion part 7.

Thus, it is possible to perform display of a position which is brighter the closer to the point-of-view, and which is darker the more remote therefrom. Thus, the insertion part 7 is expressed as a three-dimensional image 100 having depth, which is actually displayed two-dimensionally. Of course, it is optional to increase and decrease the number of gradations. Further, a color which is adopted in addition to the gradation is also formed by an arrangement of R, G and B. It is made possible to express delicate chroma or saturation and intensity or luminance.

Initialization of the image parameter such as automatic reading of the position of the initial point-of-view or the like is performed in subsequent Step S12.

If the initial position of the point-of-view is fixed, the operator must perform resetting to the portion of the point-of-view which is easy to look at. Convenience in use is lowered or reduced.

In view of the above, the position of the point-of-view desired is preserved in the form of a file (parameter file), and the file is read upon start of the program, whereby means is provided which provides ease in viewing by the operator immediately after start of the program.

Furthermore, in the present embodiment, a divided display of the scope image and the text image plane is performed. The scope image and the text image plane are divided whereby rotation and the order of enlargement and reduction of the scope image could be confirmed from both surfaces both visually and numerically.

In the subsequent Step S13, principle-origin data which store the principle for leading through the source-coil position are loaded. The data are reference data or reference information of the following relationship:

Relationship Between Magnetic-field Strength and Two Points

The creation of the reference data is performed such that the output from the single-axis source coil $16i$ is detected by the sense coil $22j$ which is produced by the three axes which extend perpendicularly to each other, to produce the spacing between the source coil $16i$ and the sense coil $22j$ on the basis of the magnetic-field strength thereof. When the spacing between both the coils is produced, solution is not directly made from distribution which indicates magnetic-field distribution created by the single-axis source coil $16i$, but a new distance calculation method has been introduced which utilizes the maximum magnetic-field strength output and the minimum magnetic-field strength output due to a difference between postures (orientations in the axis direction) of the source coil $16i$.

A graph illustrated in FIG. 16 shows data of the distance leading-through principle. This is a graph of data actually measured within the shield room. That is, when the distance between the single-axis source coil $16i$ and the three-axis sense coil $22j$ is set to various values, points at which values of the greatest magnetic-field strength (the maximum magnetic-field strength values) which are detected at the position of the three-axis sense coil $22j$ and values of the smallest magnetic-field strength (the minimum magnetic-field strength values) are measured are plotted and graphed for each change in distance value of the axial direction of the source coil $16i$. A curved line Cu on the upper side expresses the maximum magnetic-field strength curve, while a curved line Cd on the lower side expresses the minimum magnetic-field strength curved line.

The two (2) curved lines Cu and Cd are arranged such that a difference occurs in detected values depending upon orientation of the source coil $16i$ when the distance between both the coils is great. However, a difference is eliminated in detected values in accordance with the fact that a distance between the coils increases sufficiently as compared with the magnitude of the source coil $16i$. This is a result which does not contradict a qualitative physical phenomenon in which, if the magnetic field formed by the dipole is small, an equal magnetic-field surface does not fit into a spherical surface, but a distance sufficiently large with respect to the magnitude of the dipole does not almost depend upon the magnitude of the dipole so that a substantially spherical surface is formed.

Further, when a magnetic-field strength H is detected, it is possible to add a limitation that the source coil $16i$ cannot exist only within a spherical shell which is put between the minimum radius $r\_min$ and the maximum radius $r\_max$. It will be seen from the two curved lines Cu and Cd that, within the measurement range illustrated in FIG. 16, the distance within the spherical shell ($=r\_max - r\_min$) does not so much depend upon a value of the magnetic-field strength H, but is on the order of approximately 60 mm.

Figure 17A:
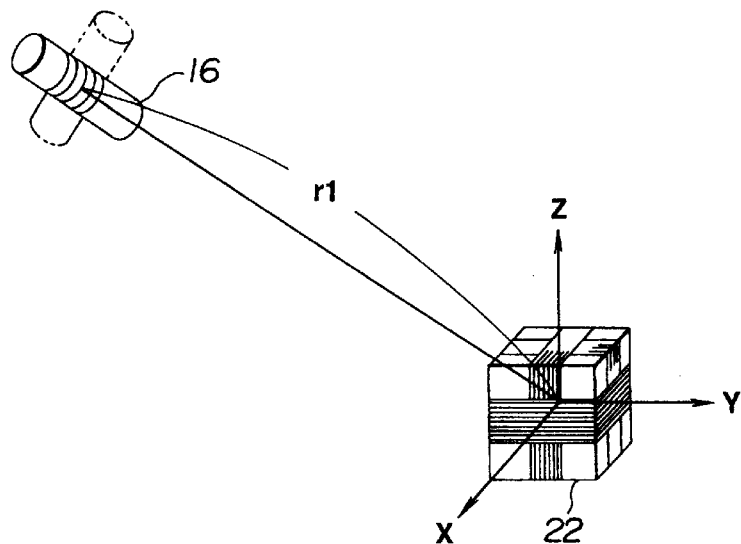
FIG. 17a is an explanatory view of a measurement method which produces data in FIG. 16, and FIG. 17b, is an explanatory view of distance calculation.

FIG. 17a shows a measurement method for producing the data in FIG. 16. As shown in FIG. 17a, the single-axis source coil 16 is arranged, for example, at the know distance r1 with respect to the three-axis sense coil 22 arranged, for example, at the origin (a center of the cube is in agreement with the origin). Orientation of the source coil 16 (the axial direction thereof) is changed at that position. The magnetic-field strength thereof is measured by the three-axis sense coil 22 which is arranged at the origin. The maximum value H1 and the minimum value H1' thereof are measured.

That is, when the orientation of the source coil 16 is changed, the magnetic field detected by the three-axis sense coil 22 is changed in accordance therewith, to thereby find out the maximum value H1 and the minimum H1' in measured values thereof.

In connection with the above, generally, when a state of the orientation of the source coil 16 indicated by the solid lines in FIG. 17a under which the axial direction of the source coil 16 is in agreement with a point on a line extending between the sense coil 22 (a center thereof) and the source coil 16 (a center thereof) to each other, it is possible to produce substantially the maximum value H1 and substantially the minimum value H1' indicated by two dot-dash lines which extend perpendicularly to the source coil 16, which is indicated by the solid lines.

Similarly, a value of the distance r1 is changed to r2, and measurement is similarly made with the distance r2 by the three-axis sense coil 22, to find out the maximum value H2 and the minimum value H2'. The distance is further changed to perform a similar measurement. The maximum value and the minimum value which are produced at the respective distances are plotted. If the maximum value and the minimum value are connected to each other by the lines such that the maximum values and the minimum values are interpolated, there are produced the curve Cu of the maximum magnetic-field strength and the curve Cd of the minimum magnetic-field strength shown in FIG. 17b. Data of these curved lines Cu and Cd are stored in data storing means such as a hard disk or the like. If operation of endoscope form display starts, the data of the curved lines Cu and Cd are transferred to a reference information storage 30b'' of the RAM in FIG. 8a, for example, and are stored therein. The CPU 30c refers to the data as occasion demands.

In this connection, the actual measured value in proportion to the magnetic-field strength which is detected by the three-axis sense coil 22 is a value in which the signals 22X, 22Y and 22Z detected by the three coils which form the three-axis sense coil 22 are squared and are summed and a value which determines the square root of 22X·22X+22Y·22Y+22Z·22Z. The determined values are calibrated by a standard magnetic-field measurement device (a gauss meter, for example), whereby it is possible to produce exact measurement values of the magnetic field.

The data illustrated in FIG. 16 are those produced as a result of the fact that such measurement is performed in detail within a magnetically shielded room.

Figure 17B:
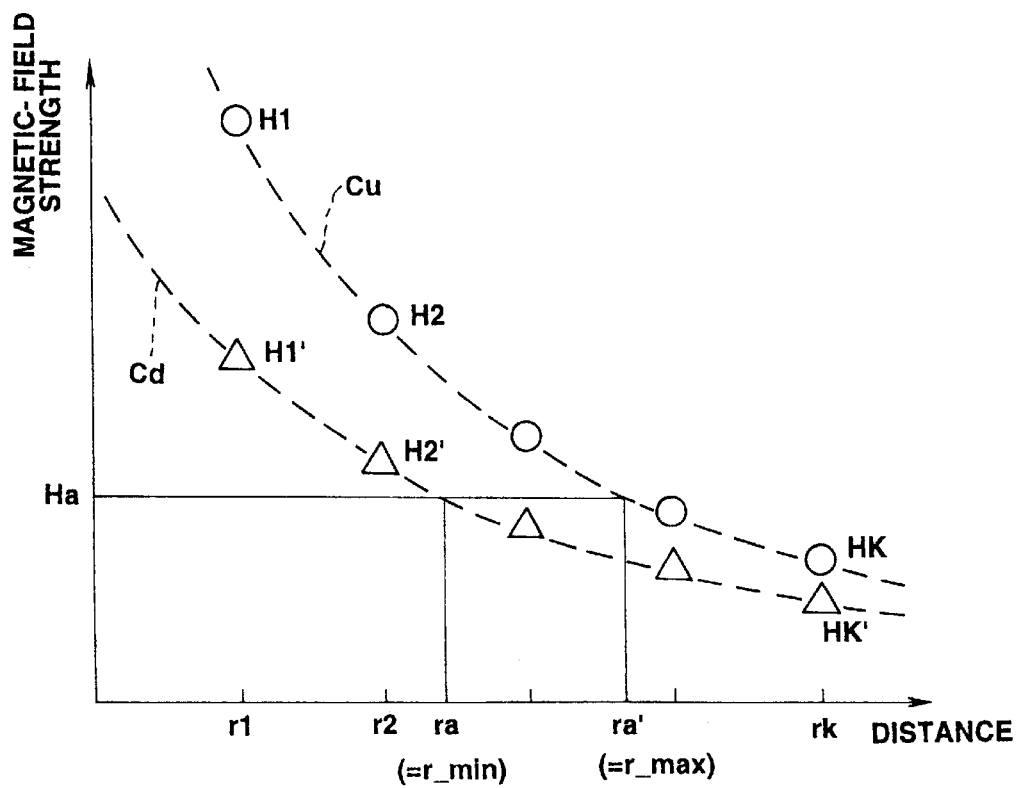

By referring to the two curved lines Cu and Cd in FIG. 17b, it is possible to estimate a three-dimensional region in which the source coil 16 exists with respect to the three-axis sense coil 22, from the magnetic-field strength which is detected by the three-axis sense coil 22.

For example, when a magnetic-field strength Ha is produced by measurement, it can be estimated that a distance corresponding to the magnetic-field strength Ha is a three-dimensional region in which the source coil 16 exists in the distance region between the distances ra and ra' in which the value of the magnetic-field strength Ha is intersected with the curved lines Cd and Cu, from FIG. 17b. That is, when a magnetic-field strength is produced, it can be estimated that a value thereof is between the minimum distance r_min and the maximum distance r_max which respectively intersect with a curved line Cd of the minimum magnetic-field strength and the curved line Cu of the maximum magnetic-field strength.

Moreover, FIG. 18 shows a comparison between a measured value within the shield room and a measured value of the magnetic-field strength at the other location (specifically, the sitting room), with respect to the maximum magnetic-field strength in case of r_max. The measured value within the shield room and the measured value within the sitting room are substantially in agreement with each other. That is, there is produced a value in which the measured value within the sitting room is substantially in agreement with the measured value within the shield room, and characteristics of the magnetic-field strength with respect to the distance of the measured value are also substantially in agreement with characteristics due to the measured value within the shield room. Although not shown, the case of the minimum magnetic-field strength also shows similar characteristics.

Accordingly, if a form of function of the curved line of the measured value within the shield room is produced beforehand, it is possible to use the function in the other environment to decide the maximum magnetic-field curve and the minimum magnetic-field curve in the environment accurately.

That is, also under a situation in which the environment of the endoscope examination is changed, by the measurement device capable of measuring magnetic field strengths in the directions of max and min at several locations under the environment, the magnetic field is beforehand measured whereby it is made possible to produce curved-line data of the maximum magnetic-field strength and the minimum magnetic-field strength under the environment. Thus, time-consuming determination of detailed data for every environment by measurement can be omitted. In this manner, FIG. 18 shows that the data are data which are extremely universal or general.

The file (max_min data file) which records therein the data of the maximum magnetic-field strength and the minimum magnetic-strength is loaded, and the correction data are also loaded from the correction data file. The following correction is performed:

Correction of Diameter of Sense Coil

It is an extremely important problem accurately producing the magnetic-field strength at the establishment position of the sense coil 22j. It is substantially impossible to manufacture the sense coil 22j which is manufactured by three axes extending perpendicularly to each other concentrically and with the same diameter. There is a difference in output detecting value due to a difference in diameter. Further, a change in output value appears due to the orientation and the direction of the source coil 16i.

In view of the above, magnetic-field detection is practically performed to investigate changing or variation of the arrangement of the source coil 16i and the sense coil 22j and in the magnetic-field detecting value. As a result of the investigation, regarding diameters having the magnitudes thereof, it has been found that only multiplication of two sets of correction coefficients separately from codes of the phase data which are produced upon magnetic-field detection can correct a difference in the magnitude of a diameter and the relationship between arrangements of both the coils 16i and 22j.

In view of the above, the correction coefficients of the phase data separately from the codes, regarding all axes which are measured beforehand is fetched by the initialization block B1. The result thereof will be described in a source-position calculation block B3 which performs magnetic field strength calculations.

After loading of the above-described data, initialization of the hardware is performed in subsequent Step S14. In Step S14, the setting contents of the source-coil switching circuit 28a, for example, shown in FIG. 8a are reset to set the source-coil switching circuit 28a to an initial condition. Further, the setting contents of the A/D converter 30a is reset to set the A/D converter 30a to a setting which corresponds to the used environment. In this manner, the hardware is set to a condition capable of being used in the form calculation, and the subsequent block B2 is operated.

B2: Hardware Control Block

First, in Step S21, the switching signal is applied to the source-coil switching circuit 28a to select the source coil 16i as described in FIG. 8a, to drive the source coil 16i. The magnetic field which is generated by the source coil 16i is detected by the sense coil 22j.

Accordingly, as shown in Step S22, the detecting signal which is detected by the sense coil 22j is sampled by the A/D converter 30a through the phase detection circuit 26. Sampled data are once written to the RAM 30b.

As shown in Step S23, it is judged whether or not drive with respect to all of the source coils 16i (the CPU 30c is built in the probe 15 of the timing control circuit 30d) ends. If the drive does not end, the timing control circuit 30d is so controlled that the subsequent source coil 16i is driven.

When all the source coils 16i are driven, amplitude data and phase data are calculated from the data in the RAM 30b, that is, PSD data passing through the phase detecting circuit 26d (refer to PSD calculation in Step S24, and the amplitude data and the phase data in Step S25 in FIG. 15).

Figure 19:
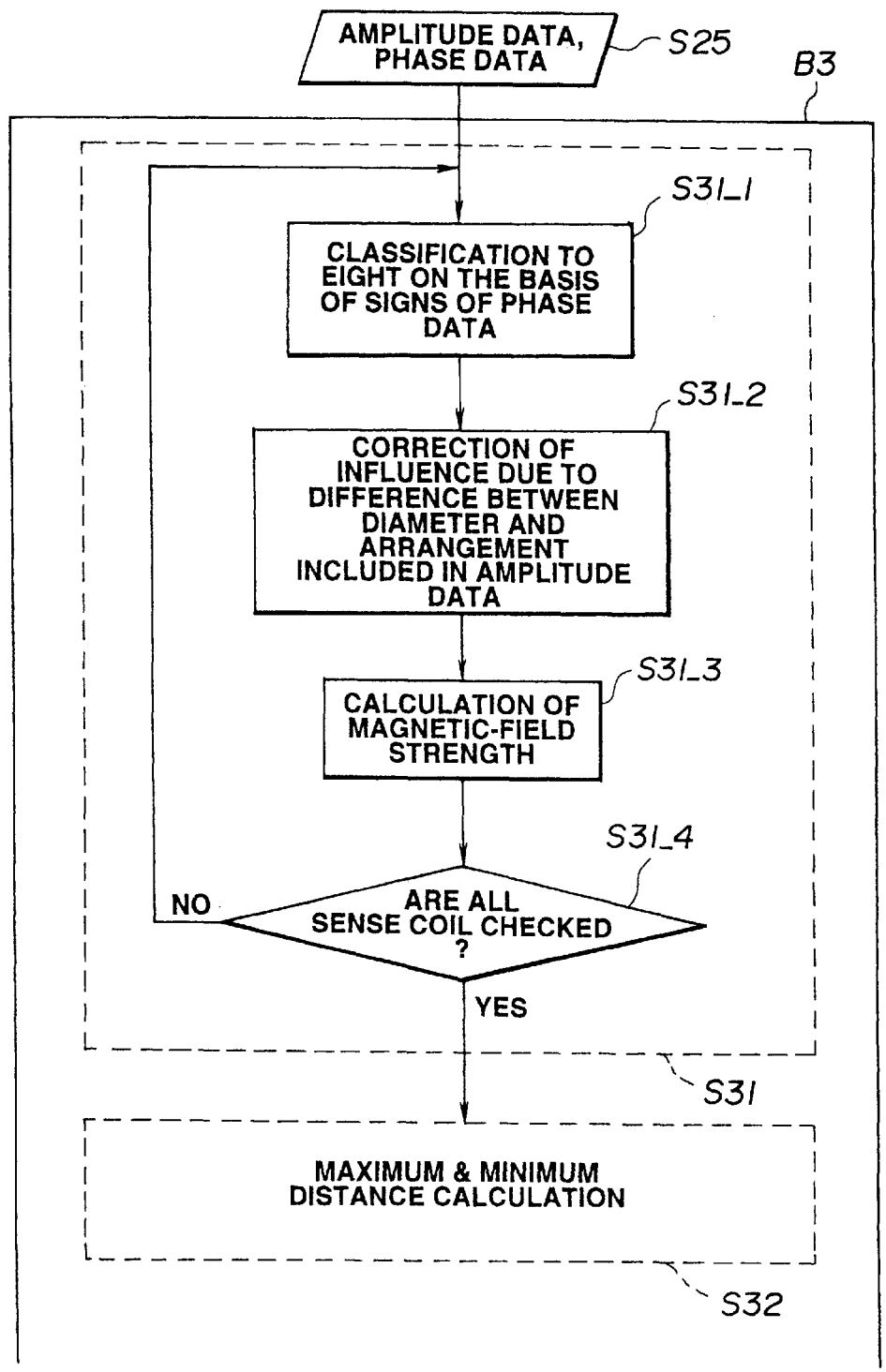

The program passes to processing in subsequent Block B3 from the amplitude data and the phase data. First, calculation of the magnetic-field strength in Step S31 is performed by the use of correction coefficients. The specific contents of a flow relating to the magnetic-field strength calculation are shown in FIG. 19. Here, the description of the flow will be added.

First, code judgment of the phase data is performed in Step S31_1.

The sense coil 22j has three single-axis coils different in diameter from each other. For this reason, if the codes of the phase data are classified with respect to respective single-axis coils, the codes are classified to eight (8) cases. This is performed like a1_1 to a1_6 as follows.

a1_1. In order to judge the codes at high speed, a condition operator which outputs 1 if + and 0 if − is created (SIG (x)→(x<0) ?0:1).

a1_2. The codes of the phase data of the minimum diameter are inspected, and the result thereof is substituted into the parameter x (x+=SIG (phi)).

a1_3. A bit of x is shifted to the left.

a1_4. The codes of the phase data of the subsequent diameter are inspected, and the result thereof is added to the parameter x.

a1_5. The bit of x is shifted to the left.

a1_6. The codes of the phase data of the maximum diameter are inspected, and the result thereof is added to the parameter x.

By doing so, the set of codes of the phase data with respect to the respective diameters can be substituted to eight (8) kinds of values of x. Thus, it is possible to perform processing at a higher speed than individual judgment of the codes.

In subsequent Step S31_2, influence of differences of the diameter and the arrangement, which are included in the amplitude data, is corrected.

In Step S31_1, since the combination of the phase data is substituted to the values of the parameter x, eight kinds of transformation equations are written in accordance with the values of x. Thus, it is made possible to multiply adequate correction coefficients by each amplitude data at high speed.

By the processing up to this point, correction of the data with respect to the difference of the diameter and the difference of the arrangement is completed.

In subsequent Step S31_3, the magnetic-field strength is calculated. Since, in Step S31_2, the influence which is given to the output by the difference in the magnitude of the diameter in each directional component and the arrangement of the coil has been able to be corrected, the square root of sum of squares of the respective components is calculated whereby the magnetic-field strength can be calculated.

By the above-described procedure, the magnetic-field strength can be calculated more accurately and at a higher speed from the output from the sense coil 22j which is manufactured by three axes which extend perpendicularly to each other.

Subsequently, calculation of the maximum distance and the minimum distance (between the source coil 16i and the sense coil 22j) of Step S32 in FIG. 15 is performed by the use of the maximum and minimum distance data (the data in FIG. 16). The Step S32 performs processing until the maximum distance and the minimum distance between the sense coil 22j and the source coil 16i are calculated by the use of the magnetic-field strength which is produced in previous Step S31.

The fact that there is the proportional relationship between the distance between two points and the magnetic field is a physical phenomenon which has widely been known generally. However, since the magnetic field which is concentrated onto a single point on a space by the single-axis source coil 16i is generally expressed by a distribution, even if the orientation of the source coil 16i is known and the magnetic-field strength is measured, it is not easy to calculate a direction and a distance in and at which the source coil 16i exists.

In view of the above, when a magnetic-field strength can be detected, if it is assumed that a distance where it is supposed that the source coil 16i is oriented in a direction in which an output of the magnetic-field strength can be taken the strongest is R_max, and a distance where it is supposed that the source coil 16i is oriented in a direction in which the output of the magnetic-field strength can be taken the weakest is R_min, a distance R-true between the true source coil 16i and the sense coil 22j can be limited to a range of $R\_min \leq R\_true \leq R\_max$.

The magnetic-field strength M produced in previous Step S31 and the magnetic-field strength data m of the R_max curved line which has already been read are compared with each other, to pick up points of $mb \leq M \leq mt$. Assuming that a location between mb and mt is changed linearly, it is assumed that a distance corresponding to the magnetic-field strength M at a point intermediate therebetween is R_max.

R_min is similarly performed. Here, the fact that the location between mb and mt is changed linearly simplifies calculation, and there is no problem even in a curved-line approximation. Further, a functional form f(x) of the R_max curved line is led, and calculation may, of course, be made on the basis of R_max=f(M).

Means for or a method of calculating the distance, which is adopted here, is a means or a method which is extremely easy because solving of a complicated distribution is not required although the value of the distance R_true is not accurately established and, in addition thereto, a means or a method which has a wide applied range which can limit an existing range of the source coil 16i even when the orientation of the single-axis source coil 16i is unknown.

Positional coordinates calculation of the source coil 16i in Step S33 is performed next. In Step S33, coordinates of the source coil 16i are calculated on the basis of the distance between the sense coil 22j and the source coil 16i.

A range within which the source coil 16i at a time of being seen from a sense coil 22j can exist is within the spherical shell which is surrounded by R_max and R_min which are produced in previous Step S32.

In order to limit the range in which the source coil 16i can exist, to a more minute or microscopic space, overlapping of the region in which the source coil 16i can exist, which is discovered from the plurality of sense coils 22j, is utilized. With respect to each of the sense coils 22j, in the existing range of the source coil 16i which is produced from the same source coil 16i, a range in which all are overlapped definitely exists, as long as the position of the source coil 16i is not moved.

A boundary of such regions is no more than a point of intersection of the radii R_max and R_min with a position of each of the sense coils 22j serving as a center. Since the boundary is the point of intersection of the ball or sphere, if there are at least three (3) sense coils 22j, the existence of the source coil 16i can be limited to the microscopic range which is surrounded by eight (8) points of intersection with R_max and R_min of each sense coil 22j serving as radii.

Assuming that the three (3) sense coils 22j are Sa, Sb and Sc, and the distance to Ra_max, Ra_min, Rb_max, Rb_min, Rc_max and Rc_min is determined, the existence of the source coil 16i is limited within the microscopic space whose apex is the following eight (8) points:

Intersection of spheres whose radii are Ra_max, Rb_max and Rc_max;

Intersection of spheres whose radii are Ra_min, Rb_max and Rc_max;

Intersection of spheres whose radii are Ra_max, Rb_min and Rc_max;

Intersection of spheres whose radii are Ra_max, Rb_max and Rc_min;

Intersection of spheres whose radii are Ra_min, Rb_min and Rc_max;

Intersection of spheres whose radii are Ra_min, Rb_max and Rc_min;

Intersection of spheres whose radii are Ra_max, Rb_min and Rc_min; and

Intersection of spheres whose radii are Ra_min, Rb_min and Rc_min.

The center of gravity of the microscopic range which is surrounded by these eight (8) points is outputted as being the positional coordinates of the source coil 16i. Moreover, the more the number of sense coils 22j increases, the region in which the source coil 16i can exist can be made narrower. Thus, it is possible to produce the position of the source coil 16i more accurately.

Since the method of limiting the source coil position is a simple arithmetic calculation such as calculation of the point of intersection of three (3) balls or spheres, time is saved, and the method an extremely superior method which enables the existing range of the source coil 16i to be limited within the microscopic range. Calculation of the positional coordinates of the source coils 16i is performed in this manner, to produce the positional coordinate data of the source coil 16i in Step S34. These data are used, and the program passes to the subsequent Block B4.

B4. Image Display Block

The block B4 is responsible for processing until a scope-form image under the inserted condition is described on the CRT on the basis of the coordinate data of the position of the source coil 16i. The coordinate data of the position of the source coil 16i are a locus along which the inserted scope passes. In view of this, the form of the scope under the inserted condition is estimated on the basis thereof. If the form of the scope under the inserted condition can be estimated, the result thereof is described on the CRT. At that time, since the three-dimensional scope form must be displayed on the two-dimensional CRT image plane, a scheme is required to display the described image more three-dimensionally.

In view of the above, in the present system, classification is performed separately according to function, and a display method is realized based on the characteristics of the respective modules.

S41 Keyboard Input Processing
S42 Scope-Image Description Processing
S43 Reference-Surface Display Processing
S44 Marker Display Processing Since all types of processing are not required for the description of the scope image, functions can be chosen or selected as occasion demands.

The method is advantageous in that more three-dimensional scope-form images can appear on the CRT whenever an auxiliary means of scope display is introduced.

Accordingly, characteristics of each of the modules will hereunder be described.

S41: Keyboard Input Processing

Here, whenever a key input corresponding to a given user command is performed, setting parameters or the like is modified in accordance with the contents thereof.

An additive function based on high demand from the user controls or influences the convenience in using the system. Further, the function selection is an easy operation, and operation is always capable of being performed as the user desires. Thus, it is required that the request contents of the user are realized at once.

Figure 20:
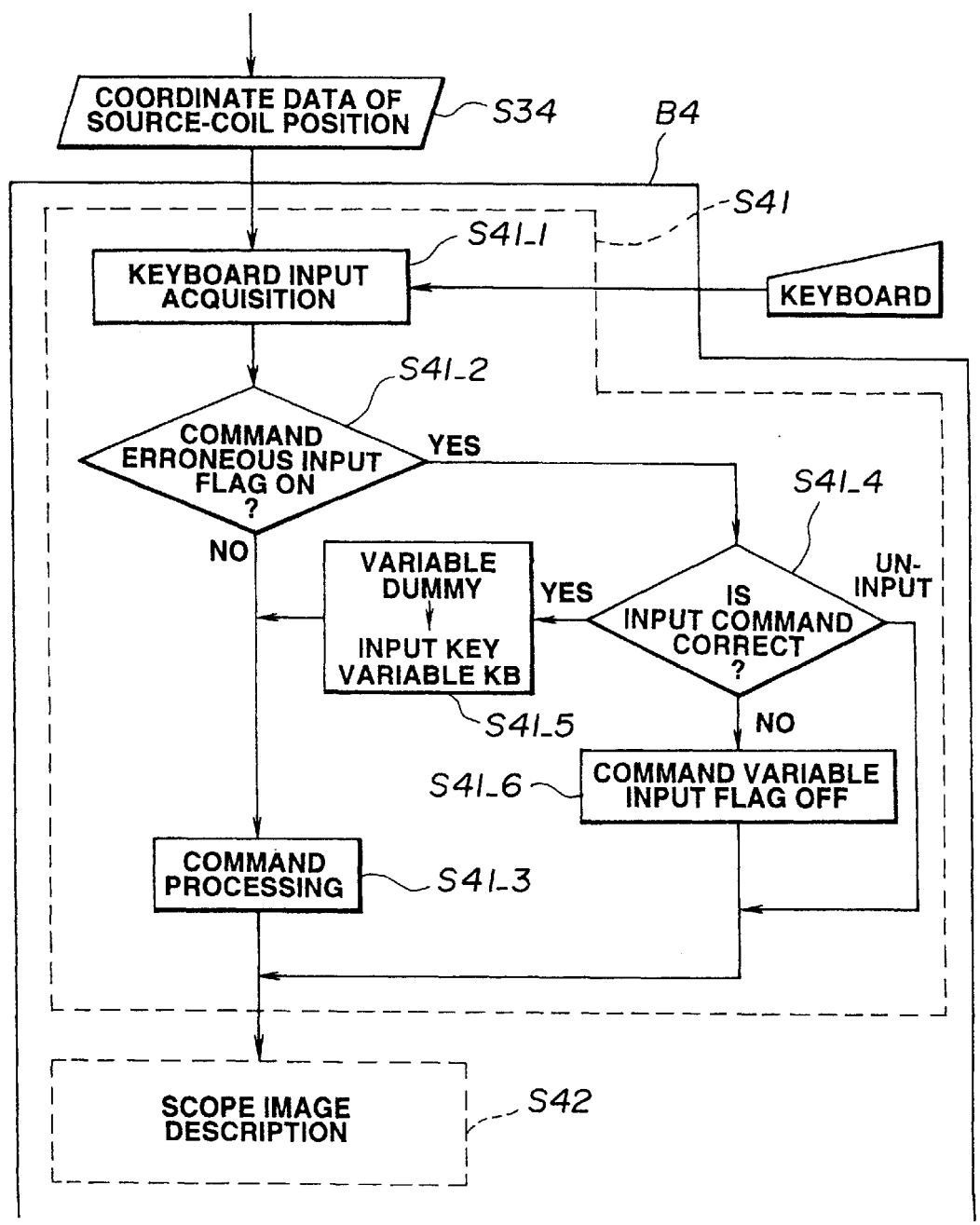

Step S41 specifically performs the processing illustrated in FIG. 20. First, as shown in Step S41_1, input acquisition from the keyboard is performed. When the key input is performed, the input contents are substituted to the input key variable KB.

Subsequently, in Step S41_2, check of command erroneous input is performed. Here, it is judged whether the inputted key is erroneous. Specifically, this is performed by check of a command erroneous input flag. When the flag is ON, judgement as to whether or not the input key is erroneous is performed in Step S41_4 of the subsequent judgment processing. Meanwhile, if the flag is OFF, a program proceeds to Step S41_3 of subsequent command processing.

In Step S41_4, confirmation as to whether the input key is in fact correct is performed. Three (3) judgment results are processed.

In case of YES: The command is processed in accordance with the key input.

The contents of the variable dummy which temporarily conserves the contents of the key input are substituted into the input-key variable KB (Step S41_5) and, thereafter, the program proceeds to Step S41_3 of the command processing.

In case of NO: The contents of the key input are canceled. The contents of the input key variable KB are canceled, and the command erroneous flag is set to OFF (S41_6).

In case of un-inputting: There is case where it is delayed for the user to take notice of erroneous input. However, also at such time, it is required that the scope image is updated. This processing copes with this. No processing is performed until judgment that the command is correct is performed, and the other command processings are inhibited.

By this procedure, even if the user mistakes the key operation, command cancellation is safely made possible.

Next, the contents of Step S41_3 of the command processing will be described.

Figure 21:
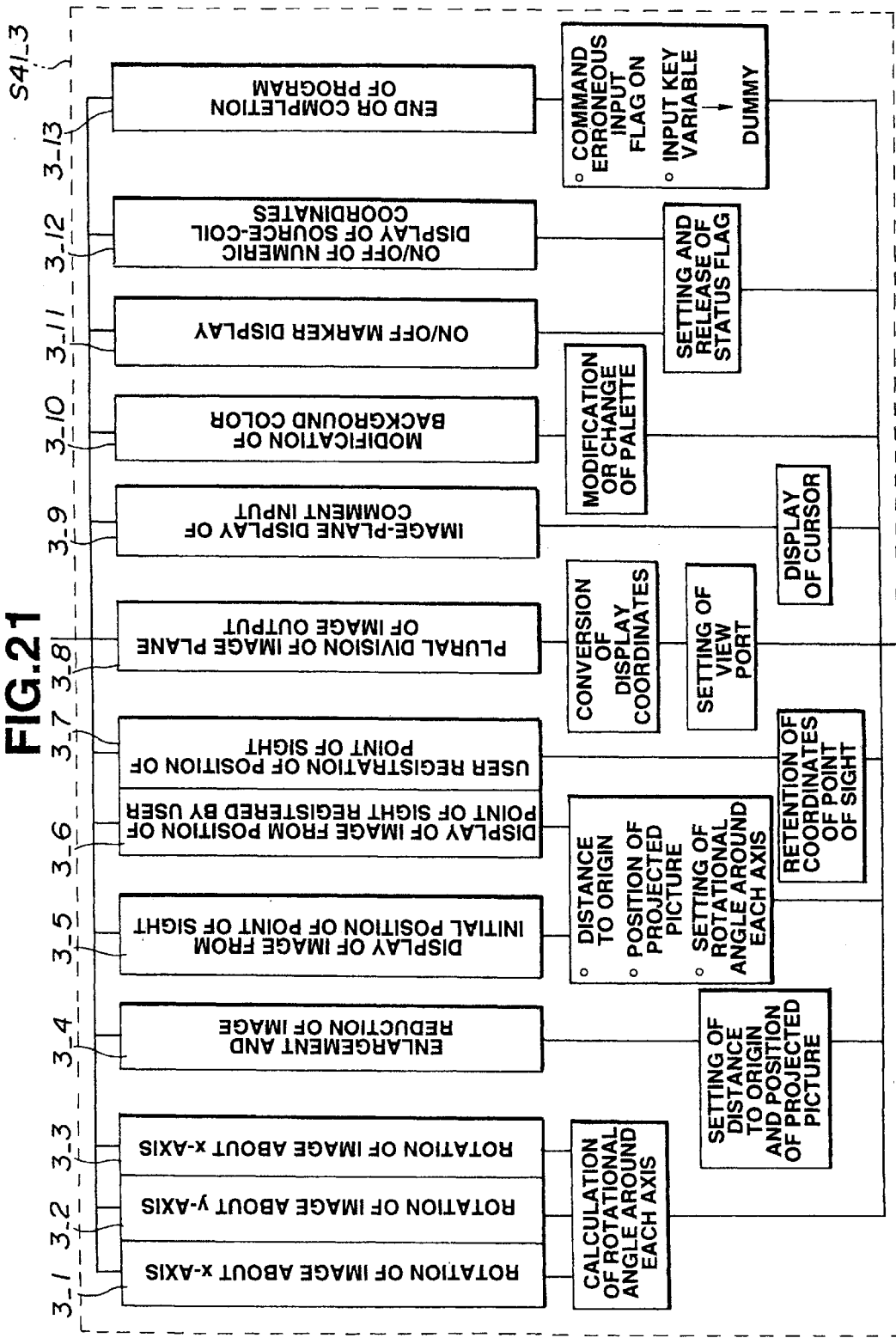

Processing here is that the inputted command is processed to reflect creation of the scope image. The specific contents of the command processing perform thirteen (13) processings 3_1 to 3_13, as shown in FIG. 21.

3_1. Rotation of Image Around x-Axis.

An image produced when a position of the point of sight is rotated around the x-axis is outputted. For example, when the x-key is inputted, the point of sight is rotated in the x-axis direction. By the coordinates of the position of the point of sight which is moved in this manner, a rotational angle is calculated or computed. The rotational angle is substituted into the variable pitch. The variable is referred to in or at the affine transformation at the time the scope image is created. Thus, an output image which is rotated about the x-axis is produced.

3_2. Rotation of Image Around y-Axis

An image produced when a position of the point of sight is rotated around the y-axis is outputted. For example, when the y-key is inputted, the point of sight is rotated in the y-axis direction. By the coordinates of the position of the point of sight which is moved in this manner, a rotational angle is calculated or computed. The rotational angle is substituted into the variable head. The variable is referred to in or at the affine transformation at the time the scope image is created. Thus, an output image which is rotated about the y-axis is produced.

3_3. Rotation of Image Around z-Axis

An image produced when a position of the point of sight is rotated around the z-axis is outputted. For example, when the z-key is inputted, the point of sight is rotated in the z-axis direction. By the coordinates of the position of the point of sight which is moved in this manner, a rotational angle is calculated or computed. The rotational angle is substituted into the variable bank. The variable is referred to in or at the affine transformation at the time the scope image is created. Thus, an output image which is rotated about the z-axis is produced.

3_4. Enlargement and Reduction of Image

An image where a distance between the origin and the position of the point of sight are moved away from each other or toward each other is outputted.

For example, when an E-key which is identified by expression of E is inputted, a distance between the position of the point of sight and the origin increases without changing of the direction. The new distance between a new position of the point of sight and the origin at this time is substituted into the variable viewpoint.

Further, correspondingly to the change of the position of the point of sight, a position of a plane onto which the three-dimensional image is projected to the two-dimensional image (project screen) is also changed, and is substituted into the variable screen. This is to regulate or adjust perspective which is in keeping with the change of the position of the point of sight. These variables are referred to upon conversion of three dimensions—two dimension projection (referred simply to as "3D→2D projection"). Thus, it is possible to produce an output image in which the image is enlarged or reduced.

3_5. Image Display from Initial Position of Point of Sight

The position of the point of sight which is changed by rotation, enlargement or reduction is returned to the initial position of the point of sight which is prescribed on the side of the apparatus, and the image looked at therefrom is outputted.

For example, if the initial position of the point of sight is set to (0, 0, 100), and the position of the point of sight is set when an R-key which is identified by expression of R is depressed, values which are calculated on the basis of the initial position of the point of sight are substituted together to the variables pitch, head, bank, viewpoint and screen. These variables are referred similarly to 3_1~4. Thus, an output image from the initial position of the point of sight can be produced. Thus, even if it is unknown in what directions the point of sight is rotated, it is possible to reset the position of the point of sight.

3_6. Image Display from Position of Point of Sight Registered by User

This function is similar to 3_5. A large difference is that the position of the point of sight is not an initial value prescribed on the side of a device, but a position of a point of sight registered by a user. A user registered method of a position of a point of view is indicated in 3_7. By this function, even after the position of the point of sight has been changed, it is possible to produce, at once, the output image from the position of the point of sight which is preferred by the user.

3_7. User Registration of Position of Point of Sight

A user can register the position of the point of sight such that an image outputted from a position of the point of sight can be looked at at an optional time. Here, if the position of the point of sight is registered, the function of 3_6 can be used.

For example, when a U-key identified by expression of U is depressed, coordinates of the position of the point of sight at that time are preserved as data. Alternatively, the variables of pitch, head, bank, viewpoint, screen and the like may be preserved.

The plurality of registered keys are prepared so that the plurality of positions of the point of view can be preserved. Moreover, it is also possible to update the data of the coordinates of the positions of the point of view which has once been preserved.

3_8. Division of Image Plane of Image Output into a Plurality of Sections

Image output is normally a single image plane. However, the image plane is divided into a plurality of sections to enable the scope image from a plurality of points of view to be outputted simultaneously.

For example, when a 2- or 4-key identified by expression of 2 or 4 is depressed, the image plane is divided into two (2) or four (4). At this time, coordinate transformation is so performed that the scope image is restored in the divided image plane, in accordance with the quantity of image-plane division. The 0-key identified by expression 0 is depressed whereby an active image plane of the image plane divided into the plurality of sections can be selected.

3_9. Image-Plane Display of Comment Input

A text output image plane is switched to the comment input image plane regarding the using situation of a list of patients and a system.

For example, a T-key which is identified by expression of T is inputted, a comment input text image-plane is overlapped over an image plane which outputs the coordinates of the position of the point of sight or the like, to urge comment input which outputs the cursor.

3_10. Modification of Background Color

When the scope image is difficult to look at because of the surrounding influence or the like, a tone of color of the background color can be modified by modification of a pallet.

For example, when a B-key which is identified by expression of B is inputted, a parameter value regarding B of an RGB pallet which determines the background color can be changed. Thus, a delicate tone of color can be modified.

3_11. ON/OFF of Marker Display

The system has a function which expresses a position of an independent coil (hereinafter, referred to as "marker") which is mounted on a finger or the like, independently of the scope image which is under the inserted condition. In case the marker is used during an operation, an M-key which is identified by expression of M, for example, is depressed whereby a position of the marker is displayed on the CRT.

This means that, when the M-key is inputted, a status flag for outputting the marker onto the CRT is set. When the status flag is set, a program routine which displays the marker is performed so that the marker is displayed. After the use of the marker, the M-key is again depressed. The status flag is released to inhibit the marker from executing the routine for outputting the marker, to thereby cancel the display of the marker.

By this function, the marker and the image output image can be compared with each other. Thus, it is possible to provide the marker as auxiliary means for knowing or learning the position of the imaged scope image.

3_12. ON/OFF of Display of Numerical Values of Source-Coil Coordinates

The image which is normally outputted is only a form thereof. However, when an N-key which is identified by expression of N, for example, is inputted, the numerical values of the coordinates of the source coil which is detected simultaneously with the image can be outputted.

Means of ON and OFF is similar to that of case of 3_11. For example, the N-key is inputted whereby the status flag for displaying the numerical values is set. If the display of the numerical values is made unnecessary, again inputting of the N-key releases the status flag, to cancel the display of the numerical values.

Thus, it is also possible to produce the numerical positional relationship in addition to the visual-sense positional relationship.

3_13. End or Completion of Program

The program ends or is completed more safety.

For example, if a Q-key is depressed, the program can be completed. In this connection, in order to avoid the program ending when the Q-key is erroneously inputted, the following countermeasure is taken:

(3_a) The command erroneous flag is confirmed.

(3_b) If the flag is OFF, the flag is turned ON, and the contents of the input key variable KB are substituted to the variable dummy.

(3_c) If the flag is ON, the command is executed in accordance with the input key variable KB.

By this procedure, it is possible to avoid erroneously ending the program during the use of the system.

As described above, since a single key is allocated, one-by-one, to each of the commands, operation is extremely easy.

When a key is depressed, it is required only that the parameter required to realize modification of the function thereof is set. Accordingly, flow of the program is not prevented. Moreover, since the parameter for realizing the functions of these commands is surely referred to anywhere during one processing (until the fact that the source coil is driven, the magnetic field is detected, the position of the source coil is detected, and the scope form is outputted in CRT therefrom.). Accordingly, a time lag until the function is realized as requested by the commands is extremely low.

In spite of the fact that the method can instantaneously cope with key input of the user, the method is superior in that influence upon the scope from painting is extremely low.

After the processing of Step S41_3, the program proceeds to scope image description processing of subsequent Step S42.

S42: Scope Image Description Processing

Here, the scope form is prepared from the coordinates of the position of the source coil which is produced by magnetic-field detection. The processing is responsible until the image is displayed on the CRT three-dimensionally. The coordinates of the position of the source coil produced are data discrete in the number of the source coil which is inserted into the scope. In view of this, on the basis of these data, the scope form which is under the inserted condition must be estimated. Further, it is the greatest point of this system that how the scope form data produced in this manner can be outputted onto the CRT as a three-dimensional form.

Figure 22:
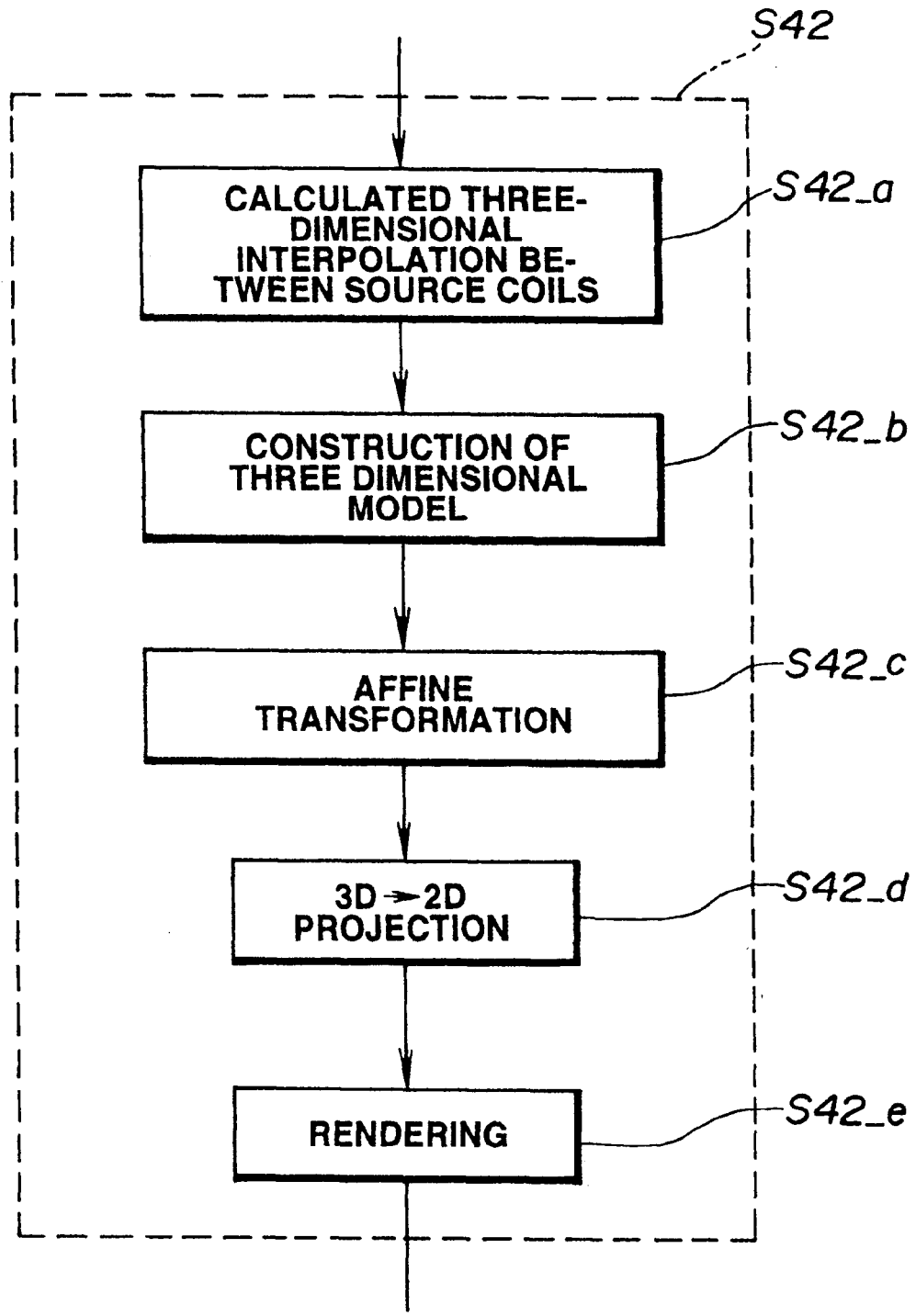

A processing flow of the scope-image description processing is as shown in FIG. 22. The detailed processing contents of each of the processings will be discussed below for every block.

S42_a: Calculated Three-Dimensional Interpolation Between Source Coils

In processing of the calculated three-dimensional interpolation between the source coils of Step S42_a, the coordinates of the source-coil position which is calculated by the magnetic-field strength detection is discrete. Accordingly, if only the calculated data are connected to each other, the locus will be squarish, and this does not deal with the scope form in which the position is continuously changed. In order to create the smooth whole scope form, the three-dimensional interpolation is executed with respect to the coordinate data of the source coil position.

S42_b: Construction of Three-Dimensional Model

Since the actual scope has a thickness, it cannot be said that connection by means of a straight line or the like having no thickness is a description of the actual scope, even if smooth data points are produced. In view of this, in processing of construction of the three-dimensional model in Step S42_b, connection between the interpolating data is performed by a columnar or n-prismatic model. Thus, display can be made correspondingly to the actual scope form also in the thickness.

S42_c: Affine Transformation

The scope form is outputted as being an image looked at from the assigned or appointed position of the point of sight. In view of this, in the processing of the affine transformation of Step S42_c, scope form model data which are produced in a reference coordinate system in the world coordinate system of rendering or deviation of the position of the source coil is converted to the visual-point coordinate system for display onto an image plane. In this connection, the visual-point position can be modified by the user. The modified contents are referred to here.

S42_d: 3D→2D Projection

The scope form is originally three-dimensional. However, the scope form must be converted to the two-dimensions, in order to output an image thereof onto a CRT picture plane. In view of this, projection transformation from the three-dimensional image of Step S42_d to the two-dimensional image is performed. At this time, far and near may be emphasized by a perspective or the like.

S42_e: Rendering

The scope form image which is produced by the processing until now is described on the CRT. Upon performing of the description, in the processing of rendering in Step S42_e, n-polygonal side-surface processing and hidden-line processing for expressing order or sequence of the loop of the scope are performed. Processing such that gradation display at the shading processing due to far and near, and adjustment of the intensity and the chroma of the scope model side surface by curvature of the scope or the like are performed, or the like may be executed to more emphasize a sense of perspective.

In connection with the above, any items described above are not necessarily required to be carried into practice.

Of course, if the above-described any items are carried into practice, the described image can be rendered on the CRT in the form including the advantages which are had by improvement items thereof. Moreover, it is not required to perform the description by the order shown in FIG. 22, but the order is modified in accordance with the model which displays the insertion-part form, whereby equivalent processing can be performed in a shorter time period.

Through these processings, it is possible to reproduce the three-dimensional scope form under the inserted condition, onto the CRT, only from the positional coordinates of the plurality of source coils.

Furthermore, in the present embodiment, the n-polygonal model and the n-polygonal connection model can be selected as display of the scope as will be described below. Accordingly, three-dimensional model construction or the like will be described along a specific example described below.

First, the n-polygonal model will be described. In the model, a cross-sectional surface of the insertion part is modeled into a regular n-angular form as shown, for example, in FIG. 14 and is displayed as an n-angular column (in FIG. 14, n=5). If the number of n increases, the n-angular form becomes circular. In this case, the n-angular column model comes into so equivalence as to be displayed as being a column.

A flow of the processing contents of the display in this model is shown in FIG. 23a~FIG. 23d.

Figure 23:
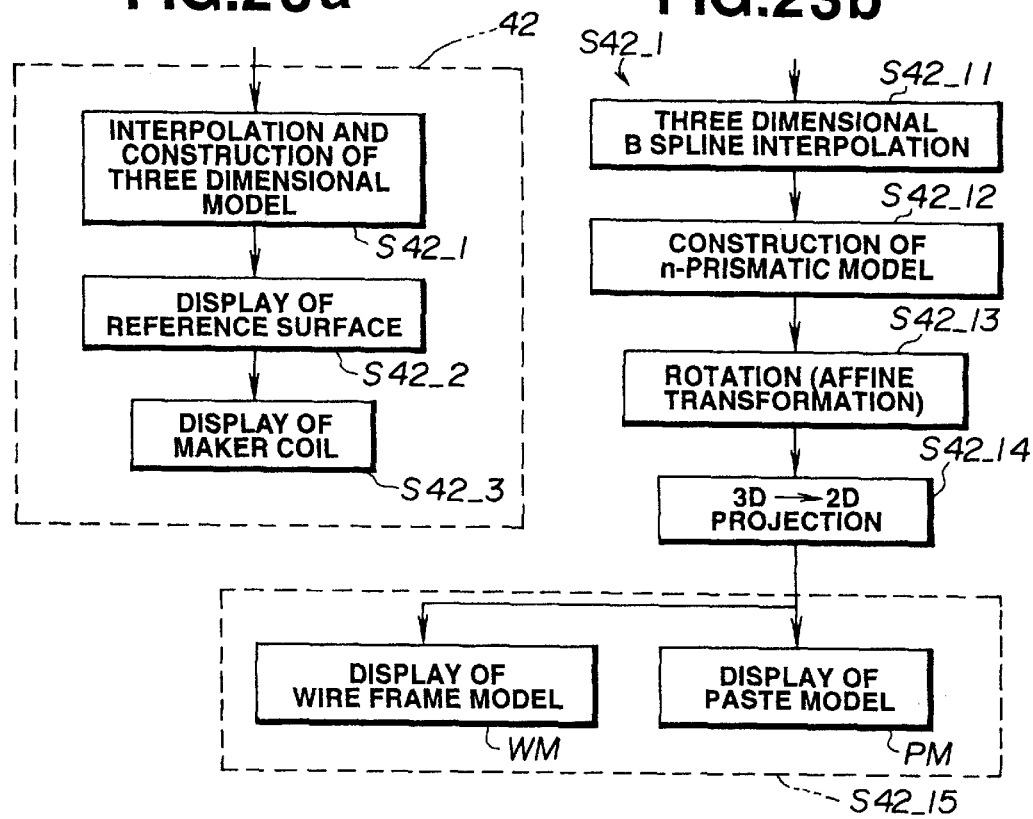

In FIG. 23a, the processings of the interpolation at Step S42_1 & the construction of three-dimensional model is performed as shown in FIG. 23b.

Here, first, the three-dimensional B-spline interpolation of Step S42_1 is practiced. The interpolation is not interpolation of a type definitely passing through an interpolation point, but one which creates a smooth curved line while passing in the vicinity of the interpolation point. As compared with a natural spline which definitely passes through the interpolation point, calculation processing thereof is easy. Of course, the natural spline may be used, and interpolation due to approximate function may be used.

The B-spline, which is relatively easy in calculation processing, is superior in that processing speed is high even if the three-dimensional interpolation is practiced.

Next, n-polygonal model construction is performed in Step S42_12.

Figure 24:
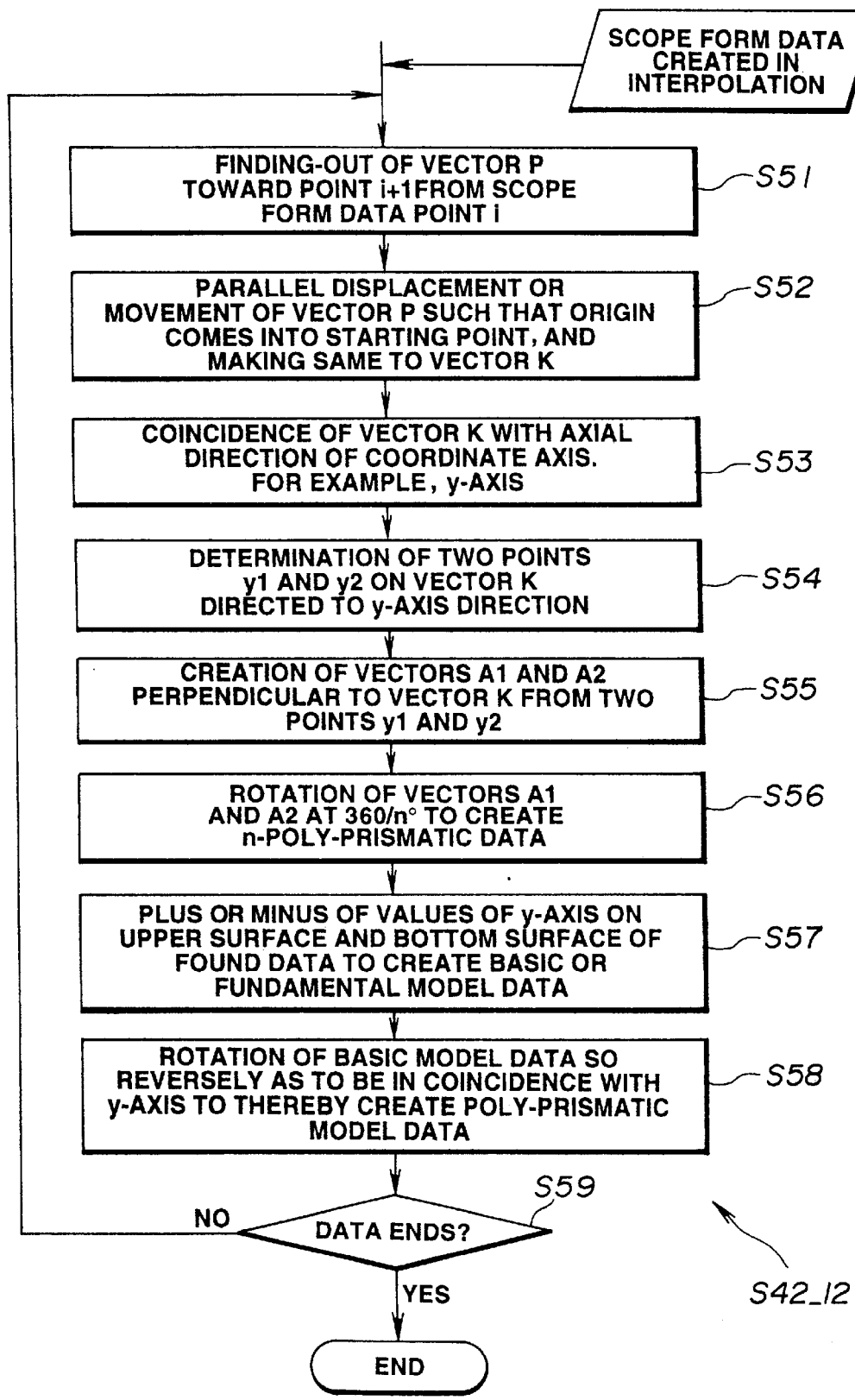

Here, a three-dimensional telescopic scope image is constructed by the n-polygonal column model (which, hereinafter, includes also a column), from the interpolation data of the coordinates of the position of the source coil. The actual processing flows as shown in FIG. 24.

When an n-polygonal columnar model is created regarding data of No. i and No. i+1 in which the coordinates of the position of the source coil are interpolated is considered.

First, a directional vector P oriented from i to a point i+1 like Step S51 and the magnitude |P| thereof are determined.

Figure 25A:
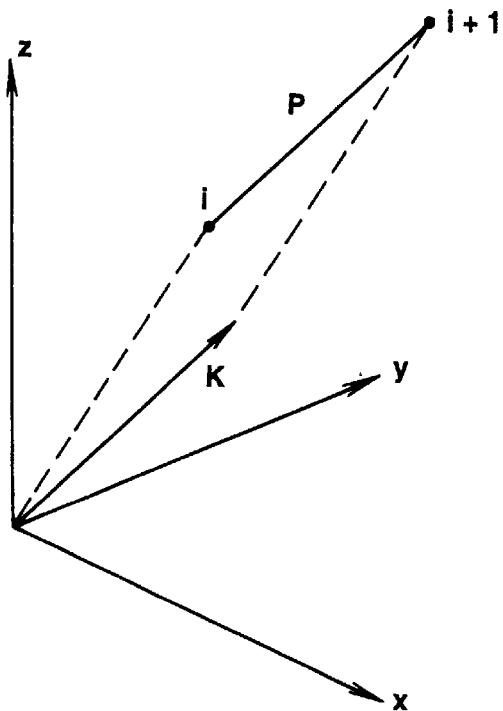
FIGS. 25a to 25c are explanatory views of origin movement in the construction of the n-prismatic model.

Next, the vector P is moved in parallel such that the origin comes into the original point like Step S52. The vector moved in parallel is assumed to be K, and the magnitude thereof is assumed to be |K|. The vector K is shown in FIG. 25a.

Figure 25B:
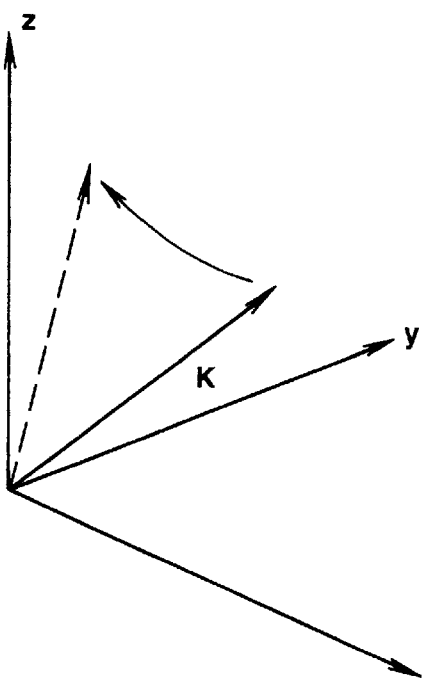
Figure 25C:
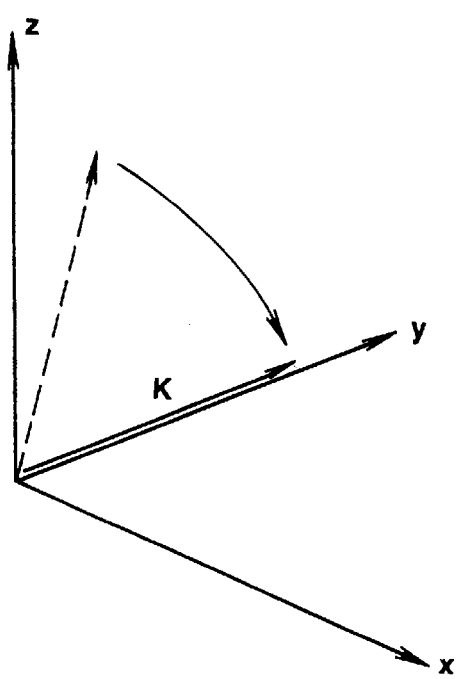

Next, the vector K is in agreement with the axial direction of the coordinate axis, for example, the y-axis (here, the vector K is first rotated around the y-axis (FIG. 25b), and is next rotated about the x-axis (FIG. 25c), whereby the vector K is in agreement with the y-axis direction).

Figure 26A:
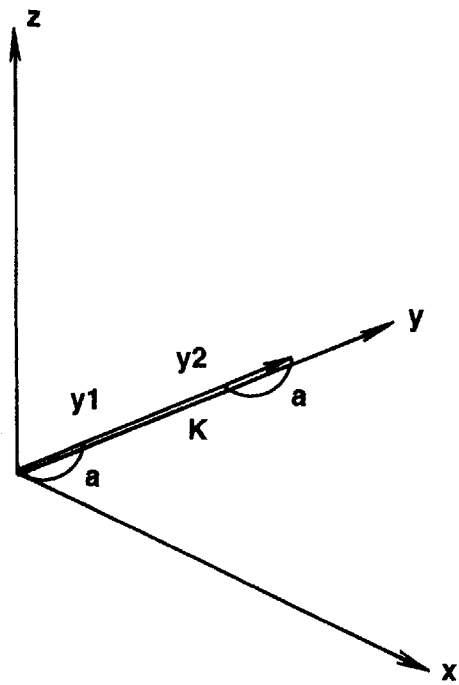
FIGS. 26a~26c are explanatory views of processing in which a vector extending perpendicularly to a vector in parallel to a y-axis in the construction of the n-prismatic model is rotated at predetermined intervals to create n-prismatic data.

Next, two (2) points y1 and y2 on the vector K oriented in the y-axis direction are determined or decided like Step S54. In this connection, a $\leq$y1<y2$\leq$|K|—a, and 2a<|K| (FIG. 26a).

Figure 26B:
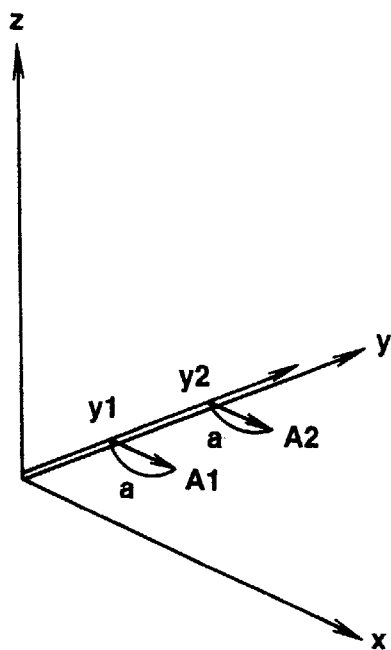

Next, vectors A1 and A2 which are perpendicular to the vector K and whose magnitudes are a are created from the two (2) points y1 and y2 like Step S55 (FIG. 26b).

Figure 26C:
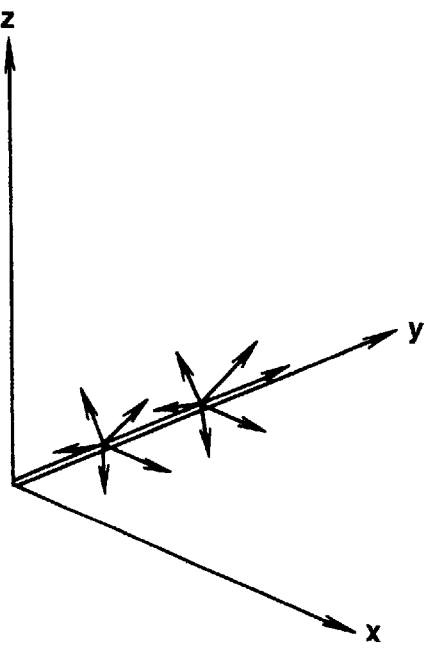

Next, the vectors A1 and A2 are rotated at intervals of $(369/n)°$ like Step S56, to produce the coordinates of A1 and A2. These are made basic or fundamental data of the n-polygonal column (FIG. 26c).

Next, values of the axis y of the upper surface and the bottom surface of the found data are added to each other or are subtracted from each other to create basic model data, as in Step S57.

Figure 27A:
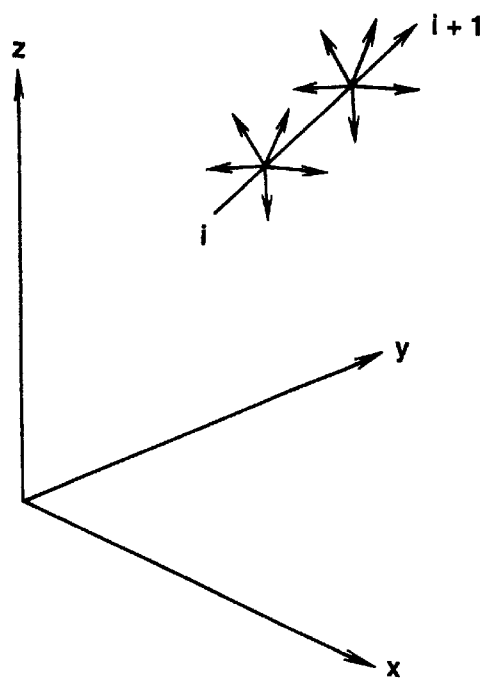
FIGS. 27a and 27b are explanatory views showing a state in which inverse transformation is made to the original vector to generate n-prismatic model data.

Next, the reverse of the conversion which is performed when the vector P is arranged properly in the y-axis direction, with respect to the basic model data which are produced like Step S58 is performed, the n-polygonal columnar model data are created around the vector P (FIG. 27a).

Figure 27B:
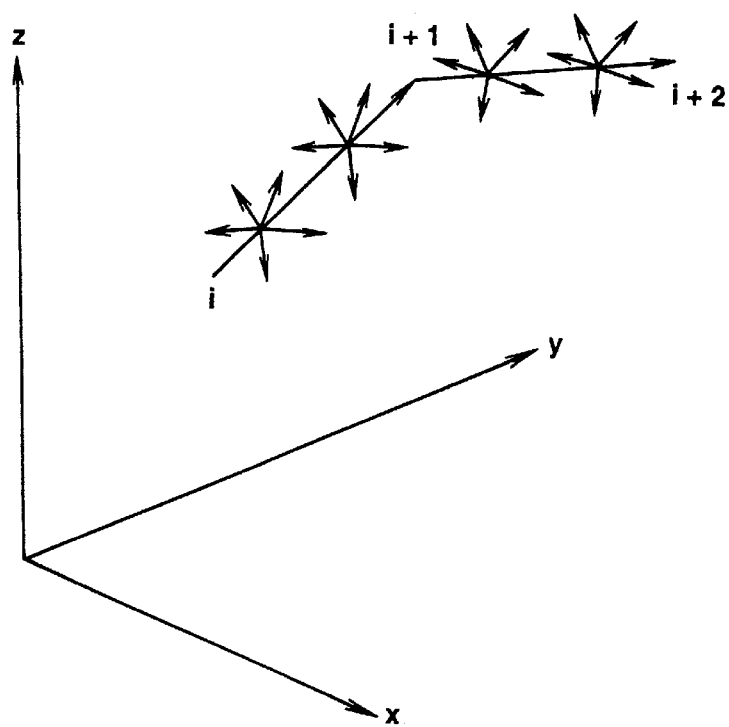

Next, when returning is again made to Step S51 by judgment of Step S59 so that similar processing is carried into practice with respect to all the interpolation data, the n-polygonal columnar model data in the form of a scope are created (FIG. 27b).

Here, a in the above-described condition of a $\leq$y1<y2$\leq$|K|—a, and 2a<|K| will be described. If the model data with respect to the vector K are created around the point i without consideration of the above condition, the model data generate overlapping like FIG. 28a so that the scope form cannot be displayed smoothly. If there is the above-described condition, the n-polygonal columnar model data are not overlapped with each other. Accordingly, the model data are connected to each other like a broken line in FIG. 28b, whereby it is possible to create the smooth n-prismatic model.

Although it is considered that operation to arrange properly the vector P along the orientation of an axis and is once again reversely converted with respect to the model data calculation is time-consuming, calculation thereof is extremely easy because expression can be made by simple rotation around each axis.

The method is superior in that the n-angular columnar model data can be calculated only by rotation about the axis.

Of course, it is difficult to calculate the transformation equation for creating the angular columnar model about the vector P, because the orientation of the vector P is not constant. However, this may be used to create the n-prismatic model.

Affine transformation of Step S42_13 in FIG. 23b is performed next. The affine transformation is one of methods which are used when the coordinate transformation of the graphic form is performed by computer graphics, and is generally performed when coordinate transformation is handled. Simple primary coordinate transformations such as parallel movement, rotation, enlargement, reduction or the like are all included in the affine transformation. FIG. 29 shows a condition or state of the affine transformation due to a rotational angle around the x-axis (pitch angle), a rotational angle about the y-axis (head angle) and a rotational angle about the z-axis (bank angle).

In this processing, the scope model data which are expressed by the aforementioned world coordinates are converted to model data which are observed from a position of a point of sight.

The position of the point of sight can be set in an optional direction. For this reason, it requires difficult processing to trace the direction the position of the point of sight is moved to move the model data in the form which follows the direction. In view of this, it is supposed that the point of sight is fixed, and the world coordinates which would originally be not moved are rotated for convenience. This gives results equivalent to that of an image in which the point of sight is moved is produced, as seen in FIG. 30.

This method can cope with the fact that the world coordinate system is rotated conveniently even when the directions from the point of sight are moved. Accordingly, the method is superior in that the time lag with respect to the movement of the point of sight can be reduced.

Next, processing of three dimensional → two dimensional projection (3D→2D projection) of Step S42_14 in FIG. 23*b* is performed.

Figure 31A:
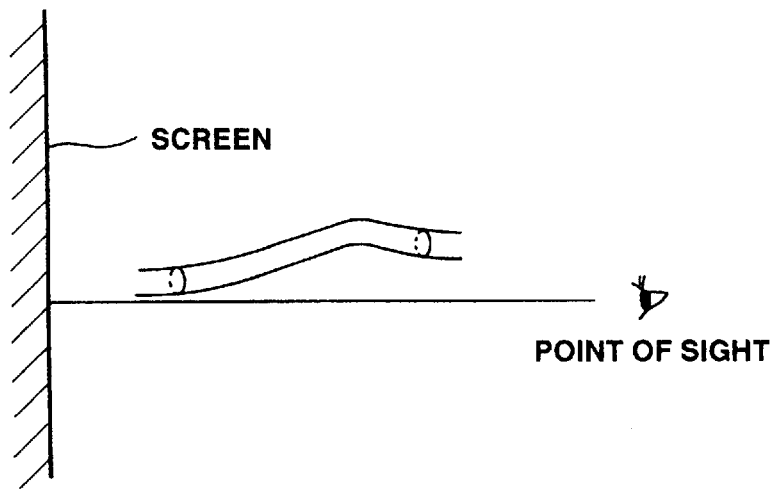
FIGS. 31a~31c are explanatory views of a state transformed in projection from three-dimensional coordinates to two-dimensional coordinates.
Figure 31B:
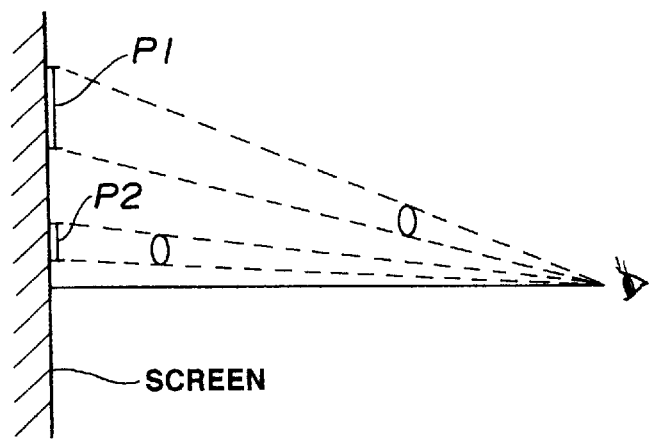

In the processing of 3D→2D projection which performs projection transformation from the three-dimensional image to the two-dimensional image a projection method indicated below is performed whereby a display can be realized by a far and near method or the like in accordance with an object or purpose.

a) In Cases Where Perspective is Applied:

The three-dimensional form is looked at larger as approaching the point of sight, and is looked at smaller as moving far from the point of sight. This can be realized by processing to convert the three-dimensional model data to the two-dimensional data. In order to project the three-dimensional coordinates to a two-dimensional plane, a screen is imaginarily or hypothetically arranged vertically with respect to the point of sight and on the opposite side of the three-dimensional image (3D image produced till S42_13) (refer to FIG. 31*a*). A projected surface or plane of an object looked at from the point of sight under such a condition is such that a projected image P1 on the side close to the point of sight comes larger than a projected image P2 on the remote side as shown in FIG. 31*b*. It is easy also to move the position of the projecting screen before and behind to vary the degree or extent of emphasis of the perspective.

This method is superior in that three-dimensional depth can easily be applied to the two-dimensional described image, and it is also easy to vary the degree of the emphasis thereof.

Figure 31C:
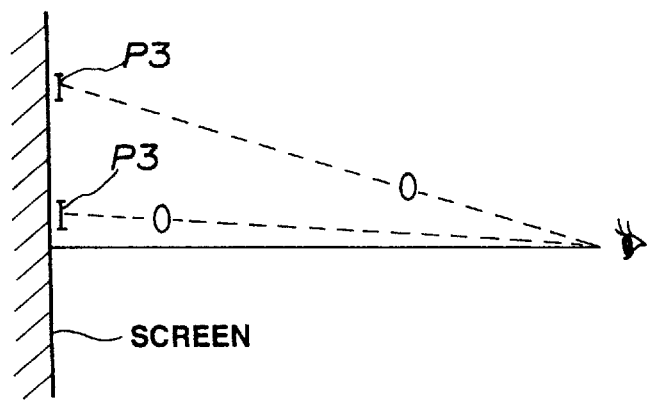

When the projecting screen is provided at an opposed position with respect to the point of sight, an angle may be applied. Since inclining the screen enables projecting the described image to vary when looked at, it is possible to confirm the emphasizing degree of the perspective.

b) When Perspective is Not Applied:

Further, in spite of the fact that the perspective is applied, a projecting method as shown in FIG. 31*c* can also be considered. Projecting the described image at this time is expressed by images of P3 which are all equal in thickness to each other, not depending upon the position of the point of sight. Since there is no perspective, a feeling of depth is lacking. However, projecting the described image is superior in that the described image does not come too large by the influence of the perspective when the point of sight is moved toward, and does not come too small when the point of sight is moved away from.

Next, processing of rendering in Step S42_15 is performed. In the present embodiment, selection can be made from processings of paste model display PM and wire-frame model display WM as shown in FIG. 23*b*.

Figure 32A:
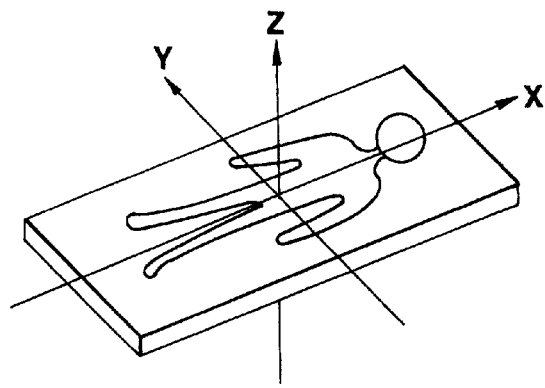
Figure 32B:
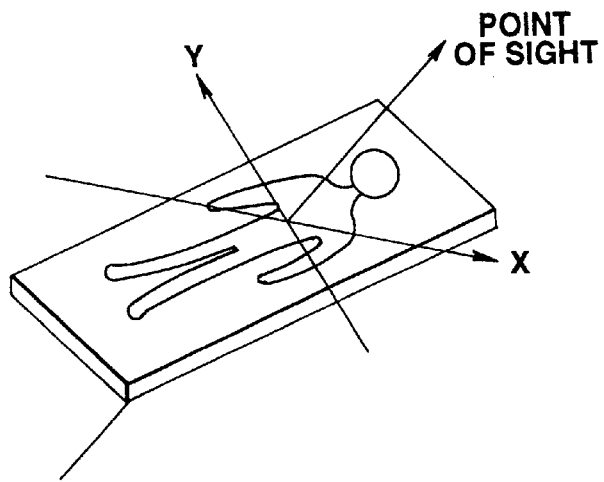
Figure 32C:
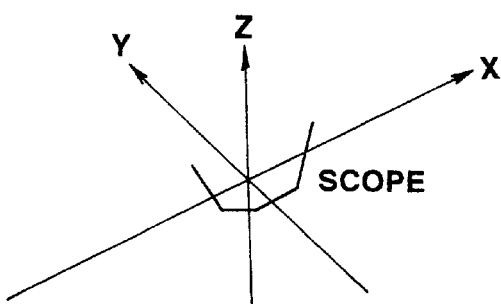

Prior to passing to the description of display by means of these models, the coordinate system of the above-described world coordinate system or the like is shown in FIGS. 32*a*~32*c*. FIG. 32*a* shows the world coordinate system which is fixed and set to the bed 4, while FIG. 32*b* shows the visual-point coordinate system which is set by the user. The origins thereof are in agreement with the origin of the world coordinate system. Further, FIG. 32*c* shows a model coordinate system which is used in display of the scope form, and is in agreement with the world coordinate system.

Figure 33:
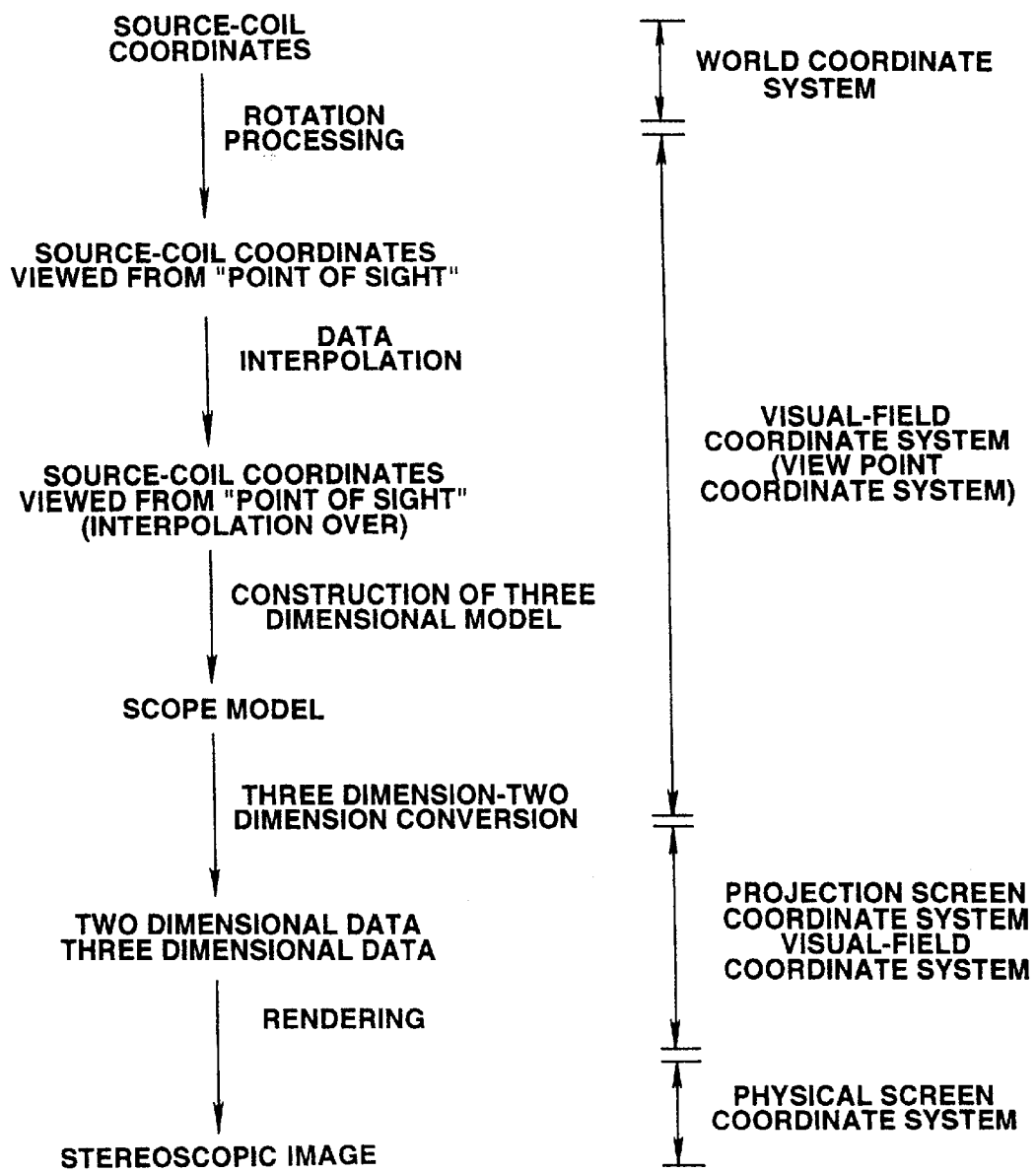

Moreover, FIG. 33 shows that the coordinate system (to the right in FIG. 33) which is adequate for each processing is adopted on the way of processing (to the left side in FIG. 33) which performs display of the scope form. For example, the source-coil coordinates are the world coordinate system, in which rotational processing is performed with respect to the source-coil coordinates, to find out the source-coil coordinates (that is, the visual-point coordinate system looked at from the "visual point" and, thereafter, data interpolation is performed with respect to the discrete source-coil coordinates to find out the source-coil coordinates looked at from the "visual point" which ends in data interpolation.

Next, in the three-dimensional model construction processing, the scope model due to the wire frame or the like is generated and, thereafter, the three-dimensional—two-dimensional transformation (perspective projection transformation) processing is performed in order to display the scope model on the two-dimensional image plane, to generate two-dimensional data and three-dimensional data to thereby rendering-process to pseudo telescopic image to display the same.

The paste model display PM in FIG. 23*b* will next be described. The model paints out the respective surfaces of the n-prism and, accordingly, is called "paste model".

Side-surface treatment of processing of the n-polygon at the time the scope form image is described on the CRT, and hidden-line or hidden-surface processing of 1_a to be described subsequently for expressing before and behind thereof in the case where the scope comes into loop will be described. Processing for emphasizing another three-dimensional feeling will subsequently be described.

1_a: Hidden-line or Hidden-surface Processing

When the scope model is displayed by the n-prism, the scope model has n-side surfaces. Of the n-side surfaces, the side surface which is actually looked at is only the side surface on the side of the direction of the point of sight. Accordingly, processing for displaying the side surface such that only the side surface on the side of direction of point of sight can be looked at, but the side surface, a side or the like which is not looked at is hidden, that is, hidden-line or hidden-surface processing (hereunder, simply referred to as "hidden-line processing") is performed.

In view of the above, sorting is made to an arrangement in which a parameter (referred to as "z-buffer", which is originated from the arrangement in which a z-value of an object is stored in a buffer memory) which indicates or expresses how each side surface is near the position of the point of sight into the buffer memory. Writing starts from the side surface in which the z-buffer is small (that is, far from the point of view). How to paste or stick with respect to the side surface is a superscription.

This method has improved processing speed, because a region to be reloaded or to be re-written is found out while a surface large or high in z-buffer is superscribed, from a surface small or low in z-buffer, to paint only the region to be reloaded.

Further, the method can be utilized also to judge which is on the upper side when the scope model is in a switching or twisted position. Generally, when the scope model is in the twisted position, it is investigated what or which is the higher. It must be judged whether a superscription may be performed, or whether a form in which the underside is passed through is.

Although the method is definite, the method takes processing time. In view of this, if the z-buffer of the whole model is all sorted, and if rendering is made from a small model, even in case of being located at the twisted position, a model which is located above is definitely described afterwards. Accordingly, it is not required to perform condition judgment. In the z-buffer method, actually, before and after judgment is performed within polygon processing with a pixel being a unit.

This is a method which is superior in that the whole form of the scope model can be created in less time.

Figure 34:
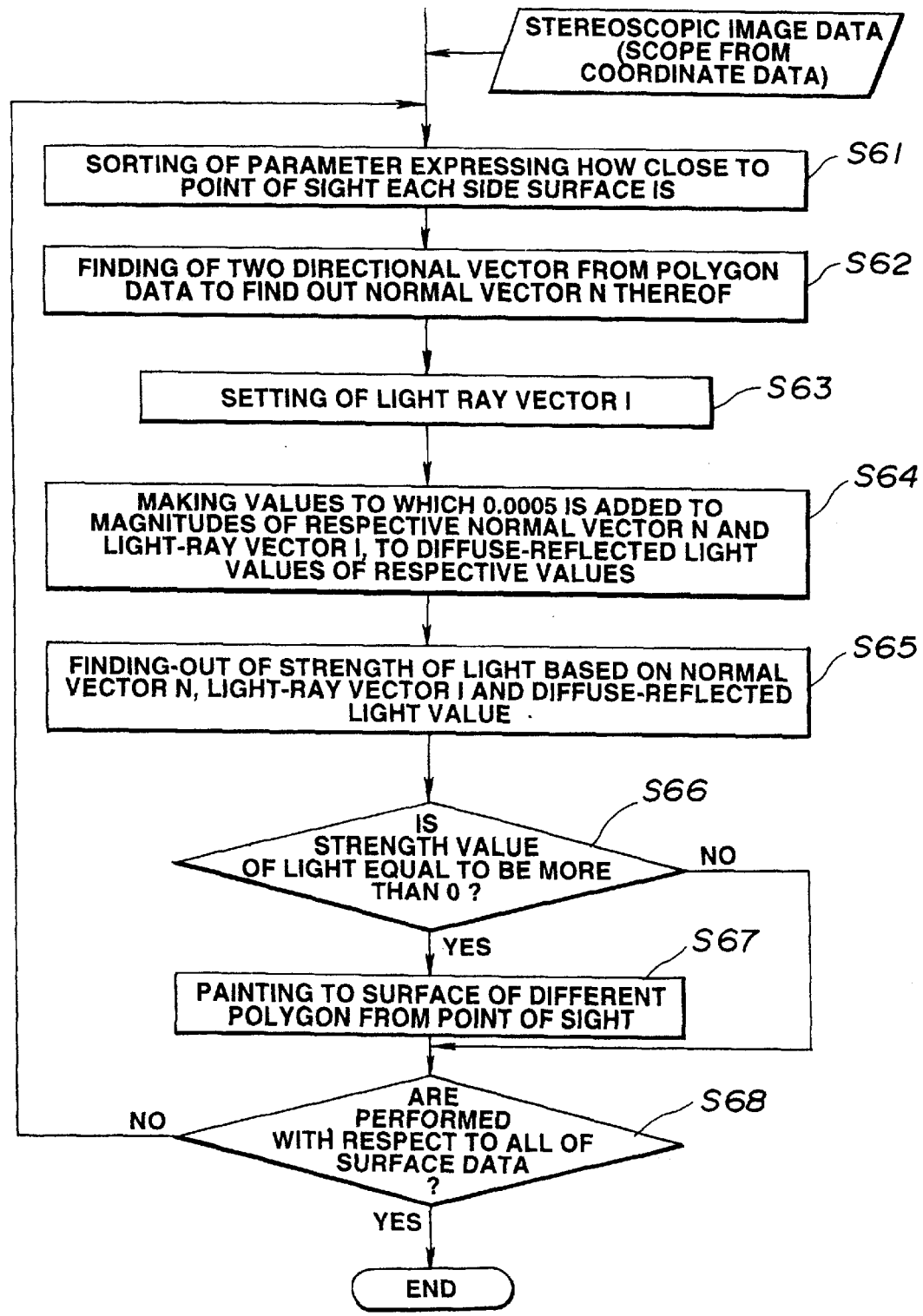

Specifically, the hidden-line processing is performed by a flow as shown in FIG. 34. First, stereoscopic image data, such as scope form coordinate data or the like, are fetched. In Step S61, a parameter (a z-buffer value of the z-buffer method which performs processing each polygon which forms each object) which indicates how each side surface is near the visual-point position is sorted, and the parameters are made to the order in which the z-buffer value is small or low. In subsequent Step S62, a two-directional vector which prescribes a surface thereof is found out from polygon data and a normal vector N of the surface is determined.

A light-ray vector I is set in subsequent Step S63. In subsequent Step S64, values in which 0.0005 is added to the respective magnitudes of the normal vector N and the light-ray vector I are made respectively to values of diffuse reflectance lights of the respective values, in order to determine an angle between the normal vector N and the light-ray vector I.

In subsequent Step S65, the strength t of a reflected light is found out from the Lambert law (an inputted light is diffused to all the directions equally) on the basis of the normal vector N, the light-ray vector I and the value of the diffuse reflectance light.

In subsequent Step S66, it is judged whether the strength value of the reflected light is equal to or greater than 0. When the strength value is equal to or more than 0, painting is made to a surface of the polygon which is far from the point of sight in subsequent Step S67. The program proceeds to subsequent Step S68 of judgment. Meanwhile, when the strength value is less than 0, a light is not applied. Accordingly, the program proceeds to Step S68. It is judged whether or not all surface data are completed. The above-described processing is applied to all the surface data, and the program ends.

Figure 35A:
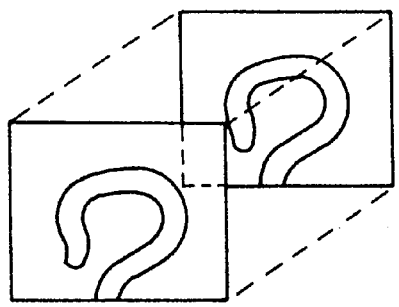
FIG. 35a is an explanatory view showing a pair of image memories.

In the present apparatus, time which is required for picture-creating of a single image plane of the scope form, onto the display device is lengthened. Accordingly, if picture-creation and easing are repeated on the same image plane, the animation image of the displayed scope appears to flicker when looked at. In view of this, as shown in FIG. 35a, a not-displayed image plane (hereinafter, referred to as "reverse image plane") is provided separately from the displayed image plane (hereinafter referred to as "front image plane"). An image plane subsequent to or next to the present front image plane is picture-created on the reverse image plane and, thereafter, is replaced with the front image plane.

Figure 35B:
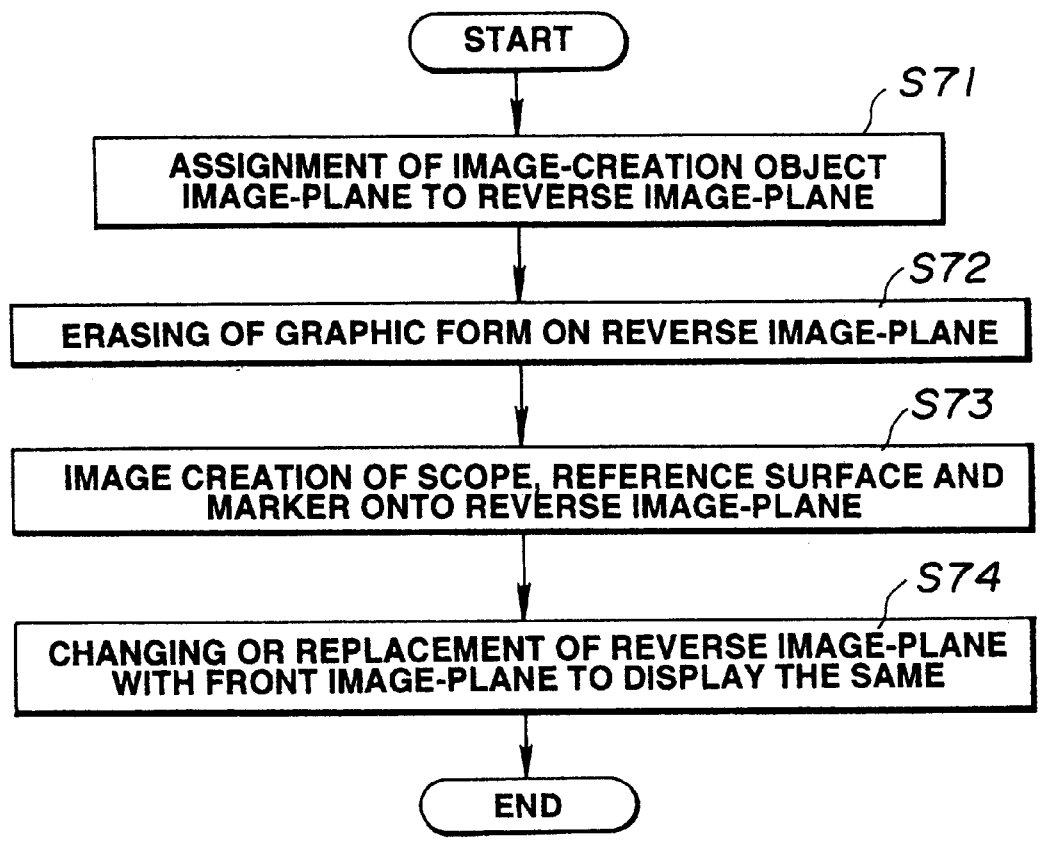
FIG. 35b is an explanatory view showing the fact that the pair of image memories are used to perform processing of flicker prevention.

A display method which uses the reverse image plane for preventing flickering from occurring will hereunder be described with reference to a flow chart shown in FIG. 35b.

First, as shown in Step S71, a picture-creation object image plane is assigned to a reverse image plane. Furthermore, in Step S72, a graphic form on the reverse image plane is erased. That is, a VRAM for the front image plane and a VRAM for the reverse image plane are prepared as VRAMs which serve as video display memories which are used for display. An objective image plane of image creation is assigned to the VRAM of the reverse image plane which is not displayed at that time during the fact that the front image plane is displayed. Further, a graphic form which is written to the VRAM of the reverse image plane is erased.

In next Step S73, required or necessary images of the scope, the reference surface, the marker or the like are image-created onto the reverse image plane which ends in erasing. If the image creation ends, the front image plane which performs display till this point of time and the reverse image plane in which a new image is described are changed to each other as shown in Step S74, and the image in which image creation ends is displayed. During the display, the reverse image plane which has been changed from the front image plane is used in subsequent image creation.

Process of image-creating a single image plane by this operation is not looked at to the user. Flickering of an animation image looked at from the user because of being instantaneously changed to the subsequent image plane is not generated or does not occur.

1_b: Three-Dimensional Feeling Emphasis Processing

Here, processing for emphasizing a three-dimensional feeling and the depth to the image due to the n-prismatic model which is constructed as being a scope form model under the inserted condition is soldered.

The scope form under being inserted is a three-dimensional form. Since, however, the medium (CRT) for display the image is two dimension, how or in what manner the three-dimensional image is displayed on a CRT largely affects convenience in use of the system. The following is an example of processing which emphasizes the three-dimensional feeling and depth.

1_c: Shading Processing

Since the scope form is three-dimensional, light and darkness are created. There is a means for displaying, in gradation, such light and darkness. There are many degrees of light and darkness, depending upon the curvature of the scope. In the utilizable number of colors, there is such a hardware limitation as sixteen (16) colors in, for example, 4096 colors. When there are few colors, there are also few colors, there are also fee in gradation capable of being used. In view of this, pallet changing or modification is carried into practice such that the gradation is effectively utilized. A tone of color is set by an angle which is formed by a light-source vector and the normal vector to a side surface of each of scope modeling and modeling.

Figure 36:
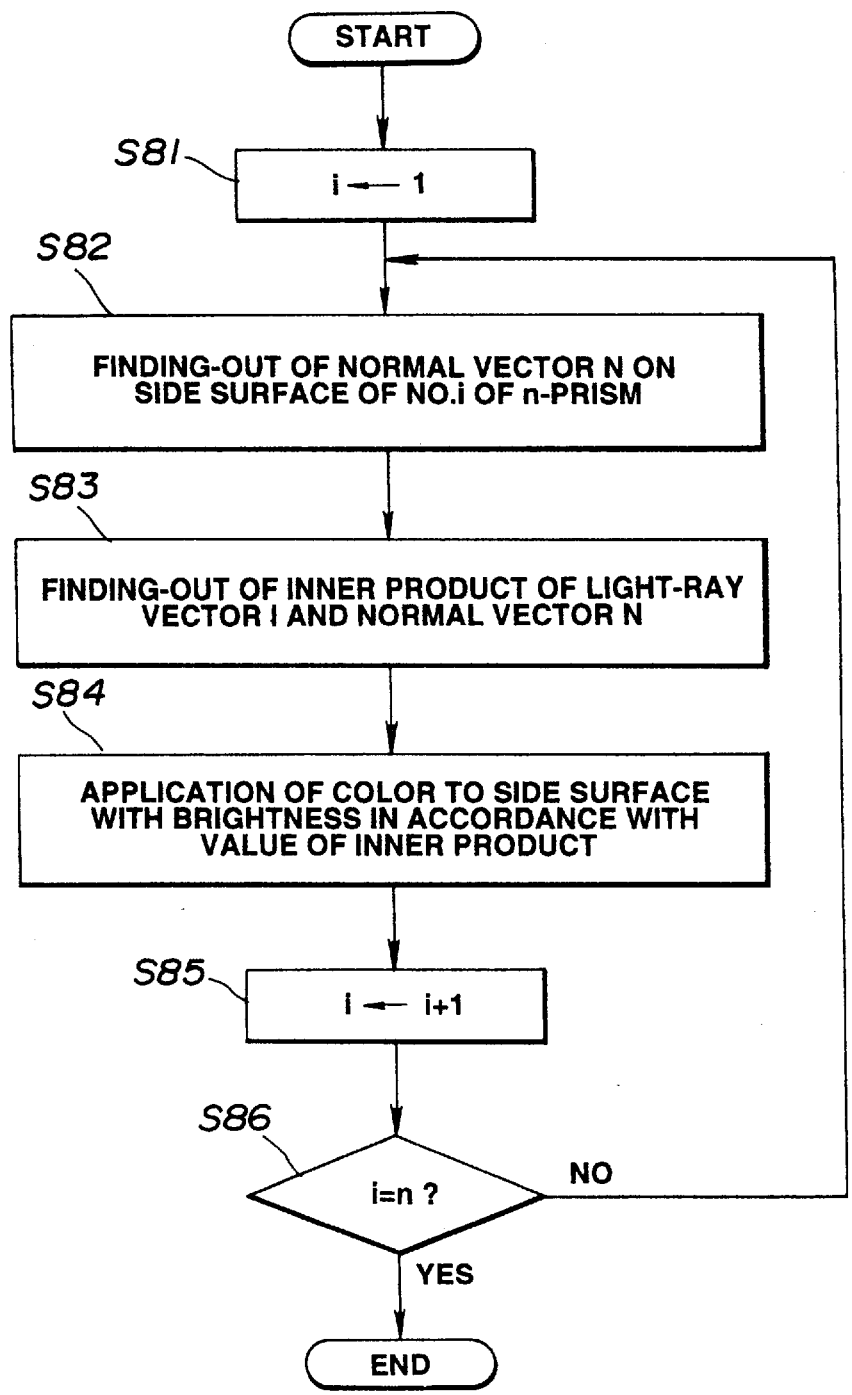

The processing is performed as shown in FIG. 36. The scope image is displayed in n-prism. First, a parameter i is set to 1 in Step S81. A normal vector N of the side surface of the number i of the n-prism is determined in subsequent Step S82.

In subsequent Step S83, the normal vector N with respect to a quadrangle which forms the side surface and the inner product of the light-source vector I are taken. The light-source vector I is assumed to be directed to the origin from the position of the point of sight.

In subsequent Step S84, color is applied to the side surface with brightness in accordance with a value of the inner product. In this case, when the inner product is 0, display is made by the darkest color, while, when the inner product=1, display is made by the brightest color. Except that, equalization is made by the utilizable quantity of gradation. Of course, a three-dimensional feeling can smoothly be expressed as the wider gradation can be set.

Subsequently, parameter i is incremented (Step S85). Judgment as to whether or not i is equal to n is then performed (Step S86). Similar processing is repeated until the side surface of No. n.

The method is superior in that, since the light-source direction and the direction of the point of sight are in agreement with each other, the direction of the point of sight is always displayed in the brightest and, in addition thereto, the three-dimensional feeling of the scope image-description can be better emphasized by the gradation display. Of course, the light-source position and the position of the point of sight may be separate from each other. At this time, the display may become dark even in a direction in front of the point of sight, depending upon the position of the light source. Accordingly, this method is particularly superior when the depth of the scope image-description is emphasized. In this connection, in order to clearly distinguish the darkest gradation color and the background color from each other, the background color may be applied.

1_d: Utilization of Intensity and Chroma of Color

When the number of utilizable colors is particularly rich, such as 256 colors in 16384 colors, for example, shading processing can be performed by a color.

Figure 37:
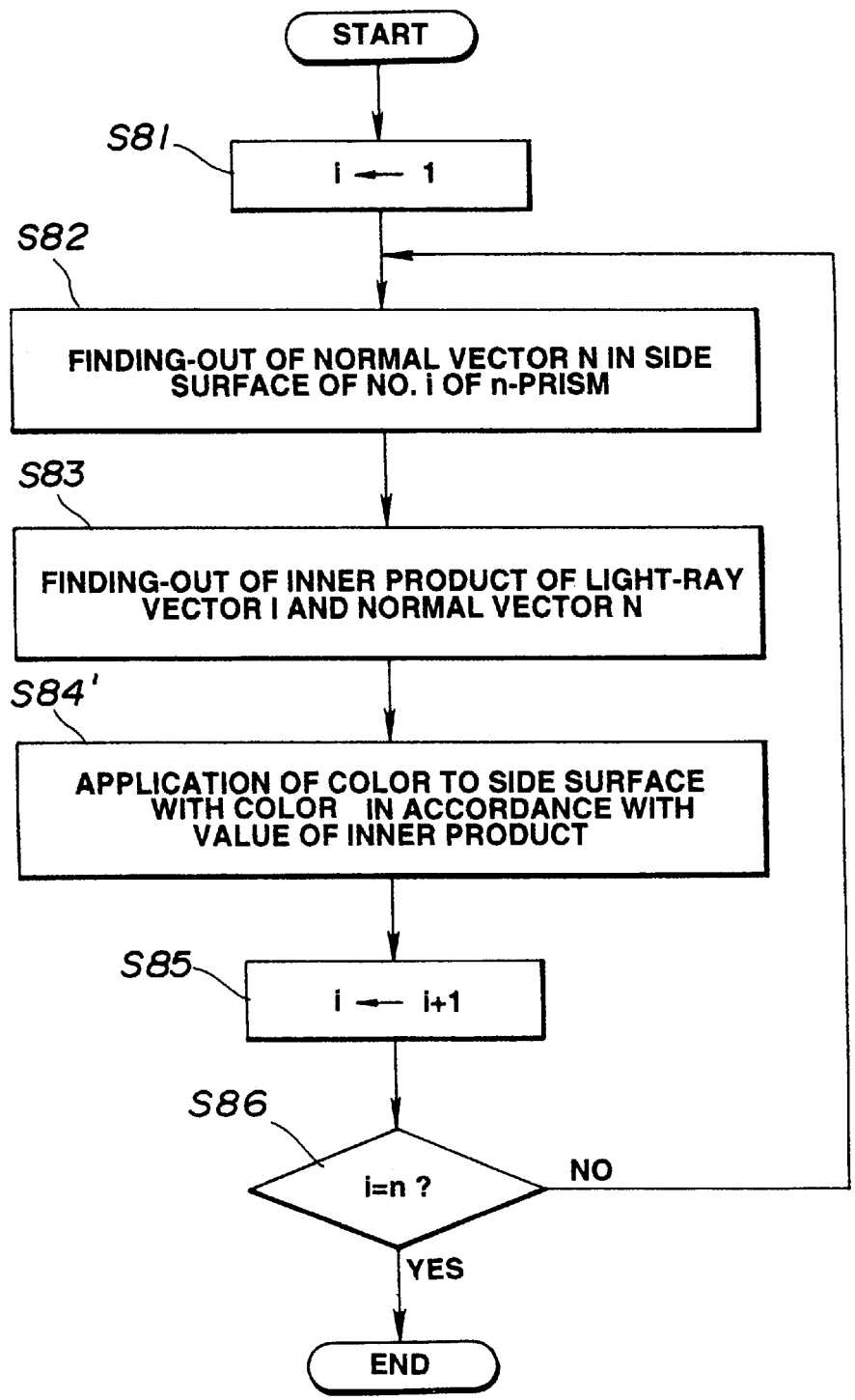

The processing contents are indicated in FIG. 37. Basically, the color is similar to shading processing. In this flow, the color is different from the shading processing only in that "brightness" in Step S84 in FIG. 35 is changed or modified to "color" in Step S84'. Accordingly, the description of a flow thereof will be omitted.

Since colors can be used in abundance, it is made possible to display the side surface of the scope model which faces toward, for example the light-source direction, by warm color, while, to display the side surface in the opposite direction by cool color. Of course, setting of color should not be limited to this.

This means that the three-dimensional feeling of the scope can be emphasized as compared with the situation where light and darkness are merely displayed, since light and darkness of the scope can be abundantly displayed in color. Further, the scope image-description is easier to observe, even where the contract of the CRT must be reduced by influence of the establishment environment of the CRT of the like.

Moreover, by combination with utilization of intensity, it is made possible to provide a more colorful or variegated display. For example, the light-ray direction is displayed by saturation, while a distance from the point of sight is displayed by intensity. By doing so, the three-dimensional feeling of the scope is made possible to be displayed by a difference in color, while the depth from the direction of the point of sight is also made possible to be displayed by a difference in intensity. Thus, a greater three-dimensional image-description can be realized. Of course, the three-dimensional feeling may be expressed by intensity, while the depth may be expressed by the saturation. The depth may also be expressed not only by the direction of the point of sight, but also by an optional direction. For example, if a difference in tone of color is applied from the bed surface in the height direction, it is possible to confirm whether the inserted condition of the scope is favorable or satisfactory, by the tone of color.

Figure 38:
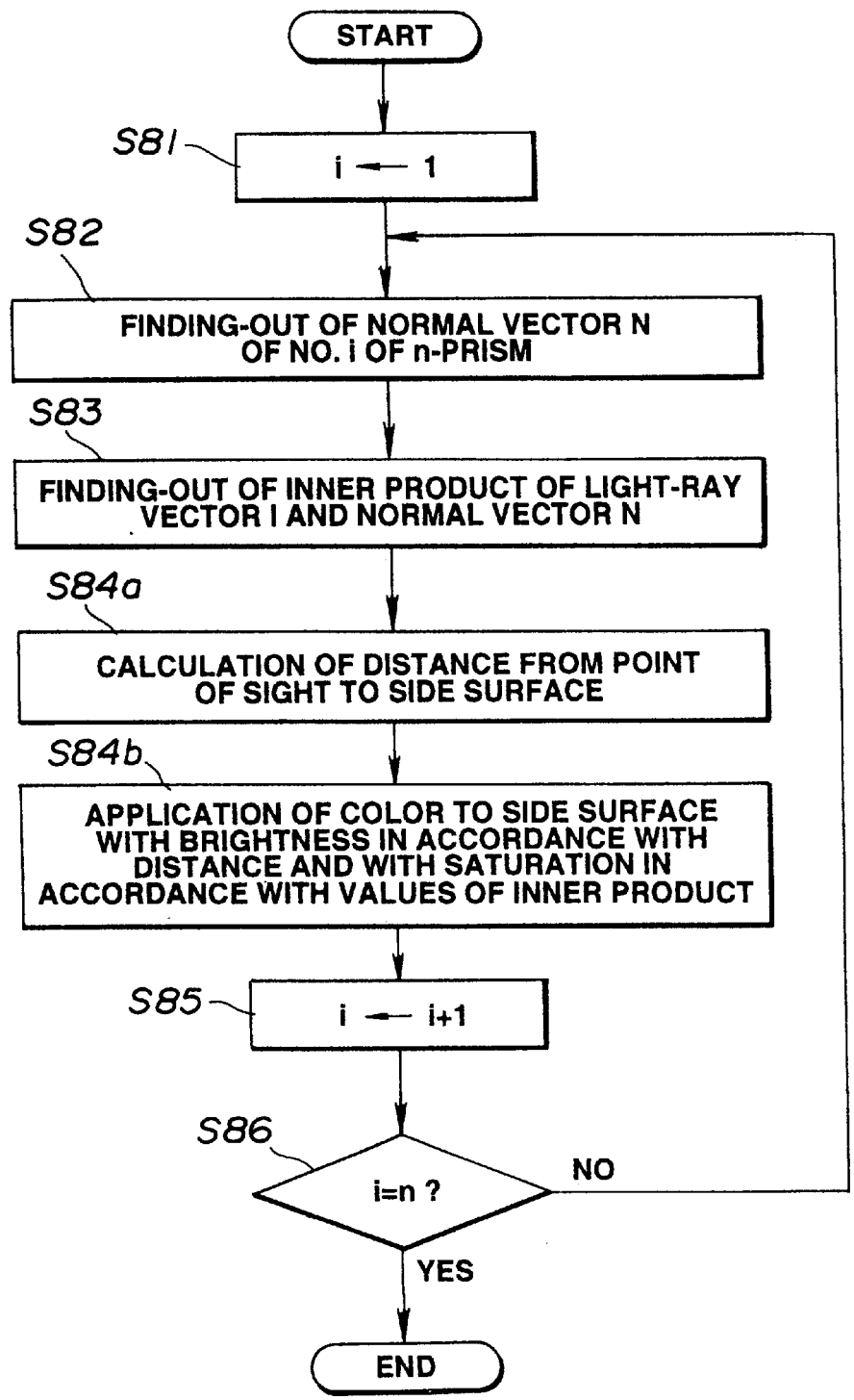

Processing which uses the chroma or saturation and the intensity is shown in a flow in FIG. 38. The flow is the same as the flow in FIG. 37 until Step S38. Processing for calculating the distance from the starting point to the side surface is performed in Step S84a in substitution for next Step S84. Processing for applying a color to the side surface by the intensity in accordance with the distance and the saturation in accordance with the value of the inner product is further performed in Step S84b.

This method is superior in that the three-dimensional feeling and the depth of the scope image can be realized by a more three-dimensional image-description, and prediction of the relative position from a position is made possible.

Processing of wire-frame model display WM will next be described.

This processing comes into the same result as that where a portion except for the side of the n-prismatic model is painted out by the background color. This can selectively be used because of shortage of processing time for painting the surface of the n-prismatic model.

In connection with the above, in this model, if writing is made in the order in which a z-buffer is small or low, a wire on the deep side of the scope model is looked up. In view of this, hidden-line processing for removing the wire is suitably carried into practice, or the wire frame is described till the model data of No. (n/2) in order from large or high z-buffer. Thus, it is possible to construct the model which is processed in hidden-line.

A flow of this display is shown in FIG. 39. First, n-prismatic modelling is performed in Step S91. In subsequent Step S92, apexes which are produced by the modeling are connected to each other by a straight line. Under the condition, the wire on the deep side of the scope model is seen. Accordingly, in subsequent Step S93, the hidden-line processing is performed whereby it is possible to produce a scope image due to the wire-frame model display WM.

Next, in FIG. 23a, Step S42_2 of display of the reference surface and Step S42_3 of display of two-point marker are performed. Processing of Step S42_2 and Step S42_3 is additional processing.

Processing of display of the reference surface facilitates visual understanding of three-dimensional display of the scope form by display of the reference plane or surface such as the bed surface or the like.

In the present embodiment, the described image which is displayed on the CRT is only the image of the scope form, and a positional relationship between the image and the internal organs within the body is unknown. Then, if the position of the point of sight is rotated, information regarding from which direction the scope form is observed, in what direction the direction of the head is oriented, and the like is only numerical information of the angle which is text-displayed. This is unsuitable for sensory judgment. In view of this, an auxiliary means which is capable of such sensory judgment is provided.

Here, realization is made as shown in FIG. 23c.

First, affine transformation in Step S42_21 is performed. In this processing, a reference display symbol of the world coordinates is transformed or converted to a visual-point coordinate system.

3D→2D projection of Step S42_22 is performed next.

Conversion processing which projects two-dimensionally is performed such that the reference display symbol which is moved or transferred to the visual point coordinate system can be displayed on the CRT.

Symbol display of the bed which comes into the reference surface of Step S42_23 is next performed. A symbol for assisting the three-dimensional described image of the scope image is displayed. A specific example of the symbol will hereunder be mentioned.

By doing so, the reference plane position, a separating condition of the scope form from the reference surface and the head direction of the patient can be visually judged. Thus, the method is superior in that a judgement reference of the position of the scope form or the like is provided.

Next, bed-surface display of 2_a or the like will be described as a specific example of the reference display symbol.

2_a: Bed-Surface Display

A reference surface which is in parallel to the x-y planar surface of the world coordinate system and which is perpendicular to the z-axis is displayed. The z-coordinates may be any position if the position is a position which can come into a reference thereof, even if the z-coordinates are the bed surface or plane (z=0). This plane is not moved together with the visual-point coordinates. That is, if the visual-point position is rotated in the x-axis direction and in the y direction, the bed plane is expressed or displayed by lines. Markers may be applied to a rectangle such as a pillow or to a direction of a right shoulder, a left shoulder or both directions thereof such that the head direction is known or understood.

This is expressed by a simple single plate and, accordingly, does not stand in the way with respect to the scope description of image. Thus, this is superior in that rotation of the point of sight can also be recognized.

2_b: Reference Marker Display

This is display represented in FIG. 40a. Here, there exist two reference markers m3 and m4 in a direction of both shoulders, and a reference marker m5 in a foot direction. The markers m3 and m4 on a shoulder are oriented perpendicularly to the z-coordinate, while the marker m5 in the foot direction is oriented perpendicularly to the x-coordinate. Accordingly, when viewed from the z-direction, the markers are indicated or expressed by line segments as shown in FIG. 40a.

For this reason, when the position of the point is rotated in the x-axis direction, the markers m3 and m4 of both the shoulders are so changed as to be displayed by the line segments. The marker m5 in the foot direction is oriented in front, and comes into a circular marker. Accordingly, a direction can be known or understood. The reason why the numbers of markers are different from each other on top and bottom is to facilitate to identify the head direction. The number of markers and the form thereof may be optional, and the fact of what markers correspond to what axes is also optional. The arrangement may be such that the markers are made to solid or stereoscope, and gradation, intensity, saturation or the like may be applied.

This method is superior in that, since the scope form and the markers are not overlapped with each other, the scope form is easily viewed.

2_c: Representation of Rectangular Parallelepipeds

This is a symbol in which frame in a z-direction is added to bed representation in 2_a so as to be represented as being rectangular parallelepipeds. The magnitude of the rectangular parallelepipeds is optional. However, if the magnitude is within a detecting range of the system or equal to or larger than the same, the scope form is displayed within the rectangular parallelepipeds. Accordingly, such a sense that the scope is under the inserted condition increases. Further, by the fact that there is also the height of a box in a z-direction, it is facilitated to estimate the z-coordinate of the model.

This method is superior in that, because it provides such a realism that the scope is under the inserted condition, the scope form is easy to be actually connected to a scope under an inserted condition.

Conversely, the arrangement may be such that a block is displayed at a corner of the scope image, and is rotated in interlocking with movement of the point of sight.

2_d: Mixture Display

The reference symbols referred to until now may be combined with each other. FIG. 40b shows where the bed-surface display of 2_a and the reference marker display of 2_b are combined with each other. By doing so, a reference with respect to the z-axis is a surface or plane display, and information of the head direction at the time of being rotated can be recognized by the marks. The other displays may be combined with each other in a manner.

Such means is superior in that the advantages of the respective symbols can be used in common.

Next, processing of marker coil display of Step S42_3 in FIG. 23a is performed.

The processing of the marker display provides processing until an independent position of the source coil is calculated, and is displayed, independently of the source coiled 16i which is inserted into the scope. Means for displaying one or more marker coils which is independently movable from the source coil 16i within the scope is provided as a means for confirming what or how position the position inserted into the scope exists.

On the actual apparatus, position calculating means is entirely the same as that which is used in the source coil 16i which is inserted into the scope. Display means is also similar to that until now. As shown in FIG. 23d, processing comes into processing affine transformation of Step S42_31→3D→2D projection of Step S42_32→marker coil display of Step S42_33.

Accordingly, here, display due to n-polygon (including also a circle) will be described as a specific example of marker coil display. If the markers are displayed in this form, it is impossible to use the large number of colors. When an apparatus arrangement which cannot but use the color the same as that of the scope form, it is possible to perform discrimination even if there is overlapping over the scope form.

This marker coil display can identify in what direction the form is viewed by the fact that the form is changed in accordance with rotation of the point of sight. At this time, the visual-point direction can be recognized from the marker coil display. However, the marker display is superior in that the marker coil display having a constant magnitude are outputted.

This also comes into expression similar to that when the marker coil display is spherical. In this connection, when the marker coil display is spherical, the gradation, information such as saturation, intensity or the like is given whereby it is also possible to display the direction of the point of sight and the depth thereof.

Such means is used, and the marker coil is moved outside the body, whereby it is made possible to recognize the position of the scope form when inserted in relation to the marker coil. Thus, it is possible to provide auxiliary means which knows the scope inserted position in relation to the actual position of the patient.

The display by the n-prismatic model has heretofore been described. However, display by an n-angular connection model will be described.

The n-prismatic model is such that, although the scope form thereof can be displayed, processing time is taken for several minutes. In view of this, n-angular connection models in which model arrangement is more simplified or abbreviated, and high-speed display is enabled are constructed, and can be selected and used (displayed).

Figure 41A:
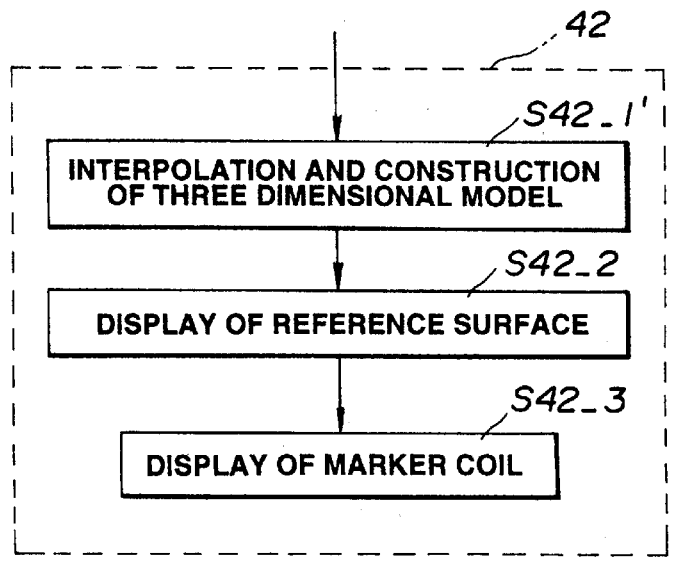
FIGS. 41a and 41b are flow charts steps involved in display by an n-prismatic connection model.
Figure 41B:
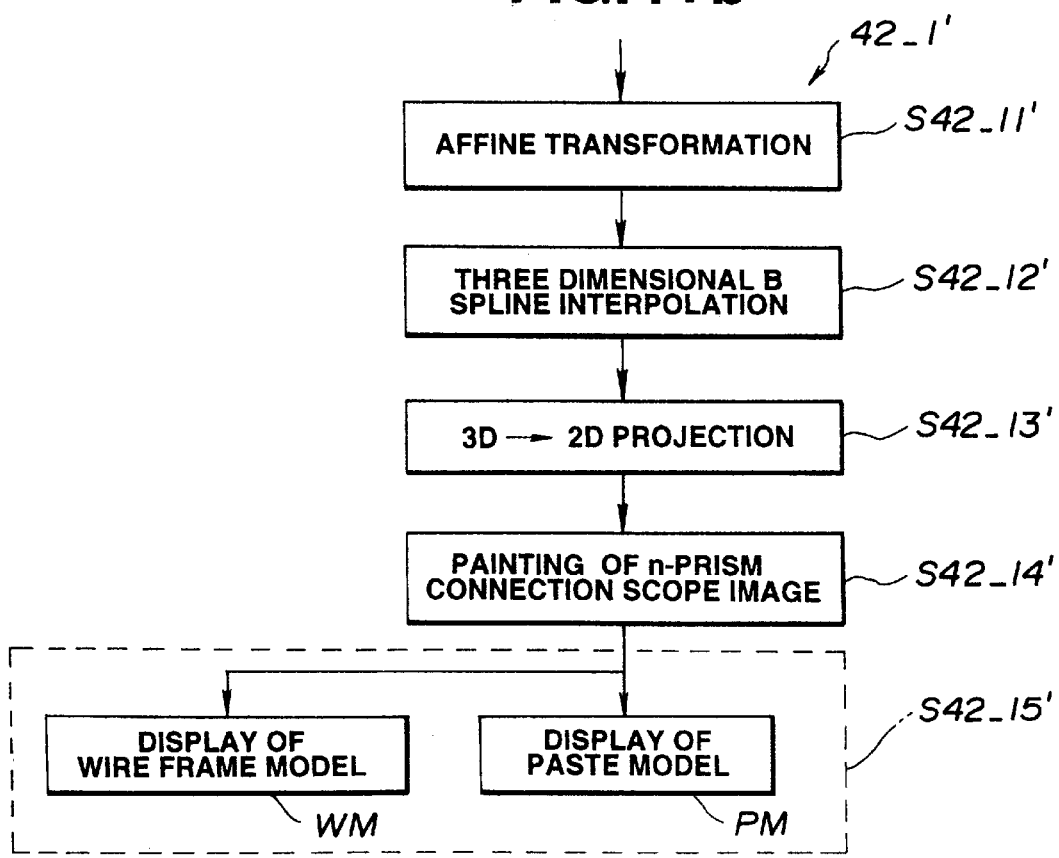

Processing flow thereof is as shown in FIG. 41a and FIG. 41b. By the processing referred to here, the basic or fundamental processing contents are the same as those when used at the n-polygonal model. In view of this, a difference therebetween will be described.

The contents of the processing of interpolation and construction of the three-dimensional model of Step S42_1' in FIG. 41a are shown in FIG. 41b. In this model, affine transformation is first performed in Step S42_11'.

The transformation is from the world coordinate system to the visual-point coordinate system, and is similar to the processing by means of the n-polygonal model (refer to Step S42_13 in FIG. 23b). In the connection, in the n-polygonal model, transformation is performed with respect to the interpolation data. However, here, transformation is carried into practice first with respect to the source-coil position data.

By doing so, the small quantity of affine transformation is dispensed with. Thus, the processing speed of the program is improved.

Three-dimensional interpolation is performed in subsequent Step S12'.

This processing is also similar to that described previously. A difference is that, in the n-polygonal model, the data are of the world coordinate system. However, here, the data are data of the visual-point coordinate system.

In subsequent Step S42_13', the 3D→2D projection is performed. This processing is also similar to that described previously. However, this time the projection has no magnitude.

In subsequent Step S42_14', construction of the n-angular connection model is performed.

Figure 42:
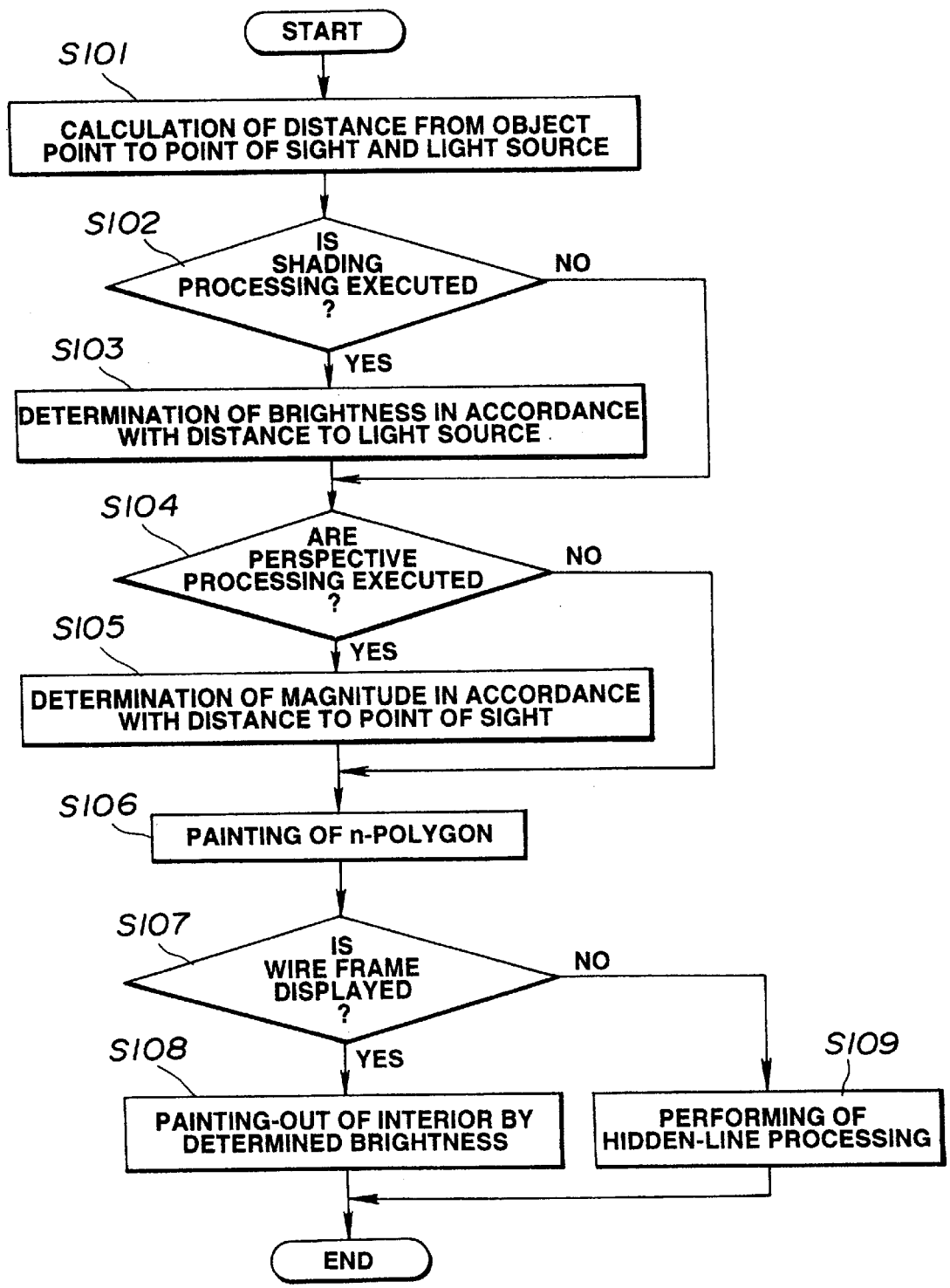

The processing contents of the n-angular connection model are shown in FIG. 42. In FIG. 42, the contents are shown including also Step S42_15' of the rendering in FIG. 41b.

First, in Step S101, distances from the objective point to the point of sight and the light source are calculated. In subsequent Step S102, it is judged whether or not the shading processing is performed. When the shading processing is performed, processing to decide brightness is performed in accordance with the distance to the light source is subsequent Step S103 and, thereafter, the program proceeds to judgment as to whether or not the perspective processing is performed in Step S104. Further, in case also where the shading processing is not performed, the program passes to the processing of judgment.

When the perspective processing is performed, processing to decide the magnitude in accordance with the distance to the point of sight is performed in subsequent Step S105 and, thereafter, the program proceeds to processing of the n-angular form painting in subsequent Step S106. In the processing of the n-angular form painting, various points are in agreement with a center of the n-angular form to perform painting in which the n-angular forms are simply connected to each other, to form an image in which the n-angular forms are connected to each other. Furthermore, when the perspective processing is not performed, the program proceeds to the process of painting.

In further subsequent Step S107, selective judgment as to whether or not the wire-frame display WM is performed is performed (that is, selection as to whether the paste model display PM is performed or as to whether the wire-frame display WM is performed is performed). When the display is not the wire-frame display WM, the program proceeds to processing of display by means of the paste model in subsequent Step S108. The interior is painted out with brightness which is decided in Step S103. Meanwhile, when the wire-frame display is performed, hidden-line processing is performed in subsequent Step S109, so that display is performed by the wire frame model.

Until now, the scope image is created in the form in which the n-angular forms are connected to each other. Moreover, the arrangement may be such that the produced point is in agreement with the center of the n-angular form model shape, and an image is outputted in the form in which "modeling" or "enrichment" is applied around the interpolation data point.

By the processings described above, the n-angular form connection model having the minimum function is outputted when NO is selected in the processing of judgment.

The method is superior in that the model excludes, to the utmost, that processing time of the n-prismatic model is taken so that display is made possible at extremely high speed (equal to or less than ½ of the processing time of the n-prismatic model).

In connection with the above, the arrangement may be such that YES is selected in the processing of judgment in the flow in FIG. 42 so that a three-dimensional feeling is emphasized in addition to additional processing similar to that upon the n-prismatic model. Basic processing is the same and, accordingly, description will briefly be made so that only differences are known.

As the additional function with respect to the n-angular form connection model, there is the following perspective processing in 4_a (when there is the magnitude) or the like.

4_a: Perspective

The reason why the perspective is not applied is that the object which performs 3D→2D conversion has no magnitude. If the object of the conversion is not made to the point, but is to the form having the magnitude, the advantages are the same as those described previously. The form may be an optional form. However, since the model has been invented or devised to realize high-speed display, it is desirable that the form has a symmetric form whose center is a point which originally performs conversion.

4_b: Hidden-Line Perspective

The processing is superior in that, since the modeling per se combines hidden-line processing with respect to the display method which paints out the interior of the n-angular form, no special processing is necessary. When the hidden-line processing is performed by the wire-frame display method, the processing can be achieved by the fact that processing to eliminate or erase an overlapping portion, or the interior of the n-angular form is once painted out by the background color and, thereafter, the wire frame is superscribed.

4_c: Shading Processing

In this model, since there exists no surface or plane of the scope, the depth of the scope model may be expressed by the shading processing. Specifically, the side which is the nearest the light source is displayed bright, the side which is the farthest from the light source is displayed dark, and a portion therebetween is displayed in gradation in accordance with the number of colors which utilizable.

At this time, the depth of the model can be expressed.

As an application, it is possible to cause a slight gradation difference to have between a central portion and an end of the model. By doing so, although gradation for indicating the whole depth decreases, the scope model is so expressed as to be bulged by the gradation difference. Accordingly, it is possible to emphasize the three-dimensional feeling of the scope.

4_d: Utilization of Saturation and Intensity of Color

This is similar to the n-prismatic model, and the same advantages can be expected.

4_e: Wire Frame Display

Here, a simple display method including the hidden-line processing function with respect to the wire frame display is provided.

The method is a method in which, first, all the wire frames are not expressed by n-angular form, but only data at the root are expressed by the n-angular form, and a semi-n-angular form is added from there toward a forward end (refer to FIG. 43a).

The method is superior in that the wire-frame form the same as that where the hidden-line processing is carried into practice can be created, notwithstanding the fact that the hidden-line processing is not carried into practice.

Moreover, the same semi-n-angular forms are not overlapped with each other, but forms including angle strains set in accordance with the curvature of the orientation of the scope may be overlapped with each other (refer to FIG. 43b).

This method is superior in that the curvature information is emphasized in addition to the advantages of the above-described means so as to approach a more practical scope image.

As described above, according to the first embodiment, the arrangement is such that the arrangement in which the source coil 16i serving as a magnetic-field generating element which generates the magnetic field is fixed to the inner wall of the probe 15 through the insulating adhesives 20 such that the form of each of the source coils 16i is not deformed is arranged within the insertion part 7 having resiliency or elasticity of the endoscope 6, the three-axis sense coil 22j serving as the magnetic-field detecting element for detecting the magnetic-field which is generated by the source coil 16i is arranged at the known position surrounding the subject into which the insertion part 7 is inserted, and the position of each of the source coils 16i within the insertion part 7 with respect to the three-axes sense coil 22j which is arranged at the known position is calculated by the position calculator 31 on the basis of the detecting signal which detects the magnetic field generated by each of the source coils 16i by the respective three-axis sense coils 22j.

Accordingly, when the insertion part 7 is inserted into the interior of the subject, even if the insertion part 7 is curved, each of the source coils 16i within the insertion part 7 is fixed by the fixing means such that there is no deformation. Thus, it is possible to detect (estimate), at high accuracy, the position of each part of the insertion part 7 of the endoscope 6 by calculation of the position of each of the source coils 16i.

Further, in the embodiment, the interval is interpolated with respect to the calculated position of each of the source coils 16i or the position of each of the parts of the insertion part 7, or the like, to estimate the form of the insertion part 6. The stereoscopic form image corresponding to the estimated form is generated. The stereoscopic form image is converted to the two-dimensional image for displaying the stereoscopic form image onto the color monitor 23 which comes into the two-dimensional display means, so as to be displayed, in a stereoscope manner, onto the monitor image plane. Accordingly, the operator observes the monitor image plane whereby it is facilitated to judge, in a visual sense manner, the form of the insertion part 7 which is inserted into the interior of the patient 5.

Furthermore, the marker display can be performed to the position corresponding to the three-dimensional position which comes into the reference which is desired by the user or the reference surface or plane such as the bed or the like, together with the image corresponding to the solid or stereophonic form of the insertion part 7. Accordingly, the monitor image plane is viewed whereby it is made possible to facilitate that the form of the insertion part 7 is grasped.

Accordingly, the insertion of insertion part 7 into the bent body cavity, or the like, is facilitated. That is, it is possible for the operator to visualize the form of the insertion part 7. Thus, it is possible to insert smoothly the insertion part 7 into the deep side within the body cavity, or it is possible to set, for the short period of time, the observation optical system (objective optical system) on the side of the forward end of the endoscope 6 to the location in the vicinity of the object part to which the endoscope inspection is performed. Furthermore, since the insertion part 7 can smoothly be inserted, a pain upon insertion with respect to the patient 5 can be relieved.

Further, by the plurality of three-axis sense coils 22j which form magnetic-field detecting means which are respectively arranged at the known positions, the strength of the magnetic field which is generated by the single-axis or three-axis source coil 16i which forms the magnetic-field generating means, the phase information in case of being driven in alternate current, and the form of the equal magnetic-field surface due to the magnetic-field generating means are considered to detect or estimate the region in which each of the magnetic-field generating means exists, to thereby estimate the three-dimensional position thereof. Accordingly, if the magnetic-field detecting means is arranged at the known positions such as four corners of the bed 4 or the like, calculation or estimation of the position is accurately made possible to the required positional detecting range, with respect to the subject such as the patient or the like on the bed 4.

That is, the plurality of (three or more) three-axis sense coils 22j are arranged on the bed 4 or the like, whereby the three-dimensional region in which the source coils 16i exist is estimated by the magnetic-field strength which is detected by each of the three-axis sense coils 22j. The existing region of the source coil 16i is estimated from the overlapping portion of the three-dimensional region which is estimated by the respective three-axis sense coils 22j. In this case, if the phase information is utilized, the situation where there is a coil out of the detecting range can be eliminated or excluded.

Moreover, in the first embodiment, the arrangement is such that the reference information from the signal corresponding to the detected magnetic-field strength is used to estimate the region in which the source coils 16i exist. Accordingly, it is possible to perform the region calculation for an extremely shorter period of time than the situation where distance calculation is performed.

Furthermore, if the number of arrangement of the three-axis sense coils 22j increases, it is possible to accurately perform positional detection of the source coils 16i, and it is possible to accurately estimate the form of the endoscope.

Further, it is also possible to display the found form of the endoscope by a form where the user looks at from a desired direction of the point of view. For example, setting is made such that the form display is performed under the condition where observation from the position of the point of view at which the inserting operation is performed, whereby inserting operation is facilitated, or the like. Thus, the present embodiment has may advantages described in the first embodiment.

Figure 10:
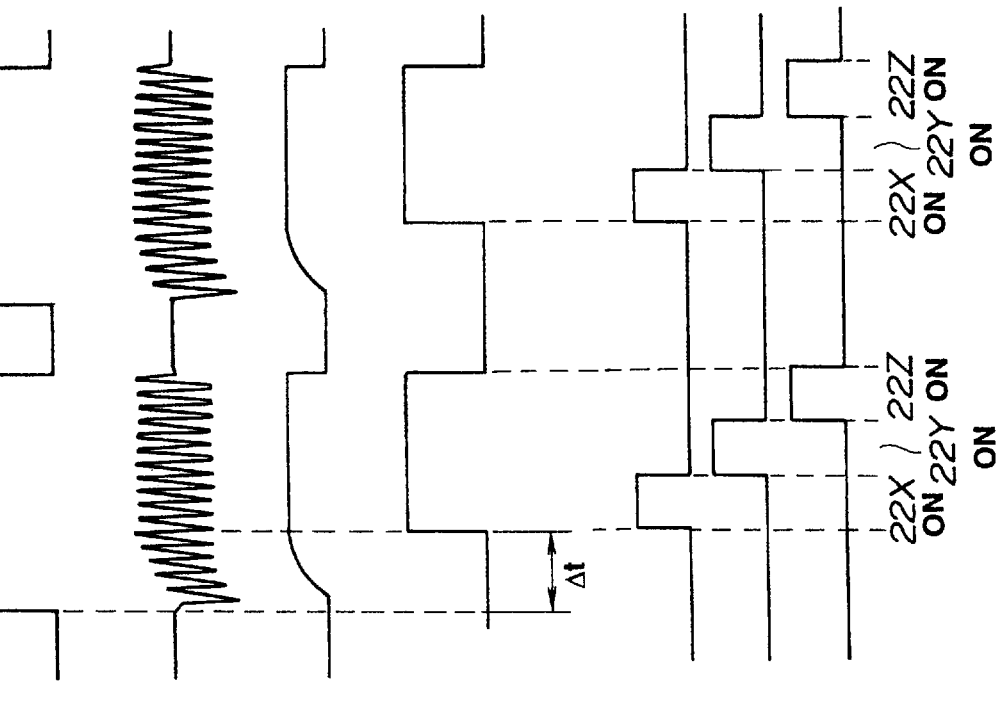

Next, a first modification of the first embodiment will be described with reference to FIG. 44. In the first embodiment, for example, as shown in FIG. 10, timing fetching or taking in the signal detected by the sense coils 22*j* has been delayed in consideration of the transient characteristic due to the source coil 16*i*.

Figure 44:
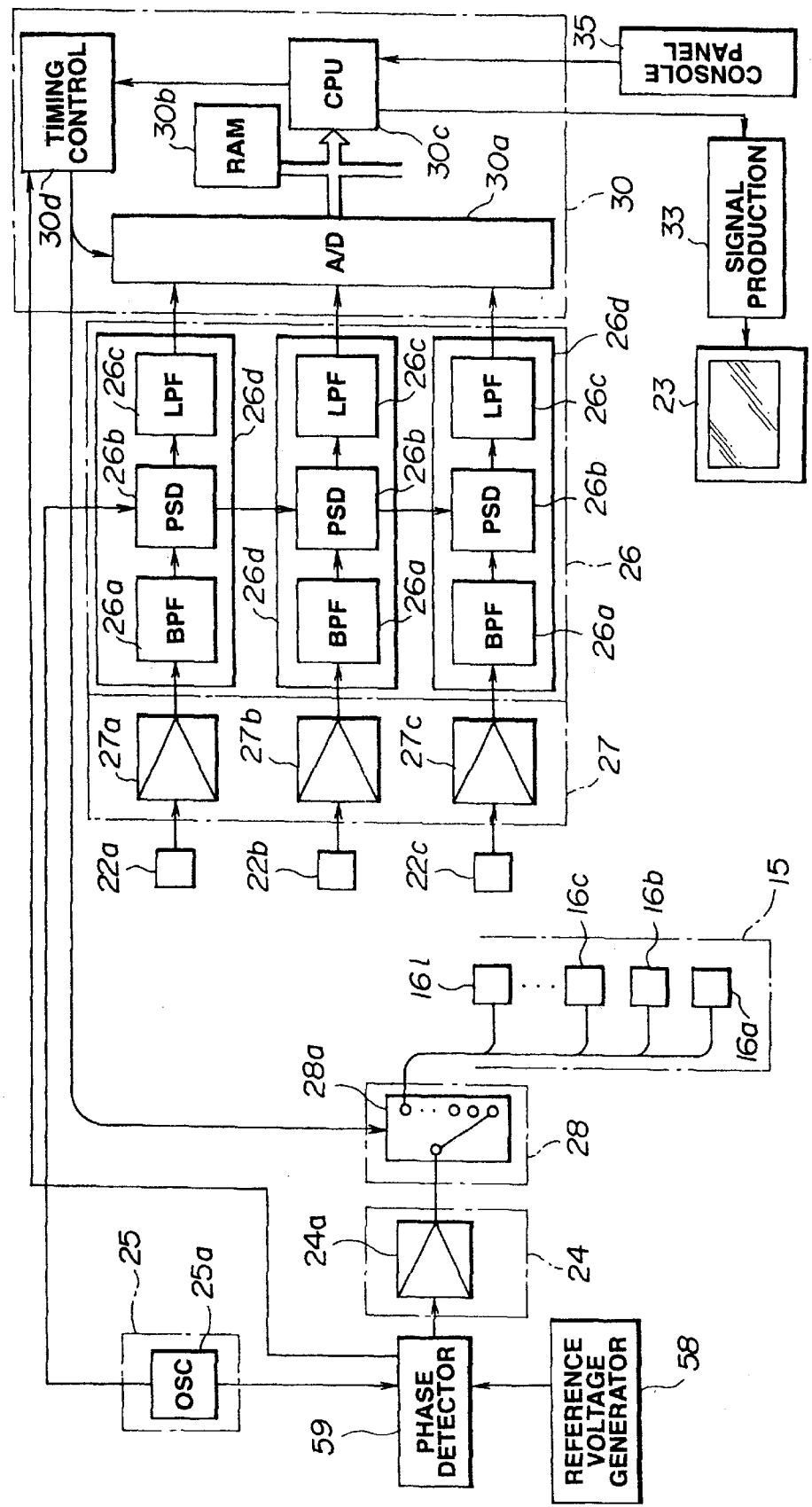
FIG. 44 is a block diagram showing an arrangement of the entire endoscope form detecting apparatus according to a first modification of the first embodiment.

By contrast thereto, in the present modification, as shown in FIG. 44, a phase detector 59 for detecting a phase comparison between a reference voltage output from a reference-voltage generator 58, and a signal output from the oscillator 25*a* and which outputs a phase angle suitable to drive each of the source coils 16*i* is arranged between the oscillator 25*a* and the amplifier 24*a*. Specifically, the arrangement is such that a drive signal is applied to each of the source coils 16*i* at timing of the phase angle which almost cancels transient response.

A reference-voltage generator 58 outputs a voltage value of a sine wave corresponding to an angle of power factor of each of the source coils 16*i*, to the phase detector 59 as reference voltage. The phase detector 59 outputs a phase detecting signal when the sine wave of the oscillator 25*a* is in agreement with the reference voltage, and the sine wave of the oscillator 25*a* passes toward the amplifier 24*a*.

Power is amplified through the phase detector 59 from the oscillator 25*a* which generates the sine wave, and drive current is supplied to each of the source coils 16*i* through contacts which are selected by a switching circuit 28*a*. The timing for supplying the drive current is performed in synchronism with the rising of the phase detecting signal which is transmitted to the timing control circuit 30*d* from the phase detector 59. Moreover, the voltage excited at both ends of the sense coil 22*j* is amplified whereby the timing at which the detecting signal detected in synchronism is read toward the CPU 30*c* through the A/D converter 30*a* is also performed in synchronism with the rising of the phase detecting signal.

Here, the phase detecting signal is produced as follows:

A signal e from the oscillator 25*a* which generates the sine wave which comes into a generating source of the drive signal can be expressed as follows:

$$e = EM \sin(\omega t + \theta) \; [V]$$

Here, Em: the maximum amplitude voltage [V], θ: initial phase [rad], ω=2πf, f: drive frequency [Hz], and t: time [s].

If it is assumed that an angle of power factor φi which is derived from pure resistance components Ri [Ω] and Li [H] for the respective source coils 16*i* are expressed as follows:

$$\phi i = \arctan(\omega i / Ri),$$

the following reference voltage:

$$V_{ref} = Em \sin \phi i \; [V]$$

and signal e [V] of a source of signal transmission are compared with each other by a comparator, whereby there can be produced a phase detecting signal when they are in agreement with each other.

The supplied drive current 1 [A] is:

$$i: A \sin(\omega t + \theta - \phi) - A \sin(\theta - \phi) \cdot \exp(-at)$$

Here, $A = Em / (R \cdot R + \omega L, \cdot \omega L)$, $a = R/L$

The above equation which expresses the drive current i indicates that the second term of the right-hand side comes into 0 when θ=φ. Accordingly, a transient direct current component is not generated. That is, coil drive under a steady condition can be performed from the switched moment.

Accordingly, it is made possible to perform reading of the detecting signal of the sense coil 22*j* toward the CPU at the same time of coil switching. In practice, reading is performed in consideration of the delay time until the voltage excited to the sensor coil 22*j* comes into an output from the synchronous detector 26*d*.

The source coil 16*i* is driven in this manner, whereby, even if switching of the number of source coils is performed, since the time from drive start to incorporation start of the detecting signal is considerably reduced, operation time of the whole system can be speeded up.

FIGS. 45*a*–45*d* are explanatory views of the timing of operation of drive of the source coils and reading of the detecting signal due to the sense coils, according to the modification. As will be seen from comparison with FIGS. 10*a*–10*d* which are timing explanatory view in the first embodiment, when the source coils are driven, a transient phenomenon is not almost generated in FIG. 45*d* and, accordingly, as shown in FIG. 45*d*, it is possible to perform reading of the detecting signal of the sense coil for a short period of time at after driving of the source coil.

Figure 46:
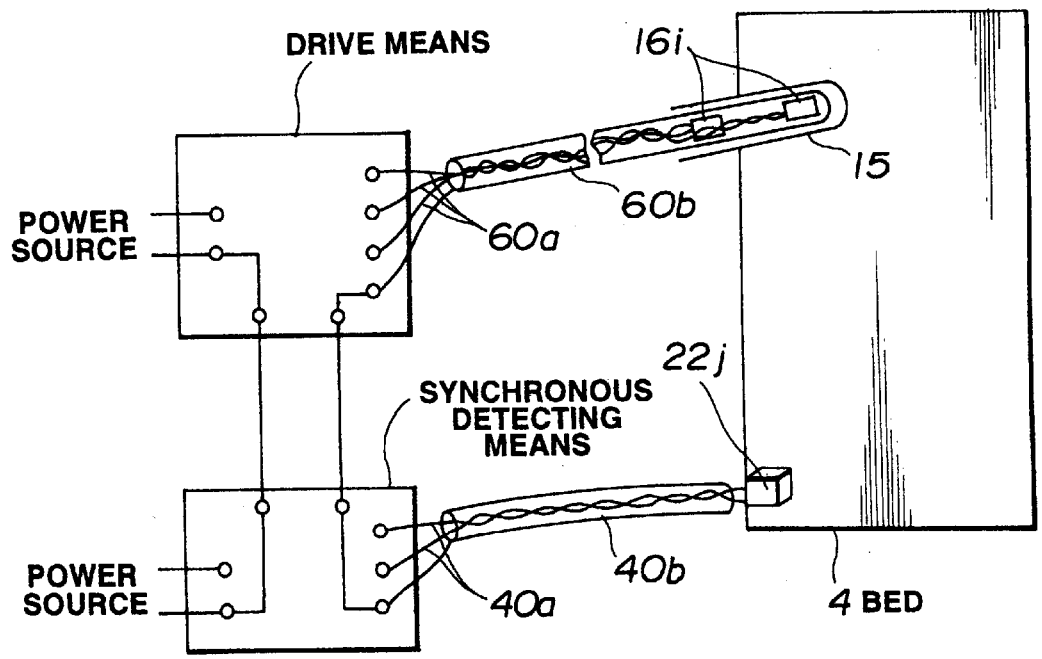
FIG. 46 is an explanatory view in which each of cables of the source coil and the sense coil is shielded.

Moreover, in the present modification, means for shielding a signal trunk line for precise measurement is provided. As shown in FIG. 46, a signal line for supplying drive current to the source coil 16*i* and a signal line for transmitting the detecting signal of the sense coil are such that every two connected coils are twisted whereby radiation from the signal lines and superimposition of the disturbances are reduced.

However, since the influence exists also in the twisted signal line to a certain degree, when the drive signal cable of the source coil approaches the sense coil, the detecting signal of the sense coil is swung to the order of 2~3 times by affection of the minute or microscopic electromagnetic wave radiated from the cable, or when a stray capacitance source such as a human body approaches the detecting signal capable of the coil, disturbance is superimposed on the signal line through the stray capacitance. Thus, an accurate measurement is impossible to perform.

The above-described problem is solved, and steady and correct or accurate measurement is performed. A specific method will next be described.

First, the drive signal cable 60*a* of the source coil 16*i* will be described. The cable 60*a* is connected to a probe 15 (indicated by a pair of source coils for simplification in FIG. 46) in which a plurality of source coils 16*i* are stored, sign wave current flows for successively driving each of the source coils 16*i*.

At this time, a component having the same frequency as the drive current, of the electromagnetic wave radiated from the signal line which is connected to each of the source coils 16*i* is superimposed on the signal line of the other source coils 16*i*, and the current flows also to the coils which are not required to be driven, to generate an undesirable magnetic field. Accordingly, the arrangement is such that, in order to absorb such an undesirable electromagnetic wave, the coil is covered with the shield 60b to the root of the coil as far as possible for each of the twisted cables, and the connecting end to the side of the drive means (for example, including the switching circuit 28, the amplifying circuit 24 or the like) is connected to the reference voltage of the drive means.

The detecting signal cable 40a of the sense coils 22j will be described next. The cable 40a has one end thereof which is connected to the three coils which form the three-axis sense coils 22j (in FIG. 46, only the pair of cables are shown for simplification). The other end of each sense coil 22j is connected to an input terminal of synchronous detecting means (amplifiers 27a~27c and the synchronous detecting circuit 26d in FIG. 8a).

The voltage which is transmitted by the cable 40a is a feeble or weak signal on the order of a few ten $\mu V$~1 Mv. Thus, there is case where the alternate current magnetic field from the source coil 16i is buried in a fluctuating portion which is superimposed on the cable 40a through the stray capacitance of the human body or the like. In view of this, the arrangement is such that, in order to absorb such unnecessary superimposing noises, the coil is covered by the shield 40b to the root of each of the coils, as far as possible, every switched cables, and a connecting terminal on the side of the synchronous detecting means is connected to reference voltage of the synchronous detecting means.

Further, the reference potential or voltage points of the drive means and the synchronous detecting means are connected to each other, and come to the same potential. With such an arrangement, influence of a leakage signal due to radiation and interference between the drive signal lines of the source coils 16i upon the sense coil 22j is almost eliminated, and influence of the sense coil 22j upon the detecting signal due to the human body is extremely reduced.

Accordingly, since it is possible to almost eliminate the noises which are included in the signal detected by the sense coil 22j, the signal component excited to the sense coil 22j by the alternate current magnetic field which is generated by the source coil 16i can accurately be measured.

A second modification of the first embodiment will next be described. The second modification provides greater accuracy of positional derivation.

When the region in which the source coil exists is accurately limited from the magnetic field strength which is produced by the sense coil which is positioned at a distance from the source coil, to calculate the three-dimensional position thereof, a minimum of three sense coils 22j are required in order to find out a narrow closed space (closed region).

However, in practice, when only three (3) sets of sense coils 22j are used, when the source coil 16i and the sense coil 22j are too close to each other, or far away from each other, there is the possibility in the single set of the three sets that the detecting signal is not surely produced. In that case, the closed space in which the source coil 16i exists cannot be limited to a narrow region. Accordingly, positional deviation of the source coil 16i is made substantially impossible.

Figure 47:
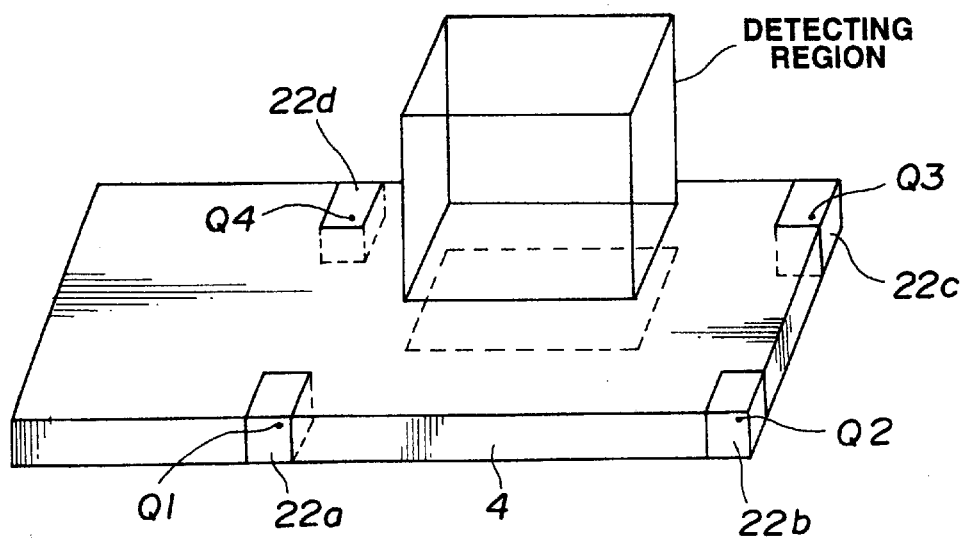
FIG. 47 is an explanatory view showing a state in which the sense coils are arranged at four (4) locations of a bed.

In view of the above, in the present modification, the positional deviation of the source coil is so arranged as to be performed always under the steady condition, not depending upon the level of the detecting signal. To this end, as shown in FIG. 47, four sets of three-axis sense coils 22j are used.

It is assumed that the detectable range of the sense coil 22j is within 30~100 cm of a radius, a required detecting region width is (x, y, z)=(40, 60, 40) [cm], and four three-axis sense coils 22j are installed on the endoscope inspection bed 4 whose size is (200×70 cm) respectively at positions whose coordinates are Qa (0, 0, 0), Qb (60, 0, 0), Qc (60, 100, 0) and Qd (0, 100, 0) [unit is cm].

Then, the required detecting region width is included in a square pole in which the four points are apexes coming into a bottom surface. In the setting, when the source coil 16i is moved within the detecting region, if distances to the four sets of sense coils 22j are within 30~100 cm, it is possible to precisely perform positional derivation.

Moreover, of the four sets, when the distance to the one set of sense coils 22j is less than 30 cm, the positional derivation is performed by the use of the detecting signal of the other three sets of sense coils 22j.

In the above-described setting, the arrangement is such that, when the distance to the one set of sense coils 22j is less than 30 cm, the other three sets have a distance equal to or greater than 30 cm. Accordingly, it is possible to produce the detecting signals of the three sets with certainty. Thus, it is possible to accurately perform positional detection (or positional estimation). Moreover, also when combination in which the distance between the source coil 16i and the sense coil 22j is greater than 100 cm is a single set, similarity is applicable to the distance less than 30 cm.

However, there may be a situation in which the distance between the source coil 16i and the sense coil 22j is greater than 100 cm is equal to or more than two sets. At this time, the drive current through the source coil 16i increases, or the sensitivity of the output from the sense coil 22j is improved, whereby measurement is again performed such that the detectable distance is lengthened, to repeat the processing until three sets or more are within the detectable range. Thus, it is possible to perform positional derivation of the source coil 22j.

In connection with the above, when the condition that two of the four sets are not utilizable for positional detection because the size of the bed 4 or detecting range of the sense coil 22j is different from the above-described value or the range, substantially the same method may be used.

For example, when the detecting region is desired to be wider, if the spacing between the sense coils 22j is increased, and if combination is made to the drive current increase of the source coil 16i and the sensitivity increase of the output form the sense coil 22j, it is possible to secure the detecting region width. However, it is impossible to widen the detecting region width as it is in the widthwise direction (y-direction) of the bed 4 equal to or more than the bed width.

In view of the above, the detectable range is shifted or deviated toward the sense coil 22j by a drive current decrease of the source coil 16i and the sensitivity decrease of the output from the sense coil 22j such that three or more sets and more are within the detectable range, whereby it is possible to perform the positional derivation or rendering of the source coil 16i.

By the method described above, it is possible to perform the positional derivation of the source coil always under the steady condition, irrespective of the level of the detecting signal. Further, in the positional derivation of the source coil in all the above-described cases, the magnitude of the closed space decreases such that the number of sets of the sense coils increases more than three sets and, accordingly, the accuracy of the positional derivation is improved. For this reason, the detecting signal of the sense coil in which the source coil exists within the detectable range are all utilized for the positional derivation, whereby it is possible to provide or produce found-out accuracy.

Figure 48:
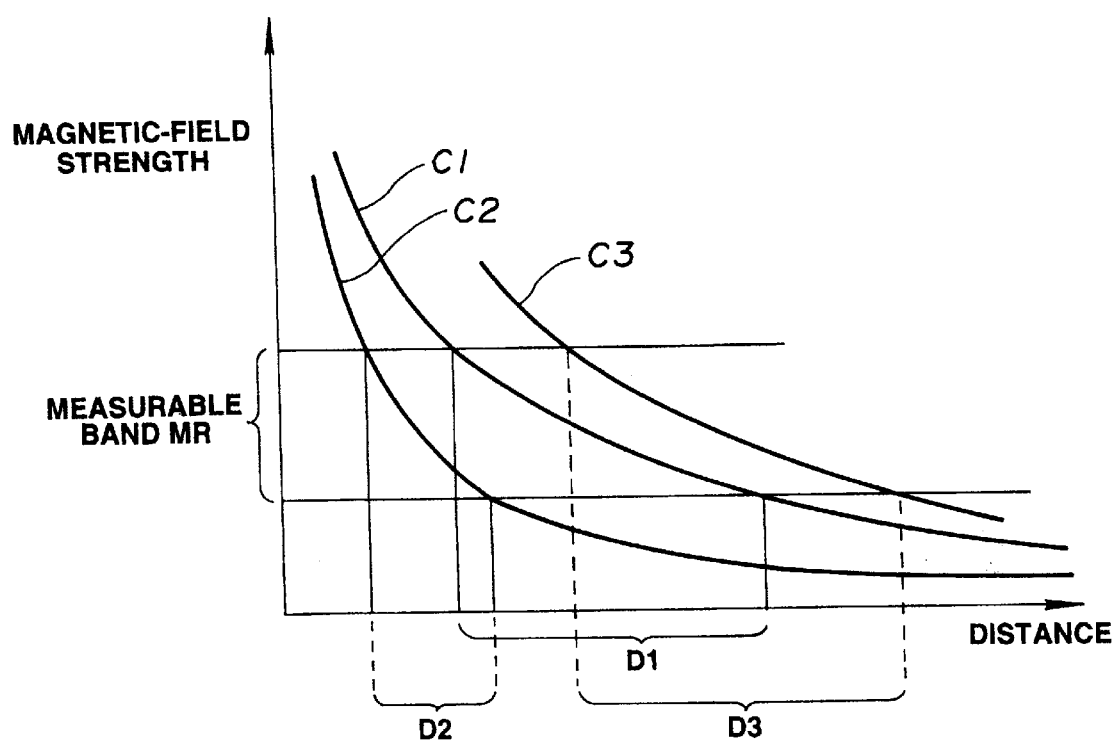
FIG. 48 is a graph showing a function in which a detecting range or scope is modified by up, down (increase, decrease) or the like of driving current in a second modification of the first embodiment.

FIG. 48 is an explanatory view of the above-described method. A curved line C1 in FIG. 48 shows a graph on the side of, for example, the maximum magnetic-field strength of measurement data of the magnetic-field strength with respect to the relative distance for calculating the relative distance which has been described in FIG. 16. When a magnetic-field value is practically detected from the detecting signal due to the sense coil 22j, a distance between the source coil 16i and the sense coil 22j exists, from the magnetic-field strength value, in a range between the curved line C1 which is intersected with the strength value, and a graph on the side of the minimum magnetic-field strength (not shown).

The signal detected by the sense coil 22j is limited in accurately detachable scope by a dynamic range of the amplifier.

For this reason, under the normal setting condition (of the sensitivity), a detecting range D1 under the normal condition indicated in a lateral axis direction comes into a detectable distance range correspondingly to an output value of a measurable range MR indicated in a longitudinal axis direction with respect to the curve line C1 (which corresponds to the radius 30~100 cm due to the sense coil 22j). In this case, if the gain of the amplifier decreases (that is, the sensitivity decreases), it is possible to shift the detectable region toward the side of a smaller region, and it is possible to shift the detectable region toward the side of a smaller radius even if the value of the drive current for driving the source coil 16i decreases.

That is, if the drive current decreases or the gain of the amplifier decreases, a range detectable by the output value due to the sense coil 22j is determined by a curved line C2 in which a value in the longitudinal axis direction of the curved line C1 decreases relatively. In this case, the detecting range is represented by D2, and detection on the side of a smaller distance is made possible.

Conversely, if the drive current increases or the sensitivity increases, the range detectable by the output value due to the sense coil 22j is determined by the curved line C3 in which the value of the curved line C1 in the longitudinal axis direction relatively increases. In this case, a detecting range is represented by D3, and detection on the side of a large distance is made possible.

Figure 49:
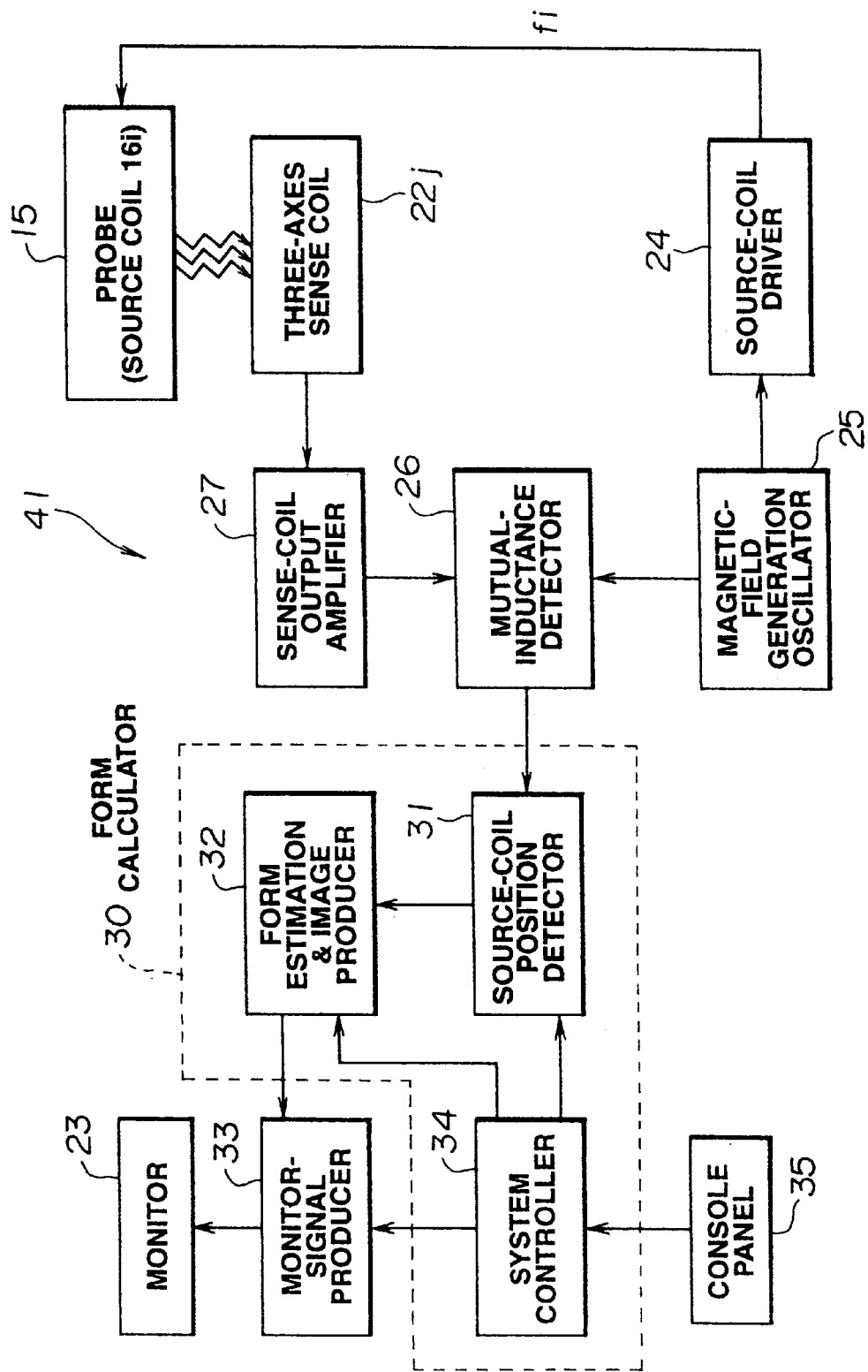
FIGS. 49 to 52 relate to a second embodiment of the invention, FIG. 49 being a block diagram showing an arrangement of the whole of an endoscope form detecting apparatus according to the second embodiment.

Next, a second embodiment of the invention will be described with reference to FIG. 49. An endoscope form detecting apparatus 41 in FIG. 49 is arranged such that the frequency of the drive signal is changed to omit the distributor 28 in FIG. 2.

Accordingly, the source-coil driver 24 outputs a drive signal having frequencies fi which are different from each other for every source coil 16i. The drive signals of the frequencies fi which are different from each other every source coil 16i are applied whereby the plurality of source coils 16i are simultaneously driven to realize high-speed processing.

In the endoscope form detecting apparatus 3 according to the first embodiment, the arrangement is such that the plurality of source coils 16i are driven in order from the coils arranged at the forward end side, or the like, by the sine wave current of a specific frequency, and by the detecting signal level of the sense coil 22j at that time, to produce detecting signals for detecting the positional coordinates of the source coils 16i one-by-one.

However, in this system, if the number of source coils 16i increases, time taken for one form detection increases. Accordingly, it is made difficult to fetch the form data at real time.

In view of the above, in the present embodiment, the data of the form calculation can be so arranged as to be fetched at the real time without influence of the number of the source coils 16i. Specific arrangement will next be shown in FIG. 50.

Figure 50:
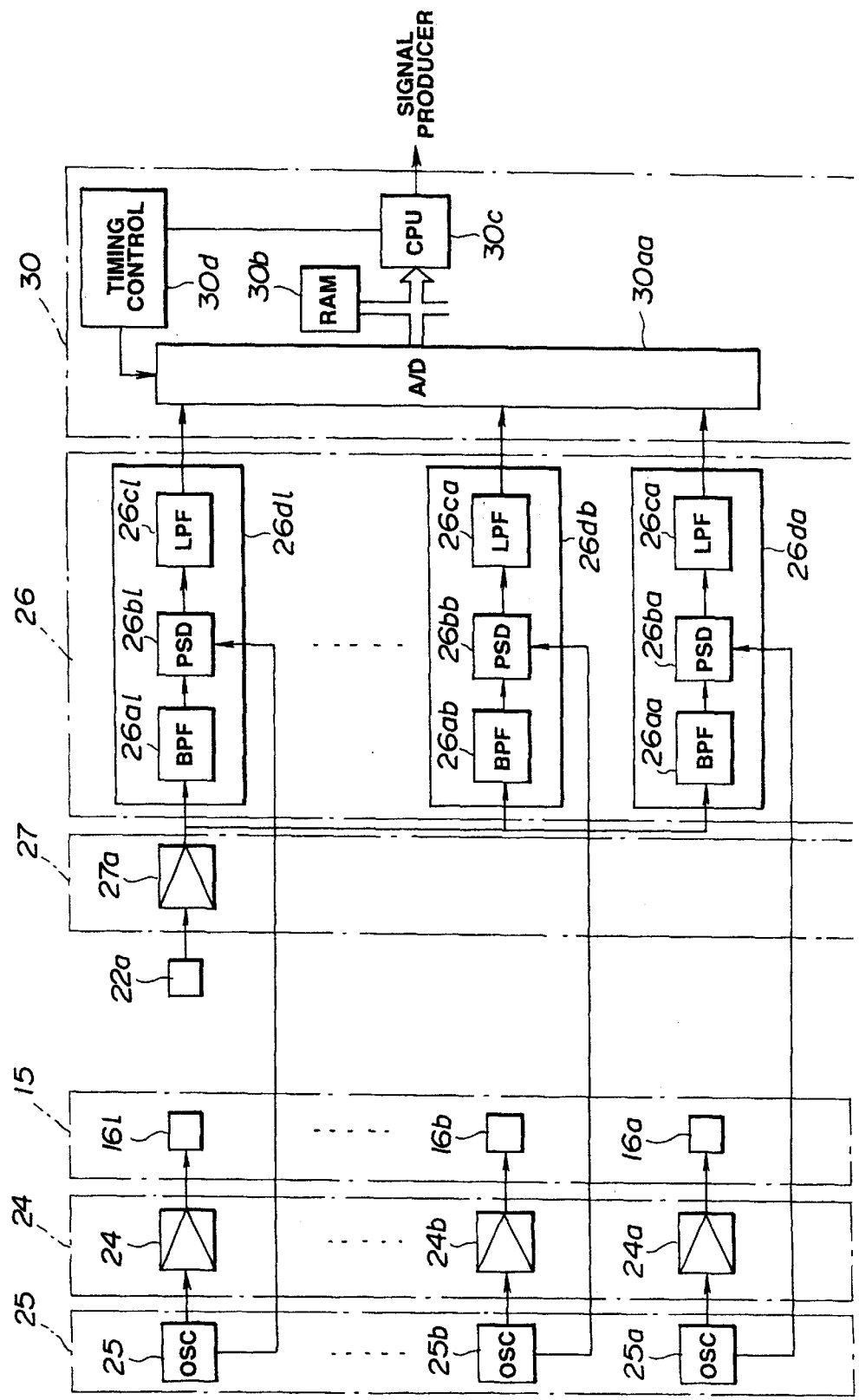

The situation where, for example, the form of the probe which builds therein twelve (12) source coils 16i is detected will be described. As shown in FIG. 50, an oscillator 25 has oscillators 25a, 25b, . . . 25l which oscillates at frequencies which are different from each other. Current is amplified by amplifiers 24a, 24b, . . . 24l which cooperate with each other to form a driver 24 and, thereafter, is simultaneously applied to the source coils 16a, 16b, . . . 16l, respectively, to generate magnetic fields of frequencies different from each other.

Meanwhile, each of the sense coils 22j generates detecting signals which are in proportion to the magnetic-field strength. The detecting signals are amplified by the amplifier 27j and, thereafter, simultaneous detection is performed, referring to the signal of the oscillator 25i by synchronous detecting circuits 26di which forms the detector 26, to extract only a signal component in proportion to the magnetic-field strength at the position of the sense coil 22j due to the source coil 16i. In this connection, a band pass filter 26ai of each of the synchronous detecting circuits 26di is set to a band which passes only a signal of the frequency of the oscillator 25i.

Each of the signals which are synchronously detected at each of the synchronous detecting circuits 26di is sampled at high speed by an A/D converter 30aj (each of the sense coils 22j comprises three coils) of, for example, 12×3 channels, and are temporarily stored in a RAM which is provided at the A/D converter 30aj or a RAM 30b which is connected to the A/D converter 30aj. The data of the RAM 30b are read onto the side of the CPU 30c. Thus, processing of positional calculation and form estimation is performed. The other arrangements are similar to that shown in FIG. 8a, and the description thereof will be omitted.

Figure 51:
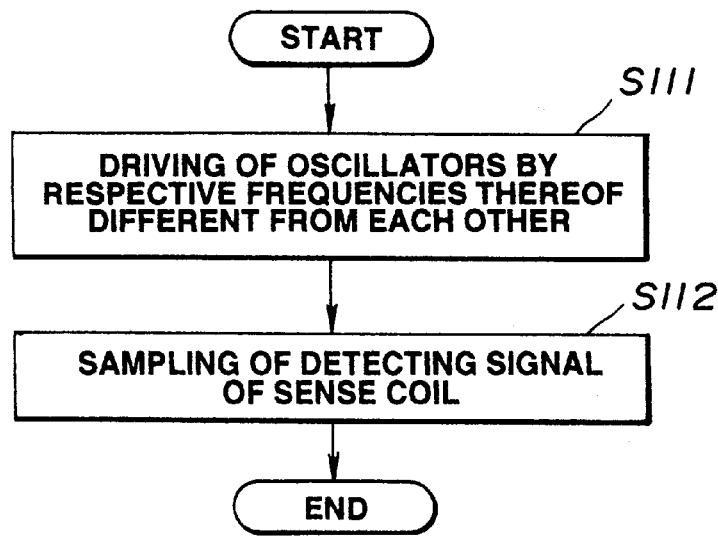

A flow indicating the processing contents of driving of the source coil 16i and data fetching at the sense coil, in the present embodiment, is shown in FIG. 51. In Step S111, the oscillators 25i are driven by the frequencies which are different from each other to cause the drive current to flow through the source coils 16i. Next, the detecting signals of the respective sense coils 22j are sampled. In this case, since a condition can be made in which the drive current flows through the source coils 16i, the detecting signals of the respective sense coils 22j can be sampled without delay only through the time of transient response. Of course, immediately after the drive current has first flowed, the transient response is considered.

As will be seen from comparison with FIG. 9, it is possible to fetch the data for positional detection or form detection for a short period of time.

Moreover, in the present embodiment, since it is possible to fetch the data for positional detection or form detection for a short period of time, in case of rapid movement of the insertion part, it is made possible to perform highly accurate form estimation.

In connection with the above, twelve (12), for example, source coils 16i generate simultaneously alternate-current magnetic fields by drive currents of frequencies (for example, 10. 0, 10. 5, 11. 0, 11. 5, 12. 0, 12. 5, 13. 0, 13. 5, 14. 0, 14. 5, 15.0, 15, and 5 [Khz]) which are different from each other and which are not integral times.

Figure 52:
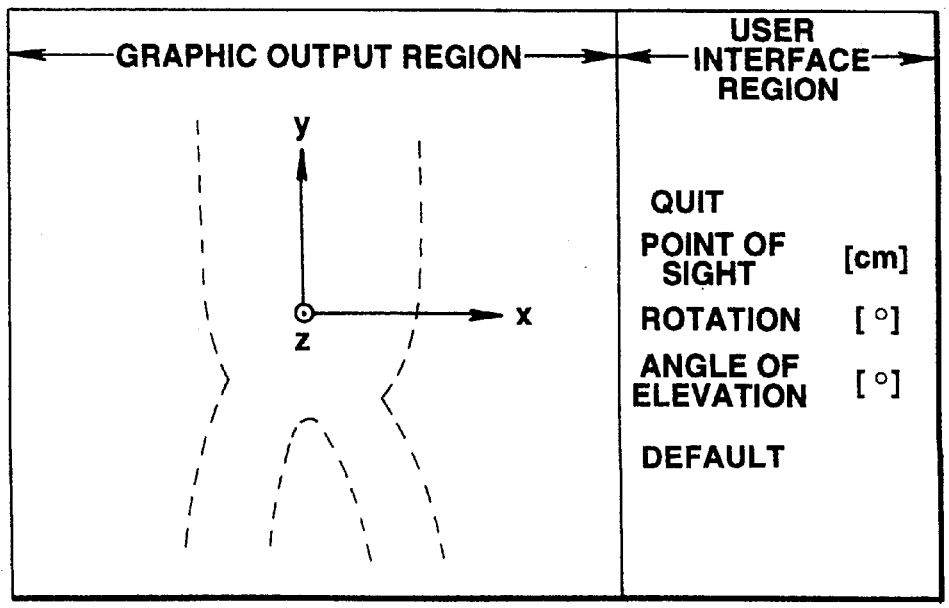

According to the above arrangement, it is possible to derive the positions of the plurality of (twelve (12), for example) source coils by time which is taken for a single source coil having the arrangement of the first embodiment. Further, in the present embodiment, when the endoscope form is displayed on the monitor image plane, the endoscope form is outputted in superimposition on a model pattern of a patient as shown in FIG. 52. In FIG. 52, the left-hand region is a graphic output region, while the right-hand region is a user interface region in which a user sets the point of sight, the rotational angle, an angle of attack formed between the visual-point position and the z-axis or the like. The other advantages are substantially similar to those in the first embodiment.

Figure 53:
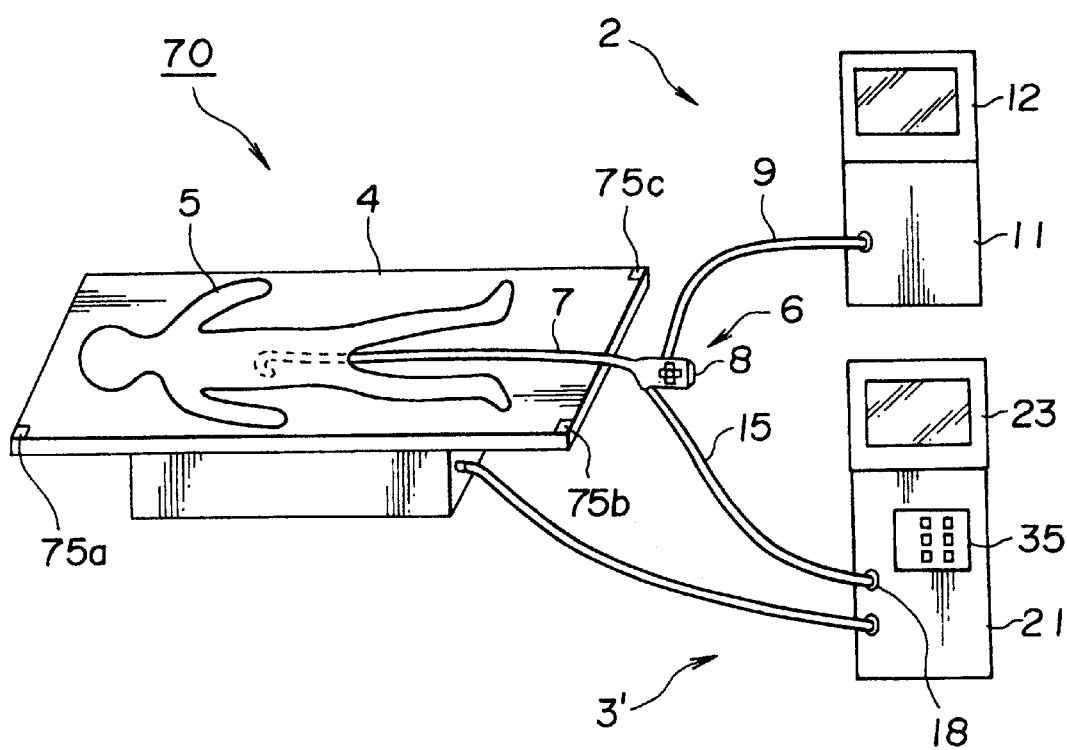
FIGS. 53 to 59 relate to a third embodiment of the invention, FIG. 53 being an arrangement view showing the whole arrangement of an endoscope system.
Figure 55A:
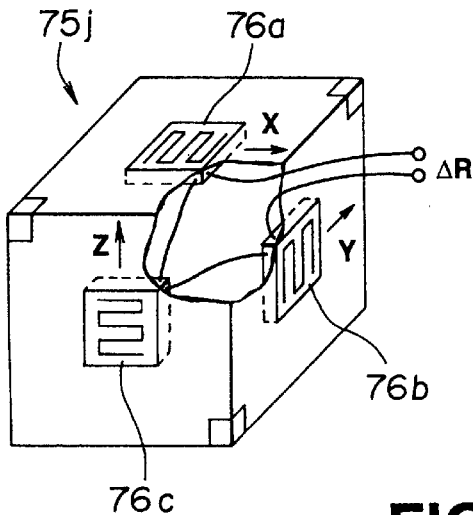
FIG. 55a is a perspective view of a sensor which is formed by a magnetic resistive element, 55b is a view showing an equivalent circuit thereof.

FIG. 53 shows an endoscope system 70 which is provided with a third embodiment of the invention. The system 70 uses a sensor 75j which is formed by magnetic resistance elements (hereinafter referred simply to as "MR element") 76a, 76b and 76c as shown in FIG. 55a, in place of the three-axis sense coil 22j, in the system illustrated in FIG. 1. The resistance elements 75a, 75b, and 75c are mounted respectively on known three (3) (or four(4)) positions at corners of the bed 4.

Figure 54:
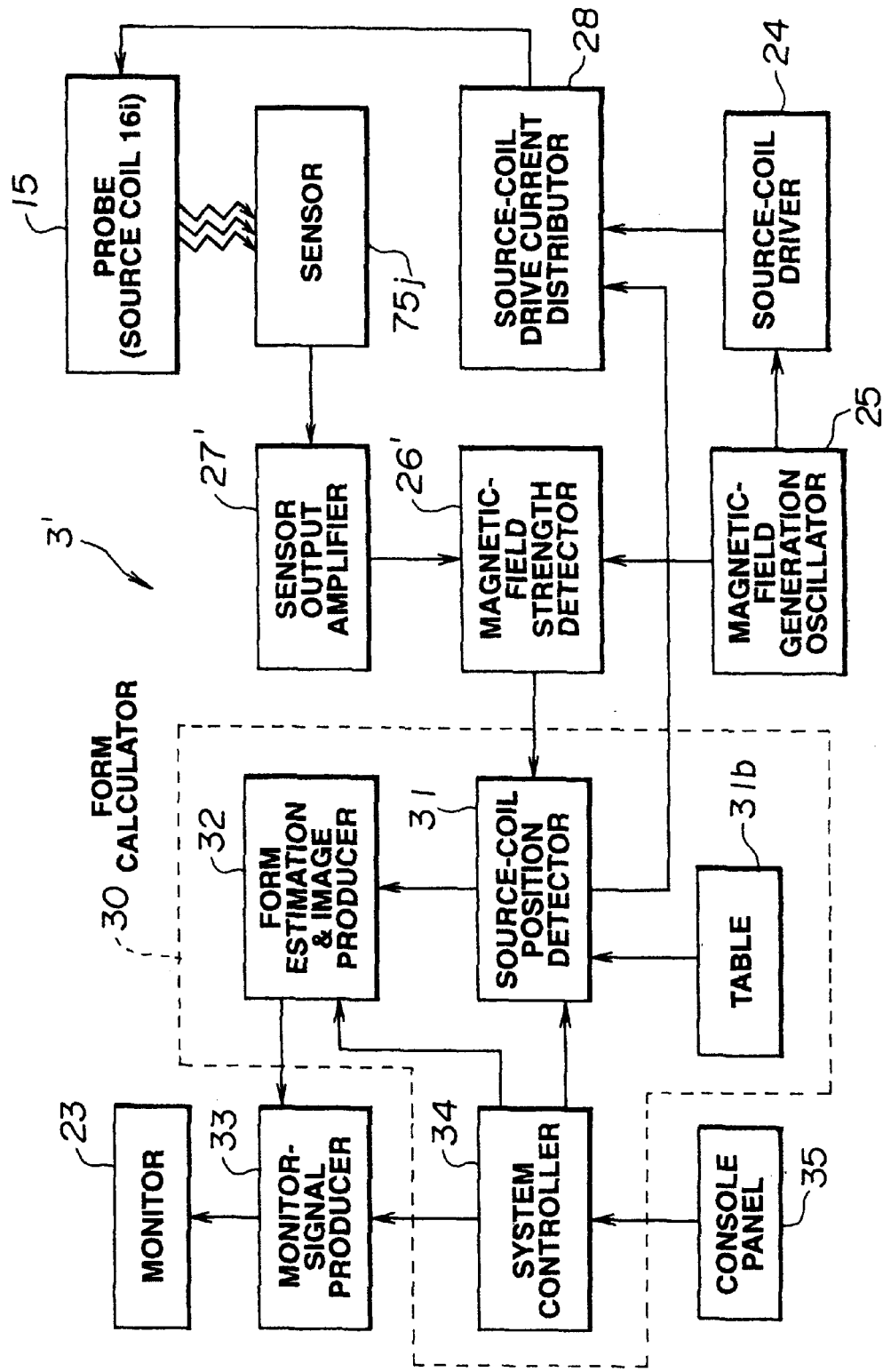

Furthermore, the arrangement of an endoscope form detecting apparatus 3' in the system 70 is shown in FIG. 54. In FIG. 54, the apparatus 3' uses the sensor 75j formed of the MR elements 76a, 76b and 76c in place of the three-axis sense coil 22j. Further, the sense-coil output amplifier 27 comes into a sensor output amplifier 27', and uses a magnetic-field strength detector 26' in place of the mutual-inductance detector 26.

Further, the source-coil position detector 31 refers to data on a table 31b which stores therein reference data, to perform positional detection or positional estimation.

As shown in FIG. 55a, each of the sensors 75j is arranged such that the three (3) MR elements 76a, 76b and 76c in which resistance values are varied in accordance with the magnetic-field strengths are mounted respectively on three planes or surfaces of a cube or a regular hexahedron, which are perpendicular to each other and which are adjoined to each other, and a sensor 75 which is formed in such a manner that these three MR elements 76a, 76b and 76c are connected in series to each other has a pair of terminals which are made to an output terminal of the detecting signal of the magnetic-field strength.

In this case, the MR elements 76a, 76b and 76c are provided such that each resistance value is varied from a reference value by magnetic-field strength components in X, Y and Z directions.

Figure 55B:
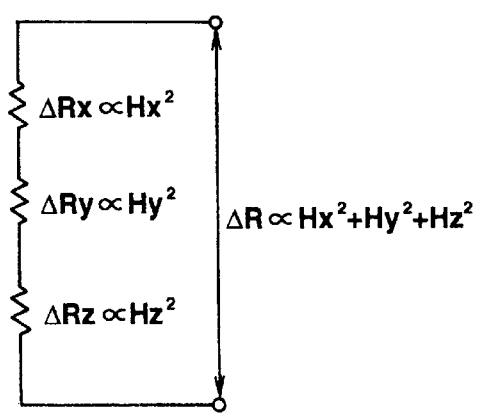
FIG. 55c is a characteristic view thereof.
Figure 55C:
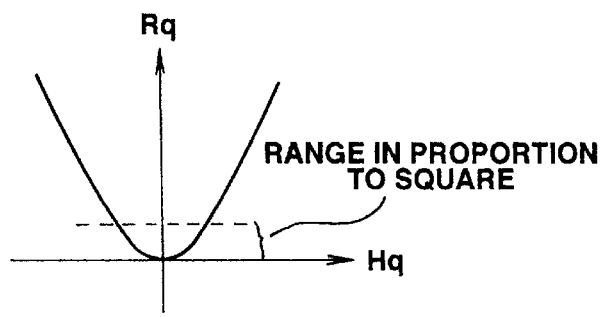

A resistance varying component $\Delta R_q$ of each of the MR elements 76q is varied in proportion to a square of the magnetic field Hq as shown in FIG. 55c. Accordingly, the resistance varying component $\Delta R$ of the pair of terminals of the sensor 75j is the sum of squares of the respective magnetic-field components Hx, Hy and Hz in x-, y- and z-directions as shown in FIG. 55b.

In the present embodiment a signal in proportion to the squared sum of the magnetic-field strength can directly be detected from the output from the sensor 75j. The signal is such that the magnetic-field strength is detected by calculation of the square root by the magnetic-field strength detector 26'.

Moreover, at the source-coil position detector 31, the data of the table 31b is referred to perform the position calculation of each of the source coils 16i.

The data of the table 31b are produced similarly to the first embodiment. That is, in FIG. 17a, the sensor 75j is arranged in place of the three-axis sense coil 22, and reference data of the curved line Cu of the maximum magnetic-field strength and the curved line cu of the minimum magnetic-field strength as shown in FIG. 17b are tabled.

Figure 56:
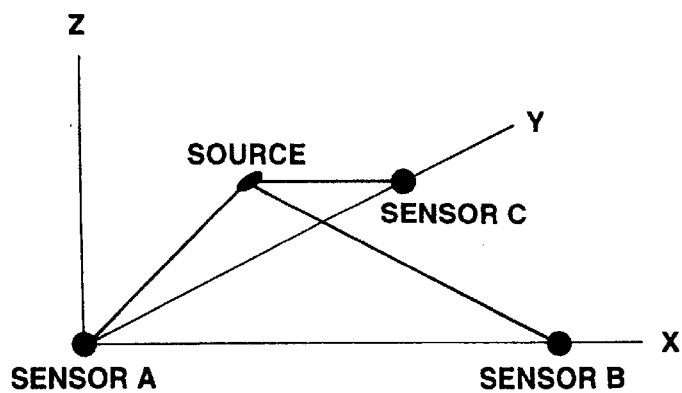

In FIG. 56, if the sensors A, B and C (corresponding respectively to 75a, 75b and 75c) are arranged at the three (3) known positions, and if one of the plurality of sources (the source coil 16i, for example) is driven, outputs corresponding to the positional relationship with respect to the source are generated at the sensors A, B and C.

The outputs from the sensors A, B and C at that time are assumed to be va, vb and vc. Further, data of the sensor outputs and spatial coordinate groups which would come into the outputs are secured into a memory or the like, concerning each of the sensors, previously.

Figure 57:
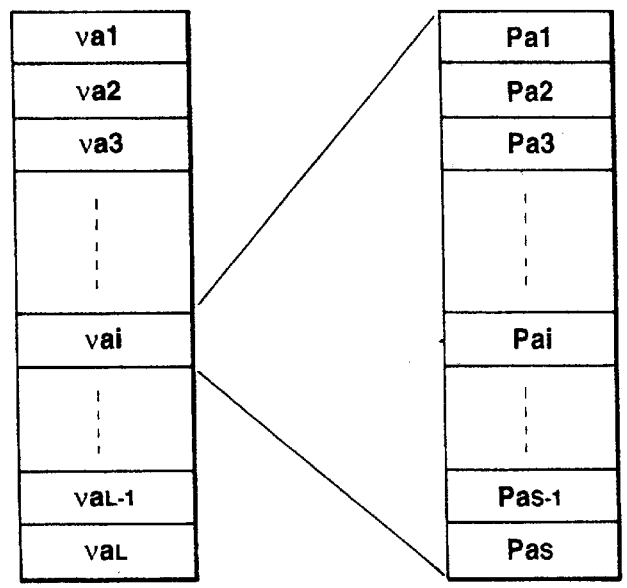

FIG. 57 shows a data table regarding the sensor A, for example. Now, a sensor output va which is produced when there exists a single source at a position, to generate the magnetic field is compared with val~vaL of the table in FIG. 57, to derive an integer 1 which satisfies $val \leq va < vak$ (k=1+1).

Similarly, integers m and n which satisfy a condition also with respect to the other sensor outputs vb and vc are determined.

Figure 58:
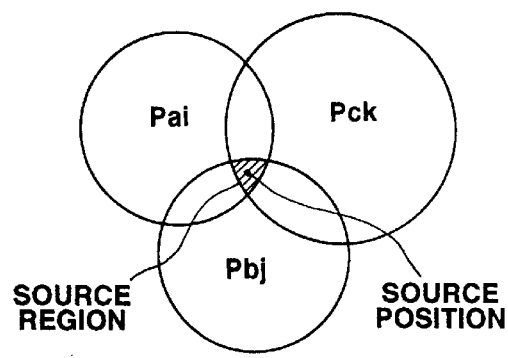

At this time, there exist spatial coordinate group Pai, Pbj and Pck corresponding respectively to the output data val, vbm and vcn which satisfy the condition. The relationship therebetween is as shown in FIG. 58. Accordingly, a three-dimensional region which is a region common to them comes into a spatial coordinate region of the source. Moreover, a gravitational center position of the region may be determined so as to come into a three-dimensional position of the source. Processing to connect the thus found plurality of spatial coordinate regions of the source (or spatial coordinate position found out from their center of gravity) to each other, or the like is performed. Moreover, by form estimation, the inserted form of the endoscope can be determined.

The three-dimensional positions or regions which are determined by FIG. 58 are connected to each other by a line or the like which passes through the gravitational center positions of the respective regions. The form of the insertion part is estimated to perform model display of the insertion-part form on the monitor image plane. When displayed more briefly, as shown in FIG. 59, the arrangement may be such that only the three-dimensional region or the three-dimensional position of the source coil estimated as shown in FIG. 58 is 3D–2D projected and is displayed on the monitor image plane to omit the model display of the insertion-part form (the dotted line in FIG. 59 represents interpolation, and display may be made with the interpolation omitted).

Since the third embodiment performs the positional detection by the use of the table substantially similarly to the first embodiment, the processing time of the positional detection or the positional estimation can be shortened or reduced. Further, since the arrangement is such that the sum of the signals which are in proportion to the root of the magnetic-field strengths in the three directions can directly be measured by the MR element, the processing of the magnetic-field strength calculation can be performed at high speed. Moreover, because the insertion-part form is displayed while omitting processing of painting the insertion-part form in the manner of the model, the summary of outline of the insertion-part form of the insertion part can be displayed with extremely high speed.

Figure 59:
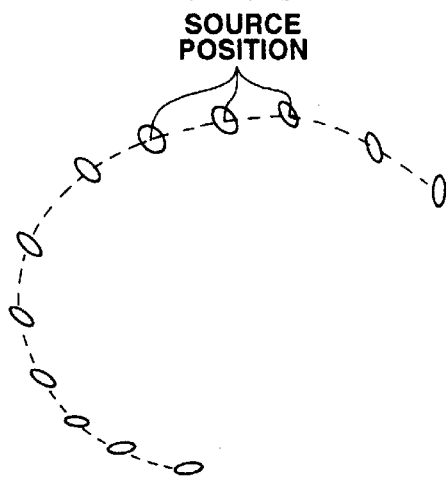

Furthermore, the arrangement may be such that, first, display is accomplished as shown in FIG. 59 and, thereafter, painting is accomplished by a model (the aforesaid n-prismatic model or the like) which is easier to be understood in a visual manner.

Figure 60A:
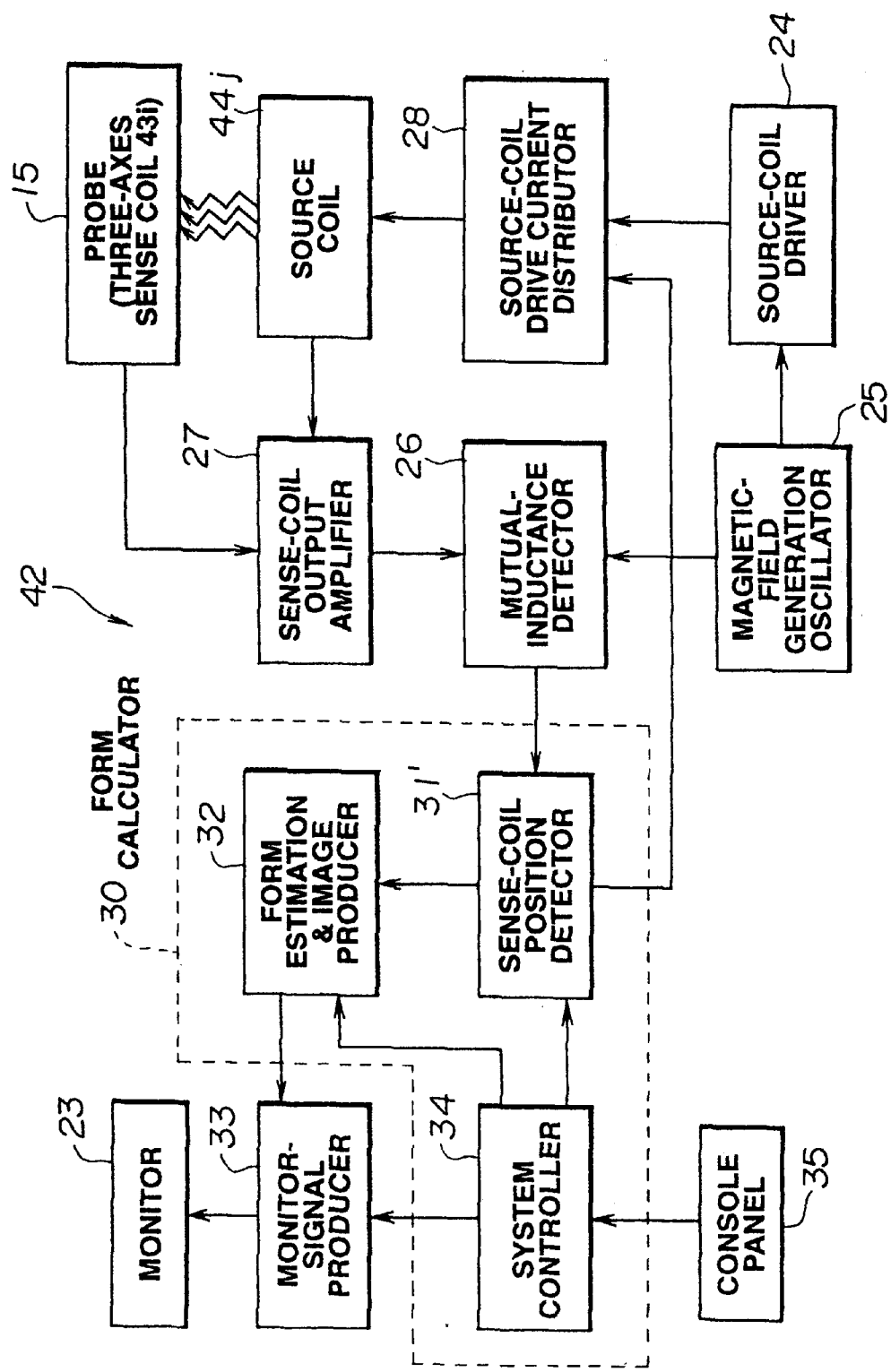
FIG. 60a is a block diagram showing an arrangement of an endoscope form detecting apparatus according to a fourth embodiment of the invention.

FIG. 60a shows an endoscope form detecting apparatus 42 according to a fourth embodiment of the invention. The third embodiment is arranged such that, in FIG. 2, the plurality of sensors, that is, the plurality of sense coils 43i, are built in on the side of the probe 15, and the magnetic-field generating source, that is, the plurality of three-axis source coils 44j, are arranged on the side of the bed. Similarly to the first embodiment, establishment is made into the endoscope 4 and to the bed 4 with respect to positions which become known.

Accordingly, the drive signals which pass through the distributor 28 are successively applied to the three-axis source coils 44 j, and the signal detected by the sense coil 43i on the side of the probe 15 is amplified by the amplifier 27. The signal is inputted to the (sense coil) position detector 31' which passes through the detector 26 to form the form calculator 30.

The position detector 31' relatively detects the position of the sense coil 43i with the three-axis source coil 44j serving as a reference.

The other arrangement is similar to that of the first embodiment. Further, the advantages of the modification are also substantially similar to those of the first embodiment.

Figure 60B:
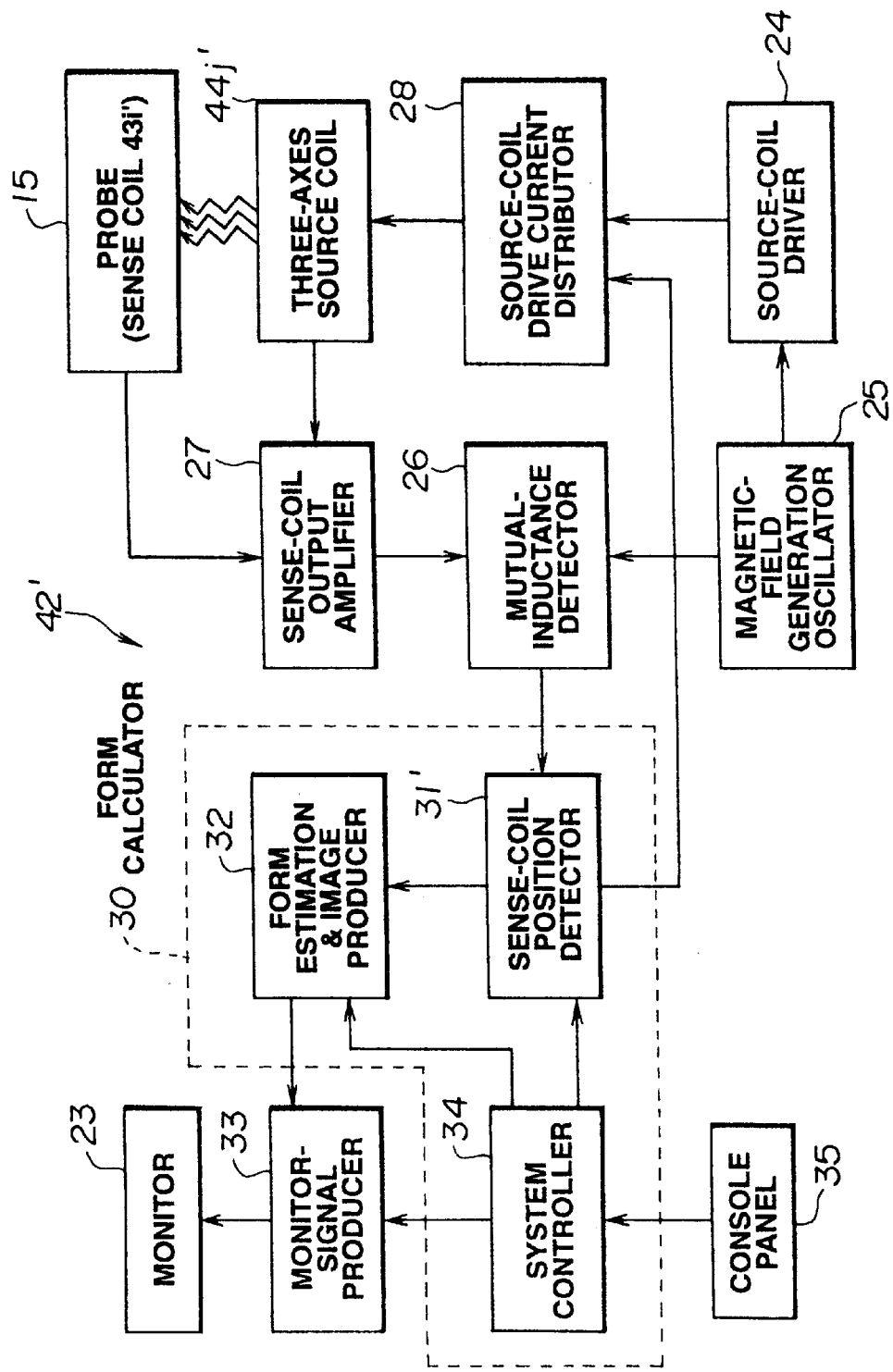
FIG. 60b is a block diagram showing an arrangement of an endoscope form detecting apparatus according to a modification of the fourth embodiment.

FIG. 60b shows an endoscope form detecting apparatus 42' according to a modification of the fourth embodiment. The modification is arranged such that, in FIG. 53a, the three-axis sense coil 43i is changed to a single-axis sense coil 43i', and the single-axis source coil 44j is changed to a three-axis source coil 44j'. The other arrangements are similar to that of the third embodiment. Moreover, the advantages are also substantially the same as those of the third embodiment.

Figure 61A:
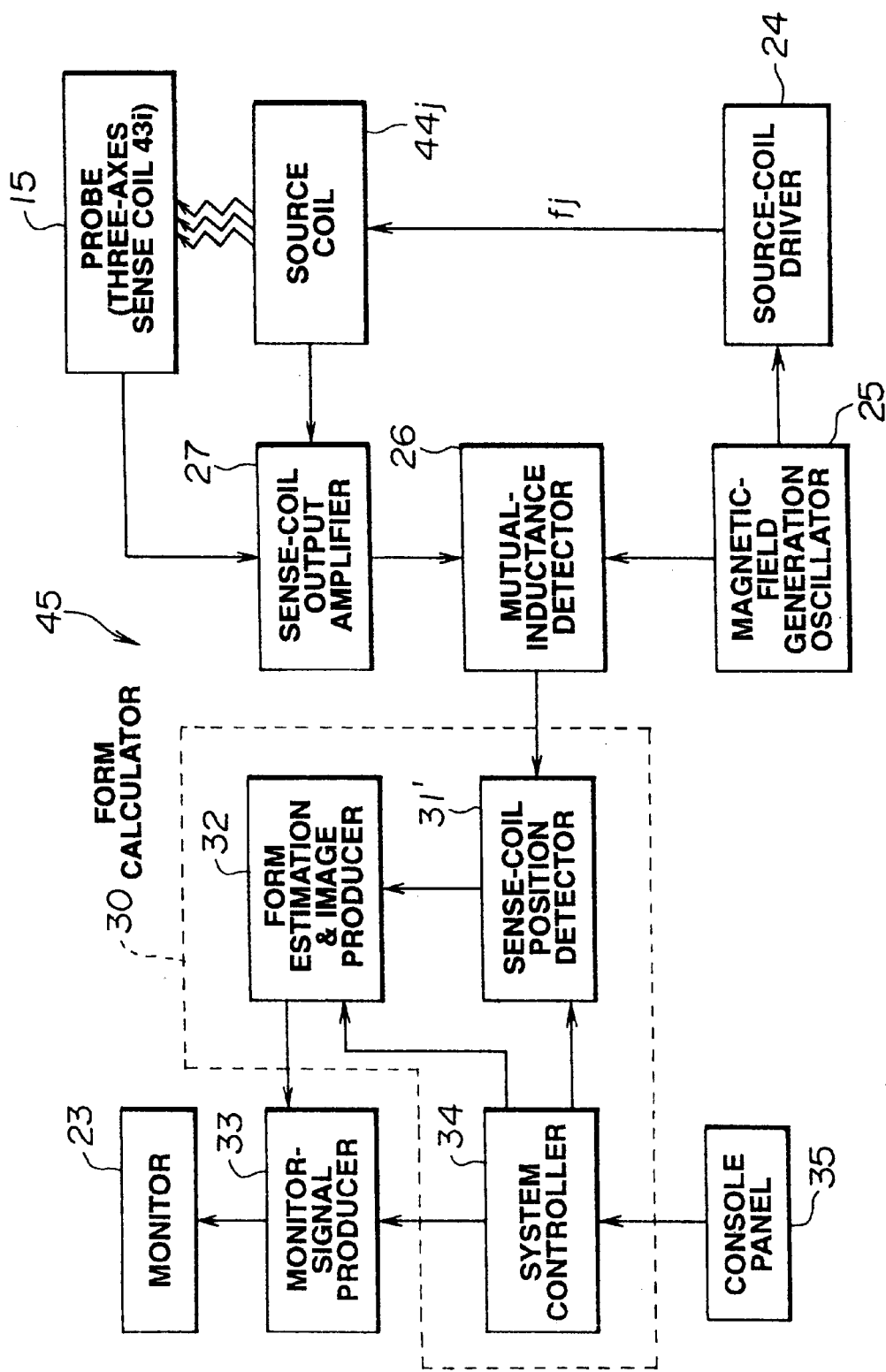
FIG. 61a is a block diagram showing an arrangement of an endoscope form detecting apparatus according to fifth embodiment of the invention.
Figure 61B:
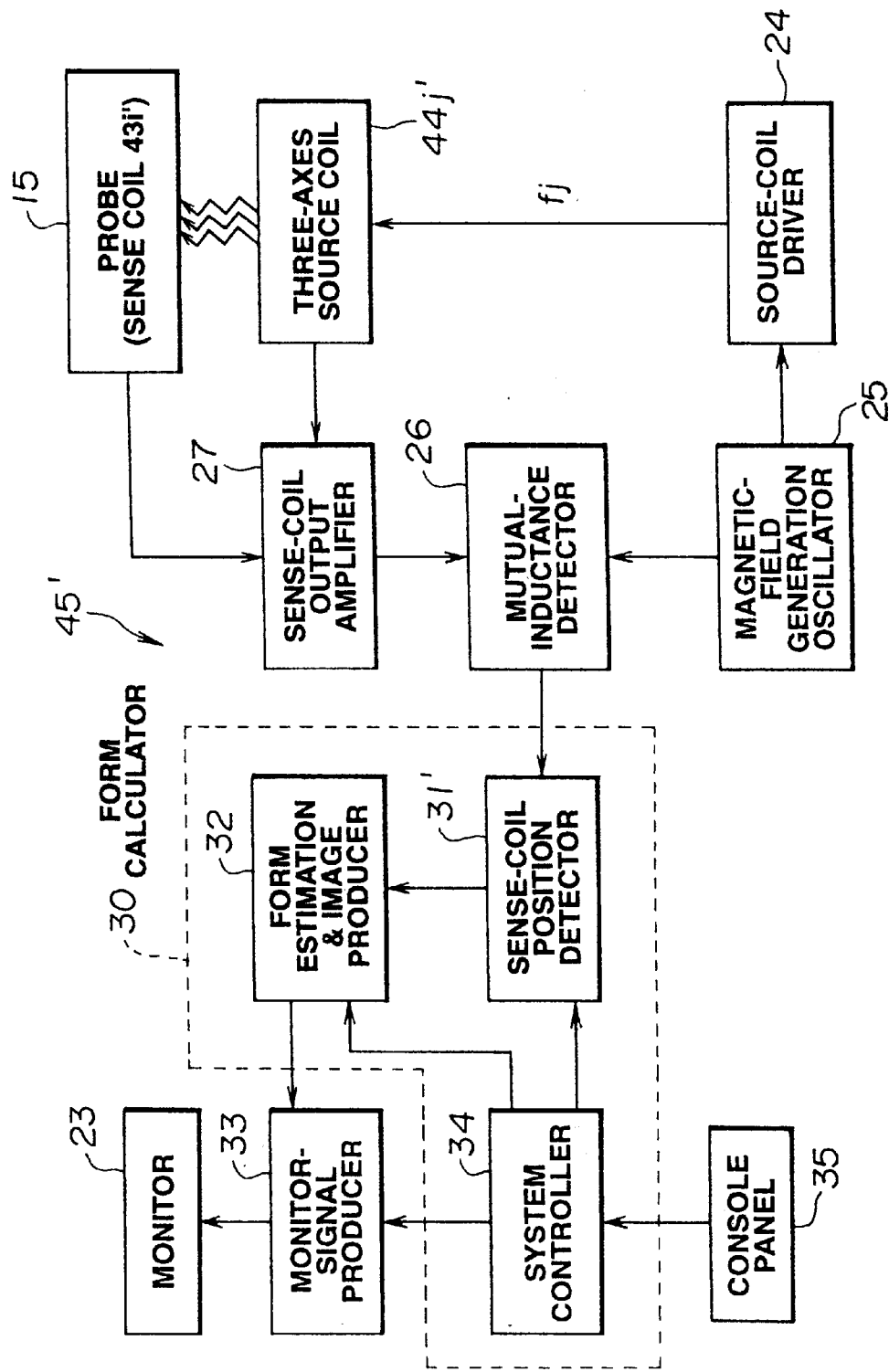
FIG. 61b is a block diagram showing an arrangement of an endoscope form detecting apparatus according to a modification of the fifth embodiment.

FIG. 61a shows an endoscope form detecting apparatus 45 according to a fifth embodiment of the invention. The fifth embodiment is arranged such that, in FIG. 60a, the frequency of the drive signal is changed to omit the distributor 28 shown in FIG. 60a.

Accordingly, a driver 24 outputs a drive signal of frequencies different from each other for each of the source coils 44j. The other arrangements are similar to that of the fourth embodiment. Advantages of the fifth embodiment are also substantially similar to those of the second embodiment.

In connection with the above, in the first to the fifth embodiments or the modifications thereof, the arrangement may be such that, after amplification, the signal from the sense coil is digital-converted to perform digital-signal processing of all the subsequent detection or the like.

Moreover, the arrangement may be such that a single source coil or sense coil is built only in the forward end of the endoscope which is the position of greatest interest. In that case, the detecting apparatus functions as an endoscope forward-end position detecting apparatus for detecting the position of the forward end of the endoscope.

Figure 62:
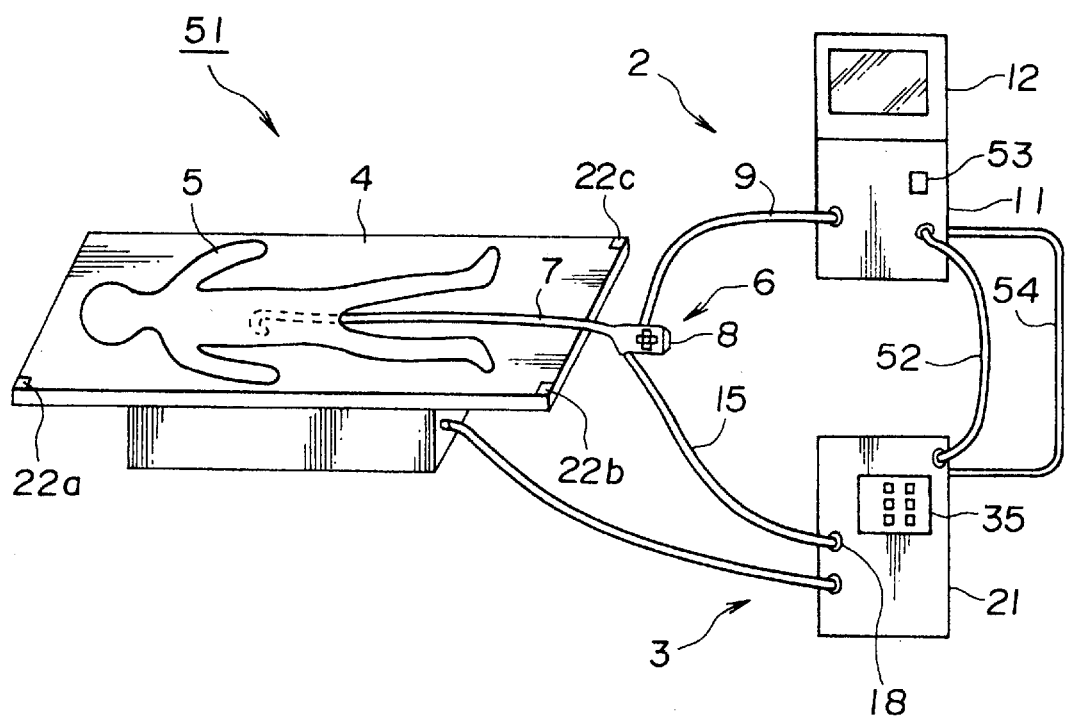
FIG. 62 is an arrangement showing an endoscope system according to the sixth embodiment of the invention.

A sixth embodiment of the invention will next be described with reference to FIG. 62. FIG. 62 shows an endoscope system including the sixth embodiment.

In the above-described embodiments and modifications, the estimated endoscope form is depicted onto the monitor 23 serving as a dedicated display apparatus. In the present embodiment, however, the image signal which is outputted to the monitor 23 is displayed in switching by the monitor 12 which displays the endoscope image. For this reason, the arrangement is such that the output from the detecting apparatus body 21 is inputted to an external image signal input end of the video processor 11 through a connection cable 52, and the changing-over switch 53 is operated whereby the endoscope image and the endoscope form can be selectively displayed on the display surface of the color monitor 12.

Moreover, the arrangement is such that, in the present embodiment, the reference signal (which determines timing of the drive signal of reading of the CCD) on the side of the video processor 11 is sent to form detecting apparatus body 21 through the cable 54. Timing at which the drive signal is applied to the source coil 16i for detection of the endoscope form is regulated so as to be performed within a period of time in which the drive signal is not outputted.

FIGS. 63a~63c show a condition of an operating period of time in the system 51. A light source within the video processor 11 successively illuminates by surface-sequential lights of R, G and B as shown in FIG. 63a. A CCD drive period of time is set to a CCD (not shown) built in the endoscope 6 in a period of time in which illumination is not performed, as shown in FIG. 63b. The CCD drive signal which drives the CCD is applied within the CCD drive period of time. An image signal (image pickup signal) photoelectrically converted by the CCD is read out.

Meanwhile, a drive-signal period of time in which the drive signal is outputted is adapted to come into a period of time other than the CCD drive period of time in which the CCD drive signal is outputted, that is, within the illumination (exposure) period of time, so that no influence is exerted by the drive signal upon the image pickup signal, and so as to prevent the CCD drive signal from extending an influence upon the detecting signal due to the sense coil. That is to say, means for solving or dissolving the mutual or interactive interference of the respective functions is constructed.

The other arrangement is similar to that of the first embodiment illustrated in FIG. 1.

According to the present embodiment, the drive signal for detection of the endoscope form can be prevented from producing excessive noise in the endoscope image signal, and the CCD drive signal can be prevented from producing excessive noise in the detecting signal due to the sense coil. The other function and advantages are substantially similar to these of the first embodiment.

In connection with the above, in the present sixth embodiment, the arrangement may be such that the endoscope form is displayed on the endoscope image, or the endoscope image is displayed on the endoscope form by a picture-in-picture system.

Further, in the sixth embodiment, when the endoscope form is detected so as not to interfere with the image pickup signal, the endoscope observation image is frozen, and noises are not mixed with the image. The setting function is put into the console panel 35 in FIG. 62. Moreover, the arrangement may be such that observation image incorporation is automatically interrupted to perform incorporation of the magnetic-field strength and magnetic-field generation for form detection every field of fetching of the image, every frame, every few frames, every few fields and every processing finishing or completion of the endoscope form representation.

Figure 64:
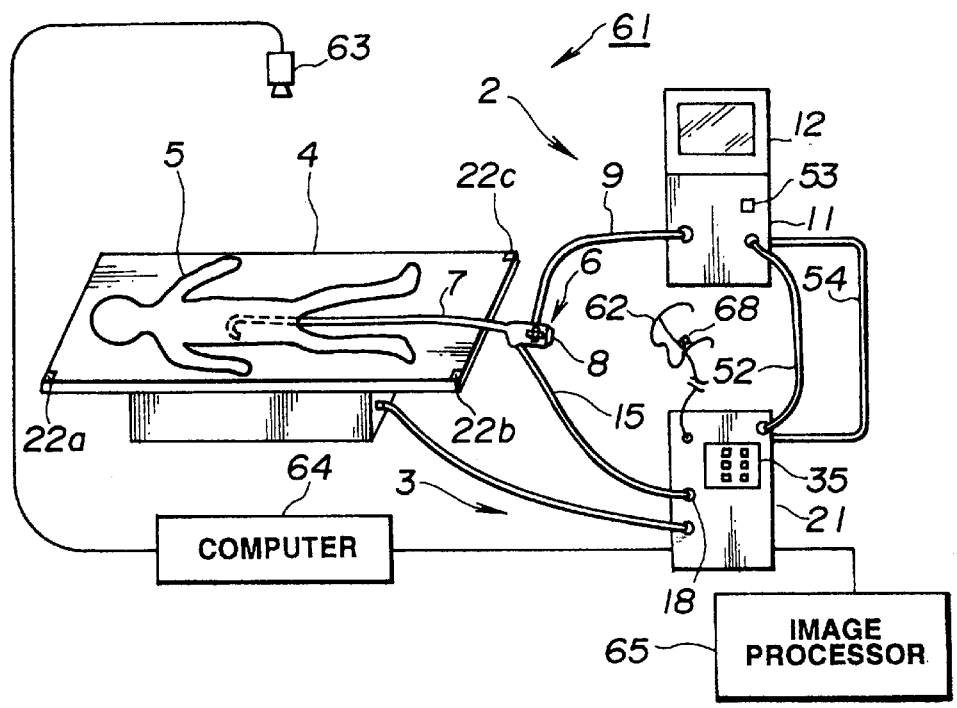

Next, an endoscope system 61 provided with a seventh embodiment of the invention will be described with reference to FIG. 64. The system 61 further comprises, in the endoscope system 51 in FIG. 62, a head mount display (hereinafter referred to as "HMD") 62, a TV camera 63 for confirmation of a position of a patient 5, a computer 64 for extracting the outline of the body of the patient 5 from the TV camera 63, and an image processing device 65 for performing virtual reality image processing.

The image processing device 65 is arranged as follows: That is, the image processing device 65 is connected to, for example, form estimation & image producer 32 (refer to FIG. 2) of the form detecting apparatus body 21. The form image which is produced by the form estimation & image producer 32 is processed in image to produce the form image for right-hand eye (or left-hand eye) observation at a position where a point of sight is slightly changed. The form image which is produced by the form estimation & image procedure 32 is outputted onto a (right-hand eye observation and left-hand eye observation) liquid crystal display of the HMD 62 through a monitor-signal producer 33. An operator in which the HMD 62 is mounted on the head can telescopically observe the endoscope form at virtual reality.

Moreover, in the present embodiment, the arrangement is such that a position of the patient 5 on the bed 4 is detected by the TV camera 63, and the image signal of the form of the body of the patient 5 is produced whereby the endoscope form can be observed at the virtual reality with overlapping over the form of the body. In this manner, the overlapping display is made to the form of the body, whereby it can be known how portion the insertion part 7 of the endoscope 6 is inserted into.

In connection with the above, one of the endoscope image and the endoscope form displayed on one liquid-crystal display of the HMD 62 (displayed in overlapping on the form of the body) can be selected and can be displayed on the color monitor 12 similarly to case of FIG. 62.

Figure 65:
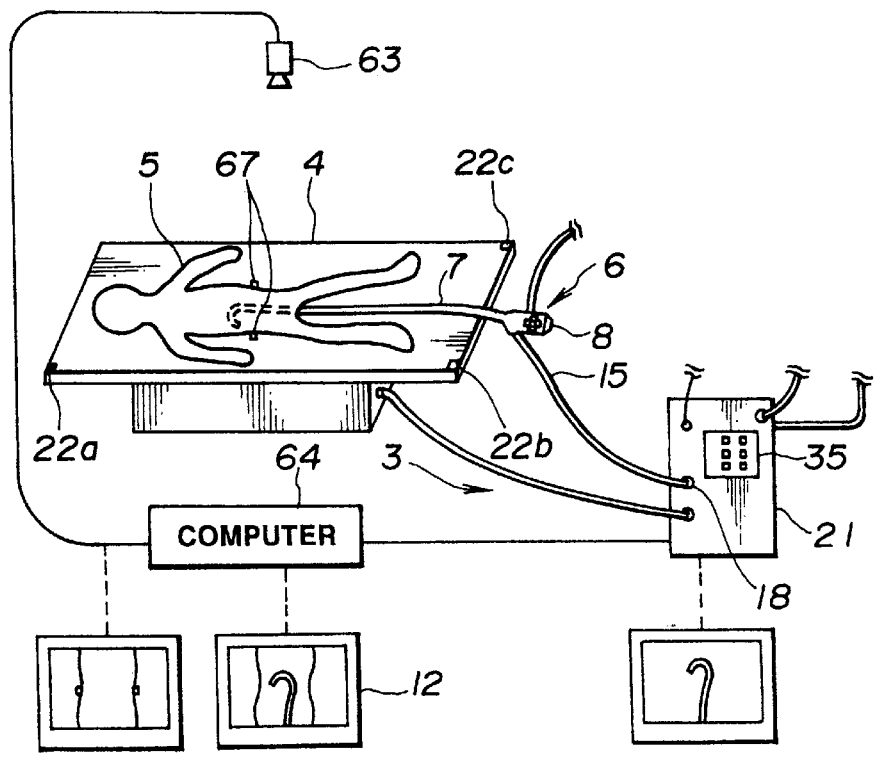

FIG. 65 is an explanatory view of a method of detecting a position of the patient 5 on the bed 4, by the TV camera 63. In FIG. 65, an image picked up by the TV camera 63 is an image indicated by broken lines below the cable in the FIG. The image due to the endoscope form detecting apparatus 3 is an image indicated therebelow. Outline extraction is performed by the computer 64. The image is displayed in overlapping relation as shown in the figure (through the monitor signal producer 33 or the like).

A body marker 67 for detecting a position and a direction is mounted on the body of the patient 5. This may be a single or a plural.

A coil for positional detection is built in the body marker 67. The establishment position of the body marker may be displayed such that a reference point such as a lateral position of a pelvis of the patient 5 or the like is provided, and is displayed in overlapping relation to the standard figure or form graphic model upon display of the endoscope form.

When the patient goes to the bed 4 for endoscope insertion, an image is taken in or fetched in the computer 64, including also the body marker 67, by the TV camera 63 for position confirmation which is provided above the bed 4. The body marker 67 which is mounted on the body of the patient 5 is a portion of the outline of the patient 5 and, accordingly, with reference to the body marker 67, only the outline image of the patient 5 is extracted and is overlapped on the form display. Thus, the outline image is extracted to the color monitor 12 or the like.

The arrangement may also be such that a direction of the patient 5 is led to or from the image or the body marker 67 which is found out magnetically, on the basis of the whole peripheral image of the body of the patient 5 which is fetched beforehand, prior to the endoscope inspection, and the overlapping image is formed in composition by the computer 64 and is displayed.

When, in fact, the color (red or the like) on the image which is fetched by the TV camera 63 is similar to the color of the endoscope which is displayed in composition by the form detecting apparatus, it becomes difficult to judge the form on the color monitor 12.

In view of the above, the user may change the color of the displayed endoscope form. Further, the thickness of the endoscope which is displayed on the color monitor 12 may also be changed.

The arrangement may also be such that, by the fact that the direction of the body of the patient 5 is detected, the image displayed on the color monitor 12 is made to an image always from the front direction of the body of the patient 5.

Naturally, the arrangement may be such that the produced image is rotated. By doing so, since conversion is possible to the image from the same location as the point of sight of the user, erroneous recognition of the endoscope form can be eliminated.

The above-described example is arranged such that the user rotates the image which is produced in putting together the observer's point of sight. However, if the sensor for position detection is mounted also on the user similarly to the body marker 67, the image can be automatically deformed such as rotation or the like.

In case of the user, there is operation of insertion of the endoscope 6. Accordingly, position movement is great, and the endoscope 6 is mounted at a location which does not interfere with movement of the user. Moreover, the position of the sensor cannot physically be made to the same location as the point of sight of the user. (The sensor must be installed in a cranium).

In view of the above, adjusting means for putting the sensor position and the point of sight together upon the use may be provided.

For example, the probe for form detection is placed on the bed 4 for endoscope inspection and is rotated, enlarged or reduced such that the displayed form comes into a similar one to practical how to see. Under this condition, a switch for visual-point correction is depressed. With such arrangement, offset adjustment of the point of sight and the sensor position are performed.

This must be performed, or is required to be performed slightly to the situation which utilizes the HMD 62 described previously. The sensor 68 may be fixed to the HMD 62. By doing so, since the eye line and the sensor position have no considerable difference therebetween, the HMD 62 can be used without substantial correction.

Whenever the position of the user is detected by the use of a magnetic sensor, magnetic association or coupling is utilized similarly to the endoscope form. However, the magnetic sensor is not driven simultaneously with detection of the position of the source coil 16i within the probe 15 for endoscope-form detection, but is driven by time sharing. By doing so, mutual magnetic interference may be reduced. FIG. 66 is a descriptive view where the magnetic sensor is driven at time sharing.

A reduced in width pulse period of time shows a period of time for driving the magnetic sensor on which the HMD 62 is fixedly mounted, while a long pulse period shows a period of time for driving the source coil 16i for endoscope form detection.

According to the embodiment, the endoscope form can stereoscopically be observed at virtual reality. Accordingly, where examination or inspection due to the endoscope 6, treatment or handling which uses the endoscope 6, or the like is performed, the operation introducing the forward end of the insertion part 7 of the endoscope 6, to a location in the vicinity of the aimed object, or the like can be performed more easily and in a reduced time or the like.

The other arrangements have advantages similar to those of the first embodiment.

In connection with the above, when the magnetic sensor which is fixedly mounted on the HMD 62 and the source coil for endoscope form detection are driven, the magnetic sensor and the source coil perform detection with respective frequencies thereof changed in place of being driven at time division or time sharing, whereby the magnetic sensor and the source coil may be simultaneously driven completely. In this case, since all the sensor positions can simultaneously be produced, even if the position, the form and the user's position vary rapidly in insertion of the endoscope, there can be produced a position and a form rapidly following the same.

These processing can use well-known orthogonal detection. However, the analog may be A/D converted to perform processing in a digital manner.

The coil for magnetic-field generation which is used for positional detection of the same and the coil for magnetic-field detection are arranged such that variation in the generated magnetic-field strength even if the same current is supplied, and variation in the produced detecting signal strength even if it is in the field of the same magnetic-field strength are generated or produced by variation in characteristics of respective cores, variation of coil, a difference in the surrounding temperature or the like.

In view of the above, the arrangement is such that a current value for generating the same magnetic-field strength is measured previously, and the variations can be corrected.

For example, a current value producing two (2) Gausses at a location of 30 cm in the axial direction from the source coil is measured, and a ratio with respect to the reference current value is stored as table values, and driving is made with the ratio. Similarly, the sense coil is also arranged such that a signal output at the two (2) Gauss magnetic field is measured beforehand, a ratio with respect to a reference value comes into a table, and correction is made by application to the detecting signal.

Since correction coefficients thereof are required to be set for each coil, the arrangement may be such that setting can be made from the keyboard which is provided on the apparatus.

Further, the arrangement may be such that the values are stored in a ROM which is provided within the connector for the probe 15, and are automatically read. Moreover, the arrangement may be such that the stored values and the set values are compressed and coded.

In the coil which is installed on the bed 4 for endoscope inspection, since combination with the apparatus does not vary except upon malfunction, varying correction amounts should be set upon assembling of the apparatus.

In this manner, the coil on the side of the bed is principally always combined with the same apparatus. Furthermore, the intervals between the respective coils in the probe 15 for form detection are assembled using previously known values. In view of this, the arrangement may be such that the probe 15 is placed on or arranged on the straight line of the bed center, and a switch for correction of the variation is depressed, whereby the variation of the respective coils within the probe 15 is corrected. Furthermore, the arrangement may be such that the correction coefficients are set or the drive current is adjusted such that the detected positions are arranged on a straight line, or that the intervals come into a known value.

By doing so, it becomes unnecessary to build the expensive ROM within the probe 15 (these are similar to case of a special endoscope for form detection).

An eighth embodiment of the invention will next be described. Generally, a detectable range of the sense coil which is used for position detection depends upon a dynamic range of the apparatus. For this reason, a dynamic range is required which can sufficiently cover a small distance in the situation where the sense coil and the source coil, in which the level of the detecting signal increases, approach each other to a situation where a distance between them is great, where the detectable signal level comes minimum.

However, in the actual endoscope inspection, the bed for inspection is used, and the patient exists on the bed. Accordingly, detection of only the region on the bed should be performed. Further, if the patient is a patient having a general conformation, a position of the endoscope which is considered in endoscope insertion comes into an extremely limited region.

That is, the arrangement should have a practically limited dynamic range. Meanwhile, if a displayed image is considered, when only the endoscope image is displayed, it is generally difficult to judge from what point of sight painting is performed.

In view of the above, in the present embodiment, display of the detectable range is prepared as one for causing the operator to confirm the direction of sight.

Figure 67:
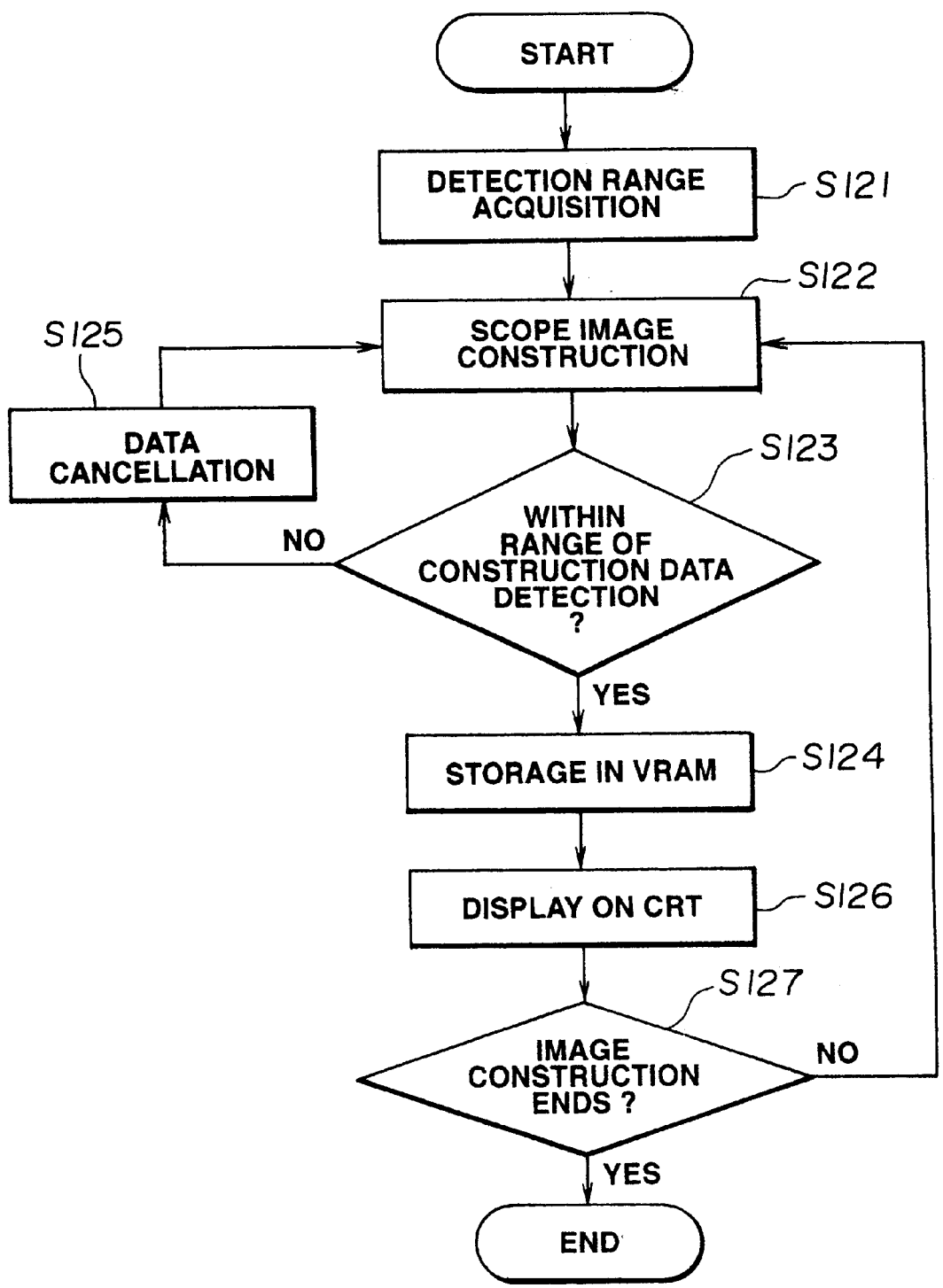
FIG. 67 is a flow chart showing the processing steps in an eighth embodiment of the invention.

If the display is within the region, it is possible to produce sufficient detecting accuracy. Accordingly, the form display of the endoscope is capable of being carried into practice only with respect to articles or objects which exist within the region. A flow of this processing is shown in FIG. 67.

Values of a rectangular parallelepipeds and the like which serve previously as a reference are set in a detecting range (detecting region), and the detecting range is acquired in Step S121. That is, the detecting range actually from the visual field coordinate system is fetched as reference data. In subsequent Step S122, construction of image cope painting starts. In this case, the positional coordinates of the endoscope which are produced by the fact that the coil position is interpolated is compared with a surface which surrounds the detecting region, to judge whether or not it is within the detecting region (Step S123).

In only the case where the comparison is judged as being within the region, the image data are stored into the VRAM (Step S124). When the comparison is outside of the region, the data are canceled (Step S125). The image data which are stored in the VRAM are displayed on the CRT (Step S126). It is then judged (Step S127) whether or not the processing of the image construction ends. This is performed until the processing ends.

In the present embodiment, display is made only in the situation where the comparison is within the detecting range. When the comparison is outside the detecting range, display is not performed, and the program ends.

Since an endoscope form which exists outside the detecting region is not sufficient in position accuracy thereof, the endoscope form is not displayed.

However, if the form which exists outside the region is not totally displayed, in the situation where almost all the endoscope is out of the region by movement of the patient or the like, the situation where almost no forms are displayed is considered.

Figure 68:
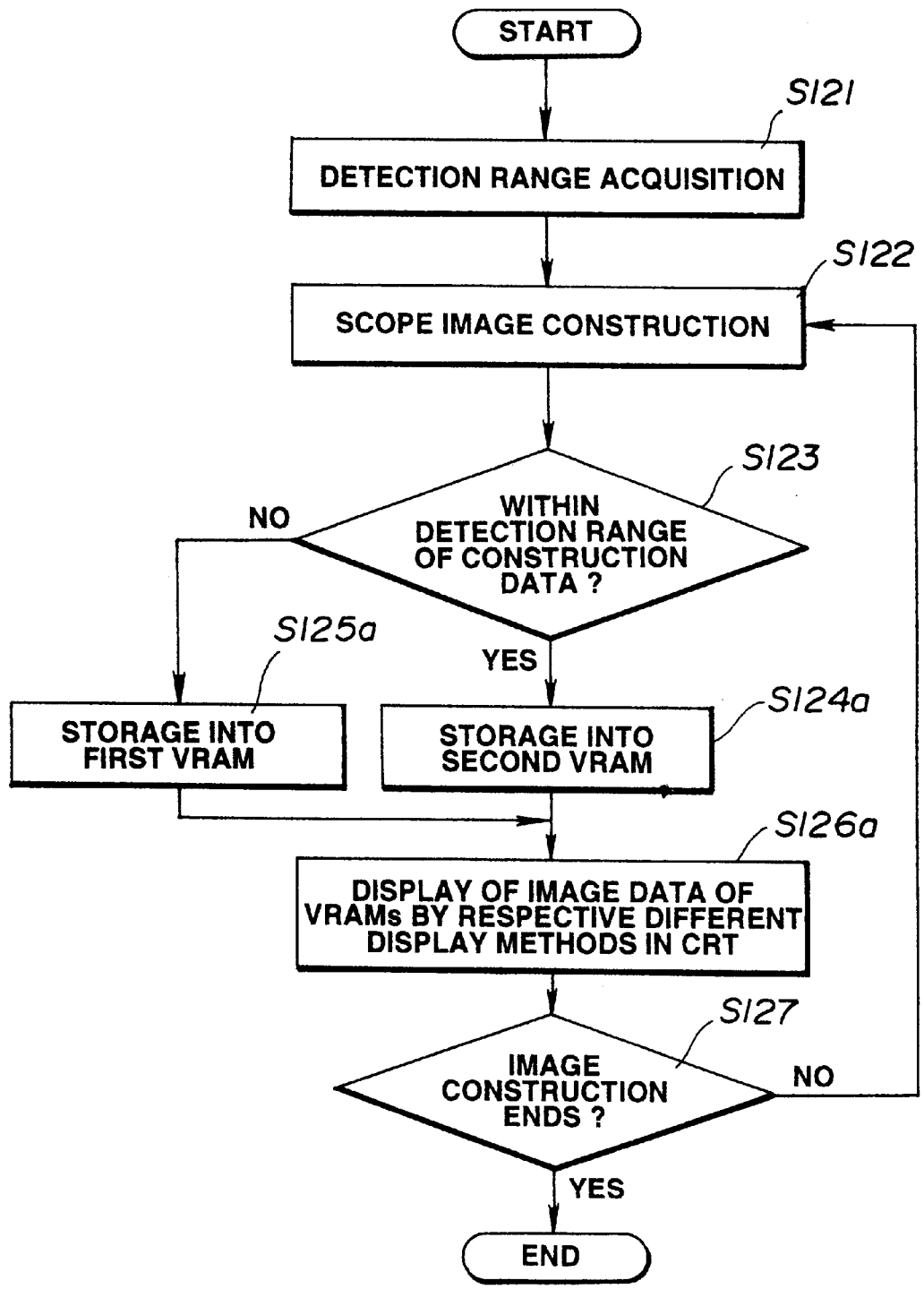
FIG. 68 is a flow chart showing the processing steps in a modification of the eighth embodiment.

In view of the above, as shown, for example, in FIG. 68, display may be performed by display methods which are different from each other in the inside and the outside of the region. In FIG. 68, in processing (Step S123) of judgment as to whether or not it is within the detecting range, in the situation of being within the range, storing is performed in a first VRAM (Step S124a). In the situation of being out of the range, storing is performed in a second VRAM (Step S125a). Image data which are stored in the first and second VRAMS are displayed onto the CRT with the display methods such as different display concentration or the like changed (Step S126a). The other processing contents are the same as those in FIG. 66.

The arrangement is not limited to one in which shading of light and the shade of the display concentration or the like is changed outside and inside the detecting range. For example, the arrangement may be such that display is made to a region outside the region by a different color system (from the inside of the region) (which is a cool color if the endoscope is a warm color system) (for example, such a LUT is prepared). Moreover, pixels which are used in painting are thinned out so that the display image is roughened. (The arrangement may be such that a display mask is prepared to take EXOR, to take OR or the like).

Since the continuous endoscope form is displayed together with the detecting accuracy, it is possible to ensure that the endoscope form can be produced.

That is, according to a painting method of the endoscope form detecting apparatus, in which the position coordinates of the endoscope which are determined by the fact that the position of the source coil is interpolated are compared with a surface which surrounds the region, and by this comparison, only where it is judged as being the interior of the region, normal painting is performed, it is possible to perform accurate form display. In this connection, the processing in FIG. 67 or FIG. 68 may be performed within Step S42 in FIG. 15 of the first embodiment.

A ninth embodiment of the invention will next be described. In the aforesaid embodiments or the like, when the endoscope form is displayed, the endoscope image is displayed as a computer graphic. By contrast, in the present embodiment, the endoscope image is displayed as, for example, an endoscope real image. The arrangement has been described in which an endoscope form which is detected is painted by a wire frame or the like within the computer, a light source is set, and the shadow processing of the set plane is performed to perform display, or the like.

However, generally, there may be a situation where, in the image processing, it becomes difficult to produce a comfortable or pleasant painting speed waiting time, by the processing speed of the computer which is required in high-speed calculation and painting ability and the capacity of the built-in memory. In this case, a model which is simple is processing is desired, in order to improve the painting speed. However, when the model which is too simplified, largely differentiated from the actual endoscope image, even if the endoscope is extracted, there is fear that the endoscope per se is difficult to be recalled.

In such a case, the embodiment is adopted whereby it is made possible to perform display in the form which is more easy to grasp the form of the endoscope and with high speed even by the computer or the like which is low in processing ability.

For this reason, in the embodiment, means for pasting a texture to display the endoscope form is arranged. The actual image of the endoscope is fetched beforehand by a scanner as the pasted texture and is stored in a ROM. Various textures are prepared as the image patterns. That is, a pattern is beforehand prepared in a high-speed semiconductor memory as the texture.

Figure 69:
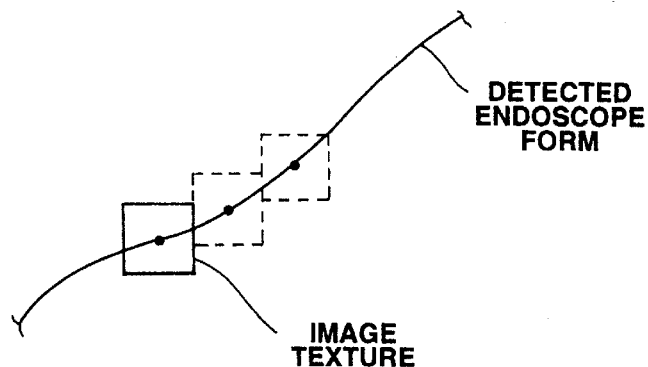
FIG. 69 is an explanatory view of a processing operation in a ninth embodiment of the invention.

As shown in FIG. 69, pasting of the texture is performed such that the coordinates corresponding to the detected position of the endoscope and the coordinates of the pattern center of the corresponding texture are in agreement with each other.

When the pasted texture is based on a square as shown in FIG. 69, a step is generated in the displayed image, depending upon the condition of the endoscope image. Accordingly, the outlines may be connected to each other by a Peje curve or a spline curve. Furthermore, a well-known ancherious may be applied.

Figure 70A:
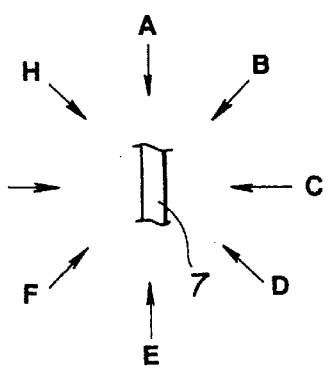
FIGS. 70a~70c are explanatory views of the sticking or paying-up texture.

The used texture is prepared such that, as shown in FIG. 70a, the used texture corresponds to the light-source direction of A to H, and the texture fetches an image of the endoscope insertion part 7.

It is needless to say that the light-source direction suitably increases and decreases in accordance with the magnitude of the stored or memory region and in conformity with the quality of the displayed image, so as to be able to prepare the texture.

Figures 70B, 70C:
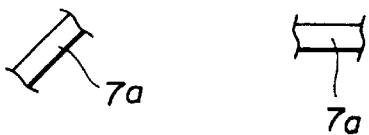

It is also possible to separately prepare an image 7a when the endoscope insertion part 7 is included, as shown in FIGS. 70b and 70c.

The more the texture in conformance with the inclination of the endoscope insertion part 7 per se (FIGS. 70b and 70c) and the textures corresponding respectively to the various light-source directions (FIG. 70a) are stored, calculation or computation for image display decreases. Higher-speed painting is made possible.

In order to cause the image of the endoscope and the background to be conspicuous, the publicly-known edge emphasis may be performed.

According to the present embodiment, the image of the ROM in which the image pattern is beforehand written is written to the VRAM which serves as the display memory for forming the image of the endoscope.

This means that data transmission between the memories should be performed which is such that the corresponding patterns are sorted and are written even after the coordinates in which the endoscope exists have been found out. Complicated calculation or computation processing becomes useless. Thus, it is made possible to perform painting at extremely at high speed.

Further, since the used texture is an object which actually uses the endoscope, it is facilitated to image the endoscope form intuitively.

Moreover, since display can be performed in color the same as the existing endoscope, it is extremely beneficial to re-construct the actual form of the endoscope within his or her head.

Next, a tenth embodiment of the invention will be described. The embodiment is so arranged that display colors are switched at predetermined lengths.

The form of the inserted endoscope insertion part is displayed on the monitor by the computer graphic. However, differentiated from the casing for the actual endoscope insertion part, display indicating an insertion length has not been performed.

For this reason, the position of the built-in coil has been expressed by the use of colors which are different from the endoscope form, or the like. However, in order to conform a length of how order is actually inserted into the body of the patient, it has been required that the operator performs judgment based on the image on the monitor.

Particularly, if the establishment intervals of the coils for positional detection are made constant, and if the position of the coil is distinguished from the other pseudo endoscope display (for example, the endoscope is expressed by a gray scale, while the coil position is expressed by a red point), it is possible to produce an inserted length based on how many coils are displayed. However, when the endoscope inspection is actually performed, since insertion of the endoscope is not an object, but observation and treatment or disposition of the tissues within the body is an object, excessive counting operation burdens the operator.

In view of the above, the arrangement is such that the endoscope form which is displayed by the computer graphic is displayed with a fundamental or basic color changed every predetermined length.

For example, a color which is separated on an order on a straight line which is drawn on a color chart due to a color displayable on an apparatus is set as a reference or basic color.

This is repeated in accordance with the painting length, whereby the colors are changed for predetermined distances.

The predetermined distances may be set by the user.

Since many painting areas can be taken more than expression or display of only the coil position by other colors, the insertion length can be easily visually understood.

It may be expressed or displayed by repetition of the change in gradation.

The pasted pattern may be changed on a white and black binary image plane.

Figure 71A:
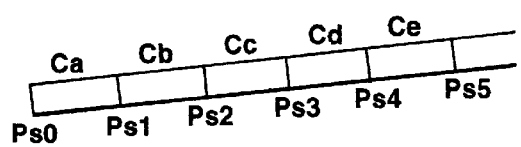
FIGS. 71a and 71b are explanatory views showing an image which is displayed by a tenth embodiment of the invention and color information stored in a memory, respectively.

For simplification, an image in which the endoscope insertion part is a straight line is shown in FIG. 71a. Colors are changed and are displayed such as Ca, Cb, Cc, Cd and Ce every predetermined length from the forward end.

Figure 71B:
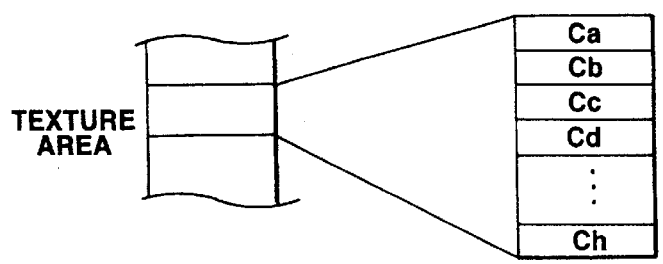

Such display is can be realized by the fact that, as shown in FIG. 71b, the data of the pasted colors Ca, ..., Ch are respectively stored at predetermined address position within the texture area, and are successively read.

Each of the patterns may freely be set by the user.

Figure 72:
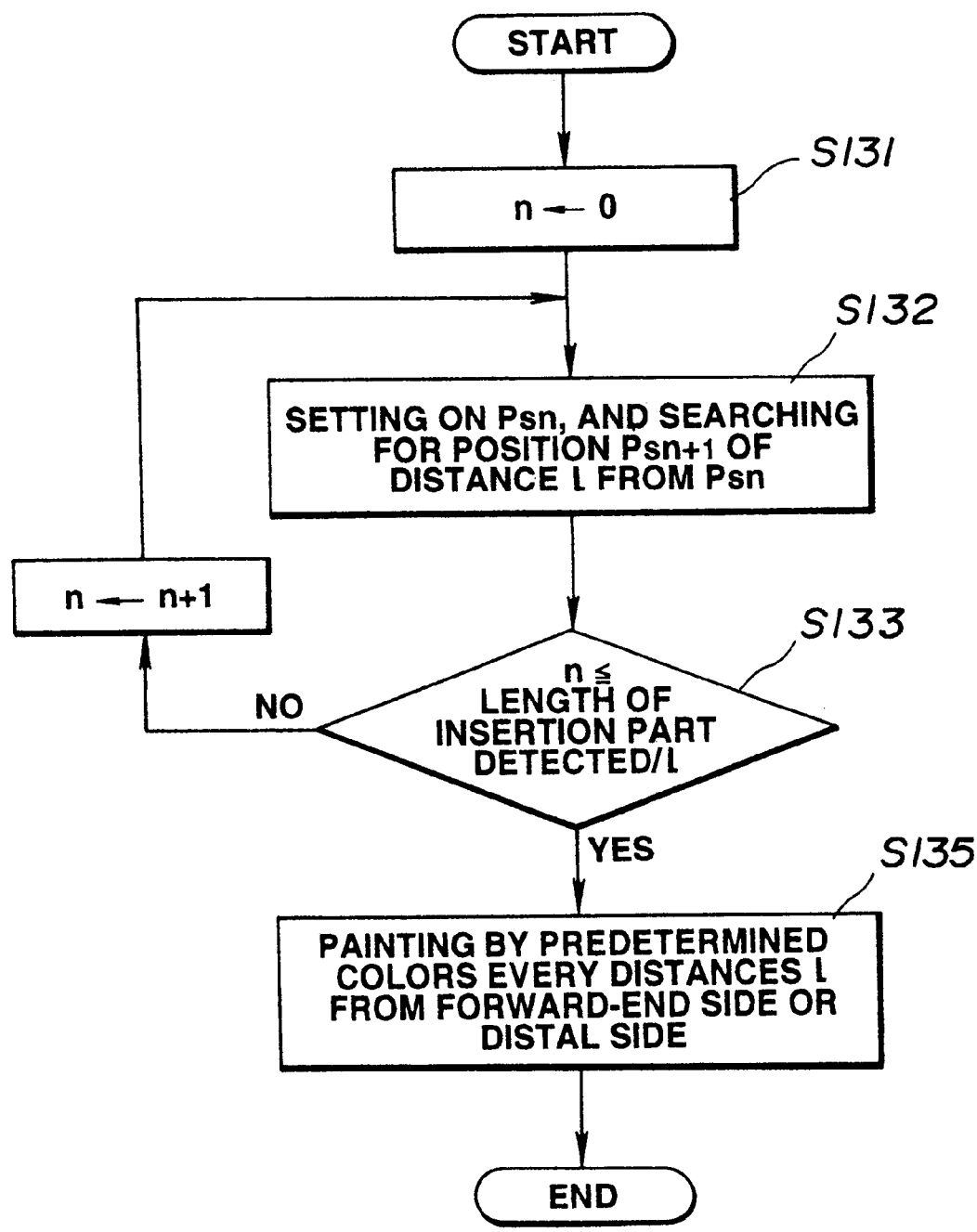
FIG. 72 is a flow chart of processing steps where color is changed every predetermined lengths, and display is made.

A fundamental or basic flow of the painting is shown in FIG. 72. First, in Step S131, a parameter n is initialized to 0.

In subsequent Step S132, since the insertion is performed from the forward end, the position of the forward end is detected. The position is made to Psn (here, n=0). A position Psn+1 on the endoscope position which comes into a distance 1 set by the user is searched, from the position Psn.

In subsequent Step S133, it is judged whether the parameter n is equal to the detected insertion-part length/1 or smaller than that (that is, n≦the detected insertion-part length/1). When this condition is satisfied, n is made to n+1 (Step S134). The program is again returned to Step S132, and similar processing is repeated.

Meanwhile, when the condition is not satisfied, the program proceeds to the next Step S135, and display is made by colors which are different from each other every the distances 1 searched from the side of the forward end. That is, display is made as shown in FIG. 71a, and the processing ends.

An eleventh embodiment of the invention will next be described with reference to FIG. 73. The embodiment is so arranged as to fetch a peripheral image to display the same.

When form display of the endoscope which is detected by the magnetism is performed by the computer graphic, an organism tissue, organization or the like is difficult to be detected. Accordingly, only the endoscope is displayed. For this reason, it is difficult to understand, in an intuition manner, the positional relationship of the organism and the endoscope.

In order to solve the same, in the first embodiment, the reference surface such as the planner surface of the bed or the like has been displayed. In this case, since it is the texture which is created by the computer, differentiated from the actual scene of the endoscope chamber, there may be case where the form is difficult to be recognized at once correspondingly to the actual endoscope. In order to prevent this, display may be made with a peripheral image fetched as in the present embodiment.

Figure 73:
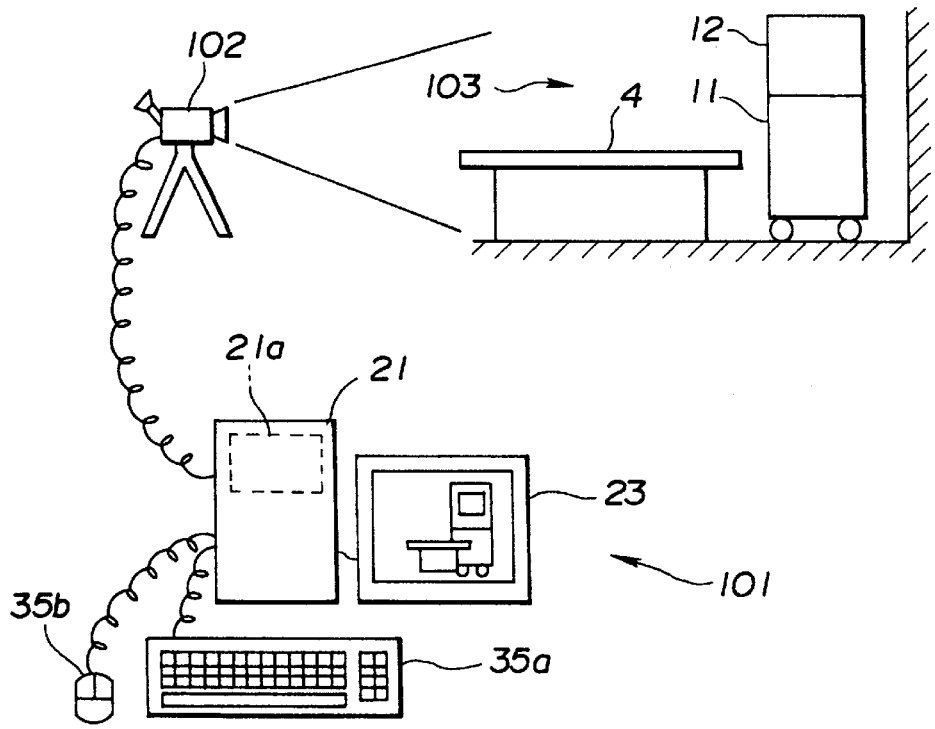
FIGS. 73 and 74 relate to an eleventh embodiment of the invention, FIG. 73 being an arrangement view of an endoscope form detecting apparatus.

In the endoscope form detecting apparatus 101 according to the eleventh embodiment of the invention, shown in FIG. 73, a video camera 102 serving as a video input device is connected to a form detecting apparatus body 21. An endoscope inspection chamber or room 103 is image-picked up by the video camera 102.

A bed 4 is arranged in the endoscope inspection chamber 103. An image of the bed 4 is image-picked up by the video camera 102, and is outputted to the form detecting apparatus body 21 as an image signal which is image-picked up. The form detecting apparatus body 21 converts the inputted image signal to a digital signal by an A/D converter within an image processor 21a, and stores the digital signal to a memory. The image in the memory is reproduced to a monitor 23 through a monitor signal generator.

Figure 74:
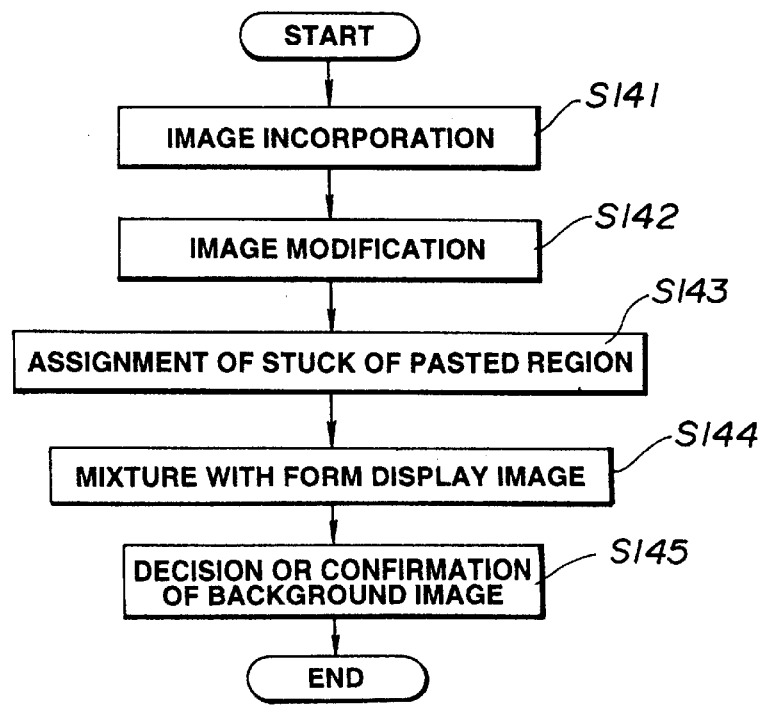

The arrangement is such that an operator operates a keyboard 35a and a mouse 35b to cause the processing shown in FIG. 74 to be performed with respect to the image displayed on the monitor 23 so as to be capable of displaying the image displayed on the monitor 23 as a background image upon display of the endoscope form.

Next, a flow of FIG. 74 will be described. First, in Step S141, fetching of the image due to the video camera 102 is performed. That is, the image signal from the video camera 102 is A/D-converted and is stored in the memory.

In subsequent Step S142, the stored image is reproduced onto the monitor, to perform processing which corrects or modifies the reproduced image. That is, unnecessary image portions or noises are modified by a photo retouch soft or the like. Of the modified images, required areas are selected by the mouse (35b), and are stored in the memory as pasting images.

In subsequent Step S143, an endoscope form detecting control program is called or invoked, and the pasting images which are stored in the memory are also read. Thus, the past region is assigned as the background image.

In subsequent Step S144, modification, enlargement and reduction are performed. After combination or amalgamation (mixture) with respect to the form displayed image of the form detecting apparatus has been performed, pasting data are defined in Step S145 whereby the background image is defined.

Thus, since the detected form of the endoscope is expressed in the background of the actual endoscope chamber, it is easy to understand the form of the endoscope within the body of the patient.

A twelfth embodiment of the invention will next be described. The embodiment is arranged such that a source coil is driven by radio without the use of a cable for driving the source coil.

In the first embodiment or the like, in order to detect the position of the source coil, the detecting signal which corresponds to the magnetic-field strength is produced by the sense coil. In this case, in order to detect minute or microscopic signals, synchronous detection is performed. In order to extract a signal the same in frequency as the drive signal of the source coil, a reference signal on the basis of the drive signal is used to perform orthogonal detection with respect to the received signal by a detection part, to produce the amplitude of the received signal and the phase with respect to the drive signal.

In this case, the drive signal is transmitted to a detection part on the side of the position detecting means or the side of the form detecting means through the cable. However, where the cable limits free movement of the operator, or where the source coil is provided on the patient as a marker, there is the possibility that free movement of the body of the patient is limited.

In view of the above, in the present embodiment, and apparatus in which a signal which produces the reference signal can be transmitted by a radio to perform positional detection by the radio will be described.

Figure 75:
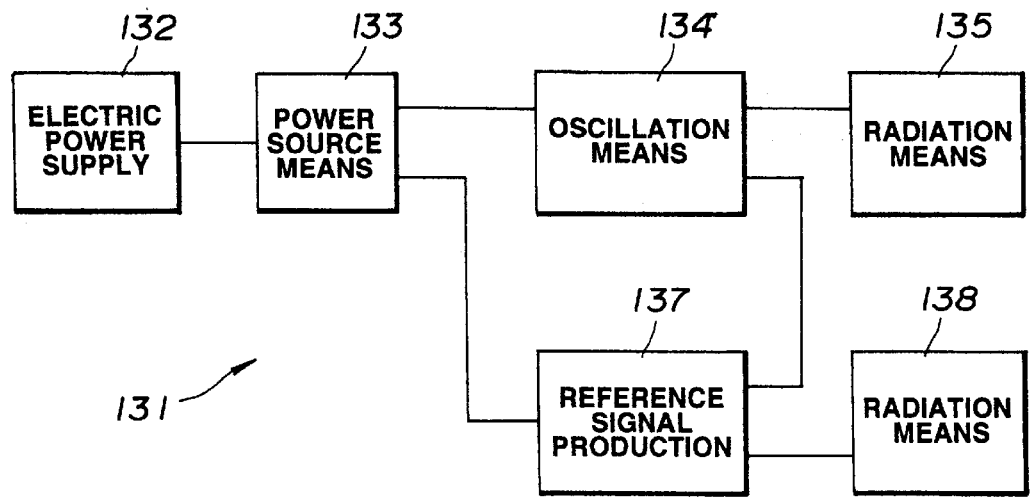
FIG. 75 is a block diagram showing an arrangement on the side of a probe in a twelfth embodiment of the invention.

FIG. 75 shows an arrangement on the side of a probe 131 which is provided with a source coil. Electric-power supply means 132 which is formed by an antenna coil or the like which generates an alternate-current signal by an electric magnetic field from a cell supplies the electric power to power source means 133. The power source means 133 produces a steady direct current source, to supply voltage required for operation of oscillation means 134 or the like.

The oscillation means 134 is caused to oscillate at a predetermined frequency. An oscillation signal thereof is applied to radiation means 135. The radiation means 135 amplifies the oscillation signal so as to come into a drive signal of the constant or predetermined level, to apply the same to the interior source coil 136*i* to thereby generate a magnetic field to the surrounding thereof.

Further, reference-signal generation means 137 for producing a reference pulse for external synchronization produces a reference pulse which comes into a reference from an oscillation signal from the oscillation means 134 to supply the same to the radiation means 138 to thereby radiate the same from the radiation means 138.

The radiation means 138 is provided with an AGC circuit for making the amplitude of the drive signal constant, to send out the reference pulse for external synchronization by the use of a diffusion spectrum method.

Figure 76:
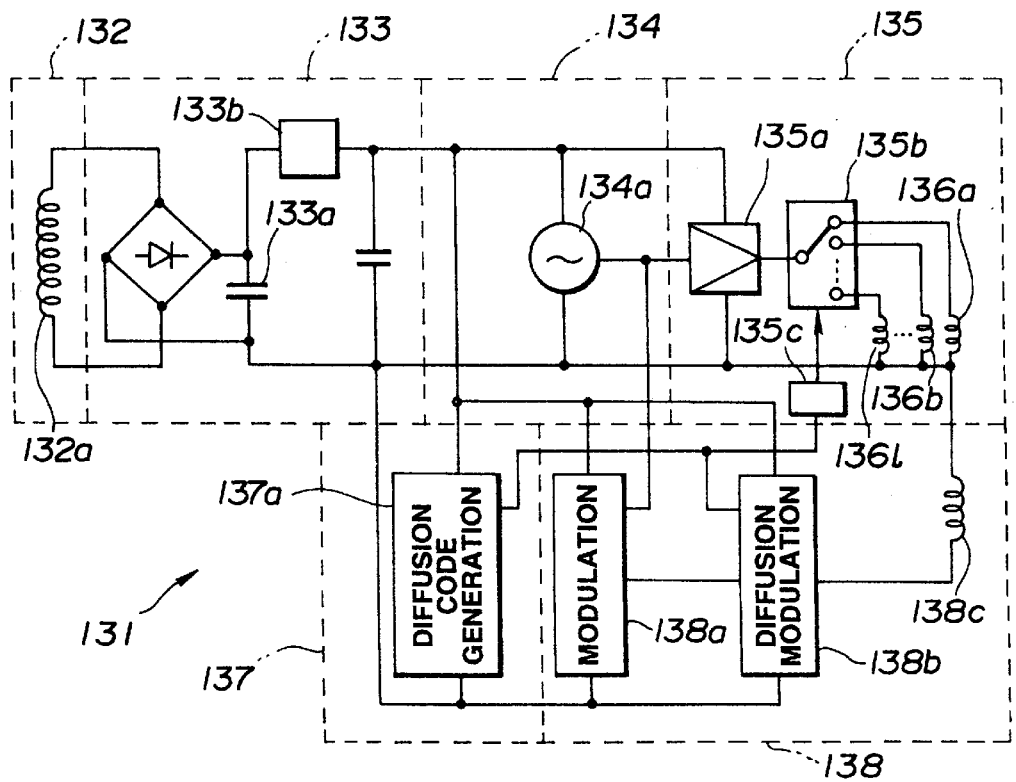
FIG. 76 is a more specific or concrete arrangement view of FIG. 75.

FIG. 76 shows an arrangement more specified than FIG. 75. The alternate current signal which is generated at the antenna coil 132*a* which forms the power supply means 132 is rectified by a direct currentization circuit 133*a* due to a rectifier and a capacity which form the electric power means 133, is converted to a direct current and is made to a direct-current power voltage by a stabilization circuit 133*b*.

The direct current power voltage is applied to the oscillator 134*a* which forms oscillation means 134, and is oscillated at a predetermined frequency. The direct current power voltage is amplified to a constant predetermined level by AGC circuit 135*a* which forms the radiation means 135. Moreover, the direct current power voltage is successively applied to the source coil 136*i* through a changing-over switch 135*b*.

Furthermore, a diffused code generator 137*a* which forms the reference-signal generating means 137 monitors the oscillation-signal output level such that the oscillation-signal output level becomes 0 when the output from the oscillator 134*a* becomes zero, and the oscillation-signal output level becomes 1 at a subsequent zero cross point, to thereby form a pulse signal. The pulse signal is FSK-modulated, for example, by a modulator 138*a*, and is further diffusion-modulated by the use of a PN code by the diffusion modulator 138*b*. The diffusion-modulated signal is amplified as occasion demands, and is radiated from the reference-pulse transmission coil 138*c*. The signal spectrum is broad.

In connection with the above, with respect to the changing-over switch 135*b*, switching is performed by a switching controller 135*c* which is formed by the use of a counter or the like which counts an output from the diffusion-code generator 137*a*.

Figure 77A:
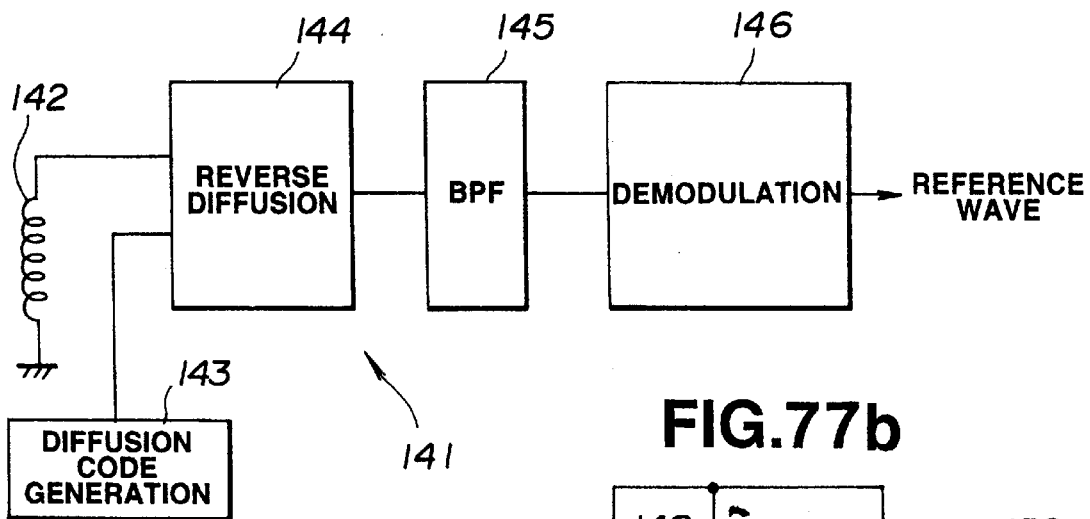
FIG. 77a is a block diagram showing an arrangement of a reference-signal production circuit.

Meanwhile, the arrangement of the reference-signal producing circuit 141 on the side of the form detecting apparatus body which is provided with the sense coil 22*j* is shown in FIG. 77*a*.

The form detecting apparatus body has a reference-signal producing circuit 141, and receives a signal which is radiated from the coil 138*c* by the antenna coil 142. The received signal is inverse-diffused by a reverse diffusion circuit 144 with reference to the PN code of the diffusion-code generator 143 similar to that on the transmission side. The received signal is filtered by a BPF 145 and, thereafter, is returned to an original signal by a demodulation circuit 146.

In order to make the demodulated signal to a pulse signal serving as the reference drive signal, a PLL loop is formed, and a phase lock to the reference frequency is performed by the PLL loop. The phase lock is applied so that the signal turned to the reference frequency comes into a reference wave (reference signal) in which reference phases become complete. The reference wave is outputted to the synchronous detection circuit, and is used for synchronous detection with respect to a detected signal detected by the sense coil.

In connection with the above, if the PN code on the receiving side is not in agreement with that on the transmission side, diffusion is performed, and a signal is not reproduced.

That is, if the PN codes of all the coils to detect the position are changed, there is no radio interference, or radio interference is eliminated and, simultaneously, it is possible to produce many reference waves without the connecting cable. That is, if applied to FIG. 50, driving of the source coil and detection due to the sense coil can simultaneously be performed by radio. In this connection, modulation and demodulation may employ any well-known systems.

Figure 77B:
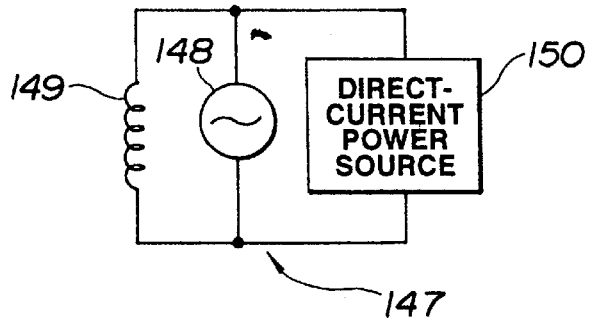
FIG. 77b is a schematic diagram of energy supply means.

In connection with the above, when the antenna coil 132*a* is adopted or employed, as shown in FIG. 76, as the electric-power supply means 132, energy supply means in which an electric magnetic field or the like is generated on the side of the form detecting apparatus or separately from the apparatus, to supply the energy to the antenna coil 132*a* is required. The energy supply means 147 comprises an oscillator 148 shown, for example, in FIG. 77*b*, a coil 149 for radiating an oscillation output thereof, and a direct-current power source 150. The direct-current power source 150 may utilize a cell or a power source which is produced by rectification or the like from a commercial power source.

The oscillator 149 is set to a frequency (for example, few 10 MHz~few 100 MHz) considerably higher than the frequency of the oscillator 134*a*, for example, and almost no influence is exerted upon a magnetic field which is generated at the frequency of the oscillator 134*a*.

In connection with the above, the waves to be modulated on the transmission side may also be the drive signal (oscillation signal) per se.

Figure 78A:
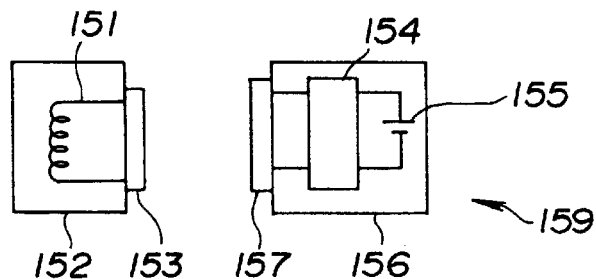
FIGS. 78a and 78b are views showing an arrangement of a magnetic-field generation unit in a modification of the twelfth embodiment.

Further, the embodiment thereof may be utilized for display of a marker. FIG. 78*a* shows a magnetic-field generation unit 159 of radio type, according to a modification of the twelfth embodiment. The magnetic-field generation unit 159 of radio type comprises a coil unit 152 and a drive unit 156.

For example, a connector 153 is provided on the coil unit 152 which builds therein the source coil 151 which is mounted on an object desired to know a position as shown in FIG. 78*a* and which is used in magnetic-field generation for detection of the position, and the connector 153 is connected by the drive circuit 154 for driving the source coil 151 and a connector receipt 157 of the drive unit 156 which builds therein the cell 155, to thereby form the magnetic-field generation means of radio type which is used in positional detection for the marker.

The drive circuit 154 and the cell 155 are arranged such that the connector receipt 157 is connected to an output end of the AGC circuit 135*a* in FIG. 76, to drive only one source coil 151 which is connected to the connector receipt 157 through the connector 153.

Figure 78B:
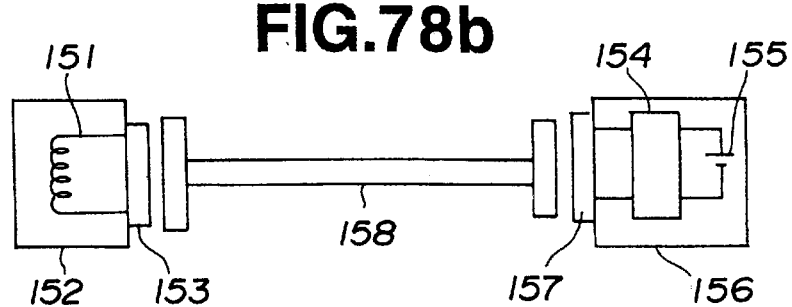

Further, as shown in FIG. 78*b*, the arrangement may be such that the coil unit 152 and the drive unit 156 are connected to each other with the coil unit 152 and the drive unit 156 separated to a position where the drive unit 156 can be installed without difficulty, through a cable 158. Connector means which can be connected to the connector 153 and the connector receipt 157 is provided at both ends of the cable 158. In this connection, the arrangement may be such that the coil unit 152 and the drive unit 156 are connected to each other by the cable 158 without the provision of the connector 153 or the like.

With the arrangement or construction, since the cable between the side of the form detecting apparatus and the side of coil which is used in the marker can be omitted, the form detecting apparatus is not almost restrained by movement of the patient in case of being mounted on the patient, and is not almost restrained by the movement of the operator on case of being used by the operator.

A thirteenth embodiment of the invention will next be described. The embodiment is so arranged as to display a position of the palm of a hand, for example, as marker display which is easy to be understood in a visual sense.

In order to realize the same, means capable of fixing at least one of the source coil and the sense coil detachably with respect to an optional position such as the palm of a hand or the like is provided.

The twelfth embodiment is provided with, in FIG. 2 of the first embodiment, for example, the palm-position detecting device 111 shown further in FIG. 79a as magnetic-field generation means for display marker.

As shown in a exploded view in FIG. 79b, the device 111 has a pair of source coils 116a and 116b for detecting the position of the palm of the hand. This pair of source coils are fixed to a location between thin flexible plates 112a and 112b (flexible material of high molecular or polymeric body such as styrene resin or the like, for example) by adhesives. Moreover, an index or parameter 114 for indicating directionality upon fixing as shown in FIG. 79a is provided on an outward surface (front surface) of one plate 112a. Further, adhesives 113 which serve as detachable fixing means are applied to a reverse surface of the other plate 112b.

As shown in FIG. 79c, by the adhesives 113, the index is adapted to be pasted on the palm of a hand (or a glove) 115 of the operator or a helper. The adhesives 113 are covered by a released paper before the use so that the released paper is torn off or peeled off just before the use. Thus, the plate can be pasted on a desired position and can fixed thereat. The arrangement may be such that, even if the adhesives are not applied, the plates may be fixed by a surgical tape or the like. Moreover, the plates may be used as body markers for confirming a position of the body of the patient.

Furthermore, the indexes 114 display the finger-tip side and the wrist side as shown, for example, in FIG. 79a so that the operator or the like can confirm a fixing direction.

The arrangement may be such that the source coils 116a and 116b which are used for detection are connected to the form detecting apparatus by the cable 117 in a manner of cable or wire type, or are connected to the drive unit as shown in FIG. 78b so that an alternate-current magnetic field can be generated in a manner of radio type (which is not connected to the form detecting apparatus). Of course, the arrangement may be such that the source coils 116a and 116b alone generate the alternate-current magnetic field as shown in FIG. 78a or the like.

It is assumed that the positions of the source coils 116a and 116b which are detected by the form detecting apparatus are P0(x0, y0, z0) and P1(x1, y1, z1).

If P01=(P1−P0), a single vector can be set. The operator pastes the vector onto the palm of a hand such that the vector is overlapped on a finger-tip direction from a wrist direction by a palm of a hand.

Figure 80:
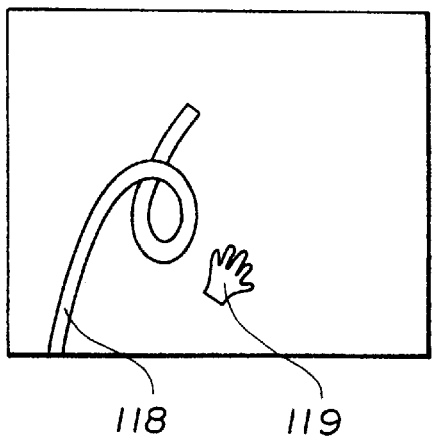
FIGS. 80a and 80b are explanatory views showing a situation where the device is displayed on a monitor image plane.
Figure 80:
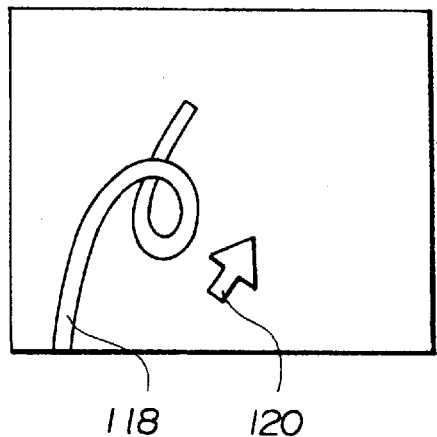

As shown in FIG. 80a, a detected position of the palm of a hand may be displayed by a graphic 119 which imitates the palm of a hand together with the image 118 of the endoscope form on the monitor image plane. As shown in FIG. 80b, the detected position of the palm of a hand may be displayed by an arrow 120.

Further, in practice, since it is means for confirming the endoscope from the outside of the body, a distance between the endoscope and the palm of hand of the operator may be displayed as auxiliary information.

Figure 81:
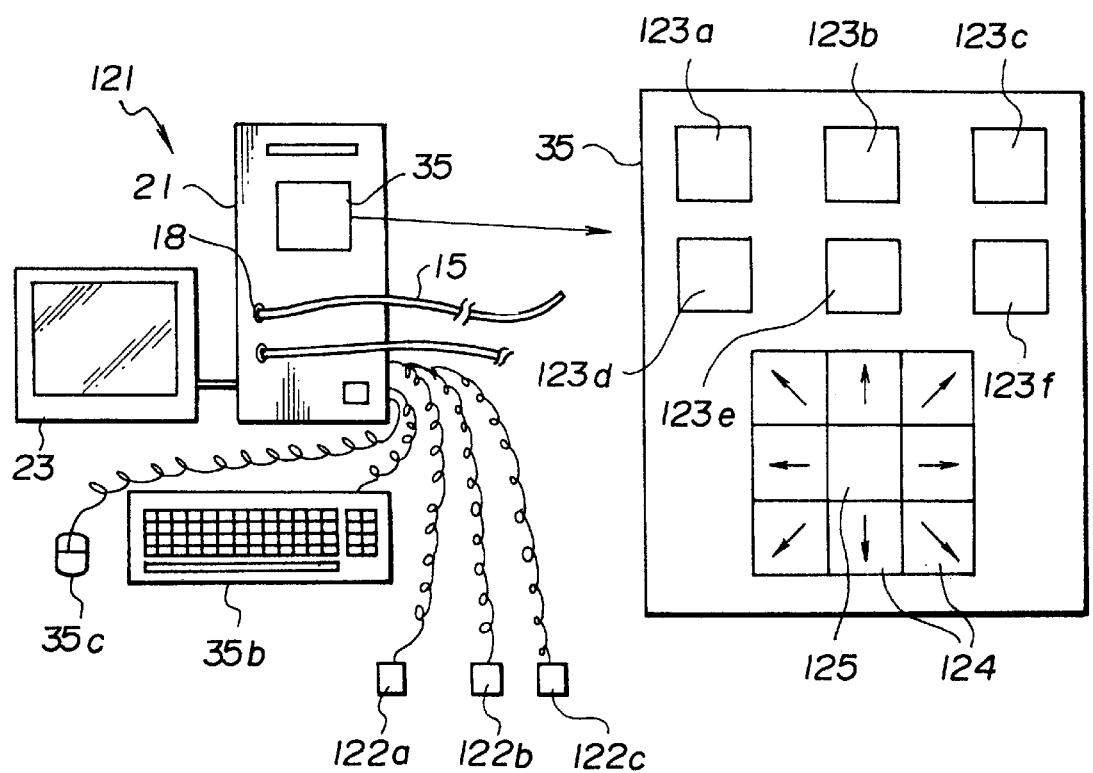
FIG. 81 is an arrangement view of an endoscope form detecting apparatus according to a first modification of the thirteenth embodiment.

FIG. 81 shows a endoscope form detecting apparatus 121 according to a modification of a thirteenth embodiment of the invention. The apparatus 121 is arranged such that, in, for example, the first embodiment illustrated in FIG. 2, coil units 122a, 122b and 122c (represented by 122q) are provided which build therein source coils, respectively, which can be used in marker display or the like. Furthermore, a keyboard 35b and a mouth 35c are connected to the form detecting apparatus body 21.

Further, as shown in an enlarged view, a user definition marker switch 123a, a body marker switch 123b, a marker setting mode ON/OFF switch 123c, an instrument or tool marker switch 123d, a hand marker switch 123e, a marker setting switch 123f (represented by 123k) or the like is provided on a console panel 35. These switches 123k are operated so that the operator can assign an optically used coil of the coil unit 122q.

Similarly to FIGS. 79a–79c, the respective coil units 122q are provided with means for causing the operator to perform pasting and fixing. Moreover, the console panel 35 is provided with a display/coil changing-over key 125, together with the cursor key 124.

Figure 82:
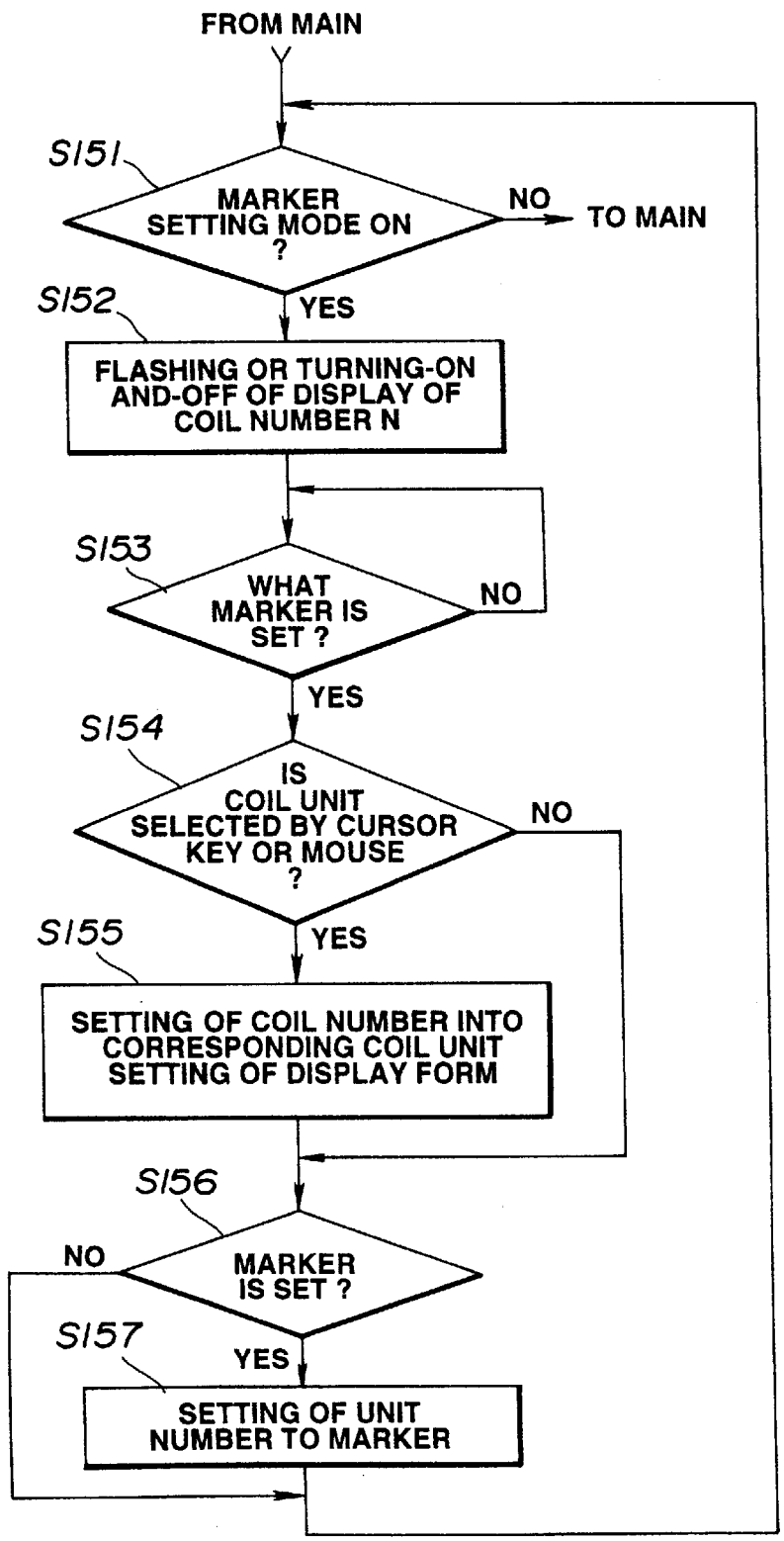
FIG. 82 is a flow chart showing the processing steps of marker setting due to operation of a console panel of the first modification.

Next, processing for setting an optional desired coil unit to the user defining marker, the body marker, the instrument marker and the like by operation of the console panel 35 will be described with reference to a flow in FIG. 82. The processing is incorporated in processing of a scope image description in Step S42 in FIG. 15, for example.

Upon operation of Step S42 (referred to as "main" in FIG. 82), the CPU monitors ON/OFF of the marker setting mode switch 123c (Step S151). If the marker setting mode switch 123c is turned ON, and if the mode is made to the setting mode, the display part corresponding to the coil unit 122q which is capable of being set as a marker is turned ON and OFF, or is displayed on the image plane of the monitor 23 by a color different from that of the coil unit.

Like Step S152, the display portion of, for example, the unit number N corresponding to the coil unit 123q is turned ON and OFF.

Accordingly, the marker switch desired to be set, such as the body marker switch 123b or the like is turned ON as the turned-ON and -OFF coil unit 123q (Step S153).

In order to know whether or not the turned-ON and -OFF coil unit 122q is the coil unit 123p (p=a, b, c) which is desired to be set by the operator, if the coil unit 123p is held and is moved above or the like the positional detecting apparatus, the display mark corresponding to the coil unit 123p is moved on the monitor image plane.

Accordingly, when the desired coil unit 123p is not selected, selection is made by a pointing device or the like such as a mouse cursor or the like, for example, or selection is made by the cursor key, or the like, to select a desired coil unit (inversion is performed by selection) (Step S154). The coil unit 123p corresponding to the unit number M is set, and a display format is set (Step S155).

Subsequently, the marker setting switch 123f is turned ON to perform setting of the marker, and marker director or registration of the desired coil unit 123p is performed (Step S156 and 157).

In this manner, the operator successively sets the necessary or required markers. For example, registration is performed as the body marker which indicates a position on the right body of the patient, the body marker which indicates a position of the left body, the body marker which indicates a position of anus, and the like.

In connection with the above, since the pattern candidates of the marker display are displayed on the monitor image plane, the display is selected by the mouse and the cursor of the display similarly to selection of the coil unit. Switching or changing-over of the function of the coil-unit selection and the display selection is performed by a display/coil switching key on the cursor center, so that the display form can be switched.

Here, case where only the position is detected has been described. However, the detected signal includes an affection or influence of change due to inclinations of the source coil and the sense coil. In view of this, it is also made possible to detect inclination.

In connection with the above, when a position rendering or derivation method which can detect also the inclination is used, the source coil or the sense coil which is installed on the palm of a hand may be one or a single.

Displays which indicate the direction corresponding to the tip of finger and the direction corresponding to the wrist as described above, respectively, are performed on the installed coil unit. The arrangement can be applied to an arrangement in which a plurality of coils are united and are constructed.

In a system for rendering only the source-coil position or the sense-coil position, in case, for example, where two source coils are used, or in a system in which the direction of the source coil is also rendered or derived, when a single source coil is used, it is impossible to define the direction in which the palm of hand is oriented. In order to decide the direction, three parameters are required. A palm-position detecting device 161 which is used where detection and painting are performed including the direction of the palm of a hand is shown in FIG. 83.

Figure 79:
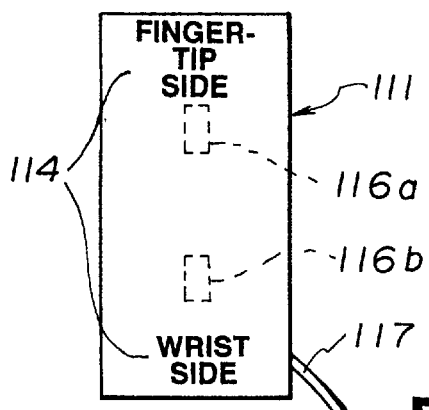
FIG. 79a is a top plan view of a palm-position detecting device in a thirteenth embodiment of the invention.
FIG. 79b is an exploded perspective view of the device in FIG. 79a, and FIG. 79c is an explanatory view showing a state where the device is mounted on a hand.
Figure 79:
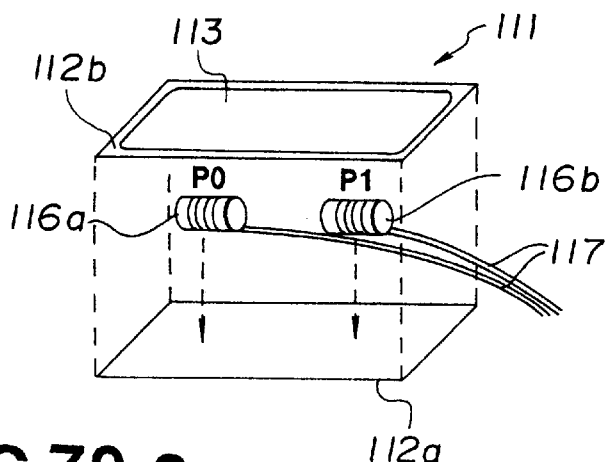
Figure 79:
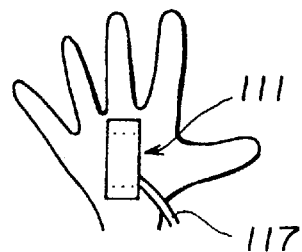
Figure 83:
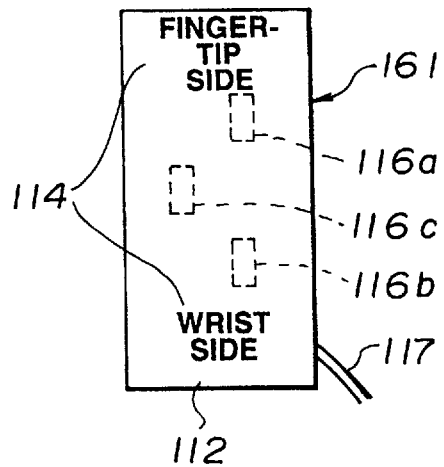
FIG. 83a is a top plan view of a palm-position detecting device in a second modification of the thirteenth embodiment.
FIG. 83b is an exploded perspective view of the device in FIG. 83a, and FIG. 83c is an explanatory view showing a state mounted on a hand.
Figure 83:
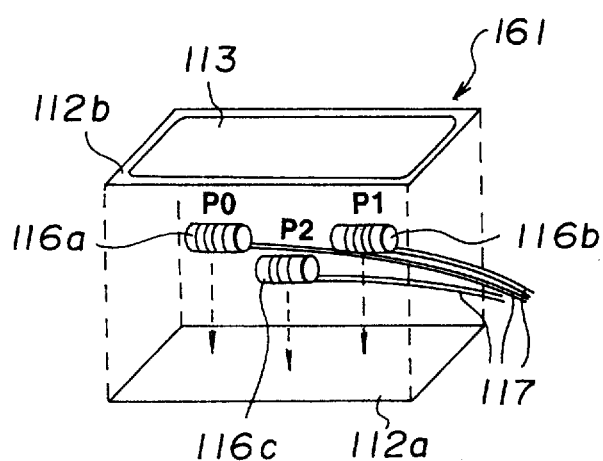
Figure 83:
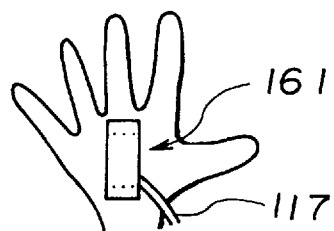

The palm-position detecting device 161 shown in FIG. 83 is arranged such that a single source coil 116c is added to the device 111 in FIG. 79. In this manner, by addition of the single source coil 116c, a single plane in which the three source coils 116a, 116b and 116c are included can be defined. Accordingly, it is possible to decide the orientation of the palm of a hand.

Thus, it is possible to detect that a change in the orientation of the palm of a hand to change the painting pattern of the displayed marker, and the stereophonic positional relationship is made easy to be grasped by the operator.

Figure 84:
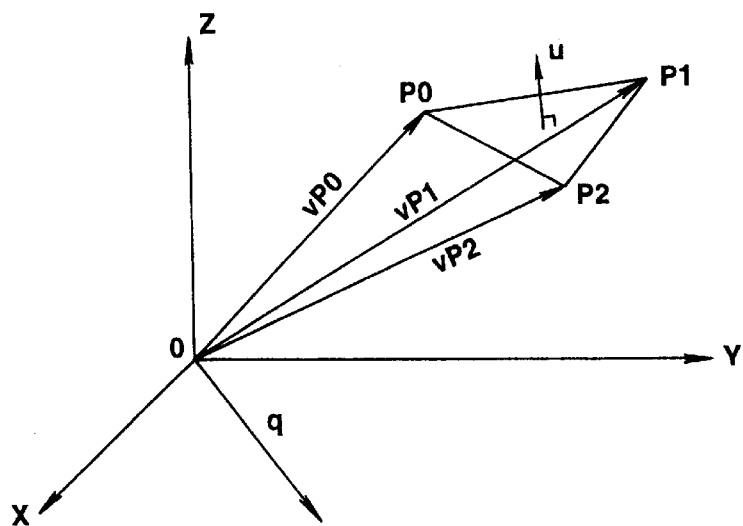
FIG. 84 is an explanatory view showing a top plan which is formed by three (3) source coils in a second modification.

As shown in FIG. 84, it is assumed that positional vectors of positions P0, P1 and P2 of the three source coils 116a, 116b and 116c and vP0, vP1 and vP2. The origin 0 is set to be the center of the bed.

At this time, $$P1P0 = vP1 - vP0 \quad (1)$$

$$P2P0 = vP2 - vP0 \quad (2)$$

Here, P1P0, for example, has a length from the position P0 to the position P1, and indicates a vector which orients a direction of the position P1 from the position P0.

Now, if it is assumed that the palm of a hand desired to be displayed and a plane including three points for detection can generally be expressed as follows, if the positional vector on the plane is, generally:

$$r = vP0 + s(vP1 - vP0) + t(vP2 - vP0) \quad (3)$$

If r=vP0, vP1 and vP2 is substituted and (3) is solved, if the respective unit vectors in the axial directions x, y and z are a, b and c, the (3) equation can be rewritten as follows:

$$la + mb + nc = 0 \quad (4)$$

(at least one of l, m and n is the integer which is not 0)

u=(l, m, n) at this time decides a directional vector which is perpendicular to a plane which includes the three points of P0, P1 and P2.

If it is assumed that the positional vector of the point of sight is q, the inner product of u and q takes a value of negative, positive and 0 depending upon the fact that an angle thereof is an obtuse angle, an acute angle or a right angle (positive in case of the obtuse angle, while negative in case of the acute angle).

By the code of the value, it is possible to judge whether the palm of a hand is oriented in the direction of sight, or whether the back of a hand is oriented in the direction of sight.

Figure 85:
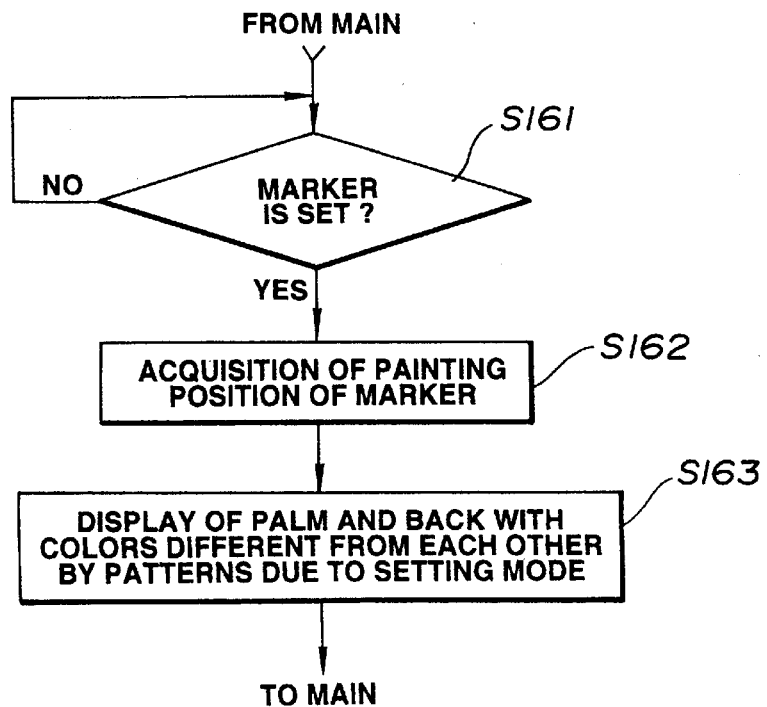
FIG. 85 is a flow chart of operation of marker display in the second modification.

In view of the above, colors displayed on the image plane is changed with respect to the palm and the back of the hand. Marker display processing is used when the device 161 is adopted in the endoscope form detecting apparatus (for example, three devices 161 are used as the coil units 122a, 122b and 122c in the apparatus 121 in FIG. 81), to perform marker display is shown in FIG. 85.

It is judged whether or not the marker is set, from the main condition (Step S161). If the marker is set, positional detection of the three source coils of the respective set coil units is performed so that the painted position of the marker is acquired (Step S161).

Subsequently, the images of the marker are displayed at the detected position by different colors in patterns corresponding to the marker setting mode with respect to the palm and the back of the hand (Step S163). After the display processing, the program is returned to the main.

When the marker is displayed in this manner, the colors may be gradually changed (For example, the displayed colors are selected from a color table so as to change from the warm color to the cool color.) in accordance with the inclined angle or the like from the palm of the hand or the surface of the back of the hand. Further, displayed form may be deformed in accordance with the angle and the position.

Figure 86:
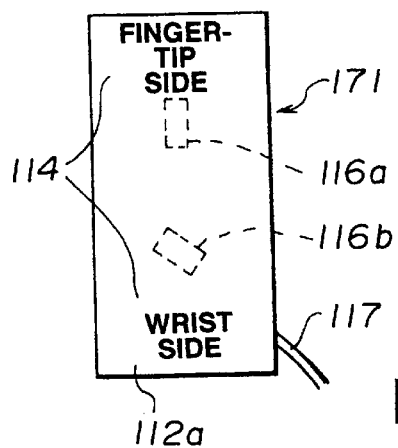
FIG. 86a is a top plan view of a palm-position detecting device in a third modification of the thirteenth embodiment.
FIG. 86b is an exploded perspective view of the device in FIG. 86a, and FIG. 86c is an explanatory view showing a condition or state mounted on a hand.
Figure 86:
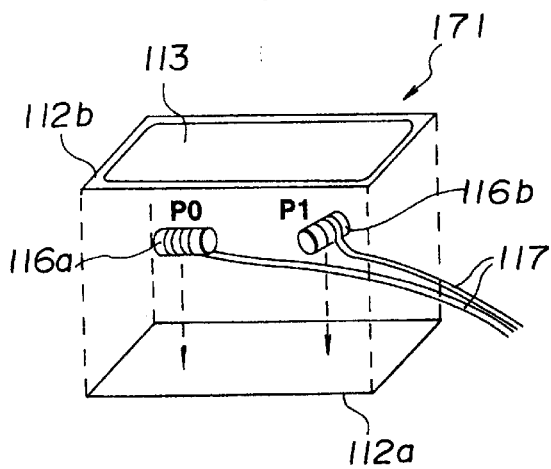
Figure 86:
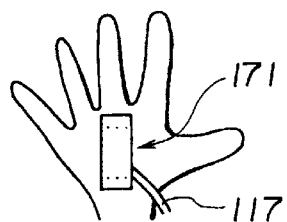

FIGS. 86a–86c shows a palm-position detecting device 171 which enables the position and the direction of the palm to be detected by the use of the pair of source coils.

The device 171 is provided respectively at positions P0 and P1 such that the pair of source coils 116a and 116b do not come into the same direction, in the device 111 and FIG. 79a. This can be pasted to the palm of the hand.

Figure 87:
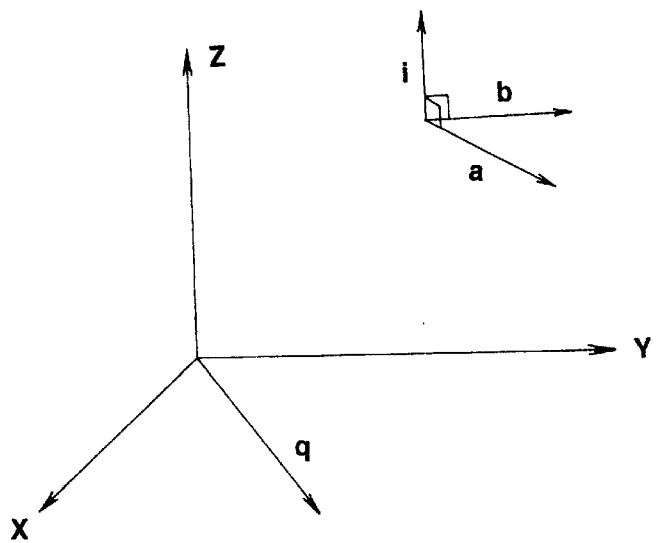

As shown in FIG. 87, if it is assumed that directional vectors of the respective source coils 116a and 116b are a and b, a vector c which reveals a plane in parallel to a and b comes into the following equation:

$$c = ga + hb \text{ (at least one of g and h is the integer which is not 0)}$$

A perpendicular of the plane comes into the vector product or outer product of a and b.

That is, a vector which is decided by i=a×b is determined. Further, similarly to the description of the case in FIG. 83, it is possible to judge the direction of the palm of the hand by positive, negative and 0 of the value w of the inner product of the vectors which show i and the direction of sight.

Figure 88:
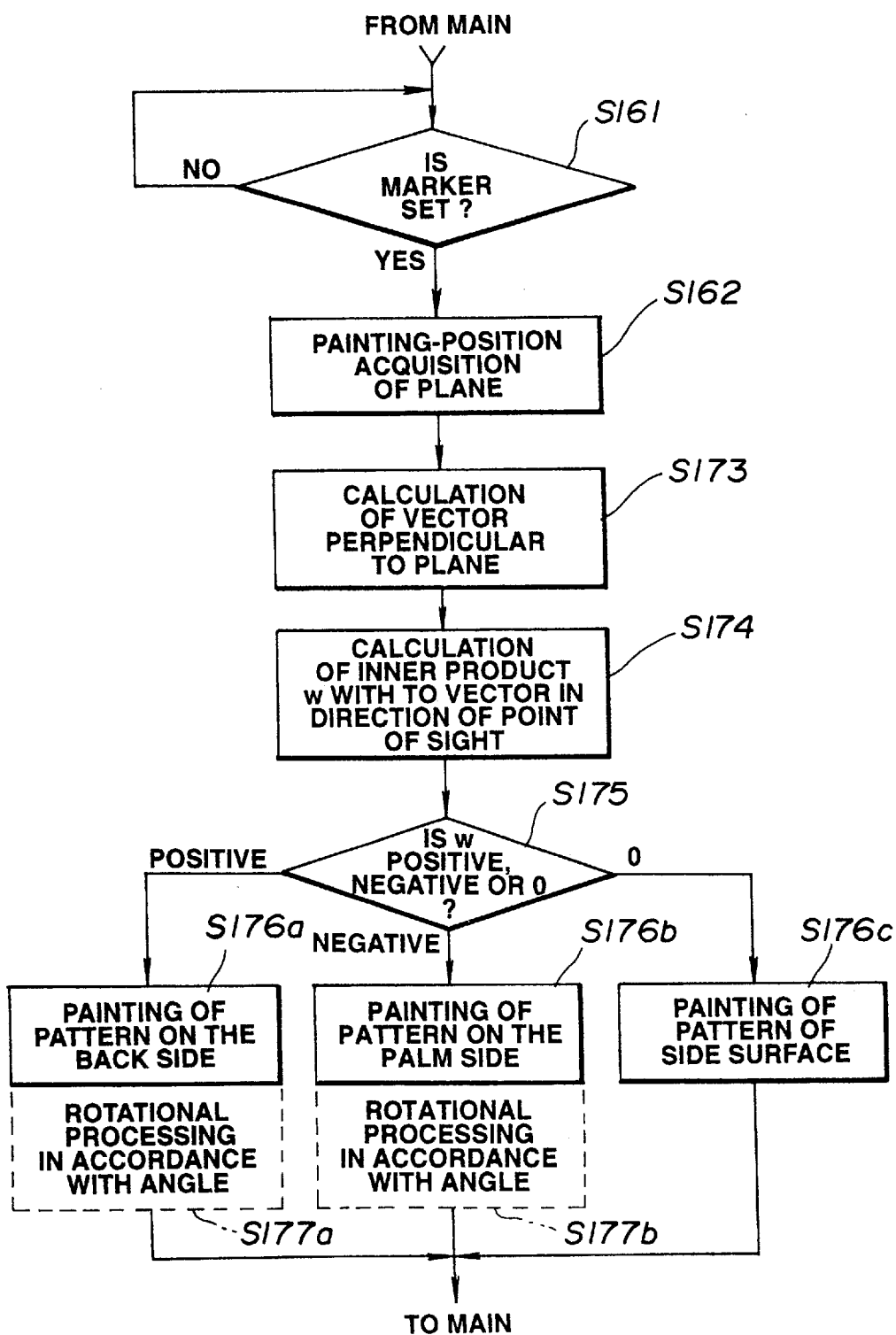
FIG. 88 is a flow chart of steps of marker display in the third modification.

FIG. 88 shows the flow of processing contents of the marker display. Similarity to FIG. 85 can be applied to FIG.

88 till Step S162. In subsequent Step S173, the vector c in parallel to the plane is calculated and, further, a vector i which is perpendicular to the vector c is calculated.

Next, a value w of the inner product between the vector i and the vector q in the direction of the point of sight is calculated (Step S174). A code of the value w is judged (Step S175). When the value w is positive, the pattern on the back side of the graphic of the marker is painted (Step S176a). When the value w is negative, the pattern on the palm side of the graphic of the marker is painted (Step S176b). When the value w is 0, the pattern on the side surface of the graphic of the marker is painted (Step S176c).

Moreover, when additional painting is intended to be performed, when the pattern on the back side is painted, the side surface pattern is rotationally processed in accordance with an angle (known from the value of w) defined between the vectors i and q so as to be returned to the main (Step S177a). Moreover, also when the pattern on the palm of the hand is painted, the side surface pattern is rotatively processed in accordance with an angle thereof so as to be returned to the main (Step S177b).

Figure 89:
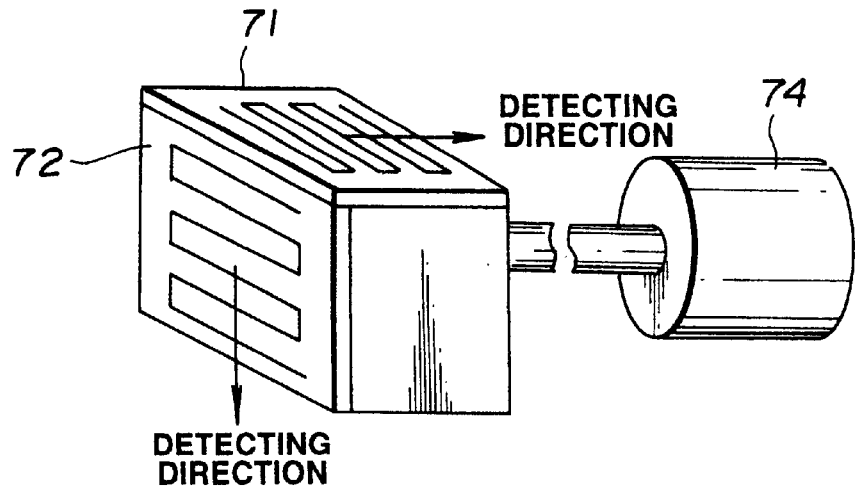
FIG. 89 is a perspective view showing a means for performing magnetic-field detection three-axis directions which is formed by a magnetic resistive element and a step motor.

In the embodiment shown in FIG. 53, three (3) MR elements are used (connected in series to each other) serving as a sensor 75j for detecting the magnetic-field strengths in three directions. However, as shown in FIG. 89, the arrangement may be such that a pair of MR elements 71 and 72 in which detecting axes extend perpendicularly to each other are installed respectively on a pair of surfaces which extend at 90 degrees, for example, these MR elements 71 and 72 are reciprocated of 90 degree rotation by a step motor 74 or a solenoid, and the magnetic-field strength is measured every rotation through 90 degrees thereof, whereby the magnetic-field strength on the spot is measured. Moreover, a hole element may be used in place of the MR element.

When the plurality of coils, the MR elements or the like are used as the positional detecting sensor, a bore is formed in core material so that connection is performed, whereby respective spacings are limited to known lengths by the elongated probe 15 or the endoscope 6, so that an attempt can be made to improve the accuracy of the produced sensor position.

When the probe 15 which is inserted into the narrow tubular space such as the channel 13 in the endoscope 6 or the like, it may become difficult to provide a positional regulation member outside the sensor in order to reduce the diameter as far as possible.

Figure 90A:
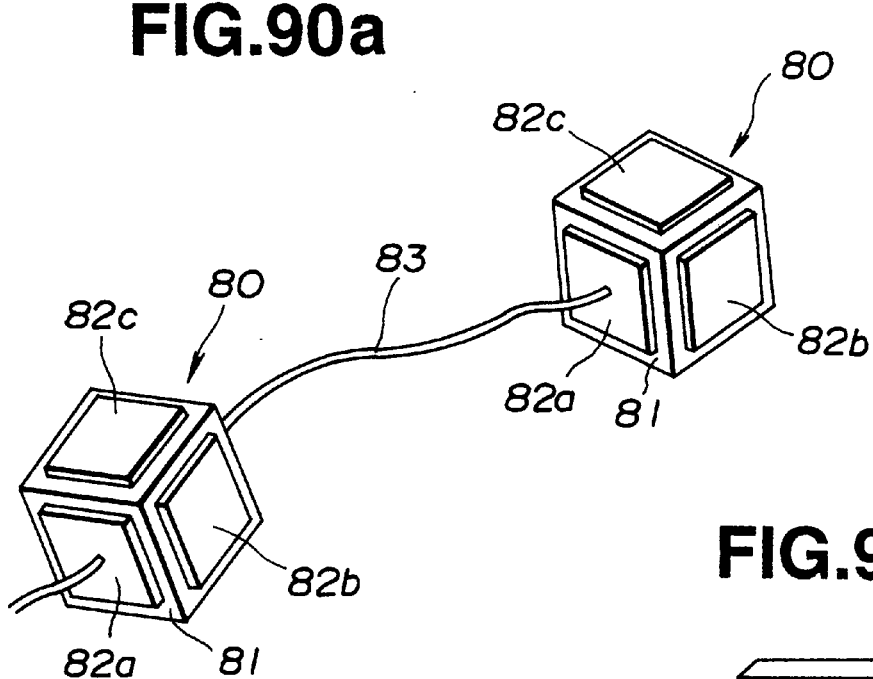
FIG. 90a is a perspective view showing a sensor to which the magnetic resistive element is connected.

For this reason, the arrangement may be such that a connecting bore, for example, is formed in the detecting part of a surface intended to be connected to each other, and the MR element is formed so as to avoid the bore. FIG. 90a shows a sensor arranged in such a manner.

Each of the sensors 80 is arranged such that the MR elements 82a, 82b and 82c are fixedly mounted by adhesives on three (3) surfaces of a cubic sensor support member 81, and are fixedly mounted on the connecting cord 83 at constant predetermined intervals.

Figure 90B:
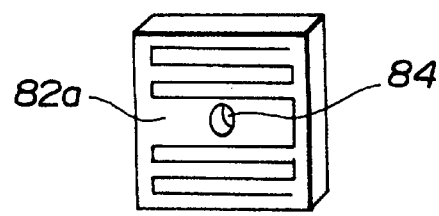
FIG. 90b is a perspective view showing the magnetic resistive element which is formed therein with a connecting hole.

In this case, as shown in FIG. 90b, a bore 84 for cord insertion is formed in a center of the MR element 82a so that the connecting cord 83 can pass through the bore 84. In this connection, the cubic sensor support member 81 is also formed therein with the bore 84' (refer to FIG. 91) for code insertion.

Figure 91:
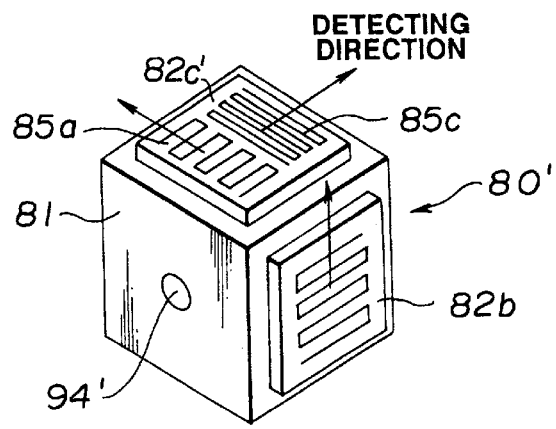
FIG. 91 is a perspective view showings a sensor in which magnetic resistive element parts different in detecting directions from each other are provided in the same plane.

Meanwhile, the connection bore 84 is not formed in the MR element 82a, but the embodiment may be constructed as shown in FIG. 91.

In a sensor 80' shown in FIG. 91, the MR element 82a and the MR element 82c in FIG. 90a are united to each other to come into an MR element 82c'. The MR element 82' is arranged such that MR element portions 85a and 85c in which the detecting directions extend perpendicularly to each other are formed on the same plane to form an MR element sensor for two direction detection.

In connection with the above, an MR element 82b for detection in a single direction is mounted on a plane which adjoins to a surface which is provided with the MR element 82' and which is not formed with the bore 84' similarly to FIG. 89a. In this manner, the MR element may not be provided on a surface which is required for connection in the sensor support element 81.

Further, in FIG. 91, the MR elements in which the detecting directions are perpendicular to each other are integrally formed on the same plane as the MR element 82c'. However, it is apparent or clear that a pair of MR elements may be mounted.

Figure 92:
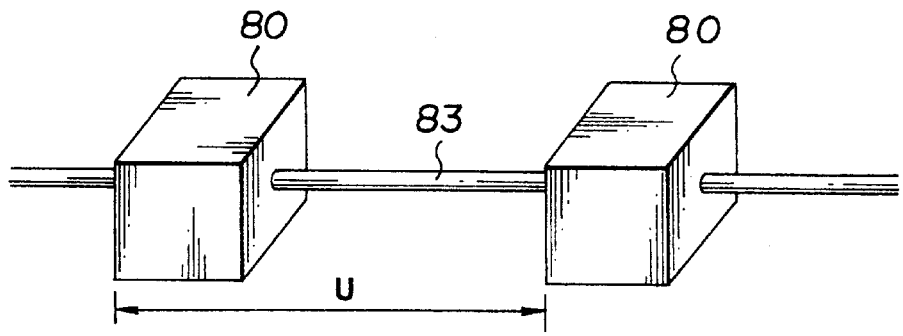
Figure 92:
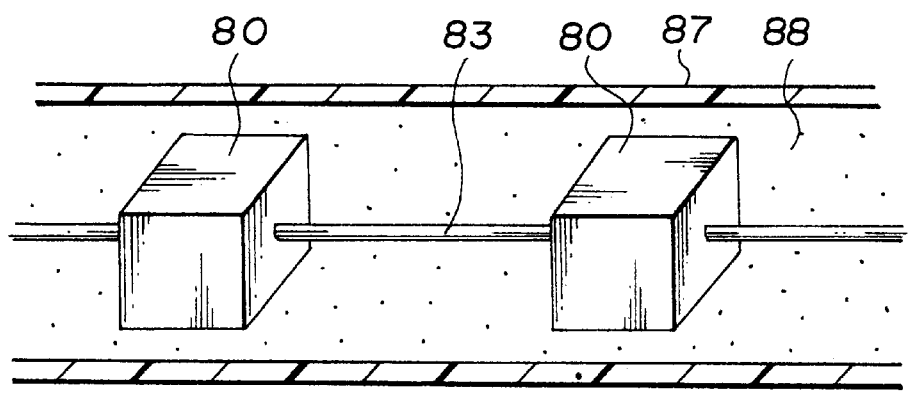

In order to position the sensor having such a structure, as shown in FIG. 92a, the interval u should be decided to adhere each sensor (80 or the like) to a fixing member such as the cord 83 or the like by adhesives. The arrangement should be such that the sensor is inserted into a tube 87 whose length is less than the entire length of the fixing member, and elastic thermosetting resin 88 or resin hardened to a condition having elasticity is filled in the tube 87 and is hardened as shown in FIG. 92b under a condition that tension is applied to the fixing member to ensure certain positioning.

Figure 93:
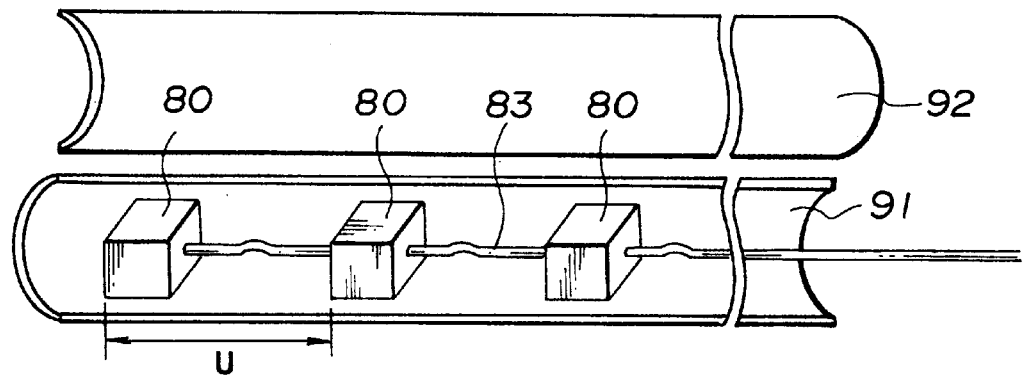
FIG. 93 is an explanatory view showing a state which performs positioning by the use of cylindrical split molds or patterns.

Moreover, the arrangement may also be such that, in order to perform positioning, as shown in FIG. 93, the sensors 80 are placed on the cylindrical split patters or split molds 91 and 92 at respective positions having predetermined intervals to close the split patterns, and insulating resin (not shown) is poured and hardened. In this case, the arrangement may form a structure in which under a condition that the lead wire is fixedly mounted on the cord 83, and the cord 83 is slightly loosened, resin is poured into and is hardened, and the lead wire is difficult to be broken in line even if the lead line is buckled. If the resin is hardened, the lead wire is inserted into an extended casing member or into a heat-contractibility casing member. In this manner, the lead wire is inserted into the casing member, whereby the strength as a probe is secured, and slippage when the lead wire is inserted into the channel can be secured by surface treatment or processing of the casing member. Further, since the interior is filled with resin, there is no situation where buckling occurs.

In connection with the above, in the above-described embodiments and the like, the description has been made such that the probe is inserted into the channel in the endoscope, and the magnetic-field generation source or the magnetic-field detecting sensor is arranged at the known position within the endoscope. However, the invention should not be limited to the arrangement. The arrangement may be such that a magnetic-field generation source or a magnetic-field detecting sensor is built in or is mounted on an outer peripheral surface of the endoscope (within the forward end, for example), or the like.

Further, the endoscope should not be limited to an arrangement which builds therein an image-pickup element such as a CCD or the like, but may be an optical endoscope (a fiber scope, for example).

Moreover, the invention should not be limited to such an arrangement that the magnetic-field generation sources or the magnetic-field detecting sensors are arranged at corners of the bed 4 or the like. The arrangement may be such that the magnetic-field generation sources or the magnetic-field detecting sensors are arranged at the periphery of the bed 4, at a position above the bed 4, or the like.

Furthermore, the invention should not be limited to such an arrangement that a single-axis or three-axis coil is used to form the source coil or the sense coil. The arrangement may be such that two-axis coil (a single coil is removed from three-axis coil) is used.

Further, the arrangement in which the coil is printed on and is formed on a flexible substrate or the like is made to a tube so as to be installed into a channel may be used as a probe for positional detection or form detection. Moreover, the arrangement may be applied to a tube in which the arrangement in which the coil is printed and formed is made to a tube to form a channel.

Moreover, the arrangement in which the coil is printed and formed on the flexible substrate or the like may be wound around the insertion part of the endoscope in the form of a spiral or the like so as to be mounted on the insertion part, and the arrangement is utilized for position and form detection.

Next, an endoscope form detecting apparatus according to a fourteenth embodiment of the invention which can prevent detecting means and internal components from failing or being damaged by interference between the endoscope internal components, the detecting means and the like due to curvature, torsion or the like of the endoscope, that is, in which an attempt can be made to increase or raise the mechanical strength with respect to curvature operation and inserting operation and to stabilize function for form insertion detection will be described.

Figure 94:
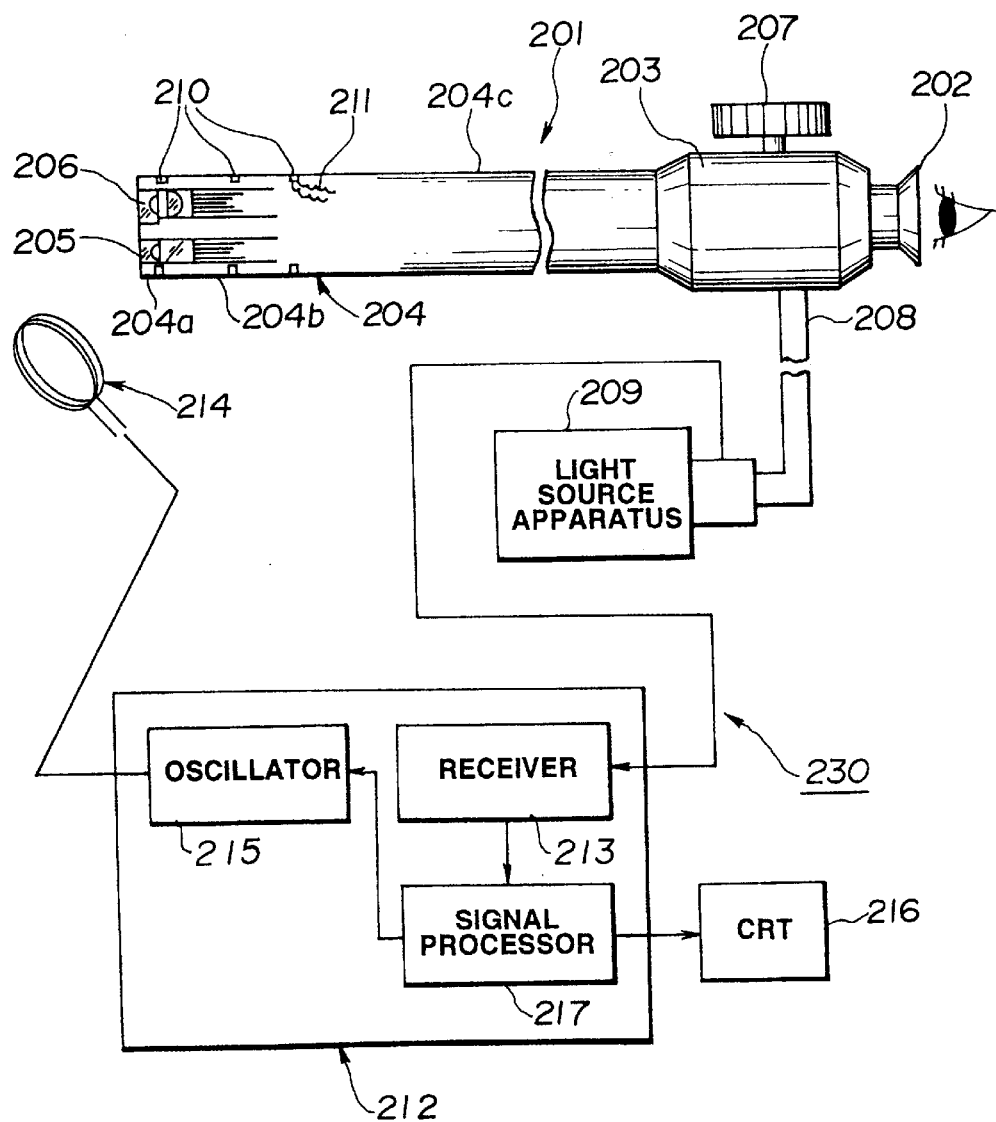
FIG. 94 is an arrangement view of an endoscope form detecting apparatus according to a fourteenth embodiment of the invention.

An endoscope form detecting apparatus 230 shown in FIG. 94 comprises an endoscope 201, a light source apparatus 209, an inserted shape detector 212, and a loop antenna 214.

The endoscope 201 is made by coupling an elongated insertion part 204 with the front end of an operation unit 203 having an eyepiece unit 202 at the back end and serving as a grip for an operator. The endoscope 201 observes or examines a region to be examined or undertakes a variety of therapeutic procedures, if necessary, when the insertion part 204 is inserted into a lumen in a body cavity perorally or per anum. The insertion part 204 is composed of a distal part 204a including a light emission window 205 for a lighting optical system and a view window 206 for a viewing optical system, a bending section 204b that can be bent, and an elongated flexible tube 204c having flexibility, which are lined up in that order from the distal end of the insertion part 204. The bending section 204b is bent by turning an angling knob 207 installed on the operation unit 203, whereby the distal part 204a is angled in a direction an operator intends.

A universal cord 208 is extending from the side of the operation unit 203, and connected to the light source apparatus 209 for supplying illumination light. The endoscope 201 shown in FIG. 94 is an optical type in which a view formed by an objective optical system lying behind the view window 206 is transmitted to the eyepiece unit 202 by means of image transmitting means, and then observed through the eyepiece unit 202. The present invention is not limited to this type of endoscope but may apply to an electronic endoscope in which a view formed by the objective optical system is photoelectrically transformed using a solid-state imaging device in order to produce an imaging signal, and the imaging signal is transmitted to an external video processor for signal processing, and then the view is displayed on a monitor.

In the insertion endoscope part 204, a plurality of coils 210 serving as a receiving antenna or magnetic field detecting means are arranged at such intervals that the coils 210 will not interfere with one another. The spacings between adjoining pairs of the coils 210 can therefore be narrowed by changing the resonant frequencies of the coils 210, whereby high-precision positional information can be acquired. The coils 210 are joined with cables 211. The cables 211 are routed to a receiver 213 in the inserted form detector 212 via the insertional part 204, operation unit 203, and universal cord 208. The coils 210 receive electromagnetic waves to generate induced electromotive voltage. The generated voltage signals are fed to the receiver 213 in the inserted endoscope form detector 212 over the cables 211.

The inserted form detector 212 includes an oscillator 215 for feeding a high-frequency signal to the loop antenna 214 serving as a transmitting antenna for radiating electromagnetic waves to the coils. The coils 210 lie within an AC magnetic field developed by the loop antenna 214 and generate induced electromotive voltage. The antenna 214 is not limited to a loop antenna but may be a square antenna or a dipole antenna. Alternatively, a plurality of antennas may be installed at the same position.

The inserted form detector 212 has a signal processor 217 for rendering a form of the insertion part 204. The signal processor 217 inputs, from the receiver 213, information concerning a strength of induced electromotive voltage varying depending on the orientation of the antenna 214 with respect to the coils 210, calculates the positions and angles of the coils 210 using the amplitudes and phases of the output signals of the coils 210 provided relative to the output of the oscillator 215, interpolates in value the information concerning calculated coordinates, and then displays a form of the insertion part on a monitor 216. For the display of a form, this embodiment adopts a dedicated monitor. Alternatively, data of a form may be synthesized with data of a viewed endoscopic image and then displayed on a monitor for displaying viewed endoscopic images.

Figure 95:
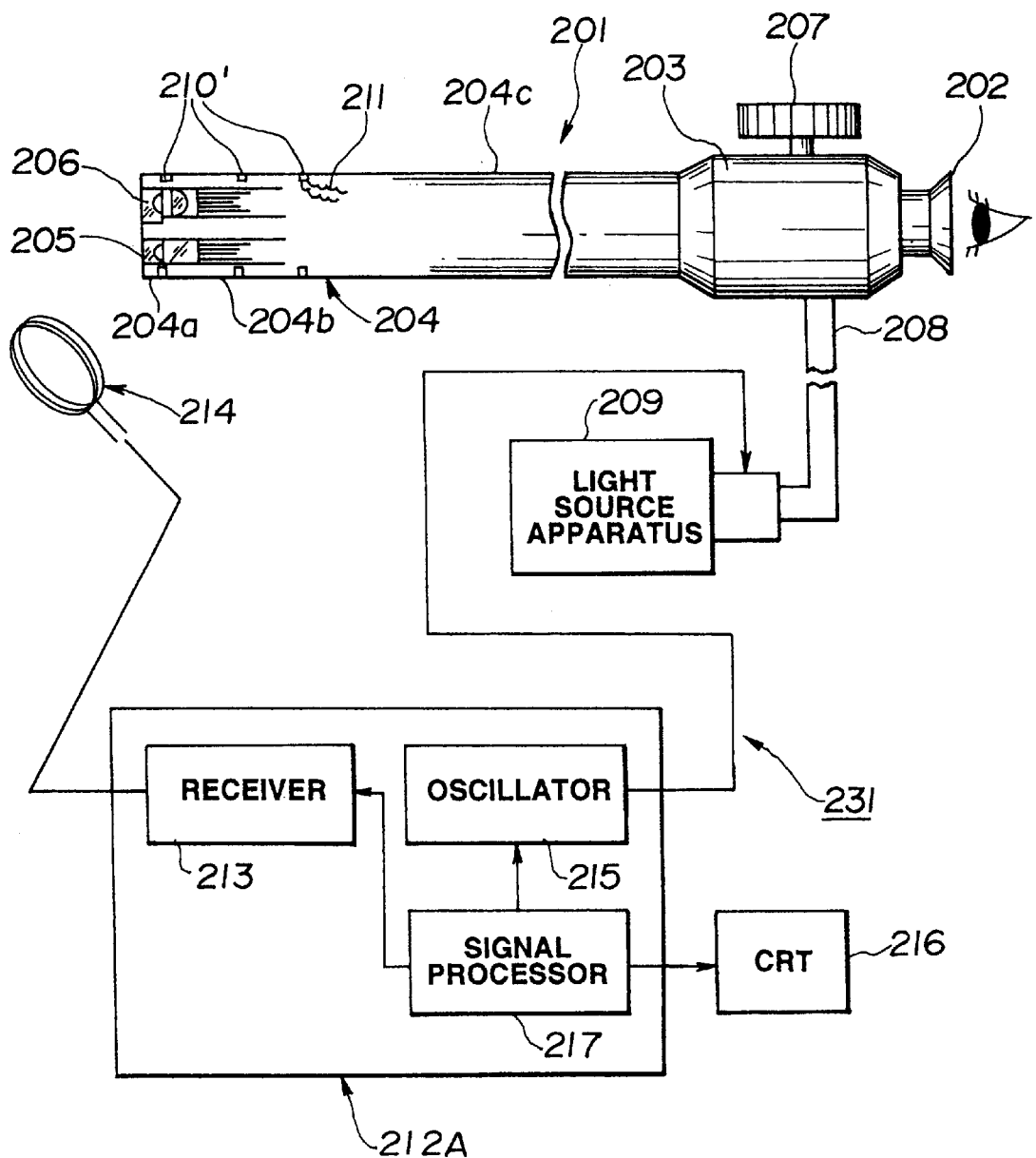
FIG. 95, is an arrangement view of an endoscope form detecting apparatus according to a fifteenth embodiment of the invention.

FIG. 95 shows an example of another configuration of an endoscope form detecting apparatus. An endoscope form detecting apparatus 231 differs from that shown in FIG. 94 in a point that coils 210' incorporated in the endoscope 201 are used as a magnetic field generator, and magnetic field detecting means installed outside the endoscope is used to detect an inserted form of an endoscope. In the apparatus 231, as shown in FIG. 95, a signal sent from the oscillator 215 is applied to the coils 210' serving as a transmitting antenna or magnetic field generating means. The loop antenna 214 lying outside the endoscope and the receiver 213 in the inserted form detector 212A are used to detect a magnetic field strength. Based on the detected value, the signal processor 217 renders a form of the endoscope similarly to that in the system shown in FIG. 94. The other components identical to those in the apparatus shown in FIG. 94 are assigned to the reference numerals. No mention will be made of these components and the operation identical to that in the apparatus shown in FIG. 94. This configuration can also display an inserted form of an endoscope on the monitor 216.

Figure 96:
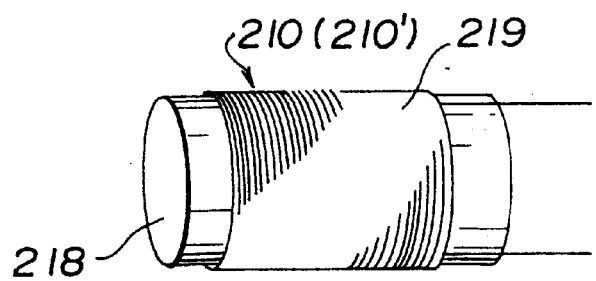
FIG. 96 is an arrangement view of a coil.

FIG. 96 shows an example of a coil 210 (or 210') incorporated in the endoscope 201. In this example, the coil 210 is a cylindrical single-core solenoid. A core 218 serving as a base material is made of a ferromagnetic material such as ferrite or Permalloy. The coil 210 is made by winding an intended number of turns of copper wire 219 about the core 218. In this case, since the copper wire 219 is coated with a given insulating material, the turns of copper wire 219 are usually in close contact with one another.

However, it is likely that the coating may develop pinholes or cracks. Then the coils 210 incorporated in the endoscope 201 are used as sensors for detecting a microscopic magnetic field as those in the configuration shown in FIG. 94, a voltage across each coil is small. The dielectric strength of each coil may therefore be small. However, in the configuration shown in FIG. 95 in which the coils incorporated in the endoscope 201 are used as a magnetic field generator and the magnetic field detecting means is installed outside the endoscope, the coils cannot help being small in size. A current value must therefore be raised so that the strength of a generated magnetic field will be greater. Thus, a satisfactory magnetic field is developed with adjoining coils spaced by a desired distance. A voltage providing the current value is applied across each of the coils 210'. The dielectric strength of each coil must therefore be high. Thus, the core 218 must have a satisfactory dielectric strength against the copper wire 219. When the coils 210' are employed for the system shown in FIG. 95, an insulating material such as Mylar film may be wound about each core before the copper wire 219 is wound about the core. For incorporating coils serving as sensors or a magnetic field generator in an endoscope, the coils must be insulated reliably so that no signal will leak out to the endoscope, or on the contrary, a signal from a living body will be not convolved into the output signals of the coils to produce noise.

For incorporating the coils 210 or 210' in an endoscope, the coils must be mechanically so strong that when the endoscope with the built-in coils is inserted into a patient, the coils will not be damaged because of the interference with optical fibers or a forceps channel lying through the endoscope and moving with bending or torsion. The reverse is also true. That is to say, a counter measure should be devised for fear that the optical fibers may be broken because of their touching the structures of coils.

Figure 107:
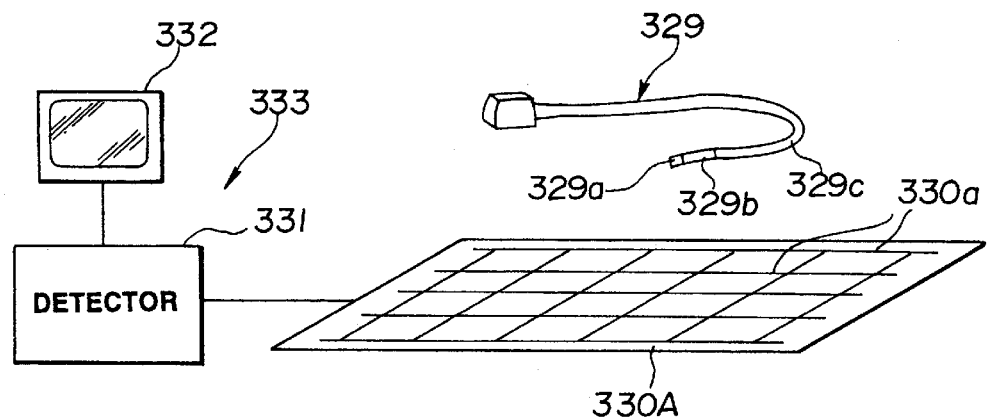

For each of the coils 210 and 210' of this embodiment, as shown in FIG. 107, the core 218 about which the copper wire 219 has been wound is coated with an insulating material 220 so as to have a curved outline. When each of the coils 210 (or 210') is connected to the inserted form detector 212 (or 212A) over connection copper wires 221 serving as connecting means, soldered points indicated with S are separated from each other and sunk in the insulating material 220. Thus, the copper wires 221 are isolated from each other and the mechanical strength of a coil is reinforced.

The insulating material 220 may be silicon or the like. For further reinforcement, the whole of a coil may be sheathed with a tube made of a high polymer material such as a heat contraction tube. Alternatively, the soldered points S may be arranged on the opposite side of a coil that is far from the inserted form detector 212 (or 212A), though the diameter of the coil gets larger by about the diameters of the connection copper wires 221. Thus, since the insulating material 220 offers as a whole opposition to the tensile forces imposed on the connection copper wires 221, the mechanical strength of the coil further improves. Even for the coil structure shown in FIG. 98, similarly to that in FIG. 97, a coil is molded with the insulating material 220 so as to have a curved surface. Alternatively, a coil may be sheathed with a tube. If the sheath of a tube provides a sufficient dielectric strength, a coil may be merely sheathed with a tube but not coated with an insulating material.

Only the portions of structures except coils in an endoscope, which may touch any other structure are formed to have a curved surface so as not to cause a mechanical damage. The other portions that cannot touch any other structure or are connected to an endoscope may have a flat surface or a surface outlined in harmony with the surface of the endoscope. The insulating material may, of course, be coated to provide an entirely curved surface.

Figure 97:
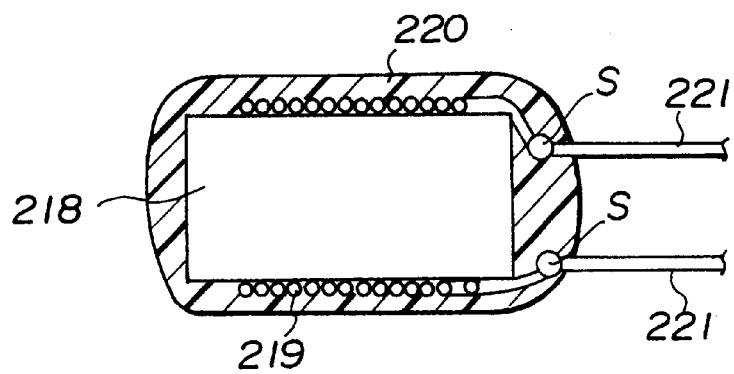
FIG. 97 is a cross-sectional view of the coil which is sealed by an insulating material.
Figure 98:
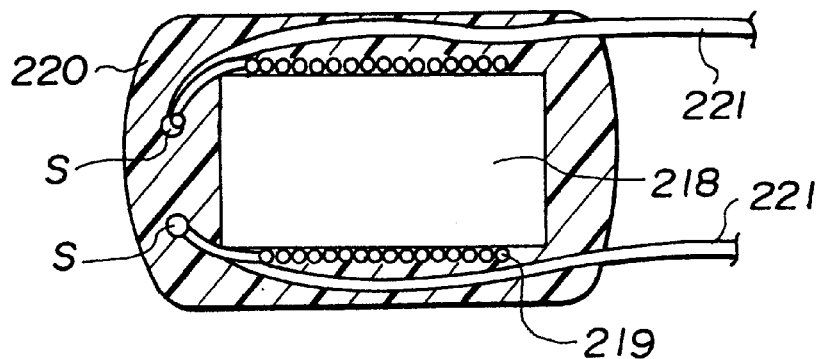
FIG. 98 is a cross-sectional view of the coil relating to an arrangement different from that shown in FIG. 97.

The inserted endoscope form detecting apparatus 230 (or 231) of this embodiment has the plurality of coils 210 (or 210') shown in FIG. 97 or 98 arranged in the insertion part 204.

In this embodiment, coils and connection copper wires joined with the copper wires of the coils are partly coated with an insulating material. The outer circumferences of the coils coated with the insulating material are shaped to have curved surfaces or not to have any projection or corner. Thus, the plurality of coils and the contents of an endoscope can be protected from being damaged due to the mutual interference resulting from bending or torsion. Thus, this embodiment provides a coil structure permitting improved mechanical strength resistive against bending or torsion of an endoscope. This results in the stable function and structure for detecting an inserted form of an endoscope.

Figure 99:
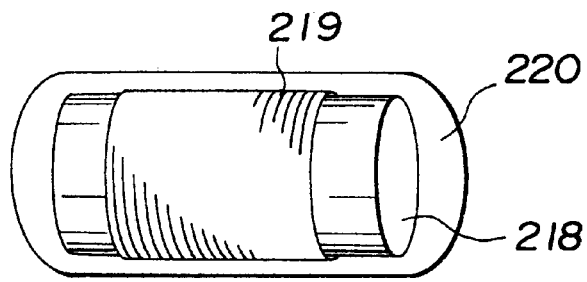
FIG. 99a~99c are arrangement views relating to a modification of the coil.
Figure 99:
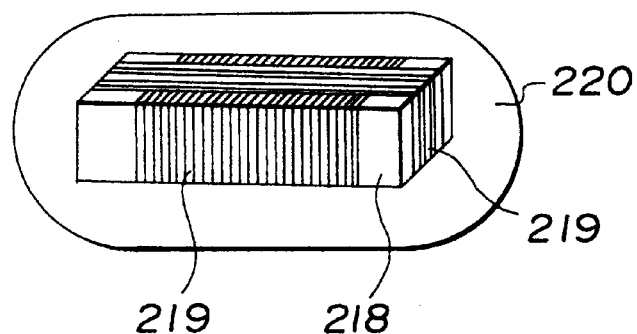
Figure 99:
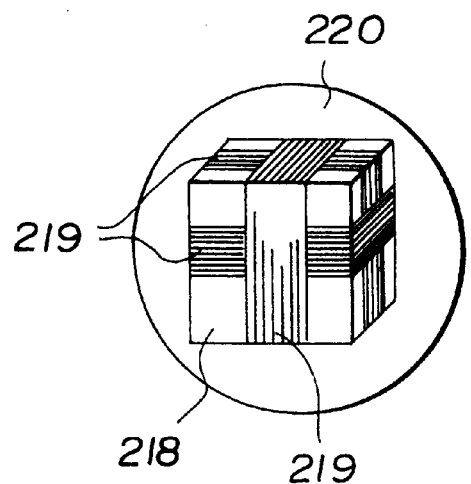

FIGS. 99a–99c show variants of a coil coated with an insulating material. FIG. 99a shows a coil having the aforesaid structure.

FIG. 99b shows a coil made by winding a number of turns of copper wire 219 bi-directionally and coated with an insulating material 220. FIG. 99c shows a coil made by winding a number of turns of copper wire 219 in three directions and coated with an insulating material 220.

Aside from the coils, the connection copper wires 221 for transferring signals between the coils and inserted endoscope form detector may mechanically interfere with other structures in the endoscope. Aside from the insulating coating applied to the copper wires 219, reinforcement insulation may be provided for the connection copper wires 221 by coating the entire lengths thereof with silicon. Alternatively, the connection copper wires 221 may be sheathed with insulation tubes in order to protect the coatings of the connection copper wires 221.

Figure 100:
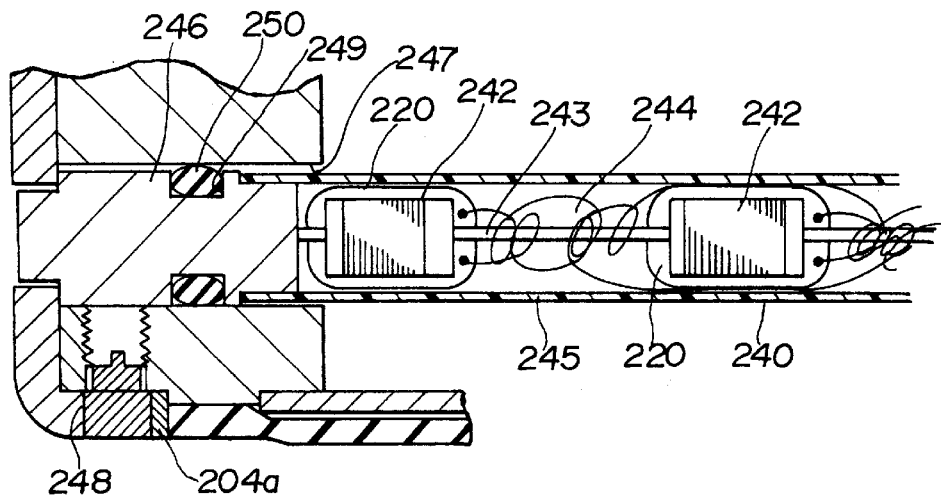
FIG. 100 is an arrangement view relating to fixing on the endoscope distal side of an imaging probe.
Figure 101:
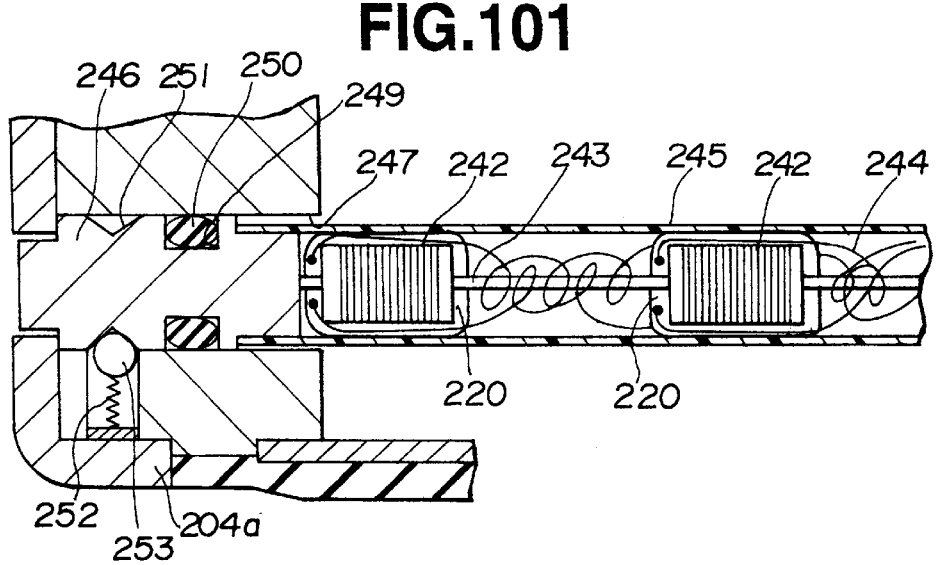
FIG. 101 is an arrangement view relating to fixing different from that illustrated in FIG. 100.
Figure 102:
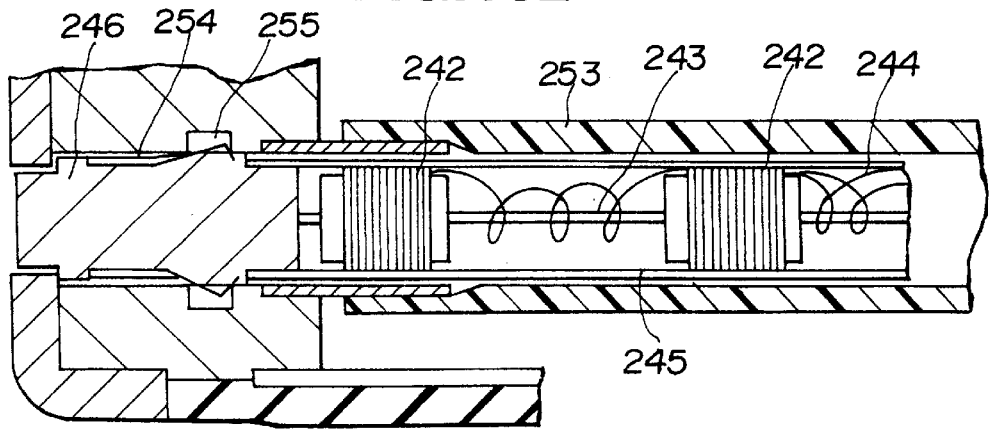
FIG. 102 is an arrangement view relating to further another fixing different from that illustrated in FIG. 100.

FIGS. 100 to 102 show structures for locking an imaging probe having a plurality of aforesaid coils therein to a distal structure of an endoscope.

An imaging probe 240 shown in FIG. 100 is inserted into and held by the insertional endoscope part 204 and electrically connected to the inserted form detector 212 (or 212A).

The imaging probe 240 comprises a distal probe member 246, a plurality of coils 242 serving as magnetic field detecting means or magnetic field generating means, a conductor 243 made of a flexible material, a signal line 244 serving as connecting means, and a casing tube 245. The coils 242 are attached to the conductor 243 at predetermined intervals using an adhesive. The distal end of the conductor 243 is locked in the distal probe member 246 mounted in the distal part 204a of the insertion part 204.

The plurality of coils 242 are sheathed with the casing tube 245 in order to protect the signal line and others. The distal portion of the casing tube 245 are fixed to the distal probe member 246.

The distal probe member 246 is inserted into a mounting hole 247 formed in the distal endoscope part 204a, and pressed radially and secured by means of a set screw 248 serving as locking means. In addition, an O-ring or any other seal member 250 is embedded in a ditch 249 bored in the middle of the outer circumference of the distal probe member 246, thus providing fluid-tight seal. Because of this structure, even when the insertion part 204 is bent during endoscopic examination, the imaging probe 240 incorporated in the endoscope 201 does not change its relative position in the axial direction with respect to the insertional part. The inserted form of the insertion part can be grasped accurately by detecting the positions of the coils.

FIGS. 101 and 102 show other structures of an imaging probe. These structures are variants of locking means for locking the distal probe member in the distal endoscope structure.

FIG. 101 shows a structure in which the distal probe member 246 is locked using a so-called ball click; that is, a ball 253 pressed by a spring 252 against a support ditch 251 formed in the outer circumference of the distal probe member 246. FIG. 102 shows an example of a structure in which an imaging probe is inserted into a forceps channel 253 formed in an endoscope. The imaging probe shown in FIG. 102 is locked by means of a plurality of plate spring members 254 attached to the outer circumference of the distal probe member 246 which are fitted into a stopper ditch 255 formed in the distal endoscope part 204a. These locking means can apply to the structure shown in FIGS. 100 and 101 in which an imaging probe is directly incorporated in an endoscope as well as the structure shown in FIG. 102 in which an imaging probe inserted into the forceps channel 253 is incorporated in an endoscope. The means for locking a distal probe member in a distal endoscope part is not limited to the foregoing illustrated examples.

The fourteenth and fifteenth embodiments have the advantages of offering improved mechanical strength by successfully protecting detecting means and the contents of an endoscope from being damaged due to the mutual interference resulting from bending or torsion of the endoscope, and of permitting a stable function for inserted shape detection.

Next, a sixteenth embodiment of the present invention will be described. This embodiment can accurately render an inserted shape of the endoscope despite the presence of stress resulting from bending or insertion of the endoscope.

Figure 103:
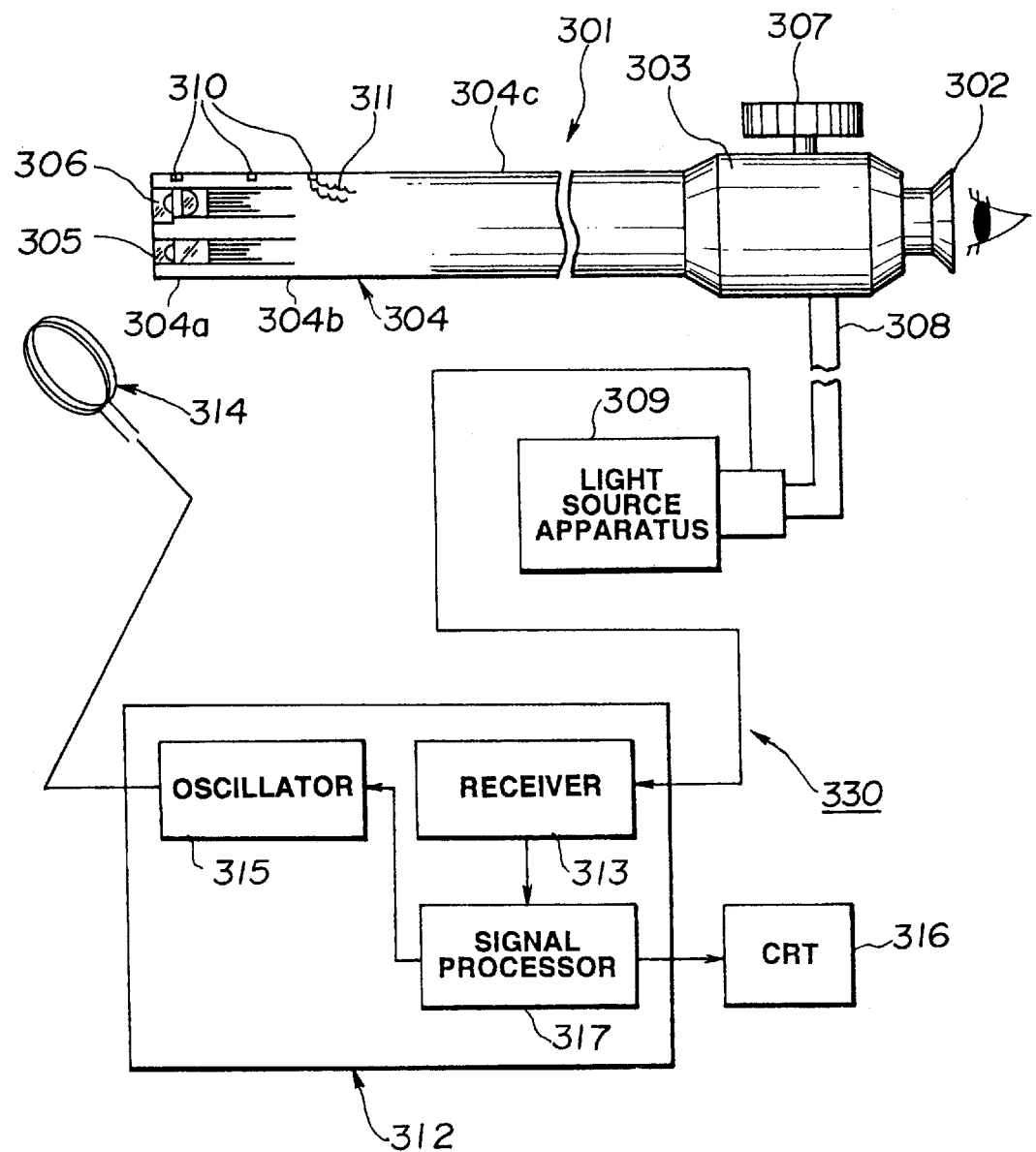

An inserted endoscope form detecting apparatus 330 shown in FIG. 103 comprises an endoscope 301, a light source apparatus 309, an inserted form detector 312, and a loop antenna 314.

The endoscope 301 is made by coupling an elongated insertion part 304 with the front end of an operation unit 303 having an eyepiece unit 302 at the back end thereof and serving as a grip for an operator. The endoscope 301 observes and examines a region to be examined or undertakes various therapeutic procedures when the insertion part 304 is inserted into a lumen in a body cavity perorally or per annum. The insertion part 304 is composed of a distal part 304a having a light emission window 305 for a lighting optical system and a view window 306 for a viewing optical system, a bending section 304b that can be bent, and an elongated flexible tube 304c having flexibility, which are lined up in that order from the distal end of the insertion part 304. The bending section 304b is bent by turning an angling knob 307 formed on the operation unit 303. Thus, the distal part 304a can be angled in a direction intended by an operator.

A universal cord 308 extends from the side of the operation unit 303, and is connected to the light source apparatus 309 for supplying illumination light. The endoscope shown in FIG. 103 is of an optical type in which a view formed by an objective optical system lying behind the view window 306 is transmitted to the eyepiece unit 302 by means of image transmitting means, and then directly observed through the eyepiece unit 302. The present invention is not limited to this type of endoscope but can apply to an electronic endoscope in which a view formed by the objective optical system is photoelectrically transformed using a solid-state imaging device in order to produce an imaging signal, and the imaging signal is transmitted to an external video processor for signal processing, and then the view is displayed on a monitor.

A plurality of coils 310 that serve as a receiving antenna or magnetic field detecting means are arranged in the insertional endoscope part 304 at such intervals that the coils 310 will not interfere with one another. The spacings between adjoining ones of the coils 310 can be narrowed by changing the resonant frequencies of the coils 310, whereby positional information with higher precision can be acquired. The coils 310 are joined with cables 311. These cables 311 are routed to a receiver 313 in the inserted form detector 312 via the insertional part 304, the operation unit 303, and the universal cord 308. The coils 310 receive electromagnetic waves to generate induced electromotive voltage. The generated voltage signals are fed to the receiver 313 in the inserted form detector 312 over the cables 311.

The inserted form detector 312 includes an oscillator 315 for supplying a high-frequency signal to a transmitting antenna for radiating electromagnetic waves to the coils; such as, the loop antenna 314. When placed in an AC magnetic field developed by the loop antenna 314, the coils 310 generate induced electromotive voltage. The antenna 314 is not limited to a loop antenna but may be a square antenna or a dipole antenna. Moreover, a plurality of antennas may be installed at the same position.

The inserted form detector 312 includes a signal processor 317 for rendering a form of an insertional endoscope part. The signal processor 317 inputs information concerning the strength of induced electromotive voltage varying depending on the orientation of the antenna 314 with respect to the coils 310, calculates the positions and angles of the coils 310 by analyzing the amplitudes and phases of the output signals of the coils 310 provided relative to the output of the oscillator 315, interpolates in value the information concerning calculated coordinates, and then displays a form of an insertional part on a monitor (CRT) 316. For the purpose of the display of a form, this embodiment adopts a dedicated monitor. Alternatively, data of a form may be synthesized with data of a viewed endoscopic image, and then displayed on a monitor for displaying endoscopic images.

FIG. 104 is a sectional view showing a locked state of a detection coil 310 in a distal endoscope part. The distal endoscope part 304a has a distal structure 318 in which image transmitting means and others are located. The tip of the distal structure 318 is shielded with a distal casing member 319. The insertion part 304 has its portion ranging from the proximal end of the distal casing member 319 through the bending section 304b to the flexible tube 304c sheathed with soft casing rubber 320. The distal structure 318 has a channel 321 opening upon the proximal space, and a projection 322 lying in the ditch 321, being formed as part or independently of the ditch 321, and serving as locking means. The coil 310 is, as shown in FIG. 105, made by winding a predetermined number of turns of copper wire 325 about a core 324. The core 324 has a fitting hole 326 into which the projection 322 of the distal structure 318 is fitted.

The coil 310 is locked in the distal structure 318 by fitting the projection 322 into the fitting hole 326. Once the coil 310 is attached to the projection 322 using an adhesive serving as locking means, the coil 310 can be locked more securely. The coil 310 is joined with a connection copper wire 327 of the cable 311 for transmitting the detected signal to the inserted form detector 312. The connection copper wire 327 is provided independently of the copper wire 325 of the coil 310, and attached through soldering or the like during assembly. Alternatively, when the coil 310 is manufactured, an extra required length of copper wire 325 may be left unwound in order to create the connection copper wire 327. Thus, the connection copper wire 327 may be formed as part of the copper wire 325.

The wire material employed may be a litz wire composed of a plurality of conductors but may not be a single-core copper wire. The wire material to be joined with the inserted form detector 312 may be a twisted pair or a shielded twisted pair.

In this embodiment, the core 324 is supported by the projection 322 in an effort to prevent dielectric breakdown or disconnection between the turns of copper wire 325 of the coil from occurring due to mechanical stress imposed on the copper wire 325. For a simpler structure, the channel 321 alone may be formed but the projection 322 may not be provided, so that the coil 310 is embedded in the channel 321 and secured with an adhesive.

In this embodiment, the axial direction of the endoscope is almost aligned with the axial directions of the coils 310. The present invention is not limited to this working mode. The coils 310 may be lined up in a direction perpendicularly to the axial direction of the endoscope.

Alternatively, the plurality of coils 310 may be lined up substantially in the axial direction of the endoscope and oriented perpendicularly thereto.

A structure for positioning and locking the detection coils 310 in the bending section of the endoscope will be described with reference to FIG. 106a. Numerous bending frames 328, which are shaped substantially annularly and combined with one another so as to rotate freely, are, as shown in FIG. 306a, arranged in the bending section 304b. The bending frames 328 are combined with one another so as to rotate freely owing to axes 328a that are fitted into holes bored in their ears. The bending frames 328 shown in FIG. 106a can be curved upward (U) and downward (D). The coils 310 are, as shown in the cross sectional view of FIG. 106b, locked in the bending frames 328 at predetermined intervals using an adhesive 323 or other locking means. In FIG. 106b, the connection copper wires for transmitting signals are not shown.

Optical fibers for guiding illumination light to the distal endoscope part or a channel for aeration or affusion, which is not illustrated, lies through the bending frames 328. The coils 310 should therefore be positioned so as not to interfere with the optical fibers or channel.

FIGS. 106c to 106f show examples of another structures for positioning and locking the coils 310 in the bending section of the endoscope. In the structure shown in the sectional view of FIG. 106c, L-shaped projections 322A are formed inside bending frames 328. In the structure shown in the sectional view of FIG. 106d, projections 322B are formed inside bending frames 328 so as to project substantially perpendicularly to the axial direction of the insertion part 304. The projections 322A or 322B are fitted into the fitting holes 326 of the coils 310, whereby the coils 310 are locked.

In the structure shown in the sectional view of FIG. 106e, recesses 322c are formed as if part of the outer circumferential walls of bending frames 328 were dented inward. The coils 310 are mounted and locked in the openings of the recesses 322C shown in the side view of FIG. 106f. In this structure, the fitting holes 326 need not be formed in the coils 310. It is, however, necessary to encapsulate the outer circumferences of the turns of copper wire 325 with an insulating material such as Mylar film, so that insulation or pressure proof can be maintained and the copper wire 325 will not be damaged.

As for the mounting site of the coils, the coils 310 can be mounted not only in the distal endoscope part 304a and bending section 304b but also in the flexible tube 304c leading to the operation unit gripped by an operator.

In this embodiment, the coils are locked securely in the insertion part using the locking means. Therefore, even if the coils are stressed due to bending or insertion of the endoscope, they are prevented from shifting. Thus, even if the insertion part changes it forms, the original positions of the coils are not shifted. The spacings between adjoining coils can therefore be reliably maintained. Conclusively, this embodiment can render a form of the insertion part accurately.

Next, a seventeenth embodiment will be described.

In the sixteenth embodiment, the coils 310 are employed as a magnetic field detecting means. A configuration in which the same kind of coils are employed as a magnetic field generator and the antenna 314 is employed as magnetic field detecting means also enables detection of a form of an endoscope. In this configuration, the coils 310 are connected to the oscillator 315 and the antenna 314 is connected to the receiver 313. FIG. 107 relates to the seventeenth embodiment, showing an exemplary example of a configuration of an inserted form detecting apparatus in an endoscope.

In a distal part 329a, a bending section 329b, and a flexible tube 329c constituting the insertional part of an endoscope 329 shown in FIG. 107, the coils (not shown in FIG. 107) serving as a magnetic field generator are arranged in the similar manner as that in the sixteenth embodiment described in conjunction with FIGS. 104 to 106f.

An inserted form detector 333 of this embodiment comprises a bed 330 for endoscopic examination on which a subject lies down, a detector 331, and a monitor 332. The bed 330 contains a mesh antenna 330a for generating a magnetic field in each of two orthogonal directions. Detected signals associated with magnetic fields are sent from the antenna 330a to the detector 331. The detector 331 renders a form using coordinates calculated using the detected signals, and displays the form on the monitor 332.

Figure 109:
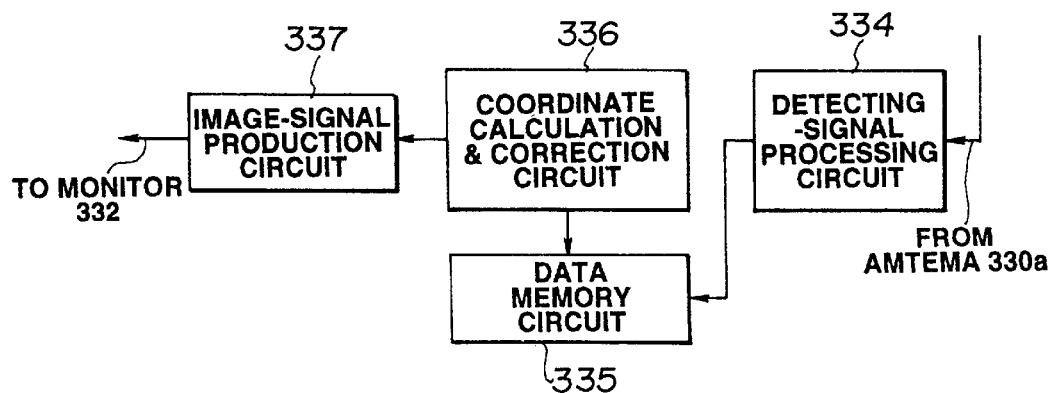

The detector 331 comprises, as shown in FIG. 109, a detected signal processor 334 for receiving detected signals from the antenna 330a, and amplifying the signals so that the signals will have an appropriate signal level or applying various processing to the signals, a data memory circuit 335 for storing data concerning a set spacing between each adjoining pair of the plurality of coils or data sent from the detected signal processor 334, a coordinate calculation/compensation circuit 336 for calculating coordinates of the plurality of coils using the data stored in the data memory circuit 335, and compensating the coordinates in value for errors or interpolating the coordinates, and an image signal production circuit 337 for producing an image signal representing a form of an insertional endoscope part by analyzing the coordinate data provided by the coordinate calculation/compensation circuit 336, and outputting the image signal to the monitor 332.

The operation of the detector 331 will be described with reference to the flow charts of FIGS. 110 and 112. The flow chart of FIG. 110 shows an overall sequence for inserted form detection which is executed by the detector 31.

Figure 110:
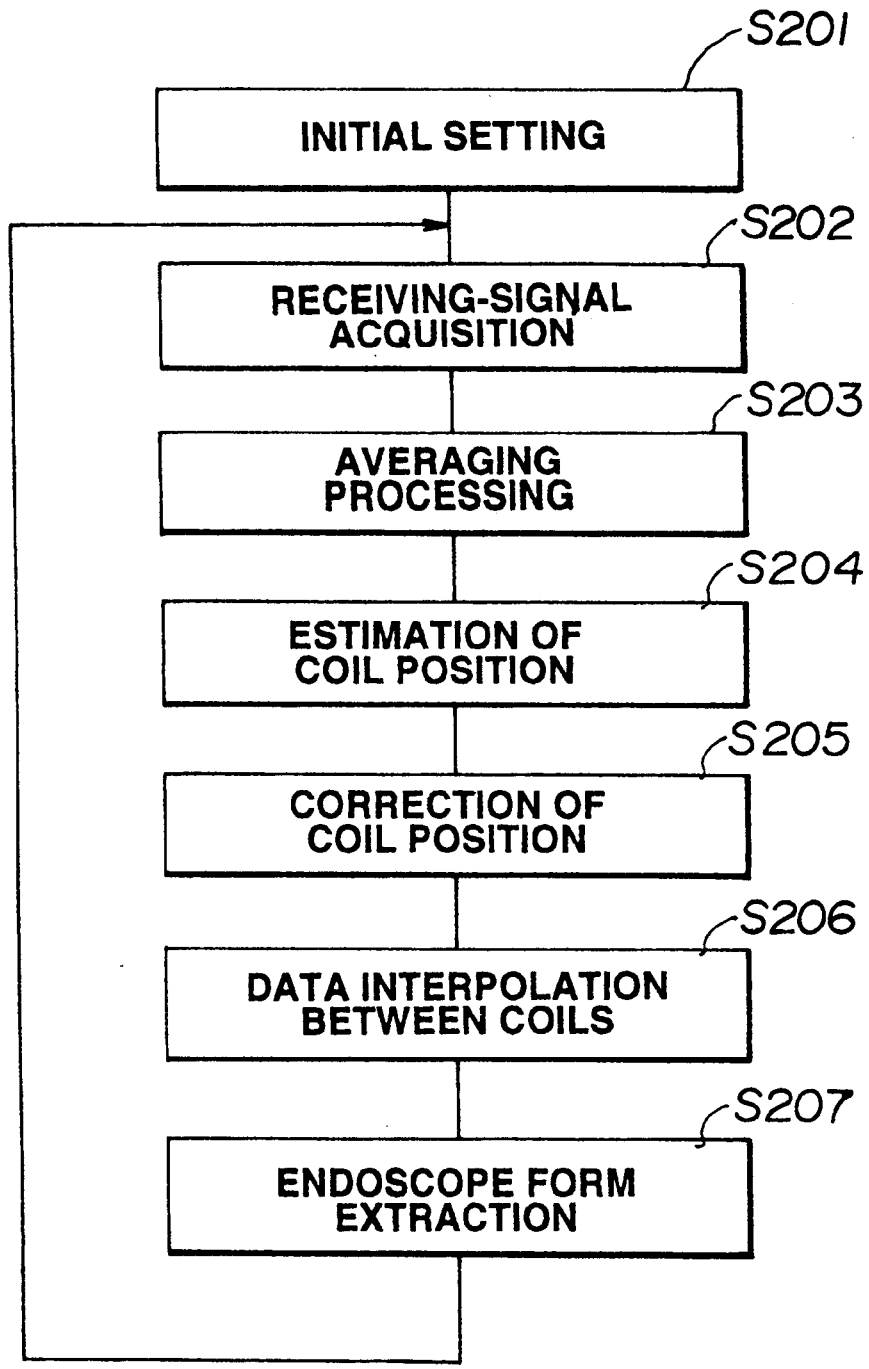

When the power supply of the detector 333 is turned on, at Step S201 in FIG. 110, an initialization routine for initializing an LSI realizing the aforesaid circuits or allocating a storage area in memory for use is executed.

At Step S202, received (analog) signals of the antenna 30a are fetched into the signal processor 334. The signal processor 334 amplifies the received signals, converts them into analog values, and applies filtering for extracting necessary frequency components, synchronism detection, fast Fourier transform (FFT), or the like to the analog values. Next, at Step S203, a plurality of received signals are averaged if needed to remove disturbance noise. The operation at Step S203 is intended to improve a signal-to-noise ratio, which can be skipped without causing a hindrance to the basic detector operation.

Control is then passed to Step S204 at which the positions of the coils are estimated using the extracted received signals. At Step S205, the coordinates of the coils estimated at Step S204 are compensated at value for errors in order to improve the precision in the positions of the coils. Specifically, the coordinates of the coils are checked and compensated in value for errors, if necessary, according to the algorithms shown in FIGS. 111 and 112.

The coils may be detected in such a state that they are concatenated and superposed on the endoscope. The coordinates of adjoining coils are interpolated in order to acquire a reliable positional information of the insertion part.

Finally, at Step S207, the image signal production circuit 337 produces an image signal representing the form of the insertion part according to the interpolated positional information, and outputs the image signal to the monitor 332.

The aforesaid sequence is repeated until the power supply is turned off. Alternatively, a Start/Stop switch may be installed in the detector 331 so that an operator can image a form of an insertional part when he/she wants to see it. Otherwise, the system may be pre-programmed so as to execute known image processing: that is, perform partial enlargement or display an obtained form as if it were seen in any direction.

Figure 111:
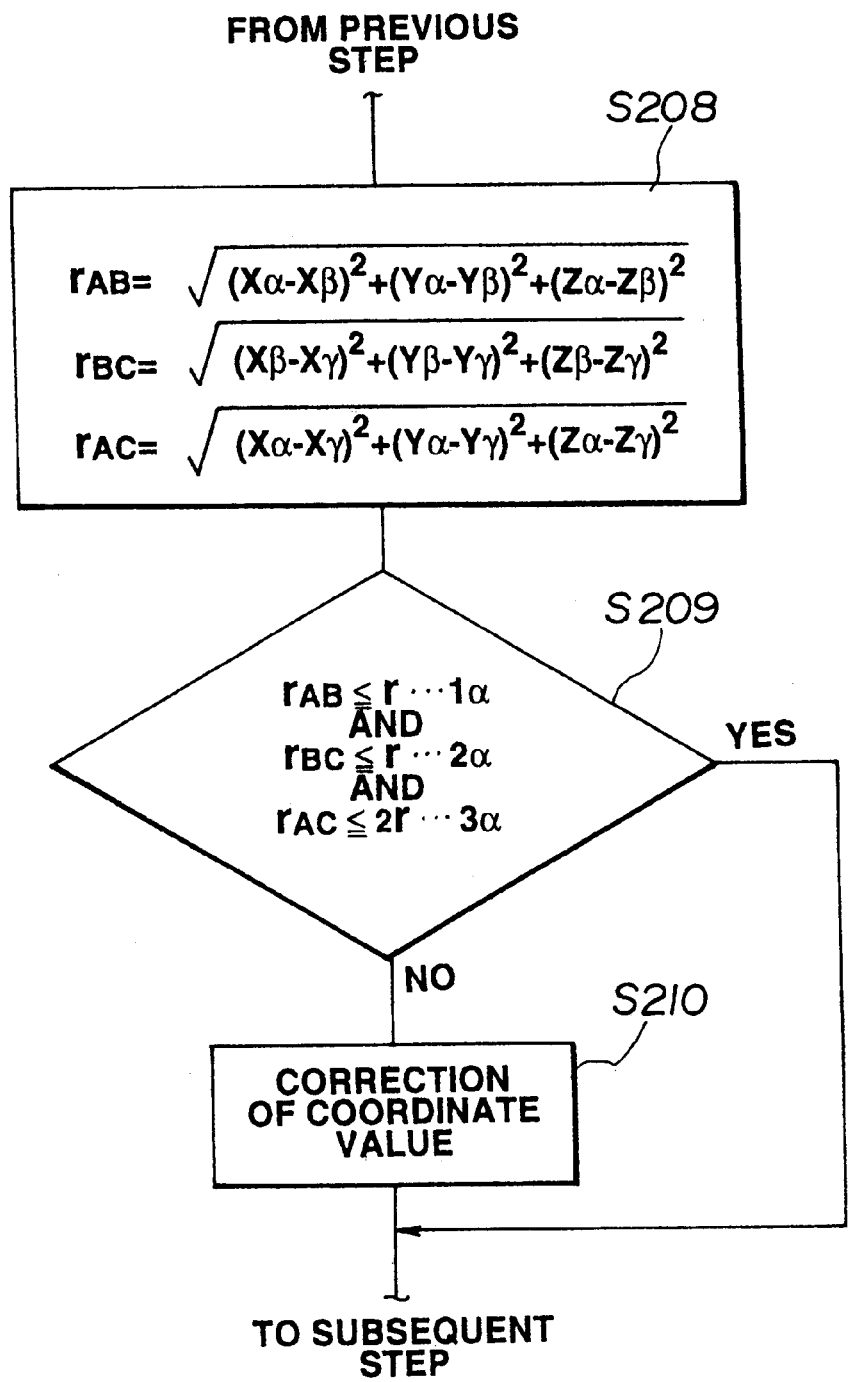

The algorithms shown in FIGS. 111 and 112 will be described. FIG. 111 is a flowchart concerning coordinate detection. FIG. 112 is a flow chart concerning coordinate compensation.

For the sake of description, the coils mounted in the distal part of 329$a$, bending section 329$b$, and flexible tube 329$c$ shall be located at (xA, yA, zA), (xB, yB, zB), and (xC, yC, zC) respectively. The positions to be detected come therefore to three.

Well-known spline interpolation or the like can be employed for estimating the intermediate positions between adjoining pairs of the coils indicated with the above three coordinates.

An insertion part of an endoscope employed for the endoscopic examination of the inferior alimentary tract is about 1 m long. For rendering the overall form, many coils 310 may be incorporated additionally in the endoscope. Spline interpolation or the like is used as described above to estimate the intermediate values between adjoining pairs of the coordinates (xn, yn, zn) indicating the positions of the plurality of coils. This enables rendering of a form of the endoscope. When the coils are arranged at regular interval, the advantages to be described below are available.

Figure 108:
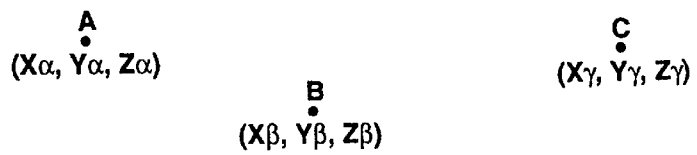

The advantages to be made available when the detection coils are arranged at regular intervals will be described. FIG. 108 is an explanatory diagram showing coordinates (x$\alpha$, y$\alpha$, z$\alpha$), (x$\beta$, y$\beta$, z$\beta$) and (x$\gamma$, y$\gamma$, z$\gamma$) shall indicate the positions of the coils A, B, and C incorporated in an endoscope. The set spacing between each adjoining pair of the coils shall measure r. The detected coordinates of the coils may include errors because of the influence of the temperature drift of a circuit for detection, disturbance noise, or the like.

Disclosure between adjoining pairs of the coils are calculated using the obtained coordinates. This is intended to detect the positions of the coils accurately. Assuming that the coils A, B and C are lined up in that order in the endoscope, a distance rAB between the coils A and B is provided as follows:

$$rAB = \sqrt{(x\alpha - x\beta)^2 + (y\alpha - y\beta)^2 + (z\alpha - z\beta)^2}$$

A distance rBC, between the coils B and C, and a distance rAC between the coils A and C are provided as follows (See Step S208 in FIG. 111):

$$rBC = \sqrt{(x\beta - x\gamma)^2 + (y\beta - y\gamma)^2 + (z\beta - z\gamma)^2}$$
$$rAC = \sqrt{(x\alpha - x\gamma)^2 + (y\alpha - y\gamma)^2 + (z\alpha - z\gamma)^2}$$

When the insertional part is linear, the set spacing between each adjoining pair of the coils in the endoscope measures r. Supposing the coordinates of the coils could have been obtained without any error, the spacing between adjoining pairs of the coils: rAB, rBC, and rAC, which are calculated using the coordinates, have the following relationship with the set spacing r:

$$r \geq rAB \tag{1$\alpha$}$$

$$r \geq rBC \tag{2$\alpha$}$$

$$2r \geq rAC \tag{3$\alpha$}$$

In other words, these three conditions are met or the result of Step S209 in FIG. 111 is in the affirmative.

If any of the three conditions is not met; that is, the result of Step S209 is in the negative, the coordinates are compensated in value for errors at Step S210. Specifically, the sequence shown in FIG. 112 is executed.

Assuming that only the condition (1$\alpha$) is met, there is a high possibility that the coordinates (x$\gamma$, y$\gamma$, z$\gamma$) of the coil contain significant errors. In this case, the coordinates x$\gamma$, y$\gamma$, z$\gamma$) are corrected to have values meeting the conditions (2$\alpha$) and (3$\alpha$). Thereafter, compensation is executed so that a form of the endoscope can be displayed. The compensation is based on, for example, three equations x$\gamma$=(x$\gamma$+x$\beta$)/2, y$\gamma$=(y$\gamma$+y$\beta$)/2, and z$\gamma$=(z$\gamma$+z$\beta$)/2. Since the coordinates (x$\gamma$, y$\gamma$, z$\gamma$) of the point C shown in FIG. 108 is regarded to contain significant errors, the coordinates (x$\gamma$, y$\gamma$, z$\gamma$) and the coordinates (X$\beta$, y$\beta$, z$\beta$) which are considered to be correct are subjected to averaging. This is intended to minimize the errors and eventually provide the coordinates with values as close as possible to true values.

When only the condition (2$\alpha$) is met, compensation is executed so that the conditions (1$\alpha$) and (3$\alpha$) will be met.

When only the condition (3$\alpha$) is met, there is a very high possibility that the coordinates (x$\beta$, y$\beta$, z$\beta$) contain significant errors. In this situation, the coordinates (x$\gamma$, y$\gamma$, z$\gamma$) are compensated in value for the errors so that the conditions (1$\alpha$) and (2$\alpha$) will be met. Using the compensated value, a form of the endoscope is displayed. Compensation is based on such equations x$\beta$={x$\beta$+(x$\alpha$+x$\gamma$)/2}/2, y$\beta$={y$\beta$+(y$\alpha$+y$\gamma$)/2}/2, and z$\beta$=(z$\beta$+(z$\alpha$+z$\gamma$)/2}/2.

When none of the conditions is met, an abnormal value flag set. With this setting, for example, no image may be displayed but received signal fetch may be rerun.

As described above, detected coordinates are compared in value with a set spacing between each adjoining pair of coils, so that detected coordinates can be compensated for an abnormal value or can be excluded from coordinate date to be handled in rendering a form. Consequently, a form of an endoscope can be displayed more correctly using a common program.

In this embodiment, three consecutive coils are selected. Aside from this combination, any combination of coils can be adopted as long as a set spacing between each adjoining pair of the coils is apparent.

A combination of coils concerned may be changed in the axial direction of an insertion part. Meanwhile, the coordinates of the coils are checked for an abnormal value. For example, when coils A, B, C, D, E, etc. are concerned, the coordinates of the coils A, B, and C are checked for an abnormal value. Thereafter, the coordinates of the coils B, C, and D are checked for an abnormal value. Thereafter, the coordinates of the coils B, C and D are checked for an abnormal value, the coordinates of the coils C, D, and E are checked therefor, and so on. When the spacings between adjoining pairs of the coils are not equal to one another, if the coordinates of a coil contain errors and are therefore corrected in value, the corrected value reflects greater influence of precision in coordinates of coil having a shorter distance to the coil concerned. This results in a larger possibility of deteriorating the precision of compensated values, which is preventable.

Figure 113:
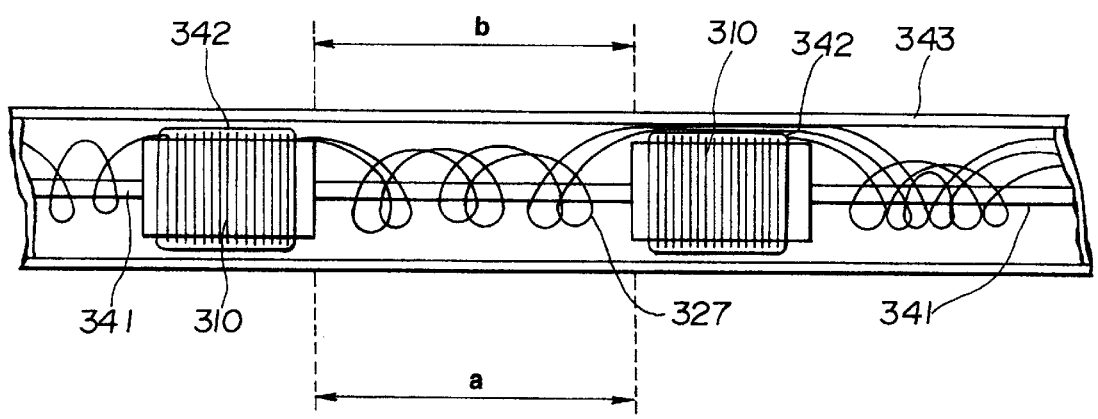
FIG. 113 is an arrangement view of an imaging probe in an eighteenth embodiment of the invention.

FIG. 113 relates to an eighteenth embodiment, showing a structure of an imaging prove having a plurality of coils therein. Coils in this embodiment may be those serving as magnetic field detecting means as described in the first embodiment or those serving as magnetic field generating means as described in the second embodiment.

Coils 310 have fitting holes 326 shown in FIG. 105. The fitting holes 326 are canalized in the axial direction of an insertion part. A conductor 341 lying along the axis of the insertion part, having flexibility, and serving as locking means is penetrating through or fitted into the fitting holes of the coils 310. The coils 310 are locked at intervals of a predetermined spacing a. The outer diameter of the conductor 341 is a bit smaller than the ones of the fitting holes 326 of the coils 310. The coils 310 are arranged at regular intervals and secured at given positions of the conductor 341 using an adhesive serving as a locking means.

As described above, the plurality of coils 310 are arranged at regular intervals. For example, when a signal generated by one detection coil is too weak to detect the position of the coil, the position of the coil concerned can be estimated using the positions of two coils located across the coil concerned. Supposing the coils are spaced irregularly, when a position of a coil separated by a large spacing from an adjoining coil and by a small spacing from the other adjoining coil is concerned, the coordinates of the coil separated by a large spacing from the coil concerned, which are regarded as correct, give greater influence on estimated coordinates of the coil concerned. This increases a possibility that the estimated coordinates of the coil concerned are mere estimates, resulting in significant errors. Compared with the situation when the coils are spaced irregularly, when coils are spaced regularly, estimated values are much closer to true values.

The portions of connection copper wires 327, which serve as transmitting means, staying on the coils 310 are attached to the coils 10 using an insulating adhesive 342. The coils 310 are encapsulated in a casing tube 343.

The adhesive 342 may not be employed, wherein the coils 310 are arranged in the casing tube 343 with their outlines sealed in close contact with the casing tube 343 using an insulating material 342. In this case, portions of the connection copper wires 327 staying on the coils 310 are sealed of by the insulating material 342.

The connection copper wires 327 lying between adjoining pairs of the coils 310 are dangled, for example, spirally and have a length b which is set to a value permitting at least $b \leq a \times 1.1$. According to this structure, the copper wires 327 are secured at the portions thereof staying on the coils. The structure can therefore prevent any connection copper wire 327 from being disconnected due to bending of the imaging probe.

FIGS. 114 and 115 relate to a variant of the eighteenth embodiment. FIG. 114 schematically shows a structure of an imaging probe mounted in an insertion part. FIG. 115 is an explanatory diagram showing the relationship between the curved state of a bending section and the lengths of coils.

An insertion part 345 shown in FIG. 114 has a built-in imaging probe 346. In the imaging probe 346, coils 310 are arranged at predetermined intervals and locked in a conductor 344 having flexibility. The components identical to those in the first embodiment are assigned the same reference numerals. No mention will be of these components and the operation identical to that in the first embodiment.

In FIG. 114, the coils are arranged so that a spacing a between each adjoining pair of the coils 310 lying the portion of the imaging probe corresponding to a bending section 347 of an endoscope, and a spacing b between each adjoining pair of the coils 310 lying in other portions thereof have a relationship of a<b. That is to say, the spacing between each adjoining pair of the coils in the bending section 347 is smaller at least than the one in a flexible tube 348. Incidentally, the coils arranged in the bending section 347 or flexible tube 348 should preferably be spaced regularly as described previously.

The inserted form detector 312 (not shown in FIGS. 114 and 115) processes signals detected by the coils 310, calculates the positions of the coils, obtain intermediate positions, at which no coils are positioned, by interpolating the calculated data, and then renders an inserted form of the whole endoscope. Herein, when the coils 10 in the bending section 347 which is curved at a smaller curvature radius are spaced more narrowly, the inserted form of the endoscope can be rendered more accurately.

The length d of each coil 310 and the width c of each bending frame 328 along the rotation axis 328a have a relationship of d<2×c. In other words, the length d of each coil 310 is smaller at least than a half of the width a of each bending frame 328 along the rotation axis 328a. Thus, the coils 310 are not overly long. This enables smooth bending.

The structure shown in FIGS. 114 and 115 can apply to the sixteenth embodiment.

As described so far, according to the sixteenth, seventeenth and eighteenth embodiments, an inserted state detecting system can render an inserted form of an endoscope accurately despite the presence of stress resulting from bending or insertion of the endoscope.

In connection with the above, in the aforesaid embodiments or the like except the fifteenth to eighteenth embodiments, the description is made to the arrangement in which the source coil serving as the magnetic-field generation element is arranged within the endoscope insertion part which has flexibility and which is inserted into the subject and is fixedly mounted such that a form thereof is not changed, or to the arrangement in which the side of the magnetic-field generation element is arranged at the known position outside the subject, and the sense coil serving as the magnetic-field detecting element, the magnetic resistance element or the like is arranged within the insertion part and is fixed such that a form thereof is not changed.

The invention should not be limited to these arrangements. The invention can be applied to a rigid endoscope having a rigid insertion part as follows.

When a plurality of rigid endoscopes are used to perform operation or inspection such as an intraperitoneal or peritoneal cavity mirror operation, it is important to correctly know the positional relationship of the forward end of the respective rigid endoscopes, in order to smoothly perform operation. In view of this, probes having a single source coil are fixedly mounted on two locations of a known portion in the vicinity of an ocular portion of the rigid endoscope which exists within the positional detection range, or a probe in which two (2) source coils are arranged at a known distance is fixedly mounted in parallel to a central axis of the rigid endoscope.

When orientation of a forward end of the rigid endoscope is changed, the neighborhood or the vicinity of the ocular portion moves considerably. Accordingly, a fixed portion of the probe is required to have resistance to a stress. The source coil is required to be fixed by an insulating member. However, the other portions are made of flexible material such that unnecessary tension is not applied when the rigid endoscope moves.

Since a distance from the position of the source coil arranged in this manner to the forward end of the rigid endoscope is beforehand known, when the positions of the pair of source coils are detected, it will be seen that the forward end portion exists at a position of the known distance on a straight line which connects the pair of source coils to each other. In this situation, it may be sufficient that the source coil is provided within the rigid endoscope and, accordingly, the invention can be used with rigid endoscopes of any thicknesses.

Moreover, the invention is not limited to an arrangement which is inserted into an organism such as a human body or the like. The invention can also be applied to an arrangement in which an endoscope is insert into an intracanal or hollow portion except the organism, or the subject (object) to be examined or inspected, one of the magnetic-field generation element and the magnetic-field detecting element is arranged within the probe having flexibility, the one element is fixed by an insulating member or the like such that a form thereof is not deformed, and the other of the magnetic-field generation element and the magnetic-field detecting element is arranged at the known position except the subject or the like.

Furthermore, the arrangement may be such that one of the magnetic-field generation element and the magnetic-field detecting element is fixed or mounted, by an insulating member or the like, at the known position such as the interior or the like of the insertion tool such as an instrument or a device for medicine or the interior of the insertion tool which is inserted for inspection or the like into the lacuna such as, for example, the interior of a plant for industrial use, by an insulating member or the like, and the position of the flexible insertion part which is inserted into the lacuna or the position of the rigid insertion part, a position on the side at hand of the insertion tool, or the like can be detected or estimated.

Also in these situations, the magnetic field which is generated by the magnetic-field generation element can be detected by the magnetic-field detecting element, the position of the probe inserted into the subject or the lacuna, or the position of the magnetic-field generation element or the magnetic-field detecting element in the insertion tool can be detected with the magnetic-field generating element or the magnetic-field detecting element arranged at the known position serving as a reference. Further, the position of at least one location of the probe or the insertion tool can be detected, the form of the probe or the insertion part can be estimated, or the estimated form can be displayed.

In the aforesaid embodiments, the signal corresponding to the magnetic field strength is produced by measurement, and the reference data which are previously found out by measurement or the like are referred to, or the like, whereby the region or the position at which the source coil 16$i$ or the like arranged within the insertion part 7 or the like exists is calculated. However, the position and inclination of the source coil 16$i$ or the like which is arranged within the insertion part 6 or the like may be derived by calculation.

Further, in the first embodiment, the coils which extend perpendicularly to the three axes are used as the three-axis sense coil 22$j$ to correct variation of size or the like thereof. However, the correction may also be applied to the source coil 16$i$ or the like.

In connection with the above, the whole form of the endoscope may be displayed. However, only a portion (forward end only, for example) in which the interest is high can be selected and can be displayed.

Moreover, only the direction of the forward end may be expressed or represented by an arrow or the like.

Only the position of the coil for detection may be expressed or represented, differentiated in color from the other endoscope form which is expressed in interpolation. Only the portion may be applied by a mark x.

A threshold value may be set by a distance from the bed, and expression or representation may be made by changing of a warm color when being remote away from the position, a cold color when being close thereto, or reverse, changing of saturation, luminosity and a hue, or the like.

Further, since the form which is detected by the form detecting apparatus reveals process of endoscope insertion, time series data thereof may be stored in a disc or the like.

In connection with the above, when one of the magnetic-field generation element and the magnetic-field detecting element is fixedly mounted on the insertion part having elasticity, of the endoscope, the one element may fixedly be mounted on the rigid forward-end rigid member which is at the forward end of the insertion part. Alternatively, the one element may be fixedly mounted, by an insulating member or the like, on a rigid curvature frame forming a bendable curvature portion by an insulating member or the like such that a form thereof is not deformed.

In connection with the above, when the magnetic-field generation element is an element for generating the magnetic field having strong directionality in a single axial direction, in a space in the vicinity of the magnetic-field generation element, it is desirable that an arrangement which can detect magnetic-strength components in three axial directions which extend perpendicularly to each other is used as the magnetic-field detecting element. When only the magnetic-field strength components in one or two axial directions can be detected, a level difference increases between case where the detected magnetic-field strength decreases extremely and case where the detected magnetic-field strength increases, largely depending upon relative orientation between the magnetic-field generation element and the magnetic-field detecting element. This is because it is almost impossible that the range of the distance between the two elements is limited to a narrow range from the detected signal.

Meanwhile, if the magnetic-field strength components in three axial directions which extend perpendicularly to each other can be detected, even when the magnetic field is strong or high in directionality, dependency of the orientation is smaller than the above case. The range of the distance between the two elements can be limited to a relatively narrow range from the detected magnetic-field strength.

Furthermore, when the magnetic-field detecting element is an element capable of detecting magnetic-field strength components in three (3) directions which are perpendicular to each other, it is desired that detecting sensitivity and sensitivity with respect to respective directions are equal to each other as far as possible. In this situation, the reason for this is that it is possible to produce the magnetic-field strength by a square root of the sum of squares of the respective magnetic-field strength components. Meanwhile, if the detecting sensitivities with respect to the respective directions are different from each other, correction is required to calculate the magnetic-field strength. However, the magnetic-field strength can be used if correction is performed.

A nineteenth embodiment of the invention will subsequently be described.

As shown in FIG. 116, an endoscope system 401 comprises an endoscope apparatus 402 which uses an endoscope 406 to conduct inspection or the like, and an endoscope form detection device 403 which is used together with the endoscope apparatus 402. The endoscope form detection device 403 detects each position within an insertion part 407 of the endoscope 406, to thereby estimate a form of the insertion part 407 from each detected position, and displays an image of the (endoscope) insertion-part form which is modeled, corresponding to the estimated form.

A patient 405 which serves as a subject is mounted on a bed 404 (for endoscope inspection). The insertion part 407 of the endoscope 406 is inserted into a body cavity in the patient 405.

The endoscope 406 is elongated, and comprises the insertion part 407 which has flexibility, a thick operation part 408 formed at a rear end thereof and a universal cable 409 which extends from a side of the operation part 408. A connector 409A at a distal end of the universal cable 409 can be detachably connected to a video processor 411.

A light guide (not shown) is inserted into the insertion part 407. The light guide is further inserted into the universal cable 409 which extends from the operation part 408. The light guide reaches the connector 409A at the distal end. An illumination light is supplied to an end face of the connector 409A, from a lamp of a light source part (not shown) which is built in the video processor 411. The illumination light which is transmitted by the light guide and which is transmitted from the distal end face which is mounted on an illumination window (which forms illumination-light output means) at the distal end of the insertion part 407 is forwardly projected.

A subject such as an inner wall within the body, an affected or diseased part or the like which is illuminated by the illumination light which is outputted from the illumination window focuses an image onto a CCD serving as a solid-state image-pickup element which is arranged on a focusing face, by an objective lens (not shown) which is mounted on an observation window which is formed adjacent to the illumination window at the distal end.

A CCD drive signal which is outputted from a CCD drive circuit within a signal processor (not shown) which is built in the video processor 411 is applied to the CCD, whereby an image signal which is photoelectrically converted (by the CCD) is read out. The image signal passes through a signal line which is inserted into the insertion part 407 or the like, and is processed by a signal processor so as to be converted to a standard image signal. The standard image signal is outputted to a color monitor 412. Thus, the CCD displays a color endoscope image which is imaged onto a photoelectric conversion surface of the CCD by the objective lens.

Further, the operation part 408 is provided with a curvature operation knob. Operation in which the knob is moved angularly is conducted whereby a bendable curvature part which is formed in the vicinity of the distal end of the insertion part 407 is capable of being curved whereby the side of the distal end thereof is curved so as to extend along the curvature. Thus, the curvature part can also be smoothly inserted into a curved passage within the body cavity.

Moreover, the endoscope 406 is formed with a hollow channel 413 within the insertion part 407. A treatment tool such as forceps or the like is inserted from an insertion opening 413a at the proximal end of the channel 413, whereby it is possible to project the side of the distal end of the treatment tool from a channel outlet in the distal end face of the insertion part 7 to conduct biopsy, treatment processing or the like with respect to an affected part or the like.

Furthermore, it is possible to insert a probe 415 for position and form detection (of the insertion part 407 which is inserted into the body cavity) into the channel 413, so that the side of the distal end of the probe 415 is set to a predetermined position within the channel 413.

As shown in FIG. 119, the probe 415 is arranged such that a plurality of source coils 416a, 416b, . . . (represented by a reference number 416i) serving as magnetic-field generation elements for generating a magnetic field are fixed within a tube 419 of a circular cross-section having insulation and elasticity, for example, under a state in which the source coils come into predetermined or constant intervals d that is, to a flexible support element 420 and the inner wall of the tube 419 by means of an insulating adhesive agent.

Each of the source coils 416i is formed by a coil in the form of a solenoid, in which a lead wire coated in insulation is wound around, for example, a hard columnar core 410 having insulation. Each of lead wires which is connected to one end of the associated source coil 416i is inserted into the support element 420. A lead wire 417 at the other end is inserted until the side of the hands within the tube 419. Further, the arrangement is such that a filler element having insulation is filled within the tube 419, and if the tube 419 is bent or curved, the tube 419 is not crushed or broken. Moreover, whenever the tube 419 is bent and is deformed, since the lead of each of the source coils 416i is wound around the hard core 410 and is fixed by the adhesive, each of the source coils 416i per se is of a structure such that a form thereof is not deformed. The arrangement is such that the magnetic-field generation function is non-variant or constant even when the tube 419 is deformed.

A position of each source 416i is set to a known position within the insertion part 407 of the endoscope 406. The position of each source coil 416i is detected whereby it is possible to detect a discrete position of the insertion part 7 of the endoscope 6 (more particularly, a position of each source coil 416i).

These discrete positions are detected whereby positions therebetween can also be estimated. Accordingly, by the detection of the discrete positions, it is possible to determine the outlined form of the insertion part 407 of the endoscope 406 which is inserted into the body cavity.

Each lead wire 417 which is connected to the associated source coil 416i is connected to a connector 418 which is provided at a proximate end of the probe 415 or which is provided at a proximate end of the cable which extends from a proximate end of the probe 415. The connector 418 is connected to a connector receptor of a body 421 of the (endoscope) form detecting apparatus. To be described subsequently, a drive signal is applied to each source coil 416$i$, to generate a magnetic field which is utilized for the position detection.

Moreover, as shown in FIG. 119, three-axes sense coils 422$a$, 422$b$ and 422$c$ (represented by 422$j$) which serve as magnetic-field detection elements for respectively detecting the magnetic field are mounted on known positions of the bed 404, for example, on three corners. These three-axes sense coils 422$j$ are connected to the body 421 of the form detecting apparatus through a cable 429 which extends from the bed 404.

As shown in FIG. 119, the three-axes sense coil 422$j$ is wound in three directions such that respective coil faces thereof extend perpendicularly to each other. Each coil detects a signal which is in proportion to the strength of the magnetic field of a component in an axial direction which extends perpendicularly to the coil face.

The above-described body 421 of the form detecting apparatus detects the position of each source coil 416$i$ on the basis of an output from the three-axes sense coil 422$j$, to estimate the form of the insertion part 407 of the endoscope 406 which is inserted into the patient 405, to thereby display a computer graphic image corresponding to the estimated form, onto the monitor 423.

Since the endoscope image detection device 403 utilizes a magnetic field, if there is metal which is not transparent to the magnetic field, a magnetic field reduction is exerted. An influence is exerted upon the mutual inductance between the source coil 416$i$ for generating the magnetic field and the three-axes sense coil 422$j$ for detection. Generally, if the mutual inductance is expressed by R+jX, the metal which is not transparent to the magnetic field exerts an influence upon both R and X.

In this case, an amplitude and a phase of a signal which are measured by orthogonal or cross detection which is generally used in the detection of the minute magnetic field are varied or changed. For this reason, in order to accurately detect the signal, it is desired to set the environment which does not exert an influence upon the generated magnetic field.

In order to realize this, the bed 404 should be manufactured by material which is magnetically transparent (in other words, material which does not affect an influence upon the magnetic field).

The material which is magnetically transparent may be, for example, resin such as Delrin or the like, wood, or any non-magnetic metal.

Practically, since an alternate magnetic field is used for the position detection of the source coil 416$i$, the bed 404 may be formed by material which does not exert a magnetic influence thereupon in a frequency of the drive signal.

In view of the above, the endoscope inspection bed 404 which is used together with the a present endoscope form detecting apparatus 403, shown in FIG. 119, is, at least, formed by non-magnetic material which is magnetically transparent in the frequency of the generated magnetic field.

In a block diagram of the endoscope form detecting apparatus 403 in FIG. 117, a drive signal from the source-coil drive part 424 is supplied to the source coil 416$i$ within the probe 415 which is set within the channel 413 of the endoscope 406. A magnetic field is generated in the vicinity of the source coil 416$i$ to which the drive signal is applied.

The source-coil drive part 424 amplifies an alternate signal which is supplied from an oscillation part 425 (for generation of a magnetic field), to output a drive signal for generating a requisite magnetic field.

The alternate signal of the oscillation part 425 is sent out, as a reference signal, to a (mutual inductance) detection part 426 for detecting the minute magnetic field which is detected by the three-axes sense coil 422$j$ provided on the bed 404.

The minute magnetic-field detection signal which is detected by the three-axes sense coil 422$j$ is amplified by an (sense coil) output amplifier 427 and, thereafter, is inputted to the detection part 426.

The detection part 426 conducts amplification and cross detection (synchronous detection), with the reference signal serving as a reference, to acquire a signal which is related to the mutual inductance between the coils.

Since there are the plurality of source coils 416$i$, there is a (source-coil drive current) distributor 428 which serves as change-over that the drive signals are successively supplied to the lead wire which is connected to each source coil 416$i$, between the source-coil drive part 424 and the source coil 416$i$.

The signal which is acquired by the aforesaid detection part 426 is inputted to a (source coil) position detection part (or a position estimation part) 431 which forms a form calculation part 430. The position detection part 431 converts the inputted analog signal to a digital signal to conduct the calculation of the position detection or the computation of the position estimation, to acquire positional information which is estimated with respect to each source coil 416$i$.

The positional information is sent to a form image generator 432 to apply graphic processing such as interpolation processing for interpolating the interval therebetween from each acquired discrete positional information, or the like, to thereby estimate the form of the insertion part 407 of the endoscope 406. An image corresponding to the estimated image is generated and is sent to a monitor-signal generation part 433.

The monitor-signal generation part 433 generates an image signal of an RGB, an NTSC, a PAL system or the like which expresses the image corresponding to the form, to output the same to a monitor 423. An image corresponding to the form of the insertion part of the endoscope 406 is displayed on a display face of the monitor 423.

In connection with the above, the position detection part 431 is such that, after calculation of one positional detection has been ended or completed, the change-over signal is sent to the distributor 428, and a drive current is supplied to the subsequent source coil 416$i$ to conduct calculation of the positional detection. The arrangement may be such that, before calculation of each positional detection is completed, a change-over signal is sent to the distributor 428, and signals which are detected by the sense coil 422$j$ are successively stored in a memory.

Moreover, a system control part 434 is formed by a CPU or the like to control operation or the like of the position detection part 431, the form image generation part 432 and the monitor-signal generation part 433. Furthermore, an operation part 435 is connected to the system control part 434. As shown in FIG. 118, an operation part 435 is formed by a keyboard 435$a$, a mouth 435$b$ and the like. The keyboard 435$a$, the mouth 435$b$ and the like are operated whereby it is also possible to conduct selection of the painted model of the endoscope form or indication in which the endoscope form displayed on the monitor 423 is displayed by the image which is against a selected visual field direction.

Particularly, in the present embodiment, the operation part 435 conducts operation of the specific key input (more particularly, of the keyboard 435$a$ in FIG. 118). The indication signal of the two-image-plane display is inputted in the system control part 434 whereby the form image generation part 432 generates an image corresponding to one visual point direction, and generates an image from a visual point direction which is 90° different from the aforesaid visual point direction, to display two images simultaneously on the monitor 423 through the monitor-signal generation part 433.

That is, the form image generation part 432 has function of a 2/1 form image mode which generates the two form images from the visual point directions extending perpendicularly to each other and the form image from the one visual point direction. The form image generation part 432 generates the 2/1 form image on the monitor 423 in accordance with the indication (selection), to display 2/1 form image which is generated by the indication, on the monitor 423. FIG. 118 shows an aspect in which the two form images in the two form image mode are displayed on the monitor 423.

The present embodiment comprises the detected-image display means (which is formed by the form image generation part 432, the monitor-signal generation part 433 and the monitor 423) for simultaneously displaying the endoscope forms, by the two-image-plane, from one visual point direction, which are 90° different from each other in this manner.

In connection with the above, the form calculation part 430 indicated by the broken line in FIG. 117 includes software. Further, in order to facilitate an understanding of the display of the endoscope form which is displayed on the monitor 423, the arrangement is such that marker probes 436a and 436b (abridged simply as "markers") which serve as auxiliary means for displaying the reference position on the displayed image plane can be connected. The markers 436a and 436b are used to simultaneously display the reference position which is optionally set by an operator, on the display image plane of the monitor 423 together with the endoscope form, to easily conduct grasping of the endoscope form.

The markers 436a and 436b are connected to the current distributor 428. Similarly to the source coil 416i within the probe 415, the drive signal is applied to the source coils within the markers 436a and 436b through the current distributor 428. In this connection, in the nineteenth embodiment, the markers 436a and 436b display the reference position on the image plane to thereby be used to facilitate the grasping of the endoscope form. A twentieth embodiment is arranged so as to be able to select also the using aspect (described later).

During endoscope inspection, since the patient 405 is on the bed 404, the position of the endoscope 406 is surely or certainly on the bed 404.

That is, if the three-axes sense coil 422j which serves as the sensor is provided on the four corners of the bed 404, the endoscope 406 (the source coil 416i therewithin) is present in a region surrounded by the sensor group. Accordingly, a quadrant in which the source coil 416i is present is limited to each of the established three-axes sense coils 422j.

Assuming that the outputs from the single three-axes sense coil 422 at the time the source coil 416i is driven are Xi, Yi and Zi, the source coil 416i is present at a distance from the three-axes sense coil 422 which serves as the magnetic field strength related or associated by $Xi^2+Yi^2+Zi^2$.

However, the one axis coil is generally expressed as a dipole, and an equi-magnetic-field surface thereof does not form into the shape of a ball or sphere, but rather into an ellipse.

For this reason, it is impossible to identify the position of the source coil 416i in which the direction or orientation of the source coil 416i is unknown, only from the equi-magnetic-field surfaces $Xi^2+Yi^2+Zi^2$ due to the single three-axes sense coil 422.

For this reason, a distance is used which is related by $Xj^2+Yj^2+Zj^2$ which are respectively measured relating to the plurality of three-axes sense coils 422j which are provided on the bed 404. In this case, since the establishment position of each of the three-axes sense coils 422j is known, it is possible to express the establishment position by a one coordinate system which is fixedly mounted on, for example, the bed 404. In this case, the reference face for the positional detection and the form detection is in the bed 404.

The magnetic field strength in which the equi-magnetic-field surface which is generated by the source coil 416i is generally expressed as being $Xs^2+Ys^2+Zs^2$ is detected by the sense coil 422j, and a distance therebetween is estimated.

Then, it such equi-magnetic-field surface which includes the magnetic field strength is determined from the magnetic field strength which is detected by the sense coil 422j, there is the sense coil 422j on the equi-magnetic-field surface with respect to the center source coil 416i. If it is assumed that the maximum value and the minimum value of the distance from the center to the equi-magnetic-field surface are respectively RmaxJ and Rminj, the sense coil 422j and the source coil 416i are present in the distance therebetween.

That is, whenever the sense coil 422j at the known position is the reference, the source coil 416i is present inside the distance of the maximum distance Rmaxj and outside the distance of the minimum distance Rminj as shown in FIG. 120.

Since the source coil 416i is present within an overlap (volume) of a spherical shell which is measured by each three-axes sense coil 422j and which is represented by Rmaxj and Rminj which correspond to Xj, Yj and Zj which are different for each three-axes sense coil 422j, it is possible to detect a center of gravity of a region as a coil position.

In this manner, the position can be determined. However, whenever a difference between Rmax and Rmin is great, there is the possibility that an error is generated.

In view of the above, it is utilized that an inclination of the source coil 416i is expressed in the phase information which is included in Xj, Yj and Zj, to determine an inclination in the volume which is previously determined.

Thus, the previous position is corrected so as to improve accuracy.

Further, since the mutual intervals between the source coils 416i is known, the previous position may be corrected by this value.

The form of the insertion part 407 of the endoscope 406 which is estimated by the plurality of positional information which is detected in this manner is displayed on the display face of the monitor 423, for example, in the left graphic output range as shown in FIG. 126 by a modeled image 500 to be described subsequently. The region on the right hand is a user interface region for setting the visual point (the distance between the position and the origin), thee rotational angle, the angle of elevation defined between the visual point position and the Z-axis, or the like which is set by the user by the key input from the keyboard 435b, or the like.

FIG. 121 shows a specific example of a structure of the marker 436a in the form of a tube. A marker body 441 is covered by a grip cover 442, and a source coil 443 is housed therein. Insulation resin 444 is filled in a periphery thereof. The source coil 443 is formed in such a manner that a lead wire 446 is wound around a core element 445 of magnetic material. The two wound lead wires 446 have ends thereof which are covered respectively by shield wires 447 which are covered by an insulation element 440. Moreover, the shield wires 447 are coated or covered respectively by silicon tubes 448. The shield wire 447 has a rearward end thereof which reaches a connector 449*a*. The connector 449*a* is fixedly mounted on a connector receiver element.

A connecting portion between the grip cover 442 and the silicon tube 448, and a connecting portion between the silicon tube 448 and the connector receiver 449*b* are prevented from being broken by a breaking prevention element 450.

FIG. 122 shows a flow in which the magnetic field which is formed by the source coil 416*i* within the scope is detected by the outside three-axes sense coil 422*j*, the position of the source coil 416*i* is acquired from the relationship between the magnetic filed strength and the distance between two points, and a form of the insertion part under being inserted (referred also to as "scope form" briefly) is displayed on a monitor (referred also to as "CRT") on the basis of each of the positional detections of the plurality of source coils 416*i*.

The whole arrangement of the flow can be largely divided into the following four blocks including B1~B4, according to the processing contents thereof.

B1: Initialization Block

Initialization operation concerning the full function of the present program is completed by this block. Specifically, memory reading of the basic or fundamental data which are used when the presence position of the source coil 416*i* is calculated, and initialization of each of various kinds of boards for controlling the hardwares, or the like is carried into practice, from setting of an initial parameter on the basis of a technique which outputs the scope form onto the CRT and phase information and amplitude information which are acquired from the magnetic field strength detected by the hardware.

B2: Hardware Control Block

In the present system, the positional coordinates of the source coil 416*i* which is arranged and fixed within the insertion part 407 of the endoscope 406 are calculated from the magnetic field strength which is generated by the source coil 416*i*, to estimate the form of the insertion part 407 of the endoscope 406 under being inserted, on the basis of the same.

The present block bears until the fact that driving of the source coil 416*i* is changed over or switched to generate a magnetic field, the generated magnetic field strength is detected by the sense coil 422*j*, and a detection output therefrom is converted to a form which can be calculated by the positional coordinates of the source coil and is outputted.

The driving change-over of the source coil 416*i* is such that it is known where in the endoscope 406 the source coil is located. As shown in FIG. 119, the sense coil 422*j* for detecting the magnetic field strength of the source coil 416*i* is manufactured such that the faces of the coil are in parallel with three axes which extend perpendicularly to each other, and is so arranged such that magnetic field strength components in three-axes directions which extend perpendicularly to each other can be detected for one sense coil 422*j*. Data of the detected magnetic field strength are separated into amplitude data and phase data which are required when the position of the source coil is calculated, and are outputted.

B3: Source Position Calculation Block

On the basis of the amplitude data and the phase data which are acquired by the magnetic field detection, at the afore-mentioned block, the relationship between the magnetic field strength and the distance between the two points is utilized to bear until the fact that the positional coordinates of the source coil 416*i* are calculated. First, correction of a difference in magnitude of a diameter of the sense coil 422*j* in each axial direction and the positional relationship between the source coil 416*i* and the sense coil 422*j* is applied, with respect to the amplitude data and the phase data, to calculate the magnetic field strength which is considered to be detected at the establishment position of each sense coil 422*j*.

From the magnetic field strength calculated in this manner, a distance between the source coil 416*i* and the sense coil 422*j* is determined. In this connection, since the posture (orientation of the solenoid-like coil) of the source coil 416*i* when inserted is unknown, only a section within a range of a spherical shell can be determined with respect to the present position of the source coil 416*i*. In view of this, three or more sense coils 422*j* are prepared, and overlap of the region of the source coil 416*i*, which is capable of being present, is determined. A position of the center of gravity of the region is outputted as representing the positional coordinates of the source coil 416*i*.

B4: Image Display Block

On the basis of the data which are acquired as representing the positional coordinates of the source coil, the scope form is constructed, and a described image thereof is outputted onto the CRT. On the basis of the data of one or more coordinates which are acquired as representing the positional coordinates of the source coil, continuous coordinates which represent a smooth line are constructed. Modeling processing for showing the scope form by the continuous coordinates is conducted (e.g., polygonal column or prism, utilization of color gradation, saturation and intensity, hidden-line processing, perspective or the like).

Moreover, the scope image model which is displayed on the CRT is capable of being rotated, enlarged or reduced in an optional direction. It is possible to also display a body marker or the like by which the visual point position of the present display and a head direction of a patient can be seen at a glance. The visual point position upon completion is automatically preserved or stored and comes into the subsequent initial visual point portion. A hot key which stores the visual point direction which the operator considers as easy to see also presents (to be described later as a second modification of the nineteenth embodiment).

More detailed contents every each block will subsequently be described.

B1: Initialization Block

In initial Step S11, initialization of graphic pages (initialization of a VRAM) is conducted. Furthermore, when the scope image which is displayed on the CRT is renewed, if a new image is superscribed, an impression of the image in which the superscription is flickered is given to the observer, and the image comes into an image which is not a smooth image. Accordingly, a plurality of graphic pages are continuously changed over to display the image, whereby smoothness like an animation is realized.

Further, setting of the used color and gradation is conducted. With regard to the number of colors which can be used, there is limitation every hardwares. In view of this, as shown in FIG. 126, if the number of colors which is allocated to the image 500 in which the insertion part 407 is modeled so as to be displayed increases and the gradation display is conducted, image display having a stereoscope is made possible. In this connection, in FIG. 126, two circles indicate a marker which indicates the reference position, and a square frame indicates the bed.

A gradation display in which the closer to the visual point, the brighter, and the farther from the visual point, the darker, is carried out whereby it is possible to express the image 500 such that the image 500 in which the insertion portion 407 is expressed two-dimensionally has a three-dimensional feeling and a depth. Of course, it is optional that the number of gradations increases and decreases. Moreover, other than the gradations, the employed color is formed by combinations of R, G and B. Thus, it is also possible to express more detailed saturation and gradation.

In subsequent Step S12, initialization of the image parameter such as automatic reading of the initial visual point position, or the like, is conducted. It is largely operator-dependent based on how the operator feels the scope image should be seen. If the initial visual point position is fixed, the operator must reset the initial visual point position, for that purpose alone, to a visual point position at which the scope image is easy to be viewed. Thus, ease of use is reduced.

In view of the above, a means is arranged in which a desired visual point position is preserved in the form of a file (parameter file), and the file is read at start of the program, whereby the scope image can be seen from a visual point position at which the operator may easily view the scope image, from the time immediately after the start of the program.

Furthermore, in the present embodiment, as shown in FIG. 126, an output region of the scope image and an output region of the text image plane are displayed in a divided display.

The scope image and the text image plane are divided from each other, whereby a degree of rotation of the scope image and a degree of enlargement and reduction can be confirmed from both the side of the visual sense and the side of the numerical values. In fact, in the two-image-plane display mode shown in FIG. 127, the scope image is simultaneously displayed on the left and on the right.

In subsequent Step S13, principle-initial or principle-origin data in which the principle for deriving or rendering the source-coil position is stored are loaded. The data are reference data or reference information Of the following relationship.

A measurement principle is to detect the output from the one-axis source coil 416i by the sense coil 422j which is manufactured by perpendicular three axes, to acquire an interval between the source coil 416i and the sense coil 422j by a magnetic-field strength thereof. Upon acquirement of the interval between both the coils, the interval is not directly solved from the distribution which indicates the magnetic-field distribution created by the one-axis source coil 416i, but a new distance calculation method is employed which utilizes the maximum magnetic-field strength output and the minimum magnetic-field strength output due to a difference in posture (orientation in the axial direction) of the source coil 416i.

That is, when the distance between the one-axis source coil 416i and the three-axes sense coil 422j is set to various values, whenever the axial direction of the source coil 416i is changed by each distance value, data of the maximum magnetic-field strength curve and the minimum magnetic-field strength curve in which points in which the largest value of the magnetic-field strength (maximum magnetic-field strength values) and the smallest value of the magnetic-field strength (minimum magnetic-field strength values) which are detected at a position of the three-axes sense coil 422j are measured are respectively plotted so as to be graphed are prepared as reference data of the distance calculation.

The reference data are used whereby it is made possible to conduct the distance calculation of the one-axis source coil 416i, from the magnetic-field strength which is detected by the three-axes sense coil 422j, as follows:

It is made possible to add such a limitation that, whenever a certain magnetic-field strength H is detected, the source coil 416i cannot present only within a spherical shell which is put between a radius whenever a value H thereof is the maximum magnetic-field strength value, that is, the minimum radius r_min in which the distance is minimized and a radius in case where a value H thereof is the maximum magnetic-field strength value, that is, the maximum radius r_max in which the distance is maximized. The limitation is conducted at the position of each sense coil 422j, whereby it is possible to limit an existence region of the source coil 416i, as shown in FIG. 120.

Data corresponding to the maximum magnetic-field strength curve and the minimum magnetic-field strength curve are stored in data storage means such as a hard disc or the like. When operation of the endoscope form display starts, the position detection part 431 refers to the same as occasion demands.

In connection with the above, an actual measured value in proportion to the magnetic-field strength which is detected by the three-axes sense coil 422j is a value which determines a square of a value 22X·22X+22Y·22Y+22Z·22Z in which signals 22X, 22Y and 22Z which are respectively detected by three coils which form the three-axes sense coil 422j are respectively squared and are summed up. The determined value is calibrated by a standard magnetic-field measurement device (a gauss meter, for example) whereby it is possible to acquire an accurate measurement value of the magnetic-field strength.

The aforesaid file (max_min data file) in which data of the maximum magnetic-field strength and the minimum magnetic-field strength are recorded is loaded, and correction data are also loaded from a correction data file. Correction or amendment of a diameter of the sense coil 422j is also conducted. Thus, it is possible to conduct highly accurate positional detection.

After loading of the aforesaid data, initialization of the hardware is conducted in subsequent Step S14. In Step S14, the setting contents of the distributor 428 in FIG. 117 are reset in an initial state. Further, the setting contents of an A/D converter (not shown) which forms the form calculation part 430 are reset in a state which corresponds to the using environment. (The number of channels thereof is set to the number of source coils and the number of used markers, for example.) Thus, the hardware is set to a state capable of being used in form calculation, and the subsequent block B2 operates.

B2: Hardware Control Block

First, in Step S21, a change-over signal is applied to the distributor 428 as described with reference to FIG. 117, to select the source coil 416i, to thereby drive the source coil 416i. The magnetic field which is generated by the source coil 416i is detected by the sense coil 422j.

Accordingly, as shown in Step S22, the detection signal which is detected by the sense coil 422j is sampled by an A/D converter through a phase sensitive detector (PSD) (not shown) which forms the detection part 426. Sampled data are once written to a memory within the form calculation part 430.

As shown in Step S23, a CPU which, for example, forms the form calculation part 430 judges whether or not driving with respect to all the source coils 416i have been ended or completed. If not completed, the CPU controls the driving of the subsequent source coil 416i.

Whenever all the source coils 416i have been driven, amplitude data and phase data are calculated from the data in the memory (the PSD data passing through the PSD) (refer to the PSD calculation in Step S24, and the amplitude data and the phase data in Step S25 in FIG. 122 ). In this connection, whenever the marker is used, similarly to the source coil 416*i* which is built in the probe 415, the drive signal is further applied to each source coil which is built in the connected marker, to calculate amplitude data and phase data with respect also to the source coil of the marker.

Transferring is made for processing of the subsequent block B3 from the above-described amplitude data and phase data. First, calculation of the magnetic-field strength in Step S31 is conducted by the use of a correction coefficient.

Subsequently, calculation of the maximum distance and the minimum distance (between the source coil 416*i* and the sense coil 422*j*) in Step S32 in FIG. 7 is conducted by the use of the maximum and minimum distance data.

Step S32 conducts processing until the fact that the magnetic-field strength acquired in previous Step S31 is used to calculate the maximum distance and the minimum distance between the source coil 416*i* and the sense coil 422*j*.

The fact that there is a proportional relationship between the distance between the two points and the magnetic-field strength is a physical phenomenon which is generally known widely. However, since the magnetic-field strength which is produced onto a one point or a single point on a certain space by the one-axis source coil 416*i* is expressed generally by a distribution, even if orientation of the source coil 416*i* is known, and the magnetic-field strength is measured, it is not easy to calculate a direction in which and a distance over which the source coil 416*i* is present.

In view of the above, whenever a certain magnetic-field strength can be detected, if it is assumed that a distance in case where the source coil 416*i* is supposed to be oriented in a direction in which an output thereof can be taken the strongest is R__max, and a distance in case the source coil 416*i* is supposed to be oriented in a direction in which the output can be taken the weakest is R__min, it is possible to limit a true distance R__true between the source coil 416*i* and the sense coil 422*j*, within a range R__min≦R__true≦R__max.

Means or a method for calculating the distance which is adopted here cannot reliably or surely find out the value of the distance R__true. However, the means or the method is an extremely easy means or method in which it is not required that complicated distribution is solved. In addition, the means or the method comes into means or a method which is wide in applied range even where, in case where, the orientation of the one-axis source coil 416*i* is unknown, it is possible to limit the existence range of the source coil 416*i*.

Subsequently, calculation of the positional coordinates of the source coil 416*i* in Step S33 is conducted. In Step S33, processing is conducted until the coordinates of the source coil 416*i* are calculated from the distance between the sense coil 422*j* and the sense coil 416*i*.

The range within which the source coil 416*i* can present at time of being seen from a certain sense coil 422*j* is within a spherical shell which is surrounded by the R__max and the R__min which are acquired in previous Step S32.

In order to limit such range within which the source coil 416*i* can be present, to a more minute space, overlap of the region in which the source coil 416*i* can be present which is determined from the plurality of sense coils 422*j* is utilized. In the region in which the source coil 416*i* is present, which is acquired from the identical source coil 416*i*, with respect to each sense coil 422*j*, a region in which all are overlapped with each other is necessarily present, as long as the position of the source coil 416*i* has not changed.

A boundary between these regions is nothing but a point of intersection of a ball or sphere having radii of the R__max and the R__min and having a center which is the position of each of the sense coils 422*j*. Since the boundary is the point of intersection of the sphere, if there are at least three sense coils 422*j*, the presence of the source coil 416*i* can be limited to a minute range which is surrounded by eight points of the sphere whose radii are the R__max and the R__min of each of the sense coils 422*j*.

This method of limitation of the source coil position is simple arithmetic calculation which calculates the point of intersection of three spheres. Accordingly, the method of limitation of the source coil position is an extremely superior method in which processing time thereof is not taken, and the method enables to limit the present region of the source coil 416*i* to one within an extremely minute region.

The calculation of the positional coordinates of each of the source coils 416*i* is conducted in this manner, to acquire the positional coordinate data of the source coil 416*i* in Step S34. Whenever the marker is used, calculation of the positional coordinates is conducted similarly also to the source coil of the marker.

These data are used to pass to processing of a subsequent block B4.

B4: Image Display Block

On the basis of the positional coordinate data of the source coil 416*i*, the block B4 shoulders processing until the fact that the scope form image under being inserted is represented or described on a CRT.

The positional coordinates of the source coil 416*i* are a locus along which the inserted scope has passed. In view of this, the inserted scope form is estimated. If the inserted form of the scope can be estimated, the result thereof is described on the CRT. At this time, since the three-dimensional scope form must be displayed by the two-dimensional CRT image plane, a contrivance is required that the described image is expressed more three-dimensionally.

Moreover, if it can instantaneously be judged that the scope image is rotated in an optional direction and in what direction a view of the scope image is now taken, convenience in use thereof is further improved.

In view of such a fact, in the apparatus 3, a display method in which classification is made as follows, depending upon the function thereof and characteristics or features every respective modules are added together is realized.

S241 Keyboard Input Processing
S242 Scope Model Description
S243 Reference Surface Display Processing
S244 Marker Display Processing Since all these processings and description are not necessary for the description of the scope image, it is possible to choose a function as occasion demands. FIG. 122 only shows keyboard input processing in S241 and processing of scope-model description in S242. After the processing in Block B4, processing of display image-plane video page setting in Step S245 is conducted. Modeled image data are set in a VRAM. Subsequently, the image data are outputted to the CRT so that the processing of the scope-image display in Step S246 is conducted. By processing of judgment as to whether or not the program is ended or completed (Step S247), the program ends when the completion is selected. If the program is not ended, the program is returned to Block B2. Similar operation is repeated. In view of this, characteristics for each module will hereunder be described.

S241: Keyboard Input Processing

Here, whenever key input corresponding to a given user command is conducted, it is shouldered until the setting parameters or the like are altered in accordance with the contents thereof.

The fact that additional function which is considered that a command from the user is high is equipped depends upon the convenience in use of the apparatus. Moreover, the function choosing or selection is easy operation, and operation is always possible when the user desires the operation. Thus, it is necessary that the requisite contents of the user are realized quickly.

Step S241 conducts input acquisition from the keyboard, to conduct processing of the command or the like corresponding to the key input.

As the command corresponding to the key input, there are rotation of the image around each of the axes X, Y and Z, enlargement and reduction of the image, image display from the initial visual-point position, image display from the visual-point position registered by the user, user registration of the visual-point position, division of the image plane of the image output into a plurality, image-plane display of the comment input, modification of the background color, ON/OFF of the marker display, ON/OFF of numerical-value display of the source coil coordinates, and the program end.

Subsequently, explanation of the nineteenth embodiment will be conducted.

Subsequent to the keyboard input processing in Step S241, the scope-model description of Step S242 shown in FIG. 122 is conducted.

A processing flow of the scope-model description is arranged such that the scope form is displayed in the one-image-plane mode as shown in FIG. 126 and is displayed in the two-image-plane mode shown in FIG. 127 in accordance with the selection of the user.

A specific example of the processing flow of the scope-model description is shown in FIG. 123.

The arrangement is as follows: That is, first, processing in which a parameter file which is required for description is loaded is conducted in Step S251. Data are loaded such as rotational angles (pitch, head and bank) around the X, Y and Z axes, visual point (view point), project screen, number of the marker mode, or the like, from the recording device of the parameter file such as a hard disc or the like. The data are temporarily written into the memory which forms the form calculation part 430. The CPU refers the data as occasion demands to conduct the processing of the description.

Subsequently, initialization of each variable is conducted in Step S252. The loaded data or the like are referred to, and the variable which is used in the description is set to an initial value. Subsequently, in Step S253, judgment as to whether or not f·10 is depressed (expressed as being f·10_key ON? in FIG. 123) which serves as a function key set to the key input of the completion of the inspection is conducted. When it is depressed, the processing of the scope-image display is ended. When it is not depressed, judgment as to whether or not the mode is the one-image-plane mode (Step S254).

The arrangement is as follows: That is, in Step S254, judgment as to whether or not the image is the one-image-plane mode is conducted by whether or not a HELP key which serves as a hot key set to a key of image-plane mode change-over is depressed. When, for example, the HELP key is not depressed, it is judged as being the one-image-plane mode. Judgment as to whether or not the HELP key is depressed (in FIG. 123, expressed as being HELP_key ON?) is conducted (Step S255) so that it is possible to conduct the change-over to the two-image-plane mode.

Specifically, for example, a two-image-plane display flag of two bits is prepared. In the initial setting, the flag is set to zero. One is added every time the HELP key is depressed. Judgment of the image-plane mode is conducted by the fact that a value of the flag is investigated. That is, when the value of the flag is zero, it is judged as being the one-image-plane mode. When the value of the flag is one, that is, is turned ON, it is judged as being the two-image-plane mode.

Moreover, the arrangement is as follows. That is, in Step 254, when it is judged as being the two-image-plane mode, judgment as to whether or not the HELP key is depressed is further conducted (Step S256). Thus, change-over to the one-image-plane mode can be conducted.

When it is judged that the HELP key is depressed in Step S255 (in the one-image-plane mode, when the key input of the change-over to the two-image-plane mode is conducted), the two-image-plane mode is turned ON in subsequent Step S257 and, thereafter, the initial setting of the two-image-plane mode is further conducted in Step S258.

First, setting of the graphic mode which is set in the one-image-plane display mode is released or canceled, and the graphic mode is set to one for the two-image-plane display mode. Moreover, a display frame is set to one for the two-image-plane display mode, and the two-image-plane display flag is turned ON.

Furthermore, in subsequent Step S259, judgment as to whether or not the head angle (the rotational angle about the Y-axis) is larger than zero is conducted. In case of being "no", the head angle is set to zero (Step S260). The program passes to processing of view-port setting of the left-hand image plane in subsequent Step S261. Meanwhile, when it is judged as being greater than zero, the program passes to processing of view-port setting of the left-hand image plane in subsequent Step S261, by the head angle.

In order to display a vertical image endoscope form (form as viewed just from the above) onto the left-hand display image plane, a region for the display is set to the left from the center of the image plane. Furthermore, the set region is cleared. Moreover, when an inspection region display frame is displayed, the frame of the inspection region is represented. In a modification to be described later, the arrangement is such that display and non-display of the inspection region display frame can be selected.

Subsequently, the scope-image representation in Step S262 is conducted.

Here, it is shouldered until the scope form is created from the source-coil position coordinates which are acquired from the magnetic-field detection, and the image thereof is three-dimensionally displayed on the CRT. The acquired positional coordinates of the source coil are discrete data of the number of source coils which are inserted into the scope. Thus, on the basis of these data, the inserted scope form must be estimated. Further, the thus obtained scope form data are outputted onto the CRT by the image which is modeled in three-dimensional form. The basic or fundamental processing contents of the modeled image representation are shown in FIG. 124.

S262_a: Three-dimensional Interpolation Between Calculated Source Coils

In processing of three-dimensional interpolation between the calculated source coils in S262_a, the source-coil positional coordinates which are calculated on the basis of the magnetic-field strength detection are discrete. Accordingly, if only the calculation data are connected to each other, the locus is squarish, and does not correspond to the scope form in which the position continuously varies or changes. In order to create the smooth overall scope form, the three-dimensional interpolation is carried into practice with respect to the data of the source-coil position coordinates.

S262_b: Construction of Three-dimensional Model

Since the real scope has a thickness thereof, even if the smooth data points are acquired, if the data points are connected to each other by a straight line or the like having no thickness, it cannot be said that the real scope is represented. In view of this, in the processing of the construction of the three-dimensional model in Step S262_b, the connection between the interpolation data is conducted by a circular cylinder or a n-prismatic model or the like. The arrangement is such that the actual scope can be displayed as corresponding to the practical scope form, also in the thickness.

S262_c: Affine Transformation

The scope form is outputted as an image which is looked at from an assigned visual-point position. In view of this, in processing of affine transformation in Step S262_c, scope-form model data which are acquired by the world coordinate system which serves as the reference coordinate system of derivation or rendering of the source-coil position are converted to a visual-point coordinate system for image plane display. In this connection, the visual-point position can be modified by the user. The modified contents are referred to here.

S262_d: 3D→2D Projection

Originally, the scope form is three-dimensional. However, in order to output the image thereof onto the CRT image plane, the image must be converted to two-dimensional. In view of this, projecting transformation to the two-dimensional image from the three-dimensional image in Step S262_d is conducted. At this time, far and near may be emphasized by perspective or the like.

S262_e: Rendering

The scope form image which is acquired by the processing until now is represented onto the CRT. When the representation is conducted, in the processing of the rendering in Step S262_e, hidden-line processing is conducted for expressing the one-side processing of the n-polygon and the order of the loop of the scope. Processing such as the fact that adjustment of the intensity and the saturation of the side surface of the scope model is conducted by the gradation display at the shading processing due to the far and near, curvature of the scope or the like, may be carried into practice to emphasize a three-dimensional feeling.

In connection with the above, it is not necessarily required to carry some of the above-described items into practice. Of course, if carried into practice, the representation can be rendered or reproduced in the form including the effects or advantages which are had by improved items thereof onto the CRT. Further, it is not required to conduct the order indicated in FIG. 124, but there is a case where the order is changed or modified in accordance with the model which displays the insertion-part form, whereby equivalent processing can be conducted in less time.

Through these processings, it is possible to reproduce the three-dimensional scope form while inserted, onto the CRT, only from the positional coordinates of several source coils.

Moreover, in the present embodiment, an n-polygonal columnar model and an n-polygonal connection model can be arranged so as to be selected as the display of the scope, as follows.

After processing of scope image painting on the left-hand image plane has been conducted in Step S262, view-port setting on the right-hand image plane is conducted in Step S263 in FIG. 123. Processing of model painting on the right-hand image plane is conducted (Step S264).

In the processing of the scope image painting on the right-hand image plane, painting is conducted by an angle in which a value of 90° is added to the head angle which is used in the processing of the painting on the left-hand image plane. Accordingly, processing is conducted in which the scope form from a visual-point direction which is 90° different from a visual-point direction of the left-hand image plane is modeled, and is painted. In Step S260, when the head angle is set to zero (painting when the left-hand image plane is looked at from the top), the right-hand image plane comes into painting when the right-hand image plane is viewed from the side.

Subsequently, after the image data which are processed in painting have been used to conduct setting of the display image-plane video page (Step S245), output is made to the CRT so that the scope image display is conducted (Step S246). In this case, the display is the scope image display at the two-image-plane mode. Two scope forms from the visual-point directions which are perpendicular to each other as shown in FIG. 127 are simultaneously displayed on the CRT.

Meanwhile, in step S255, when the HELP_key is not depressed (the one-image-plane mode), processing of the normal mode scope-image painting in Step S265, that is, processing of the scope image painting in the one-image-plane mode is conducted. The processing is similar to that in Step S262 or that in Step 264. After the processing, the image data are outputted to the CRT through the processing of the setting of the display image-plane video page in Step S245. Display of the image in which the scope is modeled by the one-image-plane mode is conducted as shown in FIG. 126.

Furthermore, in Step S256, when it is judged that the HELP_key is not turned ON (in case of the two-image-plane mode), the program passes to the processing in Step S259. Further, in Step S256, when the HELP_key is turned ON (in case where the command of change-over of the one-image-plane is inputted in the two-image-plane mode), the two-image-plane mode is turned OFF in Step S266. Moreover, after the normal scope image-plane setting has been conducted (Step S267), the program passes to the processing of Step S265 to conduct display of the scope form by the one-image-plane mode.

In a flow in FIG. 123, the scope form is displayed on the CRT by the two-image-plane mode or by the one-image-plane mode, in accordance with the key input which is selected by the user. Particularly, since, in the two-image-plane mode, the scope forms from the visual-point directions which are perpendicularly to each other are displayed simultaneously, side-by-side, as shown in FIG. 127, it is possible to accurately grasp also an amount of depth in the image from one visual-point direction, from the image from the perpendicular visual-point direction.

As described above, when the two-image plane display, normally, the image in which the visual-point direction is the vertical direction is displayed on the left hand, while the image in which the visual-point direction is the horizontal direction is displayed on the right hand. When the visual-point direction or the like is modified, the image comes into an image from a different direction in accordance with the modification.

A three-dimensional model for modeling the scope form for three-dimensional display will subsequently be described.

When the n-polygonal model is selected, the transverse cross-sectional surface of the insertion part is modeled into a regular polygon, and is displayed as an n-polygonal column, for example, as shown in FIG. 126 (in FIG. 126, n=5). If the number of n increases, the transverse cross-section comes substantially into a circle. In that case, the insertion-part form is displayed as being a cylinder.

A flow of the processing contents of the display by this model is shown in FIG. 125*a*–FIG. 125*d*.

Figure 125A:
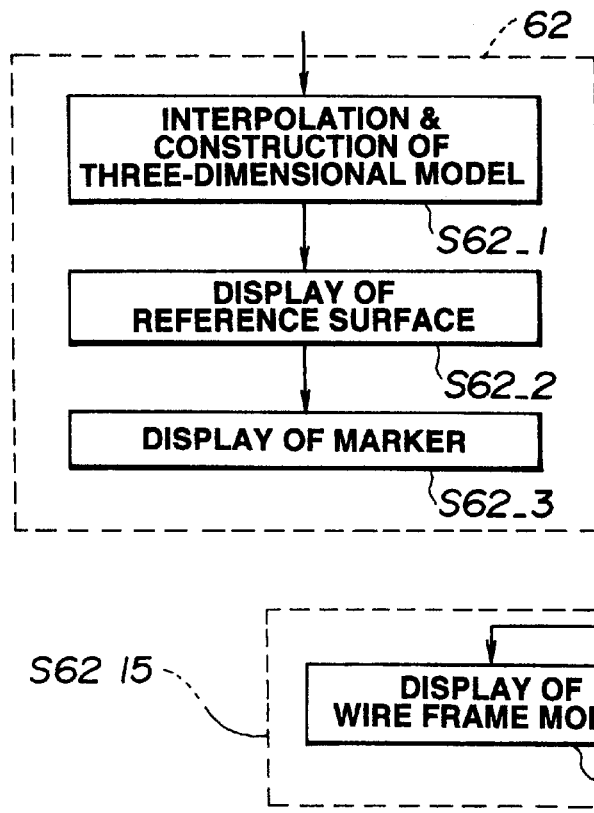
Figure 125B:
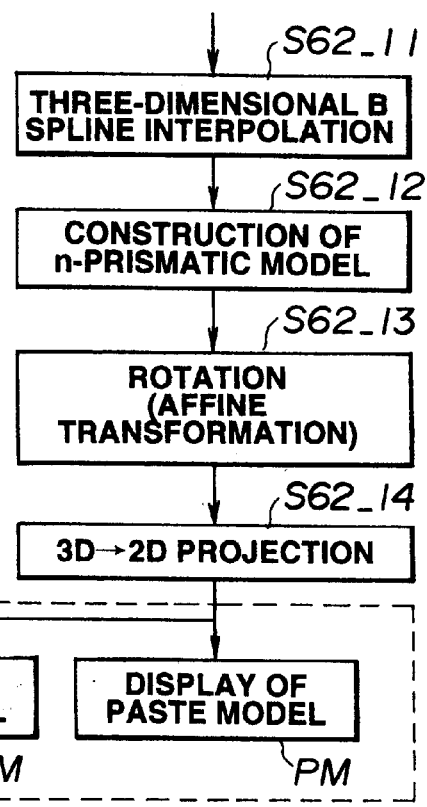

In FIG. 125*a*, processing of the interpolation & the construction of the three-dimensional model in S262_1 conducts processing shown in FIG. 125*b*.

Here, the B-spline interpolation of the three-dimension in Step S262_1 is first carried into practice. The interpolation is not a type which necessarily passes through an interpolation point, but is one which creates a smooth curved line while the interpolation passes through a point in the vicinity of the interpolation point. The interpolation is easy in calculation processing thereof, as compared with a natural spline which necessarily passes through the interpolation point. Of course, even if the natural spline is used, or even if the other interpolations are used, the interpolation may be an interpolation due to the approximate function.

The B-spline which is relatively easy in calculation processing is advantageous in that the processing speed is fast even if the three-dimensional interpolation used.

The construction of the n-prismatic model is subsequently conducted as the construction of the three-dimensional model in S262_12.

Here, a telescopic scope image is constructed by the n-prismatic model (hereinafter, also including the circular cylinder), from the interpolation data of the source-coil positional coordinates.

Affine transformation of S262_13 in FIG. 125*b* is subsequently conducted. The affine transformation is one of the methods which are used when the coordinate transformation of graphic forms is conducted by a computer graphic. When the coordinate transformation is treated, the affine transformation is generally conducted. All simple primary coordinate transformations such as parallel movement, rotation, enlargement, reduction and the like are all included in the affine transformation. In this connection, the rotational angle around the X-axis is called a pitch angle, the rotational angle around the Y-axis is called a head angle, and the rotational angle around the Z-axis is called a bank angle.

In this processing, the scope model data which are expressed by the world coordinate system (refer to FIG. 128) which is fixed to the bed 404 are converted to the model data which are [looked at] from a certain visual-point position.

The visual-point position is arranged as to be able to be set in an optional direction. For this reason, it requires extremely difficult processing that in what direction the visual-point position is moved is traced, to move the model data in the form following that direction. In view of this, supposing that the visual point is fixed, the world coordinate system which does not originally move is rotated for convenience. Thus, this gives the result similar to the fact that an image in which the visual point moves is acquired.

This method can cope with the fact that the world coordinate system is rotated for convenience in the direction the visual point moves. Accordingly, this results in as great reduction in time lag with respect to the movement of the visual point.

Processing of three-dimension—two dimension projection 3D→2D projection in Step S262_14 in FIG. 125*b* is subsequently conducted.

In the processing of the 3D→2D projection which conducts projection transformation or conversion from the three-dimensional image to the two-dimensional image, a projection method indicated below is conducted whereby a display can be realized by a far and near method or the like, in accordance with an object or purpose.

a) In Case Where Perspective is Applied

The closer to the visual point, the larger the three-dimensional form is seen, and the farther from the visual point, the smaller the three-dimensional form is seen. This can be realized by processing which converts the three-dimensional model data to the two-dimensional data.

In order to project the three-dimensional coordinates to the two-dimensional planar surface, the screen is virtually arranged vertically with respect to the visual point, and is arranged on the side opposite to the three-dimensional image (the 3D image which is acquired till S262_13). Under such a state, the projection surface of an object which is viewed from the visual point is projected such that the projected image on the side closer to the visual point is larger than the projected image on the far side, so as to be expressed by the far and near method. This method is advantageous in that a three-dimensional depth can be easily applied to the two-dimensional projected described image, and a degree of the emphasis can easily vary or change. Of course, the image may be displayed without application of the perspective.

Processing of rendering in Step S262_15 is subsequently conducted. In the present embodiment, as shown in FIG. 10(*b*), it is possible to select the rendering from the processing of the paste model display PM and the processing of the wire-frame model display WM.

The display by these models uses the world coordinate system which is fixed to the bed 404 shown in FIG. 128, and employs the other world coordinate systems in accordance with the processing contents.

For example, the source-coil coordinates are the world coordinate system. Rotational processing is conducted with respect to the source-coil coordinate, to find out the source-coil coordinate (that is, a visual-field coordinate system) which is looked at from "visual point" and, thereafter, data interpolation is conducted with respect to the discrete source-coil coordinates, to find out the source-coil coordinates which are looked at from "visual point" which is ended in data interpolation.

Subsequently, the scope model due to the wire frame or the like is generated by the processing of the three-dimensional model construction and, thereafter, in order to display the scope model to the two-dimensional image plane, the three-dimension—two-dimension transformation (perspective projection transformation) processing is conducted, to generate two-dimensional data and three-dimensional data. A pseudo-stereoscopic image is conducted in rendering processing, and is displayed.

The past model display PM in FIG. 125*b* will subsequently be described. Since the model paints out each face of the n-prism, the model is called a past model.

The side-surface processing of the n-polygon when the image in the form of the scope form is represented onto the CRT, and the hidden-line or hidden-face processing in order to express the front and back of the loop when the scope comes into the form of the loop are applied. When displayed by the n-prism, the image has n side surfaces. Of them, the side surfaces which are practically seen are only the side surfaces on the side in the visual-point direction. Accordingly, such processing resulting in a display which is conducted such that only the side surface on the side in the visual-point direction can be seen, and the side surface, the side or the like which cannot be seen is hidden, that is, hidden-line or hidden-face processing is conducted. In this case, a parameter which expresses how close to the visual-point position (referred to as "z-buffer") is sorted. This can be realized by the fact that writing is made by a superscription from the side surface in which the z-buffer is small (that is, the side surface is far from the visual point).

Processing of the wire-frame model display WM will subsequently be described.

This yields the same result as that where a portion except for the sides of the n-prismatic model is painted out by the background color. However, this is selectively used because processing time for painting the faces of the n-prismatic model is reduced.

In connection with the above, in the present model, if the z-buffers are written from the order of the small one, the wire on the side of the depth of the scope model is seen. In view of this, the hidden-wire processing for removing the same is suitably carried into practice. Alternatively, the wire frame is depicted till the model data of (n/2) in order of the large z-buffer, whereby it is possible to construct the model which is processed in hidden line.

Subsequently, FIG. 125a conducts Step S262_2 of the reference-surface display and Step S262_3 of the marker display. Processings in these Steps S262_2 and S262_3 are additional processings.

The processing of the reference-surface display is such that the reference surface such as the bed surface or the like is displayed. Thus, the processing of the reference-surface display shoulders an auxiliary role to facilitate understanding, in a manner of visual sense, the three-dimensional display of the scope form.

If the described image which is displayed on the CRT is only the image in the form of the scope, the positional relationship between the image and the internal organs within the body is unknown. Then, if the visual-point position is rotated, information regarding from what direction the scope form is viewed, in what orientation the direction of the head is oriented and the like is only information of a numerical value of the angle which is displayed in text. This is unsuitable for sensitive judgment. In view of this, auxiliary means is provided which can sensitively conduct such judgment.

Figure 125C:
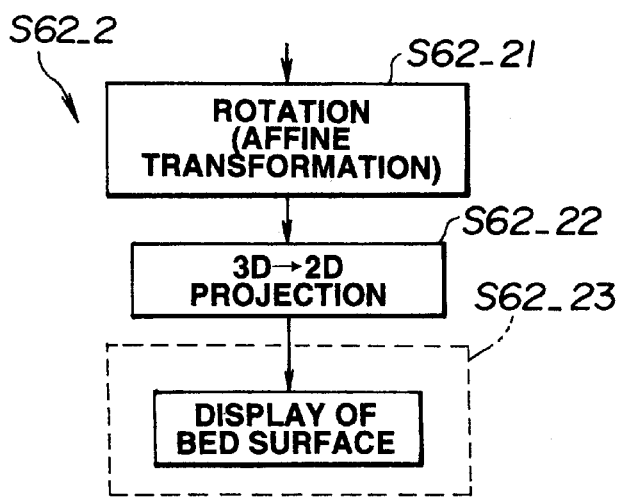

Here, this is realized as shown in FIG. 125c.

First, affine transformation in Step S262_21 is conducted. In the processing, a reference display symbol of the world coordinate system is transformed to the visual-point coordinate system.

Subsequently, the 3D→2D projection in Step S262_22 is conducted.

Transformation processing projected to the two-dimension is conducted so that the reference display symbol which is transferred to the visual-point coordinate system can be displayed in CRT.

Subsequently, symbol display of the bed or the like which comes into the reference surface of Step S262_23 is conducted.

Such a symbol as to assist or subsidize the three-dimension described image of the scope image is displayed. As a specific example of the symbol, there is, for example, the bed-surface display or the like. This will be described later.

Thus, it is possible to visually judge a separating condition or state of the scope form from the reference surface position and the reference surface, and a direction of the head of the patient. Thus, this is advantageous in that the judgment reference of the position of the scope form or the like is provided.

As a specific example of the reference display symbol, the bed surface display, for example, will subsequently be described.

A reference surface which is parallel to an X-Y plane of the world coordinate system and which is perpendicular to the Z-axis is displayed. Even if the Z coordinates are the bed surface (Z=0), if the Z coordinates are a position which can come into a reference thereof, the Z coordinates may be any position. This surface is not moved together with the visual-point coordinates. That is, if the visual-point position is rotated in the X-axis direction and the Y-direction, the bed surface is expressed by a line. A marker may be applied in the direction of a rectangular pillow or in a direction of a right-hand shoulder and a left-hand shoulder or in a direction of both such that the head direction is known or seen.

This is advantageous in that, since this is expressed by a single plate, there is no interference with the image described on the scope, and it is possible to also recognize rotation of the visual point. In this connection, other than this, display of the reference marker, and display of rectangular parallelepipeds in which a frame in the Z-direction is added to the bed display, or the like, may be conducted.

Processing of the marker display in Step S262_3 in FIG. 125a will subsequently be conducted.

The processing of the marker display shoulders until the fact that, apart from the source coil 416i which is inserted in the scope, an independent source coil position is calculated, and is displayed. As a means for confirming the position inserted into the scope, a means is provided for displaying one or more markers which are capable of being moved independently from the source coil 416i within the scope.

Figure 125D:
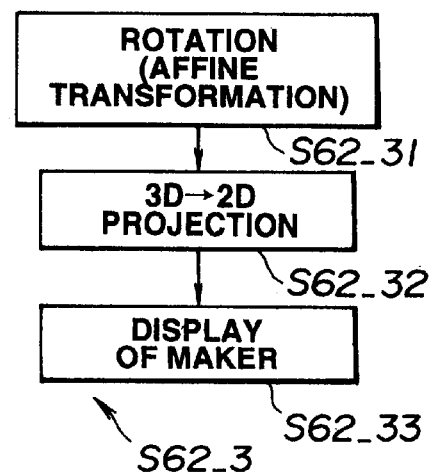

On the actual apparatus, the position calculation means is wholly identical with that which is used in the source coil 416i which is inserted into the scope. Display means is also similar to that until now, and comes into processing such as affine transformation in Step S262_31→3D→2D projection in Step S262_32→marker display in Step S262_33, as shown in FIG. 125d.

Accordingly, here, as a specific example of the marker form output, a display due to the n-polygon (including also a circle) will be described. If the display of the marker is displayed in this form, a large number of colors cannot be used. When an apparatus arrangement which cannot but use the color identical with that of the scope form, if the display of the marker is overlapped with the scope form, it is possible to distinguish the same from each other.

This marker display has the following advantage. That is, the form is changed in accordance with the rotation of the visual point, whereby it is possible to recognize from what direction the marker display is seen. Furthermore, correspondence or equivalence may be made such that it always comes into the front with respect to the visual point. At this time, the visual-point direction cannot be recognized from the marker. However, the marker always having a constant magnitude is outputted.

Moreover, this results in an expression similar to that in case where the marker is a sphere. In this connection, if the marker is the sphere, information such as gradation, saturation, intensity or the like is given whereby it is also possible to express the direction and the depth of the visual point.

Such means is used, and the marker is moved outside the body, whereby it is possible to confirm the position of the form of the inserted scope in relation to the marker. Thus, it is possible to provide auxiliary means for knowing the insertion position of the scope, in relation to the actual position of the patient.

As described above, according to the nineteenth embodiment, since a means is provided for modeling the scope form when looked up from the visual-point directions which are 90° different from each other, to simultaneously display the same by two image planes stereoscopically, the operator or the like can accurately grasp, in a visual sense, the scope form from the image of the scope form from the visual-point directions which are perpendicular to each other (which are displayed simultaneously), even when the depth form in the image of the scope form when seen from one visual-point direction is difficult to be known accurately.

Accordingly, when an operation is conducted such that the distal-end side of the insertion part inserted into, for example, the patient is guided to an objective or intended part, since the stereophonic or stereoscopic form of the insertion part can be accurately grasped, it is possible to conduct the activity or operation for introduction to the intended part easily and smoothly. Thus, it is possible to improve the operability with respect to the endoscope inspection which uses the endoscope.

Further, since the display means such as the marker or the like is provided, grasping of the stereophonic form including the directionality of the scope form from the display position of the marker on the image of the scope form is made more easily.

Moreover, a function which conducts ON/OFF of the display of the inspection-range reference frame may be provided as the first modification of the nineteenth embodiment. The arrangement of the first modification is substantially the same as that of the nineteenth embodiment. That is, in the arrangement shown in FIG. 117 or FIG. 118, the system control part 434 shoulders such processing as to turn ON or OFF the display of the inspection-range reference frame in accordance with indication (selection) from the operation part 435.

Particularly, in the two-image-plane display, since the information from two directions is displayed, it is apparent from which direction the endoscope is painted under the initial state.

For this reason, case is also assumed where the display per se of the inspection-range display frame which facilitates to identify in what direction the endoscope is seen is felt troublesome or cumbersome. In view of this, setting can be made so as not to display the inspection-range display frame. A flow of the processing is shown in FIG. 129

Operation up to Step S253 is the same as that shown in FIG. 123. When the end or completion is not selected in Step S253, ON/OFF judgment of the flag of the display in the inspection-range reference frame is conducted in subsequent Step S271. The judgment conducts change-over of the display of the inspection-range reference frame, depending upon whether or not the HOME_CLR key, for example, which is set to the hot key of the change-over of the display in the inspection-range reference frame is depressed.

When the HOME_CLR key is not depressed, the display flag of the inspection-range reference frame is turned OFF. In further subsequent Step S272, it is judged whether or not the HOME_CLR key is depressed (in FIG. 129, abridged as being "HOME_CLR ON?"). Step S272 of the judgment is provided for the purpose that the flag is changed over from OFF to ON. When the flag is turned OFF, processing of the scope model painting is conducted in Step S242' (more specifically, Step S242' corresponds to Step S254~Step S267 in the whole of Step S242 in FIG. 123) similar to Step S242 shown in FIG. 123. In this case, the display of the scope image is conducted as shown in FIG. 130a by the mode which does not display the inspection-range reference frame. FIG. 130a shows the display of the one-image-plane mode.

When the display flag of the inspection-range reference frame is turned ON in Step S271, judgment as to whether or not the HOME_CLR key is depressed in Step S273 is further conducted. When the HOME_CLR key is not depressed, the processing of the cube painting within the inspection range is conducted in Step S274 and, subsequently, the processing of the scope model painting in Step S242' is conducted. In this case, as shown in FIG. 130b, display of the scope image is conducted together with display of the cube that comes into the inspection-range reference frame. FIG. 130b also shows the display in case of the one-image-plane mode.

When the HOME_CLR key is depressed by the judgment in Step S273, the flag is set to OFF in Step S275, and the processing of the scope model painting in Step S242' is conducted.

Moreover, when the HOME_CLR key is depressed in Step S272, the display flag of the inspection-range reference frame is turned ON in Step S276. The operation passes to the processing of the cube painting within the inspection range in Step S274. The processing passes to the processing of the scope model painting in Step S242'.

According to the first modification of the nineteenth embodiment, it is possible to freely conduct that the inspection-range reference frame is displayed to display the scope form in accordance with the selection of the user or that the inspection-range reference frame is not displayed to display the scope form. Thus, the selection range of the user can be expanded or widened. It is possible to improve the convenience of use with respect to the user. This embodiment has other advantages similar to those of the first embodiment.

A second modification of the nineteenth embodiment will subsequently be described. The modification is arranged so as to be provided with a memory function of a view state of the user setting of the endoscope form and function of processing of being set to the view state of the user setting. Specifically, by the Input of a TAB_key serving as the hot key which conducts ON/OFF of the memory of the view state of the user setting of the endoscope form, the memory of the view state of the user setting of the endoscope form is conducted. Furthermore, the input of a /_key serving as the hot key which converts the endoscope form to the stored view state causes processing to convert the endoscope form to the view state. An arrangement of a hardware in the second modification is similar to that in the nineteenth embodiment, but the processing contents thereof are different in part therefrom.

A flow of the processing contents in the second modification is shown in FIG. 131. Operation until Step S253 is the same as that in FIG. 129. Subsequent to Step S253, judgment as to whether or not there is a key input is further conducted in Step S15. That is, since the keyboard input can be conducted after Step S253, judgment as to whether or not there is the key input is conducted.

When there is no key input, the program is returned to the display routine of the endoscope form in Step S16. Subsequently, processing for display of the scope model on the CRT is conducted by the processing of the scope model display in Step S17, and the program is returned to Step S253. In this connection, in the processing of the display routine of the endoscope form in Step S16 and the processing of the display of the scope model in Step S17, processings the same as those in Step S242', Step S245 and Step S246 in FIG. 129 are briefly shown.

Meanwhile, when it is judged that there is the key input in Step S15, judgment as to whether it is the TAB_key or the /_key is conducted in Step S18a and Step S18b.

When it is judged as being not the TAB_key or the /_key in Step S18a or Step S18b, the program passes to the processing in Step S16.

Further, when it is judged as being the TAB_key, a state of the view parameter of the display of the present or current endoscope form which is set and used by the user at the time the TAB_key is depressed is written to the file or the like by the processing of the current user setting view memory in subsequent Step S19a, and is stored (or is recorded). Subsequently, the program passes to the processing in Step S16.

Meanwhile, when it is judged as being /_key, the view parameter of the visual-point setting at a time of the display of the endoscope form which is stored by the operation of the TAB_key is read out from the file or the like, by the processing of the stored user setting view-parameter setting, in subsequent Step S19b. The view parameter is set to each parameter upon the display of the endoscope form. Subsequently, the program passes to the processing of the display routine of the endoscope form in Step S16. In this case, display of the endoscope form is conducted by each parameter which is read out from the file.

According to the second modification, when the user displays the endoscope form and there is the view state which is suited for the operator, if the TAB_key serving as the hot key for storing the view state is depressed, it is possible to store the view parameter. When the display is desired, if the /_key serving as the hot key for being set to the view parameter is depressed, it is possible to be set to the view parameter. Thus, it is possible to display the endoscope form at the subsequent parameter by the processing of the display routine of the endoscope form.

Accordingly, according to the second modification, without such troublesome operation to conduct setting of each parameter of the display every the endoscope form is displayed is conducted, the endoscope form can be displayed by the view parameter which is denied by the operator. Thus, it is possible to provide the environment which is superior in convenience for use with respect to the display of the endoscope form.

A third modification of the nineteenth embodiment will subsequently be described. The modification is arranged such that, by input of the hot key, the endoscope form can be rotated ±90° in the horizontal direction and displayed. Specifically, when key input of ROLLUP is conducted, the endoscope form is rotated +90° in the horizontal direction and displayed. When key input of ROLLDOWN is conducted, the endoscope form is rotated −90° in the horizontal direction and displayed.

The arrangement of a hardware of the third modification is similar to that of the nineteenth embodiment, but the processing contents thereof are different in part therefrom. A flow of the processing contents in the third modification is shown in FIG. 132. Step S15, Step S16 and Step S17 are similar to those in FIG. 131. In Step S15, when it is judged that there is the key input, it is judged whether it is the key input of the ROLLUP or the key input of the ROLLDOWN. In case of the key input of ROLLUP, the head angle serving as the rotational parameter of the display of the endoscope form in the horizontal direction is set to +90° in Step S20a (that is, set to a value in which the head angle is rotated 90° in the positive direction about the Y-axis). In case of the key input of ROLLDOWN, the head angle is set to −90° in Step S20b (that is, set to a value in which the head angle is rotated 90° in the negative direction). Thereafter, the program passes to the display routine of the endoscope form in Step S16.

The other parameters for the form display are used as is (without being changed). According to the third modification, even in the one-image-plane mode, the key input of the ROLLUP or the ROLLDOWN is conducted whereby it is made possible to display the endoscope form from a direction which is perpendicular to a visual-point position in the form display which is prior to the key input. Thus, the third modification has such a merit that the form grasp is further facilitated, or the like.

That is, in the two-image-plane mode, the image from the set visual-point direction and the image from the visual-point direction which extends perpendicularly thereto are also simultaneously displayed. However, also in the one-image-plane mode, the aforesaid hot key is depressed whereby it is possible that switching can be made to the image from the visual-point direction which extends perpendicularly to the aforementioned visual-point direction, and the image can be displayed. In the two-image-plane mode, the user interface region on the right-hand side of the image plane is normally used as the graphics output region, and two image planes which are perpendicular to each other are put side-by-side in the left and the right and are displayed. Accordingly, it is impossible to grasp the setting state of the image numerically. However, where switching is made, in the one-image-plane mode, to the display from the perpendicular visual-point direction by the input operation of the hot key, the setting state is numeric and is in an always displayed state on the right-hand side. Accordingly, it is also possible to conduct numerical grasping.

Furthermore, when an image is recorded by picture photograph or a still image, or the like, information of the setting state can simultaneously be recorded. Accordingly, it is easily comprehended in what or how state the image is recorded. Thus, this is convenient.

In the third modification, it is possible to display the image under a state in which the head angle is rotated +90° or −90° by the hot key. However, the third modification may be arranged such that the image under a state of being rotated +90° or −90° similarly also to the pitch angle that is the rotational angle of the X-axis or the bank angle that is the rotational angle of the Z-axis can be displayed. For example, when the hot key which modifies the pitch angle to conduct the display can be used, since, in addition to the two visual-point directions perpendicular to each other which are displayed in the two-image-plane mode, an image from the visual-point direction further perpendicular thereto can be displayed, the form is further facilitated to be grasped. In this connection, the arrangement may be such that the pitch angle can be changed also with respect to one or two images in the two-image-plane mode, and the image or images can be displayed.

A twentieth embodiment of the present invention will subsequently be described.

The twentieth embodiment has means for or function of being able to select and set the use form of the marker, and the means or the function will hereunder by described.

The arrangement of the embodiment is substantially the same as that of the nineteenth embodiment. That is, the arrangement of the embodiment is similar to that in FIG. 117 or FIG. 118. In the present embodiment, the system control portion 434 conducts such processing that the using form of the connected marker is selected and set by the indication (selection) from the operation part 435 (more specifically, the keyboard 435a), and the marker is displayed on the monitor 423 in accordance with the selection. The contents of the processing in this case are shown in a flow in FIG. 133.

Processings until Step S253 are the same as those in FIG. 123. When completion is not selected in Step S253, judgment as to whether or not a f·9_key which serves as a function key corresponding to key input of a preset image plane which is capable of conducting modification of a marker mode in Step S280, or the like, is depressed.

When the f-9__key is depressed, the setting of the marker mode in Step S281 is conducted. In the preset image plane, modification of date and time and modification of the marker mode are possible. An item to be modified is selected by an arrowed key, a cursor or the like is set to a position of the modification of the marker mode, and a return key is depressed, to thereby be set to the marker mode.

If set to the marker mode, the program passes to the judgment (selection) processing of the marker mode in Step S282.

In the selection processing of the marker mode, the kind of the markers and the display form (base model) which are used in identification are selected by, for example, the number of the marker mode. For example, judgment is made depending upon whether or not the number of the marker mode is zero. If the number of the marker mode is zero, the mode does not display the marker. In a case other than zero, the mode is set to a display mode in accordance with the number of the marker mode, in display-mode setting processing in Step S283. Specifically:

If the number of the marker mode is one as shown in Step S283a, the mode becomes a one-hand-marker display mode, and a mode in which the marker is displayed by a circle.

If the number of the marker mode is two as shown in Step S283b, the mode becomes a one-body-marker display mode, and a mode in which the marker is displayed by a square.

If the number of the marker mode is three as shown in Step S283c, the mode becomes a two-hand-marker display mode, and a mode in which the marker is displayed by a square and a circle.

If the number of the marker mode is four as shown in Step S283d, the mode becomes a one-body-marker+a one hand marker display mode, a mode in which the body marker is displayed by a square and a mode in which the hand marker is displayed by a circle.

Here, what is the body marker indicates that the marker comes into the reference position of the painting. For example, assuming that the marker coil is installed at the position of the anus, the endoscope form to the side of the body from this position is painted. In this case, the endoscope form in the Y-coordinate which is greater than a value of the Y-coordinate in which the marker coil is installed is painted (as shown in FIG. 128, the side of the head is set in a positive direction of the Y-coordinate).

Alternatively, from the source coils on the side of the probe, the source coil which is present on the inside of the detection region more than the marker coil is painted together with the painting of the marker coil, with the position of the marker coil serving as a boundary position of the painting range. In this case, the source coil within the probe which comes into a range on the outside of the detection region more than the marker coil is not painted.

Further, when the detection region is set, if the marker coil is set on the outside more than the detection region, painting is made only by the source coil within the probe within the detection range.

Meanwhile, the hand marker mode is a painting mode which displays a position of the merely detected marker coil.

In subsequent Step S284, judgment is made regarding whether or not the mode is the body-marker display mode. If it is judged that it is not this mode, the mode becomes the hand-marker display mode. Accordingly, in subsequent Step S285, processing of the hand-marker painting is conducted. The processing conducts the following a~e (indicated by such a description that the processing can be applied also to processing of marker painting in Step S290).

a. The detected marker data are converted in conformity with the set visual point:

b. If the two-image-plane mode, conversion processing rotating further 90° is added:

c: The marker data on a space is constructed by the detection marker data and the base model data.

d: The marker data are converted to the two-dimensional coordinates by perspective projection conversion; and e: The marker data are converted to actual display coordinates of the monitor on the basis of the converted data, to display each of the marker data.

If the processing of the hand marker painting is conducted in Step S285, processing of the scope model painting is conducted in subsequent Step S286. The position of the hand marker is displayed on the CRT, and the modeled image of the scope is displayed. In this connection, when the number of the marker mode is zero in the judgment of Step S282, the program passes to Step S286, and the scope is displayed by the modeled image without the fact that the marker painting is not conducted.

Meanwhile, when it is judged as being the body-marker display mode in Step S284, comparison in the Y-coordinates, that is, comparison of a body-marker coordinate value<a scope coordinate value is conducted in Step S287. By the comparison, the source coil which satisfies the condition which is located on the inside of the detection region more than the body marker is extracted. Judgment as to whether or not the number of scope data≧3, which satisfies this condition (that is, whether or not the number of source coils≧3, which satisfies this condition) is conducted in subsequent Step S288.

When the judgment is satisfied, the scope model painting is conducted in subsequent Step S289. The marker painting is further conducted in subsequent Step S290. Processing of the marker painting also conducts the above-described a~e.

Meanwhile, when the condition of the number of scope data≧3 is not satisfied by the judgment in Step S289, only the marker painting is conducted in Step S290, without the fact that the scope-model painting is not conducted. This is because, if the number of scope data is less, form estimation which is high in accuracy cannot be conducted and, accordingly, the scope-model painting is not conducted.

In connection with the above, the processing of the scope-model painting in Step S286 and Step S289 conducts processing similar to processing except for the processing of the marker painting in Step S242' in FIG. 129. This is because, in the twentieth embodiment, the processing of the marker painting is described separately from the processing of the scope-model painting.

In the nineteenth embodiment, the two hand markers are displayed as shown, for example, in FIG. 126. On the contrary, in the twentieth embodiment, the image 500 of the scope form when one is set to the body marker, and the body marker is displayed by a square comes into one shown, for example, in FIG. 156. Thus, a scope form portion of the Y-coordinate position (an upper one in FIG. 156) larger than the Y-coordinate position of the body marker m shown by the square is displayed. In this connection, display of a scope distal-end part in the image 500 will be described subsequently.

According to the twentieth embodiment, since display means for displaying the marker by a desired marker mode is provided, the grasp of the stereoscopic form which includes the directionality of the scope form is more facilitated from the reference display position of the marker on the image of the scope form. Other advantages are similar to those of the nineteenth embodiment.

A modification of the twentieth embodiment will subsequently be described. The modification is provided with a marker-position memory mode which stores a reference marker position of an anus or the like in addition to the other functions of the twentieth embodiment. The arrangement is such that, in the memory mode, by the input operation of the hot key, the marker position at that time is stored, and marker display is conducted on the stored marker position upon the display of the endoscope form (for example, by a mark which is different from the hand marker or the like, but which is easy to be identified).

Specifically, when the number of the marker mode is 5 and 6, the function is added. When one marker coil is connected, the number of the marker mode is 5, while when two marker coils are used the number of the marker mode is 6. The arrangement of the modification is the same as that of the twentieth embodiment, and is such that processing to which function is further added is conducted. A flow of the processing contents in the modification is shown in FIG. 134.

The processing shown in FIG. 134 is as follows. That is, the display-mode setting processing in Step S283 in FIG. 133 is changed to the contents in Step S283' shown in FIG. 135, and Step S311 of judgment processing as to whether or not it is the position memory mode and Step S312 which conducts anus marker display (such as is used as a reference marker in a manner of a body marker) to the stored marker position which is conducted whenever the judgment result thereof is ON are interposed between Step S288 and Step S290 in FIG. 133.

That is, the processing until Step S282 is the same as that in FIG. 133. Whenever the number of the marker mode is other than 0 in the selection processing of the marker mode in Step S282, the display-mode setting processing in step S283' shown in FIG. 135 is conducted. In the processing, whenever the number of the marker mode is 1~4, setting is made to the display mode in Step S283a~Step S283d similarly to FIG. 133.

Further, whenever the number of marker mode is 5 or 6, the mode comes into a position memory mode in which the marker is one or two. Setting is made to the display mode of a position memory mode (one marker) shown in Step S283e or a position memory mode (two markers) shown in Step S283f.

After processing of the setting of the corresponding display mode has been conducted by the numbers of marker mode 1~6 in this manner, processing is conducted which conducts judgment as to whether or not an INS_key serving as a hot key which conducts ON and renewing of the position memory mode shown in Step S283g is turned ON.

Whenever the number of marker mode is 5 or 6 is selected and whenever the INS_key is depressed, processing of the current marker-position memory is conducted as shown in Step S283h, thereby storing a marker coil position (a coordinate value) at the same time the INS_key is depressed, to an another area or the like of the memory. Subsequently, as shown in Step S283i, processing in which setting is made to the number 1 as the marker mode is conducted by the processing of the marker mode setting (processing which is set to 3 in case of two markers). The state comes into a state capable of being used as a hand marker and, thereafter, the program passes to subsequent Step S284.

Specifically, whenever the number of marker mode 5 or 6 is selected, when the hot key which conducts ON of the position memory mode is depressed, memory of the marker position at that time is conducted. Subsequent to the memory operation, it can be used as one or two hand markers (when the number of marker mode 5 or 6 is selected, the arrangement may be such that it can be used as a hand marker other than time at which the hot key is depressed. That is, the arrangement may be such that it can be used as a hand marker before and after the time the hot key is depressed).

In Step S284, judgment as to whether or not it is the body-marker display mode is conducted. Whenever the selected number is 1~4, it is similar to FIG. 133. However, whenever the number is 5 or 6, processing similar to the body marker is conducted with respect to the stored marker position (in this connection, the marker which is used for selection as to whether the number is 5 or 6 is processed as being the hand marker, as described in the marker-mode setting in Step S283i).

Specifically, whenever the selected number is 1 or 3 (in this case, including also the marker which is used in selection of the number 5 or 6 and which comes into the hand marker by the marker-mode setting), the program passes to processing in Step S285. Whenever the selected number is 2, 4, 5 or 6, the program passes to processing in Step S287.

In Step S287, whenever the number is 2 or 4, it is similar to FIG. 133. Also whenever the number is 5 or 6, processing of Y-coordinate comparison is conducted similarly to the case where the number regards the body marker in which the number is 2 or 4, with regard to the stored marker position. In subsequent Step S288, judgment as to whether or not the number of scope data is equal to or more than 3 is conducted. Whenever the number of scope data is equal to or more than 3, processing of the scope painting is conducted in Step S289. Whenever the number of scope data is less than 3, processing of the scope painting is not conducted, but the program passes to subsequent Step S111.

Whenever it is judged as being the position memory mode as to whether or not it is the position memory mode in Step S111, the anus marker is displayed as the reference marker shown in Step S112, at a position of the marker position which is stored (as a reference coordinate position) by input operation of the hot key (whenever the number is 6, the marker display is conducted by an easily-identified mark which expresses the reference coordinate position at an another position of the marker position which is stored in addition to the anus marker). The program passes to subsequent Step S290.

In the processing of the marker painting in Step S290, the body marker is painted. Whenever the number 5 or 6 is selected, the program passes to subsequent Step S245.

In connection with the above, during time operated by the memory mode in which the number is 5 or 6, after start-up of the system, switching is made to another image plane. Even if a return is again made to the main display, the reference coordinate position which is stored by the hot key is held. Specifically, the stored reference coordinate position is effective.

When the hot key is subsequently depressed, the memory contents of the marker position which are stored until now are renewed, and a new marker position is stored. That is, no change is made until resetting is subsequently made by the hot key.

According to the modification, if the position memory mode is selected, and the hot key is depressed at the position which is desired as being the reference position such as an anus or the like, the reference position is stored. It is possible to always display the marker at the reference position. Subsequently, the marker which is used in memory setting of the reference position can be used for display or the like of another position as a hand marker.

For this reason, it is possible to use both the function as the body marker and the function of the body marker to be had by one marker. Thus, it can effectively utilized for display of the reference position or the like. Moreover, even if the marker is not fixed to the reference position and used as the body marker, if the hot key is depressed under a state in which the marker is merely set to the reference position, the reference position can be displayed without moving.

In connection with the above, a plurality of reference positions may be stored by a single marker as the marker-position memory mode. In this case, the number of the stored reference positions may be selected and set. Further, display release or cancellation of the display thereof may optionally be conducted with respect to the stored and displayed reference position. In this case, the arrangement may be such that, whenever the marker is set to the displayed marker position, and the stored reference position and a new reference position are judged as being coincident with each other on the basis of comparison therebetween by input operation of the hot key, the contents thereof are erased and are not displayed.

In connection with the above, the above description covers the situation where the number of the marker is at least 2. However, of course, the invention should not be limited to this. Even if the number of the marker is equal to or greater than 3, principal processing is the same as that described before. Only the number of processings substantially the same as before almost increases. That is, it is possible to set the number which uses the marker. It is also possible to set the contents thereof (the number used as the body marker).

Moreover, the number of the markers which can be set and used may be independent from the number of the marker coils connected. However, the arrangement may also be such that, because the connected marker coil is automatically detected by the fact that the coil is successively scanned to apply voltage and whether or not current actually flows, and it is possible to limit the mode of the marker capable of being set in accordance therewith.

A twenty-first embodiment of the invention will subsequently be described. The embodiment freezes the form display. Patients almost always move a little. In this case, the detected endoscope image minutely moves, and it is therefore difficult to grasp the form. In view of this, the present embodiment is arranged such that the form image which is displayed continuously is frozen to facilitate understanding of the endoscope form.

FIG. 136 shows a flow of processing of the operation to conduct freezing to display the form in the present embodiment. Processing until Step S253 is the same as that in FIG. 113. When the f·10_key is not depressed, judgment of the freeze mode ON/OFF is conducted in subsequent Step S291. Moreover, it is also possible to pass to the processing in Step S271 in FIG. 129 or Step S280 in FIG. 133.

The above-described judgment of the freeze mode ON/OFF is judged by a freeze flag. Whenever the freeze flag is OFF, when, for example, the vf·2_key which comes into one of function keys, is depressed, the freeze mode is turned ON, and the freeze flag is turned ON. Moreover, when a vf·2_key is depressed, the freeze mode is released, and the freeze flag is turned OFF.

Whenever it is judged that the freeze mode is turned OFF in Step S291, that is, during an animation mode, processing of acquisition of twelve point data of the source coils which are mounted within the scope is conducted in Step S292.

After the processing of acquisition of the data with respect to all the source coils which are mounted within the scope has been conducted, judgment as to whether or not the vf·2_key is depressed is conducted in subsequent Step S293.

If the vf·2_key is not depressed, judgment as to whether or not a CTRL+arrow key or CTRL++ (or –) key serving as an indication key of rotation zoom of the scope image is depressed is conducted in subsequent Step S294. If these keys are depressed, an input parameter is changed or varies correspondingly to the depressed key (Step S295), and rotation or zoom is conducted. The program passes to the processing of the scope model display in Step S101, and the scope form is displayed on the CRT. The processing of the scope-model display briefly expresses the processing after Step S242' in FIG. 129, for example.

In Step S293, whenever the vf·2_key is depressed, processing to set the freeze mode to ON is conducted (Step S296). The freeze flag is turned ON to make the mode the freeze mode. In case of being set to the freeze mode, fetching of data of twelve points is not newly conducted for display of the scope form, but the data for the form display which is acquired before the freeze time are used to conduct the display of the scope form, onto the CRT.

Meanwhile, whenever it is judged that the freeze mode is turned ON in Step S291, judgment as to whether or not the vf·2_key is depressed is conducted in further subsequent Step S297. Whenever the vf·2_key is not depressed, judgment as to whether the CTRL+arrow key or the CTRL+plus (or minus) key serving as the indication key of rotation zoom of the scope image is depressed is conducted in subsequent Step S298.

When depressed, the input parameter is changed correspondingly to the depressed key (Step S299), and the rotation or the zoom is conducted. The model of the scope is displayed on the CRT. Whenever the key is not depressed in Step S298, the scope model is displayed on the CRT without being rotated or zoomed.

Furthermore, in the judgment in Step S297, in case where vf·2_key is depressed, the freeze mode is turned OFF in subsequent Step S300. The scope model is displayed on the CRT by an animation mode.

According to the twenty-first embodiment, it is possible to freely select the display of the scope form at the frozen mode and the display of the scope form at the animation mode. Accordingly, if the display at the animation mode is selected, it is possible to conduct the display of the scope form under a state close to the real time.

Meanwhile, whenever the display at the freeze mode is selected, it is possible to display the scope form as a still image. For example, whenever motion of the patient is a concern, such as when the form display is conducted at a part or the like close to the heart, the freeze mode is selected whereby it is possible to display the scope form under the still image. Accordingly, it is possible to easily grasp the scope form without being affected by the motion of the patient. Moreover, during the freeze mode, the form data just before the same are used in case where the freeze mode is selected. Since the processing of the acquisition of the form data and the form calculation which are changed every moment after selection are dispensed with, it is possible to conduct the display of the scope form for a short period of time, as compared with the case of the animation mode. Other advantages are similar to those of the first modification of the nineteenth embodiment and the twentieth embodiment.

In connection with the above, the arrangement may be such that, even when the freeze mode is selected, the time interval of the data renewal of the scope form whenever the scope form is displayed by the freeze mode can be set on the side of the user. That is, the arrangement may be such that, whenever set to the freeze mode, the scope form can be continued to be successively displayed by the still image at new form data every set time, in addition to the mode in which the scope form is continued to be displayed by the still image at one form data, until the freeze mode is released.

The twenty-first embodiment is provided also with the flow function in FIG. 129 and FIG. 134. Characteristics and typical function thereof will hereunder be described, including also the function which is indicated by a flow and function which is not indicated by a flow. First, the embodiment has the following characteristics:

(1) A dedicated (source) probe 415 is inserted into the channel 413 for the treatment tool of the endoscope 406 which is inserted into the patient body, or a dedicated endoscope (the source coil is provided within the insertion part of the endoscope despite the fact that the probe 415 capable of being installed in the channel 413 is used) is used, whereby the insertion form of the endoscope is detected three-dimensionally so that it is possible to display the insertion form of the endoscope by a continuous image.

(2) A dedicated marker (which may be a marker shown in FIG. 121, or which is a marker having a structure different from that shown in FIG. 121) is mounted whereby it is possible to determine the arrangement relationship with respect to the endoscope form, on an image plane.

(3) It is possible to rotate or zoom the displayed form image of the endoscope, within the assigned range.

(4) It is possible to return the form image which is moved by the rotation and one zoom, the initial state.

(5) It is possible to freeze the form image which is continuously displayed.

(6) It is possible to superscript the comments on the displayed form image.

(7) It is possible to display the following items on the image plane:
Date and time
Patient data (patient ID, name, sex, age and birth)
Comments (8) The following items can be inputted modified on the image plane:
Patient data (patient ID, name, sex, age and birth)
Comments (9) The patient data can previously be inputted, and the contents thereof can be listed.

(10) It is possible to set date time.

(11) It is possible to set the mode which uses the marker.

(12) It is possible to input display the characters on the full image plane.

(13) It is possible to erase all the characters which are displayed on the image plane.

(14) It is possible to use a stop watch on the image plane.

(15) It is possible to use the following functions in combination with a multi video processor:
It is possible to select display non-display of the form image of the endoscope on a color monitor.
It is possible to freeze the displayed form image on a color monitor.

Typical examples of function and specific display image planes in that case will subsequently be shown.

FIG. 137 shows more specific display examples in FIG. 126. That is, FIG. 137 shows normal display image planes in which form images are displayed on a display surface of the color monitor 423. The form image is displayed on a graphic output region (referred also to as "scope image display frame") G. Date and time, and the patient data (patient ID, name, sex, age and birth) are displayed on a date & patient data output region D & P on the graphic output region G. A main hot key, and corresponding set information and comments are displayed on a user interface region (referred also to as "comment display frame) K on the right side of the graphic output region G.

Further, in FIG. 137, two hand markers which indicate, for example, the reference position are displayed. On the drawings subsequent to FIG. 138, for simplification, a transcription of the above-described output regions G, D & P and K will be omitted.

In FIG. 137, the data input of the date & patient data output region D & P is selected by operation of the mouth or the keyboard, for example, whereby, as shown in FIG. 138, it is possible to input the name of the patient data, for example. Of course, it is also possible to conduct input of the other data and modification of the data.

Functions set by the function key will subsequently be described.

[f·1] . . . Stop watch

1. When the function key [f·1] is depressed once, a stop watch starts. At this time, time is displayed on an upper part of the comment display frame K on the right of the image plane. FIG. 139 shows the display image plane when the stop watch starts.

2. When the function key [f·1] is depressed once more, the stop watch stops. FIG. 140 shows the display image plane when the stop watch stops.

3. When the function key [f·1] is depressed once more, the display of the stop watch is erased.

[f·2] . . . Erase of Full Characters

1. When the function key [f·2] is depressed once, all the characters on the image plane are erased. FIG. 141 shows the display image plane under a state in which all the characters on the image plane are erased.

2. When the function key [f·2] is further depressed once, the image plane is returned to the display of the initial state.

In connection with the above, the patient data, the comment and the like which are inputted on the image plane prior to the fact that the function is used become null by the use of the function, and will not be displayed if returned to the display under the initial state.

[f·3] . . . Expanded Comment Input

1. When the function key [f·3] is depressed once, the comments can become to be inputted within the scope-image display frame.

Under the state, a [SHIFT]+arrow key ([→], [←], [↑] and [↓]) is depressed whereby it is possible to input [→], [←], [↑] and [↓] within the scope-image display frame.

2. When the function key [f·3] is depressed once again, it is returned to a normal display state, while the input characters are left. FIG. 142 shows the display image plane in which the comments of tip and [→] are inputted in order to show the distal end of the insertion part.

In connection with the above, whenever the [SHIFT] key is not depressed, and the arrow key ([→], [←], [↑] and [↓]) is depressed, the cursor is moved according to the orientation of the depressed key. The arrangement is such that, when the function is used to conduct the comment input within the scope-image display frame G, it is impossible to conduct "[SHIFT]+arrow key ([→], [←], [↑] and [↓]) . . .

rotation zoom of the scope image". Accordingly, setting is previously made, and then, the expanded comment input is conducted.

[f·4] . . . Title Screen Display

1. When a function key [f·4] is depressed once, switching is made to an input image plane of a title screen so that a text can be inputted. FIG. 143 shows the title screen image plane.

2. When the function key [f·4] is further depressed once, the title screen input image plane disappears, and the image plane is returned to the normal display state. Since the text which is inputted at this time is backed up, the same text is displayed also upon subsequent calling.

In connection with the above, the arrow key ([→], [←], [↑] and [↓]) is used for movement of the cursor.

[f·5] . . . Pre-input Of Patient Data

1. When the function key [f·5] is depressed once, switching is made to a patient-data list image plane. FIG. 144 shows the patient-data list image plane.

2. When the function key [f·5] is further depressed once, the patient-data list image plane disappears, and the image plane is returned to the normal display state.

3. When the number which is desired to be registered to "Seq. No." on the image plane of the patient-data list is inputted by the number from 1~20, and the return key is depressed, a patient-data pre-input image plane is which the data input every each patient is pre-conducted is called. The data can be registered. FIG. 145 shows the patient-data pre-input image plane.

Furthermore, when a [HOME CLR] key serving as an all-data erasing key is depressed at the time of input waiting of "Seq. No.", it is possible to erase all the patient data from 1~20.

4. On the data input image plane every each patient, it is possible to input the followings:

| <ITEM> | <FORM> |
|---|---|
| Patient ID | → To 15 English Numerical Characters |
| Name | → To 20 English Numerical Characters |
| Sex | → To 3 English Numerical Characters |
| Age | → To 3 English Numerical Characters |
| Birth | → DD/MM/YY (D: Date, M: Month and Y: Year) |

Selection of the items is conducted by depression of top and bottom arrow keys ([↑] and [↓]) or a return key.

In connection with the above, right and left arrow keys ([→] and [←]) are used for movement of the cursor.

5. If the input is ended or completed, the function key [f·6] is depressed, and they are registered to the patient data. If registered, the image plane comes into the patient-data input image plane of subsequent "Seq. No.". Accordingly, the function key [f·6] is depressed repeatedly until "Seq. No." comes into 20. Alternatively, a function key [f·9] is depressed. Thus, pre-input function is ended. In connection with this, since the registered patient data are backed up, the same patient data are displayed also at a subsequent list.

[f·7] . . . Selection Of Patient Data

1. When the function key [f·7] is depressed once, switching is made to the patient-data list image plane.

2. When the function key [f·7] is depressed once again, the patient-data list image plane disappears, and the image plane is returned to the normal display state.

3. When the number which is desired to be selected to "Seq. No." on the image plane of the patient-data list is inputted by the number from 1~20, and the return key is depressed, data for each patient are called to a top of the normal image plane so that display of the patient data can be conducted. That is, it is possible to select the patient data. FIG. 146 shows the patient-data list image plane in which the patient data which are inputted on the patient-data pre-input image plane in FIG. 145 is selected and displayed.

When the [HOME CLR] key is depressed upon selection of "Seq. No.", all the patient data from 1~20 can be erased.

[f·8] . . . Display Switching Of Cursor

1. When the function key [f·8] is depressed once in the normal display image plane or in the comment expanded display image plane, the cursor is displayed. The cursor is then in a position where a blinked portion can be inputted. FIG. 147 shows the display image plane of the cursor.

2. When the function key [f·8] is depressed once again, switching is made to a pre-set image plane for conducting modification of the initial setting. On the pre-set image plane, it is possible to conduct modification of date and time and modification of the marker mode so as to be able to correspond to a used place (country), summer time or the like.

As has been described in FIG. 134 and FIG. 135, it is possible to select the marker mode from a single hand marker, a single body marker, a two-hand marker, a hand marker+a body marker, a memory marker position (one-marker mode) in which a marker position is stored, and a memory marker position (two-marker mode) in addition to the mode in which the marker is not used.

Selection of the items is conducted by depression of the top and bottom arrow keys ([↑] and [←]) or the return key. FIG. 148 shows the pre-set image plane. In this connection, the right and left arrow keys ([→] and [←]) are used for movement of the cursor.

2. When the function key [f·9] is depressed once again, the pre-set image plane disappears. The image plane is returned to the normal display state, and comes into the modified setting. Further, if any items are not modified, the image plane is returned to the normal display state while being the previous setting.

[CTRL]+[→]
[CTRL]+[←]
[CTRL]+[↑]
[CTRL]+[↓] . . . Rotation Zoom Of Scope Image
[CTRL]+[+]
[CTRL]+[−]
[vf·1]

1. When a [CTRL]+the right and left arrow keys ([↑] and [↓]) are depressed, the scope image is rotated about the center of the Y-axis. FIG. 149 shows a form image where, for example, FIG. 146 is rotated 50° about the Y-axis. In the comment frame, the amount of rotation is displayed.

2. When the [CTRL]+the top and bottom arrow keys ([↑] and [↓]) are depressed, the scope image is rotated about the center of the x-axis. FIG. 150 shows a form image where, for example, FIG. 146 is rotated −75° about the x-axis. In the comment frame, the amount of rotation is displayed.

3. When the [CTRL]+[+] key is depressed, the scope image goes away. Moreover, when the [CTRL]+[−] key is depressed, the scope image approaches. FIG. 151 shows a form image in case where the [CTRL]+[+] key is depressed to conduct a zoom-out (reduction), while FIG. 152 shows a form image in case where the [CTRL]+[−] key is depressed to conduct a zoom-in (enlargement).

In FIG. 151, a view point which indicates a distance increases, while, in FIG. 152, the view point decreases.

4. When the function key [vf·1] is depressed, a visual point which is modified by the above-described operation of 1~3 is returned to the initial setting.

[vf·2] . . . Freeze Of Scope Image

1. When the function key [vf·2] is depressed once, one scope image is frozen.

2. When the function key [vf·2] is further depressed once, the freeze is canceled or released.

[vf·3] . . . Display Switching Of Scope Image

1. When the function key [vf·3] is depressed once, the scope image which is displayed by the wire frame is painted out and is displayed. The form image which is shown subsequent to FIG. 137 (to FIG. 152) is displayed by the wire frame (showing an example of the wire frame display in a circle in which a part of FIG. 152 is enlarged). However, [vf·3] is depressed whereby the scope image is painted out and is displayed as shown in FIG. i53.

2. When the function key [vf·3] is depressed once again, the painting-out is canceled, the form image is displayed by wire frame.

(5) Other Functions

Image output operation by a multi video processor

[vf·4] . . . Freeze Of Video Image

When the function key [vf·4] is depressed once, the scope image which is displayed on the video monitor is frozen. When the function key [vf·4] is depressed once again, the freeze is canceled

[vf·5] . . . Superimposition Of Video Image

When the function key [vf·5] is depressed once, the video image (endoscope image) is superimposed upon the scope image which is displayed on the video monitor. When the function key [vf·5] is depressed once again, the superimposition is canceled.

In connection with the above, these functions cannot be used if connection to the multi video processor can conduct video signal output.

During the endoscope inspection, naturally, an operator observes the practical endoscope image plane, and attention is paid to the presence of a lesion part. For this reason, the image which is projected onto the plurality of monitors is observed, thereby enlarging the burden on the operator becomes large or is enlarged. Accordingly, in order to improve this, the image can be superimposed within the display image plane of the endoscope image to display the scope form.

In this case, whenever the output from the endoscope form detection device is a signal different from the general video signal, the signal is converted to the normal video signal and is outputted. A device called a scan converter is used for the conversion. Operation of the scan converter which is a device different from the endoscope form detection device is controlled through an RS-232C or the like from a personal computer within the form detection device, whereby the operation of the scan converter can be operated.

The endoscope form detection device is connected to the multi video processor through the aforesaid scan converter so (also, the endoscope form is) arranged as to be displayed on the video monitor, whereby freeze or the like of the video image can be controlled as mentioned previously.

Furthermore, it is possible also to control the superimposition of the video image. Whenever the output from the endoscope form detection device is the signal of the standard the same as the general video signal, the endoscope form detection device is connected to the multi video processor without the intervening of the scan converter. Thus, it is possible to realize the similar function.

In connection with the above, in recent years, since there is hardware in which the normal video signal is fetched so as to be displayed on an image plane of a personal computer or a work station (specifically, a device capable of conducting highspeed A/D conversion), the arrangement may be such that such device is used to conversely display the endoscope observation image onto the monitor of the form detection device.

[HELP] . . . Scope Image Two-Image-Plane Display

1. When the [HELP] key is depressed once, the scope image is displayed simultaneously in two directions including a horizontal direction and a vertical direction. FIG. 154 shows the image plane of the scope image two-image-plane display. Under a state in which a visual-point direction is not modified, a scope form in the vertical direction (from a Z-direction) is normally displayed on the left side, while the scope form in the horizontal direction (from an X-direction) is displayed on the right side.

In the scope image two-image-plane display mode, the function of [vf·1]~[vf·5] and the inspection end function of [vf·10] are functioned similarly to the normal one-image-plane display mode.

2. Further, the rotation zoom function of the scope image functions simultaneously in two image planes.

In this connection, the comments which are inputted on the image plane before the function is used become null by the use of the function, and are not displayed.

[HOME_CLR] . . . Inspection Range Reference Surface

Display On/Off

1. When a [HOME_CLR] key is depressed once, display of a cube indicating an inspection-range reference frame is not conducted. FIG. 155 shows an image plane under a state in which an inspection-range reference frame is not displayed, that is, the inspection-range reference frame is erased, but display of the scope image is conducted.

2. When the [HOME_CLR] key is further depressed once, switching is made to a state which displays the inspection-range reference frame.

In connection with the above, in the above description, it has been described that, in the two-image-plane mode, the scope forms in the directions 90° different from each other in the direction of the view point can be displayed. However, the embodiment includes also an arrangement which can display the scope forms in two directions which are 90° different from each other in the direction of the view point. Moreover, the arrangement may be such that, in the two-image-plane mode, the date & patient data and the like can simultaneously be displayed, and the display/non-display of the data can be selected.

Under a state in which the scope forms are displayed in the directions which are 90° different from each other in the direction of the visual point in the two-image-plane mode, it is also possible to simultaneously alter or modify the direction of the visual point. Furthermore, it is also possible to modify the direction of the visual point only of the image of one scope form. In this case, the two images are in a state in which the directions of the visual point are 90° different from each other.

In connection with the above, in the one-image-plane mode, the scope form is displayed in the graphic output region G under the date & patient data output region D & P, as shown in FIG. 137. However, the scope image may be displayed in a region which includes the date & patient data output region D & P. These may be selected and displayed. Further, the scope form may be displayed in a region which includes also the graphic output region G and the user interface region K. Moreover, the scope form may be displayed in the maximum display region (or the maximum display image-plane size) which includes three regions D & P G and K.

In this manner, since the third embodiment is provided with various functions with regard to the display method or the like, the form grasping within the body of the patient may be easily understood from the displayed endoscope form.

In connection with the above, in the above-described embodiments or the like, the direction of the scope form, or the like, is easily grasped from the display of the marker, or the like. However, as shown in FIG. 156, the distal end side, for example, of the displayed endoscope form is displayed by a display method (for example, only the most distal end is displayed by color different from that of the other portions, that is, a displayed color is modified. In addition thereto, the arrangement may be such that a painting model is modified such that, in the case where an arrow indicating the most distal end is displayed, the most distal end is displayed by turning-ON and -OFF thereof, and the other portions are displayed by the wire frame, display is made by a paste model in which the distal end part is painted out) which is different from the other portions, whereby it is possible to easily grasp or judge the distal-end side from the displayed image and, thus, the grasping of the scope form can easily be conducted.

In connection with the above, if the number of the arrangement of the three-axes sense coil 422$j$ increases, it is possible to conduct positional detection of the source coil 416$i$ further accurately. It is also possible to estimate the endoscope form accurately.

The endoscope form detecting apparatus 501 according to the twenty-second embodiment shown in FIG. 157 comprises the endoscope 502, the light-source device 503, the insertion form detection part 504, the monitor 505, the antenna coil 506, and the scanning device 507 for scanning the antenna coil 506.

The endoscope 502 has the insertion part 508, the operation part 509, the ocular part 511, and the light guide cable 512 which extends from the ocular part 511. The light guide cable 512 has one thereof which is connected to the light source device 503, whereby an illumination light is supplied from a lamp within the light source device 503. The illumination light is outputted forwardly from an illumination window in the distal end part 513 of the insertion part 508.

An objective optical system is arranged in an observation window which is located adjacent to an illumination window. An image due to the objective optical system is transmitted to the end face on the side of the ocular part, through the image guide so as to be able to be observed by naked eyes through the ocular window. Further, the angle knob 514 which is provided on the operation part 509 is operated in angular movement, whereby it is possible to curve the curvature part 515 which is provided adjacent to the distal end of the insertion part 508. Thus, the arrangement is such that the distal end part 513 which is located adjacent to the curvature part 515 can be oriented to a direction which is desired by the operator.

The branched other end of the light guide cable 512 is connected to the insertion form detection part 504.

The insertion form detection part 504 has the oscillator 521. The oscillation output from the oscillator 521 is supplied to the antenna coil 506. Further, the insertion-form detection part 504 has the CPU 522 for controlling operation of the insertion form detection part 504. The CPU 522 drives controlling transistors Tri (i=1, 2, 3, ..., N) which are connected to the output port 523, to send a selection signal to couplers CPi (i=1, 2, 3, ..., N) within the endoscope 502.

A signal which is detected by loop coils LCi (i=1, 2, 3, ..., N) connected to the couplers CPi is transmitted through a coaxial cable 525. The signal is inputted to a receiving circuit 527 through the matching transformer 526 to which a rearward or proximal end of the coaxial cable 525 is connected. After the signal has been amplified, or the like, the signal is converted to a digital signal by the A/D converter 528, and is inputted to the CPU 522.

The CPU 522 conducts computation of the form detection from a signal which is inputted such that the memory 529 is used in a work area, or the like, to output the computation result to the form signal generation circuit 531 for generating an image signal corresponding to the form. The image signal which is generated by the form signal generation circuit 531 is outputted to the color monitor 505. The form of the detected insertion part is displayed on a display image plane.

Moreover, the CPU 522 is connected to the scanning circuit 507 through the antenna scanning drive circuit 532, to conduct such control or the like that setting is made under a state in which the signal which is detected in such a manner that orientation of the antenna coil 506 due to the scanning circuit 507 through the antenna scanning drive circuit 532 is altered or changed comes into the maximum or the minimum.

The insertion form detection part 504 is connected to the endoscope 502 through the coaxial cable 525 and a control line CLi for transmitting the selection signal. As shown in FIG. 158, the control line CLi and the coaxial cable 525 are inserted into the insertion part 508.

The insertion part 508 shown in FIG. 158 comprises the flex 541 made of a helical metallic band, the blade 542 made of a metallic network tube which covers an outer peripheral surface thereof, and the tube 543 made of resin covering the outer peripheral surface of the blade 542.

Since, normally, the insertion part 508 is covered by the blade 542 which is made of the metallic band or strip, it is isolated from electromagnetic wave invading the insertion part 508 from the outside. For this reason, the present embodiment has a structure in which the blade 541 is cut off to provide a window Wi so that the electromagnetic wave can be invaded. The present embodiment is arranged such that a loop coil LCi for detection of the electromagnetic wave which is emitted to the atmosphere from the antenna coil 506 is arranged on a ring-like portion between the flexes 541 on the inside of each window Wi, and the electromagnetic wave due to the antenna coil 506 can be received through the window Wi.

A signal which is induced to the loop coil LCi is transmitted to a coupler CPi. The control line CLi and the common coaxial cable 525 are connected to each of the couplers CPi. A signal induced to the loop coil LCi which is connected to the coupler CPi connected to the control line CLi to which the selection signal is applied is transmitted by the coaxial cable 525. FIG. 159 shows an arrangement of the coupler CPi.

The coupler CPi comprises the matching transformer 551 for conducting alignment in impedance between the loop coil LCi and the coaxial cable 525, and the diode switch circuit 552 for outputting a signal from only the loop coil LCi which is selected by the selection signal of the control line CLi, to the coaxial cable 525.

The diode switch circuit 552 comprises the diode 553 and the condenser or the capacitor 554 provided between the matching transformer 551 and the coaxial cable 525, and the impedance element Z such a resister connected between a connection point between the diode 553 and the capacitor 554 and the distal end of the control line CLi, or the like. The diode switch circuit 552 is so arranged as to send a selection signal of an "H" level to the coupler CPi through the control line CLi, to thereby turn ON the diode 553 to set the loop coil LCi to an electric conduction state with respect to the coaxial cable 525, so that a signal induced to the loop coil LCi can be sent to the side of the coaxial cable 525.

Operation of the embodiment will subsequently be described. A signal indicating selection is outputted to the output port 523 by the CPU 522. The transistor Tr1, for example, is turned ON by the signal, and current flows from a power source end Vcc of the "H" level to the control line CL1. The current flows to the diode 553 through the impedance element Z of the coupler CP1. The current flows in a forward direction of the diode 553, whereby a minute signal which is induced to the loop coil LC1 is transmitted in a reverse direction of the diode 553, and is transmitted to the coaxial cable 525 through the capacitor 554.

The signal which is transmitted by the coaxial cable 525 is inputted to the receiving circuit 527 within the insertion form detection part 504, and is amplified. Thereafter, a signal intensity of the loop coil LC1 is transformed or converted to a digital signal by the A/D converter 528 and, thereafter, the digital signal is fetched to the CPU 522.

The CPU 522 drives the scanning device 507 through the antenna scanning drive circuit 532 such that the signal intensity is maximized or minimized, to scan the loop antenna 506.

The CPU 522 conducts computation which calculates a distance range from the loop antenna 506 of the loop coil LP1 under a state in which the signal intensity is maximized or minimized. The signal intensity either maximized or minimized, whereby it is possible to reduce a width of the distance range in which the loop coil LP1 is to reside, from a known position (however, orientation is different depending upon scanning) of the loop antenna 506.

When computation of the distance range in which the loop coil LP1 is to reside is ended, a subsequent transistor Tr2 is turned ON, to conduct computation of a distance range in which the loop coil LP2 is to reside.

In this manner, when computation of the distance range in which all the loop coils LP1, LP2, ..., LPN are to reside is ended, the CPU 522 conducts processing or the like in which the model form of the insertion part 508 is painted, from each of the positions of the loop coil LPi. An image signal corresponding to the model form is outputted to the color monitor 505 through the form-signal generation circuit 531. The detected model form of the insertion part 508 is displayed.

In connection with the above, the coupler CPi may be provided within the insertion part 508, or may be provided within the operation part 509. Furthermore, a non-conductive reinforced fiber such as a glass fiber or the like may be used in place of the flex 541 and the blade 542 within the insertion part 508. In case where the non-conductive reinforced fiber is used in place of the blade 542, it is unnecessary to provide the window Wi.

According to the present embodiment, since the non-scanning antenna or standard antenna for transmission is provided on the outside of the endoscope 502, there are the following merits as compared with case where the non-scanning antenna for transmission is provided on the inside of the endoscope 502.

Since high-frequency power for transmission is not required to be sent to the endoscope 502, it is possible to reduce high-frequency leakage current.

Further, in FIG. 157, the description has been made to case of the endoscope 502 of the optical system. However, it is possible to reduce the affection or influence of a noise which is given to an image pickup element, with respect to case of an electronic endoscope.

A twenty-third embodiment of the invention will subsequently be described. The embodiment is arranged such that a curvature part of the endoscope is utilized for receiving antenna.

As shown in FIG. 160, the curvature part 561 is arranged such that the insulating piece 562 in the form of a ring, which is formed by plastics or the like and the antenna piece Ai made of metal are rotatably connected to each other in a longitudinal direction of the curvature part 561, alternately, by the rivets 564. A light guide, an image guide, an angle wire or the like (not shown) is inserted into the inside of the insulating piece 562 and the antenna piece Ai which are connected to each other, and the coupler 565 and a feeder Fi connected to the coupler 565 are inserted thereinto.

Outer peripheral surfaces or the insulating piece 562 and the metallic antenna piece Ai are covered by the tube 571which is made of a non-conductive reinforced fiber, and the outside of each thereof is covered by the tube 572 made of rubber.

The coupler 565 in the present embodiment is so arranged as to have functions of a plurality of couplers CPi shown in FIG. 159 (refer to FIG. 163). Each of the feeders Fi which extend from the coupler 565 is connected to the antenna piece Ai.

As shown in FIG. 161 and FIG. 162, the antenna piece A1 is arranged such that a part of a metallic ring is cut out so as to be formed into a C-ring form. The insulation plate 566 is fitted in or immersed in the cut-out portion. The insulation plate 567 which is fixed inside thereof to the insulation plate 566 by adhesives or the like is fixed to the antenna piece A1 by a plurality of caulking pins 568.

As shown in FIG. 162, the feeder Fi is connected, by solder or the like, to a portion of the antenna piece A1 on both sides which put therebetween the insulation plate 567.

As shown in FIG. 163, the coupler 565 is so arranged as to unite or combine the plurality of couplers CPi described with reference to FIG. 159. The diode of the diode switch circuit 552 which is selected by the control line CLi is conducted so that the signal which is induced to the antenna piece Ai is inputted to the receiving circuit through the coaxial cable 525.

The arrangement of the insertion form detecting part or the like according to the present embodiment is similar to that of the twenty-second embodiment Moreover, function or operation of the form detection is similar to that of the twenty-second embodiment.

According to the present embodiment, there are the following advantages.

Since the curvature piece which forms the curvature part of the endoscope is utilized as the antenna, it is unnecessary or is not required to provide a separate antenna. Thus, it is possible to apply the curvature piece also to an endoscope having a thin curvature part.

Detection of the state of the curvature part is important to decide the insertion direction or the like of the insertion part. However, the curvature part makes it difficult to arrange the antenna because the curvature piece is arranged. According to the present embodiment, since the curvature piece is utilized also to the antenna, it is possible to conduct the form detection of the curvature part, without the fact that the curvature part becomes thick.

In connection with the above, embodiments or the like arranged such that the above-described embodiments or the like are combined with each other partially or the like belong to the present invention.

In connection with the above, embodiments or the like arranged such that the above-described embodiments or the like are combined with each other partially or the like belong to the present invention.

What is claimed is:

1. An endoscope position detecting apparatus comprising:
   an endoscope having a flexible insertion part which is insertable into an object to be examined, said endoscope having illumination-light emitting means for emitting an illumination light toward a distal end of said insertion part, and an objection optical system for observing an illuminated subject;
   a first position estimation element including a magnetic-field generation element for generating a magnetic field to an environment arranged on said insertion part for estimating a position of said first position estimation element by application of a drive signal;
   a second position estimation element including a magnetic-field detection element for detecting the magnetic field generated by said magnetic-field generation element, said second position estimating element being installed at a known position outside said subject and which is used for estimation of said position of said first position estimation element with respect to said known position;
   position estimation means for estimating a position of said first position estimation element which is arranged within said insertion part with respect to said known position outside of said subject from a detection signal which is detected by said magnetic-field detection element on the outside of the subject;
   insertion-part form estimation means for estimating a form of said insertion part which is inserted into said object to be examined from the position which is estimated by said position estimation means; and
   display means for displaying a form of said insertion part which is estimated by said insertion-part form estimating means, by two images corresponding respectively to cases where directions from an observation point which observes said insertion part are different from one another,
   wherein said position estimation means initially changes orientation of said magnetic-field generation element to determine a maximum value and a minimum value of the magnetic-field strength which can be detected by said magnetic-field detection element, and sets said maximum value and said minimum value to reference information whenever a distance between said magnetic-field generation element and said magnetic-field detection element is changed, to decide a range in which a distance between said magnetic-field generation element and said magnetic-field detection element exists, with reference to said reference information with respect to the magnetic-field strength determined from the detection signal which is detected by said magnetic-field detection element, to thereby estimate a position of said magnetic-field generation element within said insertion part.

2. An endoscope position detecting apparatus according to claim 1, wherein said display means simultaneously displays the two images corresponding to two directions from the observation point in which the direction from said observation point are perpendicular to one another.

3. An endoscope position detecting apparatus comprising:
   an endoscope having a flexible insertion part which is insertable into an object to be examined, said endoscope having illumination-light emitting means for emitting an illumination light toward a distal end of said insertion part, and an objective optical system for observing an illuminated subject;
   a first position estimation element including a magnetic-field generation element for generating a magnetic field to an environment arranged on said insertion part for estimating a position of said first position estimation element by application of a drive signal;
   a second position estimation element for estimating said position of said first position estimation element with respect to a known position of said subject from a detection signal which is detected by a magnetic-field detection element on the outside of said subject;
   position estimation means for estimating a position of said first position estimation element which is arranged within said insertion part with respect to said known position outside of said subject from a detection signal which is detected by said magnetic-field detection element on the outside of the subject;
   insertion-part form estimation means for estimating a form of said insertion part which is inserted into said object to be examined, from the position which is estimated by said position estimation means; and
   display means for displaying an image corresponding to a form of said insertion part which is estimated by said insertion-part form estimating means;
   a reference-position setting element formed by one of said magnetic-field generation element and said magnetic-field detection element, in order to display the set position as a reference position on said image by said display means; and
   reference-position display means for displaying the reference position corresponding to the position of said reference-position setting means onto said image,
   wherein said position estimation means initially changes orientation of said magnetic-field generation element to determine a maximum value and a minimum value of the magnetic-field strength which can be detected by said magnetic-field detection element, and sets said maximum value and said minimum value to reference information whenever a distance between said magnetic-field generation element and said magnetic-field detection element is changed, to decide a range in which a distance between said magnetic-field generation element and said magnetic-field detection element exists, with reference to said reference information with respect to the magnetic-field strength determined from the detection signal which is detected by said magnetic-field detection element, to thereby estimate a position of said magnetic-field generation element within said insertion part.

4. An endoscope position detecting apparatus according to claim 3, including identification means which is utilized for identification of a range which displays said image with said reference position serving as a reference.

5. An endoscope position detecting apparatus comprising:
   an endoscope having a flexible insertion part which is insertable into an object to be examined, said endoscope having illumination-light emitting means for emitting an illumination light toward a distal end of said insertion part, and an objective optical system for observing an illuminated subject;

a first position estimation element including a magnetic-field detection element for detecting the magnetic field which is generated by a magnetic-field generation element by application of a drive signal, said first position estimation element being arranged on said insertion part for estimating a position of said first position estimation element;

a second position estimation element including said magnetic-field generation element for generating a magnetic field to an environment installed at a known position outside said subject and is used for estimation of said position of said first position estimation element with respect to said known position;

position estimation means for estimating a position of said first position estimation element which is arranged within said insertion part with respect to said known position outside of said subject from a detection signal which is detected by said magnetic-field detection element on said insertion part;

insertion-part form estimation means for estimating a form of said insertion part which is inserted into said object to be examined, from the position which is estimated by said position estimation means; and display means for displaying a form of said insertion part which is estimated by said insertion-part form estimating means, by two images corresponding respectively to cases where directions from an observation point from which said insertion part is observed are different from one another, wherein said position estimation means initially changes orientation of said magnetic-field generation element to determine a maximum value and a minimum value of the magnetic-field strength which can be detected by said magnetic-field detection element, and sets said maximum value and said minimum value to reference information whenever a distance between said magnetic-field generation element and said magnetic-field detection element is changed, to decide a range in which a distance between said magnetic-field generation element and said magnetic-field detection element exists, with reference to said reference information with respect to the magnetic-field strength determined from the detection signal which is detected by said magnetic-field detection element, to thereby estimate a position of said magnetic-field detection element within said insertion part.

6. An endoscope position detecting apparatus according to claim 5, wherein said display means simultaneously displays the two images corresponding to the two directions from the observation point in which the directions from said observation point are perpendicular to one another.

7. An endoscope position detecting apparatus comprising:

an endoscope having a flexible insertion part which is insertable into an object to be examined, said endoscope having illumination-light emitting means for emitting an illumination light toward a distal end of said insertion part, and an objective optical system for observing an illuminated subject;

a first position estimation element including a magnetic-field detection element for detecting a magnetic field which is generated by a magnetic-field generation element by application of a drive signal, said first position estimation element being arranged on said insertion part for estimating a position of said first position estimation element;

a second position estimation element including said magnetic-field generation element arranged outside of said subject for estimating said position of said first position estimation element with respect to a known position of said subject from a detection signal which is detected by the magnetic-field detection element on the insertion part;

position estimation means for estimating a position of said first position estimation element which is arranged within said insertion part with respect to said known position outside of said subject from a detection signal which is detected by said magnetic-field detection element on the outside of the subject;

insertion-part form estimation means for estimating a form of said insertion part which is inserted into said object to be examined, from the position which is estimated by said position estimation means; and display means for displaying an image corresponding to a form of said insertion part which is estimated by said insertion-part form estimating means;

reference-position setting element formed by one of said magnetic-field generation element and said magnetic-field detection element, in order to display the set position as a reference position on said image by said display means; and reference-position display means for displaying the reference position corresponding to the position of said reference-position setting means onto said image, wherein said position estimation means initially changes orientation of said magnetic-field generation element to determine a maximum value and a minimum value of the magnetic-field strength which can be detected by said magnetic-field detection element, and sets said maximum value and said minimum value to reference information whenever a distance between said magnetic-field generation element and said magnetic-field detection element is changed, to decide a range in which a distance between said magnetic-field generation element and said magnetic-field detection element exists, with reference to said reference information with respect to the magnetic-field strength determined from the detection signal which is detected by said magnetic-field detection element, to thereby estimate a position of said magnetic-field detection element within said insertion part.

8. An endoscope position detecting apparatus according to claim 7, including identification means which is utilized for identification of a range which displays said image with said reference position serving as a reference.

* * * * *